US012528763B2

(12) United States Patent
Lee et al.

(10) Patent No.: US 12,528,763 B2
(45) Date of Patent: Jan. 20, 2026

(54) HETEROCYCLIC COMPOUND AND ORGANIC LIGHT-EMITTING DEVICE COMPRISING SAME

(71) Applicant: LT MATERIALS CO., LTD., Yongin-si (KR)

(72) Inventors: Gi-Back Lee, Yongin-si (KR); Ji-Yeon Park, Yongin-si (KR); Won-Jang Jeong, Yongin-si (KR)

(73) Assignee: LT MATERIALS CO., LTD., Yongin (KR)

( * ) Notice: Subject to any disclaimer, the term of this patent is extended or adjusted under 35 U.S.C. 154(b) by 702 days.

(21) Appl. No.: 17/614,794

(22) PCT Filed: Oct. 20, 2020

(86) PCT No.: PCT/KR2020/014305

§ 371 (c)(1),
(2) Date: Nov. 29, 2021

(87) PCT Pub. No.: WO2021/080280

PCT Pub. Date: Apr. 29, 2021

(65) Prior Publication Data

US 2022/0267251 A1 Aug. 25, 2022

(30) Foreign Application Priority Data

Oct. 25, 2019 (KR) ........................ 10-2019-0133970

(51) Int. Cl.
*C07C 211/61* (2006.01)
*C07C 255/58* (2006.01)
(Continued)

(52) U.S. Cl.
CPC .......... *C07C 211/61* (2013.01); *C07C 255/58* (2013.01); *C07D 307/91* (2013.01);
(Continued)

(58) Field of Classification Search
CPC ... C07C 211/61; C07C 255/58; C07C 13/567; C07C 211/54; C07D 307/91;
(Continued)

(56) References Cited

U.S. PATENT DOCUMENTS 4,356,429 A 10/1982 Tang
9,260,390 B2 2/2016 Kato
(Continued)

FOREIGN PATENT DOCUMENTS

CN 109928887 A * 6/2019 ........... C07C 211/61
CN 111662187 A * 9/2020 ........... C07C 211/54
(Continued)

OTHER PUBLICATIONS

Machine-generated English-language translation of CN-111662259-A.*
(Continued)

*Primary Examiner* — Vu A Nguyen
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

11 Claims, 3 Drawing Sheets

(51) Int. Cl.

| | |
|---|---|
| ***C07D 307/91*** | (2006.01) |
| ***C07D 333/76*** | (2006.01) |
| ***H10K 50/13*** | (2023.01) |
| ***H10K 50/17*** | (2023.01) |
| ***H10K 50/18*** | (2023.01) |
| ***H10K 85/60*** | (2023.01) |

(52) U.S. Cl.
CPC ......... *C07D 333/76* (2013.01); *H10K 85/622* (2023.02); *H10K 85/624* (2023.02); *H10K 85/626* (2023.02); *H10K 85/633* (2023.02); *H10K 85/6574* (2023.02); *H10K 85/6576* (2023.02); *C07B 2200/05* (2013.01); *H10K 50/13* (2023.02); *H10K 50/171* (2023.02); *H10K 50/18* (2023.02)

(58) Field of Classification Search
CPC .. C07D 333/76; C07D 209/70; C07D 209/86; C07D 219/02; C09K 11/06; H01L 51/006; H01L 51/504; H01L 51/0054; H01L 51/0056; H01L 51/0073; H01L 51/0074; H01L 51/0058; H01L 51/00; H01L 51/50
See application file for complete search history.

(56) References Cited

U.S. PATENT DOCUMENTS

| | | | |
|---|---|---|---|
| 9,882,142 B2 | 1/2018 | Mujica-Fernaud et al. | |
| 2016/0254450 A1 | 9/2016 | Herron et al. | |
| 2020/0152874 A1* | 5/2020 | Park | H10K 85/633 |
| 2022/0238811 A1* | 7/2022 | Park | H10K 85/633 |

FOREIGN PATENT DOCUMENTS

| | | | | |
|---|---|---|---|---|
| CN | 111662259 A | * | 9/2020 | C07C 211/54 |
| EP | 2 468 725 A1 | | 6/2012 | |
| JP | 2016-537331 A | | 12/2016 | |
| KR | 10-2015-0036654 A | | 4/2015 | |
| KR | 10-2018-0015546 | * | 2/2018 | C07C 211/54 |
| KR | 10-2018-0015546 A | | 2/2018 | |
| KR | 10-2020-0127628 A | | 11/2020 | |
| KR | 10-2020-0131681 A | | 11/2020 | |
| WO | WO 2010/110553 A2 | | 9/2010 | |
| WO | WO 2012/026780 A1 | | 3/2012 | |
| WO | WO 2018/225991 A1 | | 12/2018 | |

OTHER PUBLICATIONS

Machine-generated English-language translation of CN-111662187-A.*

Chiba, T., Pu, YJ., Kido, J. (2018). White OLED (WOLED) and Charge Generation Layer (CGL). In: Adachi, C., Hattori, R., Kaji, H., Tsujimura, T. (eds) Handbook of Organic Light-Emitting Diodes. Springer, Tokyo.*

International Search Report (PCT/ISA/210) issued in PCT/KR2020/014305, dated Feb. 9, 2021.

Kuwabara et al., “Thermally Stable Multilayered Organic Electroluminescent Devices Using Novel Starburst Molecules, 4,4',4"-Tri(N-carbazolyl)triphenylamine (TCTA) and 4,4",4"-Tris(3-methylphenylphenyl-amino)triphenylamine (m-MTDATA), as Hole-Transport Materials,” Advanced Materials, vol. 6, No. 9, 1994, pp. 677-679.

* cited by examiner

【FIG. 1】
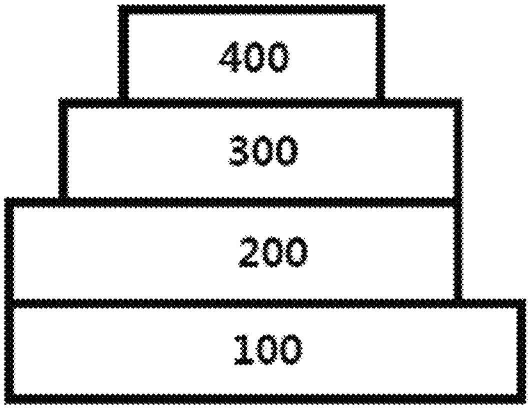
【FIG. 2】
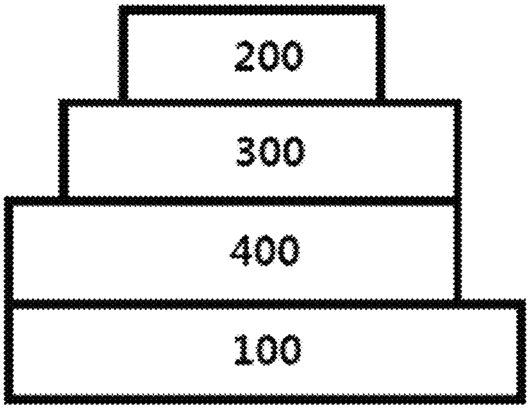

【FIG. 3】
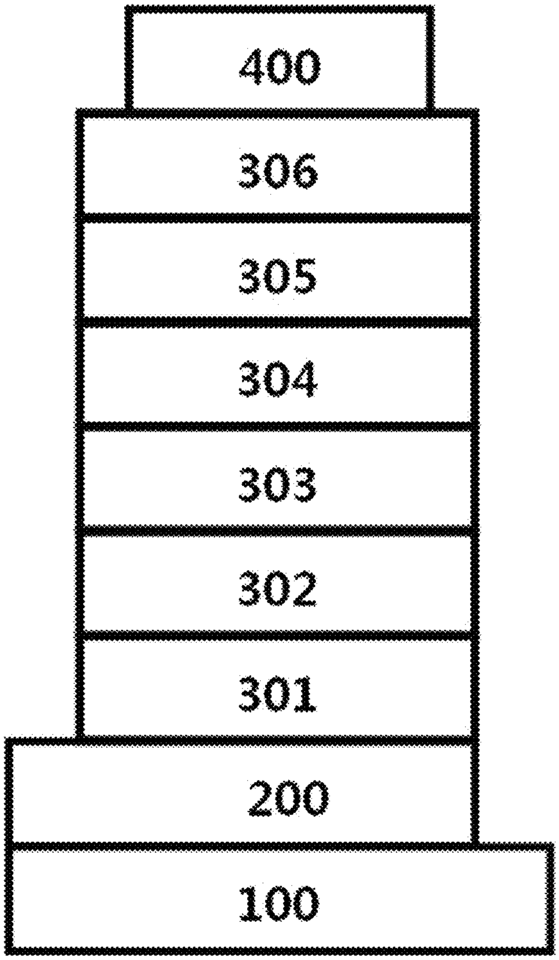

【FIG. 4】
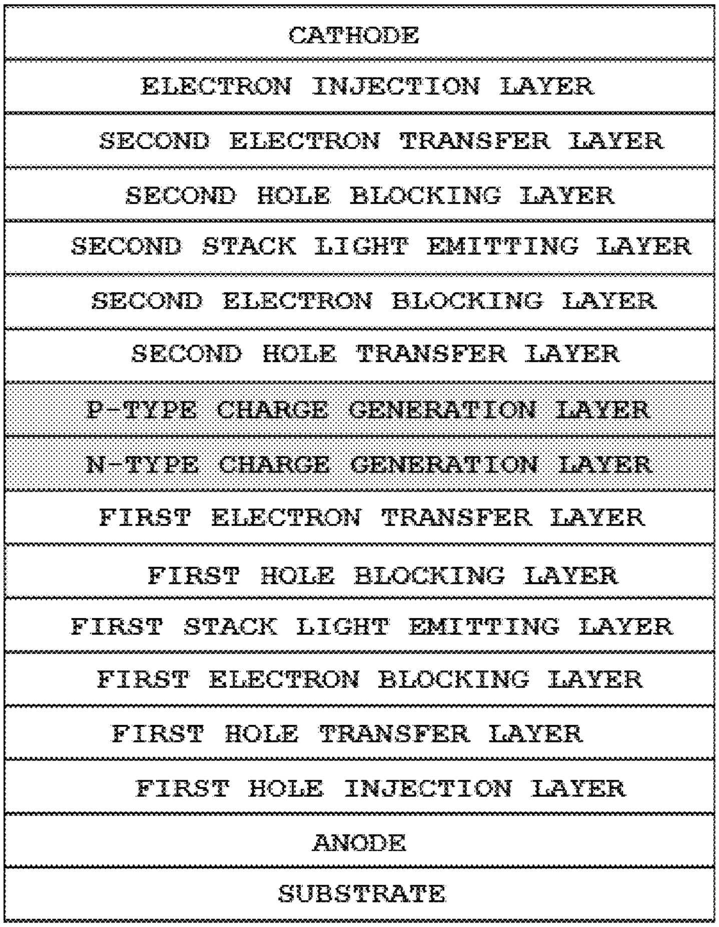

HETEROCYCLIC COMPOUND AND ORGANIC LIGHT-EMITTING DEVICE COMPRISING SAME

TECHNICAL FIELD

This application claims priority to and the benefits of Korean Patent Application No. 10-2019-0133970, filed with the Korean Intellectual Property Office on Oct. 25, 2019, the entire contents of which are incorporated herein by reference.

The present specification relates to a heterocyclic compound, and an organic light emitting device comprising the same.

BACKGROUND ART

An organic electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents

U.S. Pat. No. 4,356,429

DISCLOSURE

Technical Problem

The present disclosure is directed to providing a heterocyclic compound, and an organic light emitting device comprising the same.

Technical Solution

One embodiment of the present application provides a heterocyclic compound represented by the following Chemical Formula 1.

[Chemical Formula 1]

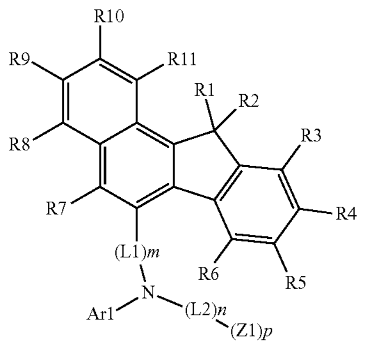

In Chemical Formula 1,

R1 and R2 are the same as or different from each other, and each independently a halogen group; a substituted or unsubstituted C1 to C60 alkyl group; a substituted or unsubstituted C6 to C60 aryl group; or a substituted or unsubstituted C2 to C60 heteroaryl group, L1 and L2 are the same as or different from each other, and each independently a direct bond; a substituted or unsubstituted C6 to C60 arylene group; or a substituted or unsubstituted C2 to C60 heteroarylene group, Ar1 is a substituted or unsubstituted C6 to C60 aryl group, Z1 is a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; or —P(═O)RR', R3 to R11 are the same as or different from each other, and each independently selected from the group consisting of hydrogen; deuterium; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(═O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring, R, R' and R" are the same as or different from each other, and each independently hydrogen; a substituted or unsubstituted C1 to C40 alkyl group; or a substituted or unsubstituted C6 to C40 aryl group, and m, n and p are an integer of 1 to 6, and when m, n and p are 2 or greater, two or more substituents in the parentheses are the same as or different from each other.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. In the organic light emitting device, the compound is capable of performing a role of a hole injection material, a hole transfer material, a hole blocking material, a light emitting material, an electron transfer material, an electron injection material, a charge generation material or the like. Particularly, the compound can be used as a hole transfer layer material or an electron blocking layer material of the organic light emitting device.

When using the compound represented by Chemical Formula 1 in the organic material layer, a driving voltage of the device can be lowered, light efficiency can be enhanced, and lifetime properties of the device can be enhanced by thermal stability of the compound.

The compound represented by Chemical Formula 1 has an amine-based substituent at a specific position on the skeleton having a fused fluorene group, and when included in an organic light emitting device, superior efficiency and driving are obtained through adjusting band gap and T1 value by strengthening hole properties Particularly, when using the amine derivative as a hole transfer layer, an unshared electron pair of the amine improves the flow of holes enhancing hole transfer capability of the hole transfer layer, and when used as an electron blocking layer, deterioration of the hole transfer material caused by electrons invading the hole transfer layer can be suppressed, and by combining the amine moiety with a substituent with enhanced hole properties, planarity of the amine derivative and the glass transition temperature increase, which increases thermal stability of the compound.

In addition, hole transfer capability is enhanced through adjusting band gap and T1 value, and molecular stability increases as well, and as a result, the device can have lowered driving voltage, enhanced light efficiency, and lifetime properties of the device can be enhanced due to thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0% or a hydrogen content being 100%.

In other words, an expression of "substituent X is hydrogen" does not exclude deuterium such as a hydrogen content being 100% or a deuterium content being 0%, and therefore, may mean a state in which hydrogen and deuterium are mixed.

In one embodiment of the present application, deuterium is one of isotopes of hydrogen, is an element having deuteron formed with one proton and one neutron as a nucleus, and may be expressed as hydrogen-2, and the elemental symbol may also be written as D or 2H.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

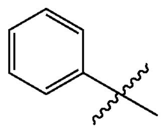 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

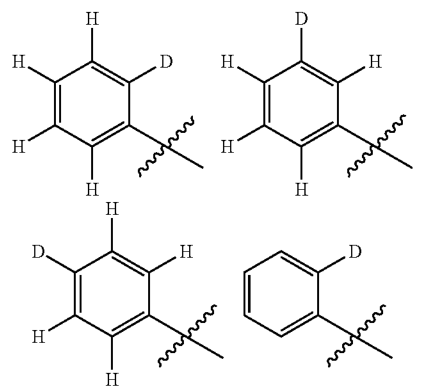

-continued

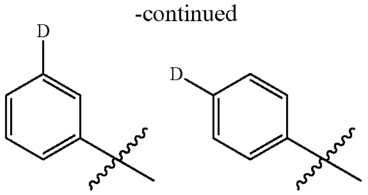

In addition, in one embodiment of the present application, “a phenyl group having a deuterium content of 0%” may mean a phenyl group that does not comprise a deuterium atom, that is, a phenyl group that has 5 hydrogen atoms.

In the present specification, the term “substitution” means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, “substituted or unsubstituted” means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the phosphine oxide group is represented by —P(═O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —$SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted, the following structures may be included, however, the structure is not limited thereto.

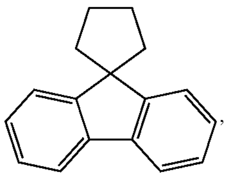,
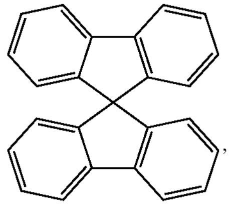,
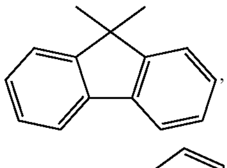,
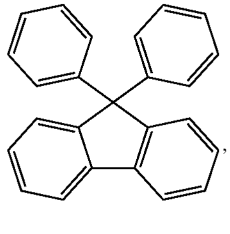,
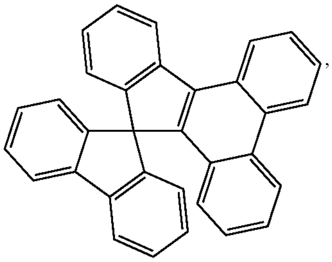,

-continued

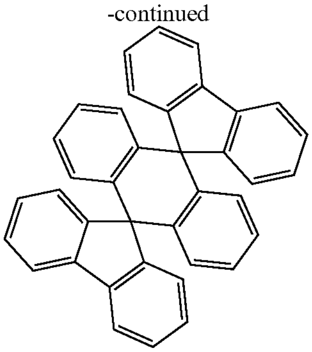

In the present specification, the heteroaryl group comprises S, O, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

One embodiment of the present application provides a compound represented by Chemical Formula 1.

In one embodiment of the present application, Chemical Formula 1 may be represented by any one of the following Chemical Formula 2 to Chemical Formula 4.

[Chemical Formula 2]

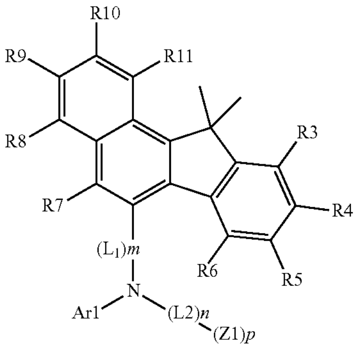

[Chemical Formula 3]

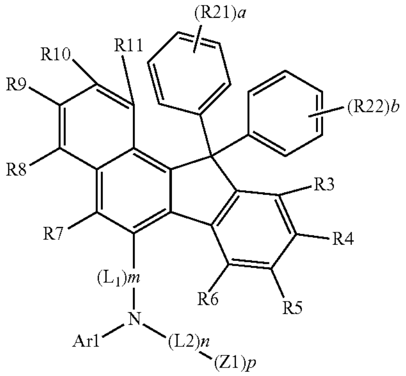

-continued

[Chemical Formula 4]

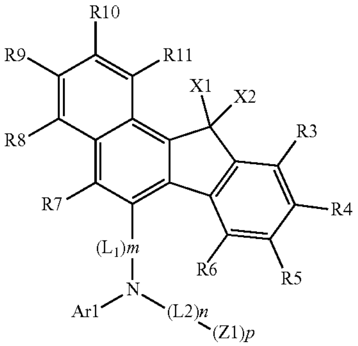

In Chemical Formulae 2 to 4,

R3 to R11, L1, L2, Z1, Ar1, m, n and p have the same definitions as in Chemical Formula 1, X1 and X2 are the same as or different from each other, and each independently a halogen group, R21 and R22 are the same as or different from each other, and each independently hydrogen; a halogen group; a substituted or unsubstituted C6 to C60 aryl group; or a substituted or unsubstituted C2 to C60 heteroaryl group, and a and b are each an integer of 1 to 6, and when a and b are 2 or greater, substituents in the parentheses are the same as or different from each other.

In one embodiment of the present application, Ar1 may be a substituted or unsubstituted C6 to C60 aryl group.

In another embodiment, Ar1 may be a substituted or unsubstituted C6 to C40 aryl group.

In another embodiment, Ar1 may be a substituted or unsubstituted monocyclic or polycyclic C6 to C40 aryl group.

In another embodiment, Ar1 may be a substituted or unsubstituted monocyclic or polycyclic C6 to C30 aryl group.

In another embodiment, Ar1 may be a monocyclic or polycyclic C6 to C30 aryl group unsubstituted or substituted with one or more substituents selected from the group consisting of a C1 to C20 alkyl group and a C6 to C30 aryl group.

In another embodiment, Ar1 may be a phenyl group; a biphenyl group; a naphthyl group; a dimethylfluorenyl group; a diphenylfluorenyl group; a dimethyl-11H-benzo[a]fluorenyl group or a spirobifluorenyl group.

In one embodiment of the present application, the dimethyl-11H-benzo[a]fluorenyl group may satisfy the following structure.

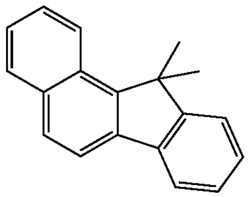 [SMILES: CC1(C)c2ccccc2-c2ccc3ccccc3c21]

In another embodiment, Ar1 is a substituted or unsubstituted monocyclic or polycyclic C6 to C12 aryl group, or may be represented by the following Chemical Formula 5 or Chemical Formula 6.

[Chemical Formula 5]

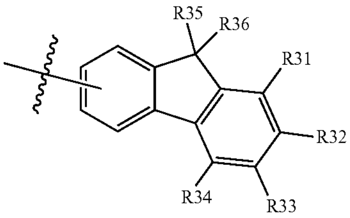

[Chemical Formula 6]

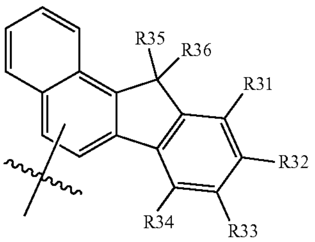

In Chemical Formula 5 and Chemical Formula 6,

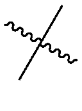

means a position linked to N of Chemical Formula 1,

R35 and R36 are the same as or different from each other, and each independently a substituted or unsubstituted C1 to C60 alkyl group; or a substituted or unsubstituted C6 to C60 aryl group, or adjacent groups bond to each other to form a substituted or unsubstituted C6 to C60 aromatic hydrocarbon ring or a substituted or unsubstituted C2 to C60 heteroring, and R31 to R34 are the same as or different from each other, and each independently selected from the group consisting of hydrogen; deuterium; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(═O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group.

In another embodiment, Ar1 is a monocyclic or polycyclic C6 to C12 aryl group, or may be represented by Chemical Formula 5 or Chemical Formula 6.

In another embodiment, Ar1 is a phenyl group; a biphenyl group; or a naphthyl group, or may be represented by Chemical Formula 5 or Chemical Formula 6.

In one embodiment of the present application, Ar1 may be represented by any one of the following structural formulae.

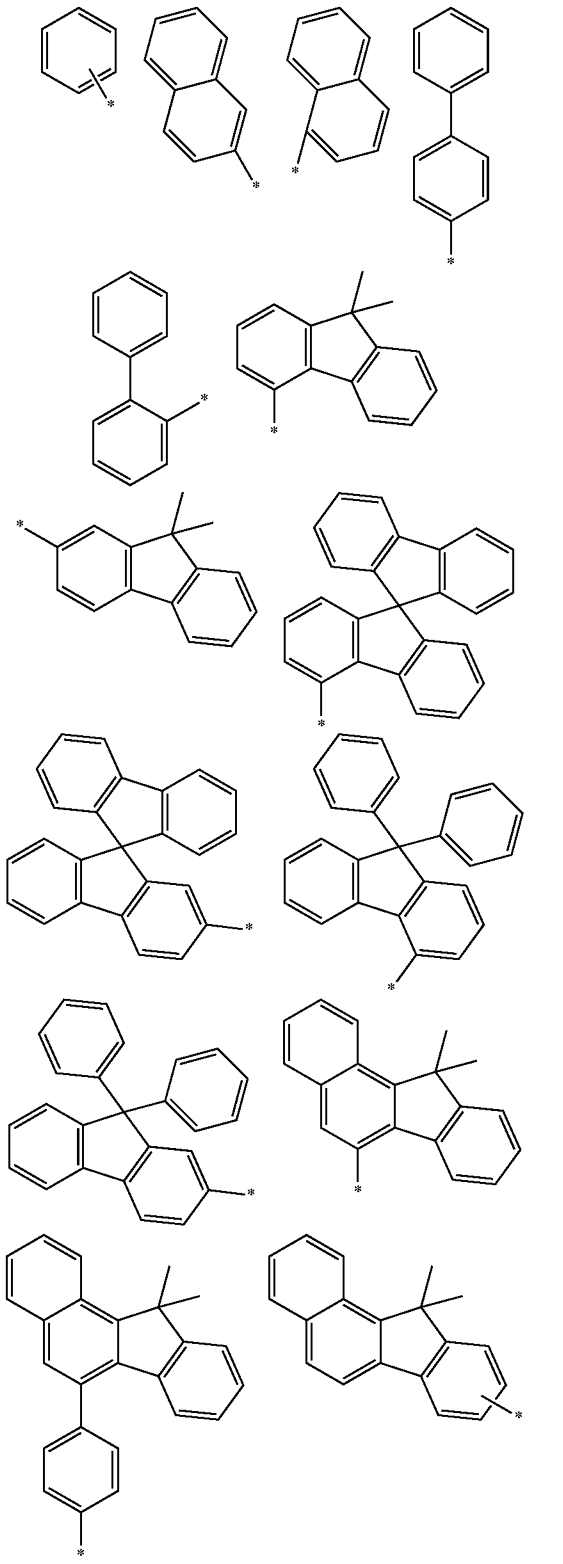

In the structural formulae, * means a position linked to N.

In one embodiment of the present application, R1 and R2 are the same as or different from each other, and may be each independently a halogen group; a substituted or unsubstituted C1 to C60 alkyl group; a substituted or unsubstituted C6 to C60 aryl group; or a substituted or unsubstituted C2 to C60 heteroaryl group.

In another embodiment, R1 and R2 are the same as or different from each other, and may be each independently a halogen group; a substituted or unsubstituted C1 to C40 alkyl group; a substituted or unsubstituted C6 to C40 aryl group; or a substituted or unsubstituted C2 to C40 heteroaryl group.

In another embodiment, R1 and R2 are the same as or different from each other, and may be each independently a halogen group; a substituted or unsubstituted linear C1 to C40 alkyl group; or a substituted or unsubstituted monocyclic C6 to C40 aryl group.

In another embodiment, R1 and R2 are the same as or different from each other, and may be each independently a halogen group; a substituted or unsubstituted linear C1 to C20 alkyl group; or a substituted or unsubstituted monocyclic C6 to C20 aryl group.

In another embodiment, R1 and R2 are the same as or different from each other, and may be each independently a fluoro group (—F); a linear C1 to C20 alkyl group; or a monocyclic C6 to C20 aryl group.

In another embodiment, R1 and R2 are the same as or different from each other, and may be each independently a fluoro group (—F); a methyl group; or a phenyl group.

In one embodiment of the present application, L1 and L2 are the same as or different from each other, and may be each independently a direct bond; a substituted or unsubstituted C6 to C60 arylene group; or a substituted or unsubstituted C2 to C60 heteroarylene group.

In another embodiment, L1 and L2 are the same as or different from each other, and may be each independently a direct bond; or a substituted or unsubstituted C6 to C60 arylene group.

In another embodiment, L1 and L2 are the same as or different from each other, and may be each independently a direct bond; or a substituted or unsubstituted C6 to C40 arylene group.

In another embodiment, L1 and L2 are the same as or different from each other, and may be each independently a direct bond; or a substituted or unsubstituted C6 to C30 arylene group.

In another embodiment, L1 and L2 are the same as or different from each other, and may be each independently a direct bond; or a substituted or unsubstituted monocyclic or polycyclic C6 to C30 arylene group.

In another embodiment, L1 and L2 are the same as or different from each other, and may be each independently a direct bond; or a monocyclic or polycyclic C6 to C30 arylene group.

In another embodiment, L1 and L2 are the same as or different from each other, and may be each independently a direct bond; a phenylene group; or a biphenylene group.

In one embodiment of the present application, R3 to R11 are the same as or different from each other, and each independently selected from the group consisting of hydrogen; deuterium; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(═O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring, and R, R' and R" are the same as or different from each other, and may be each independently hydrogen; a substituted or unsubstituted C1 to C40 alkyl group; or a substituted or unsubstituted C6 to C40 aryl group.

In another embodiment, R3 to R11 are the same as or different from each other, and may be each independently selected from the group consisting of hydrogen; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(═O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group.

In another embodiment, R3 to R11 are the same as or different from each other, and may be each independently hydrogen; a halogen group; —CN; a substituted or unsubstituted C6 to C60 aryl group; or a substituted or unsubstituted C2 to C60 heteroaryl group.

In another embodiment, R3 to R11 are the same as or different from each other, and may be each independently hydrogen; a halogen group; —CN; a substituted or unsubstituted C6 to C30 aryl group; or a substituted or unsubstituted C2 to C30 heteroaryl group.

In another embodiment, R3 to R11 are the same as or different from each other, and may be each independently hydrogen; a fluoro group (—F); or —CN.

In one embodiment of the present application, Z1 may be a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; or —P(═O)PRR'.

In another embodiment, Z1 may be a C6 to C60 aryl group unsubstituted or substituted with deuterium, a C1 to C20 alkyl group or a C6 to C40 aryl group; or a substituted or unsubstituted C2 to C60 heteroaryl group.

In another embodiment, Z1 may be a C6 to C40 aryl group unsubstituted or substituted with deuterium, a C1 to C20 alkyl group or a C6 to C40 aryl group; or a substituted or unsubstituted C2 to C40 heteroaryl group.

In another embodiment, Z1 may be a monocyclic or polycyclic C6 to C40 aryl group unsubstituted or substituted with deuterium, a C1 to C20 alkyl group or a C6 to C40 aryl group; or a substituted or unsubstituted C2 to C40 heteroaryl group comprising O or S as a heteroatom.

In another embodiment, Z1 may be a monocyclic or polycyclic C6 to C40 aryl group unsubstituted or substituted with deuterium, a C1 to C20 alkyl group or a C6 to C40 aryl group; or a C2 to C40 heteroaryl group comprising 0 or S as a heteroatom.

In another embodiment, Z1 is a phenyl group unsubstituted or substituted with deuterium; a biphenyl group; a naphthyl group; a phenanthrenyl group; a triphenylenyl group; a terphenyl group; a dimethylfluorenyl group; a diphenylfluorenyl group; a spirobifluorenyl group; a dimethyl-11H-benzo[a]fluorenyl group; a dibenzofuran group; or a dibenzothiophene group.

In one embodiment of the present application, X1 and X2 are the same as or different from each other, and may be each independently a halogen group.

In another embodiment, X1 and X2 are the same as or different from each other, and may be each independently —F; —Cl; —Br; or —I.

In another embodiment, X1 and X2 are the same as each other, and may be —F; —Cl; —Br; or —I.

In another embodiment, X1 and X2 are the same as each other, and may be —F.

In one embodiment of the present application, R21 and R22 are the same as or different from each other, and may be each independently hydrogen; a halogen group; a substituted or unsubstituted C6 to C60 aryl group; or a substituted or unsubstituted C2 to C60 heteroaryl group.

In another embodiment, R21 and R22 may be hydrogen.

In one embodiment of the present application, R35 and R36 are the same as or different from each other, and each independently a substituted or unsubstituted C1 to C60 alkyl group; or a substituted or unsubstituted C6 to C60 aryl group, or adjacent groups may bond to each other to form a substituted or unsubstituted C6 to C60 aromatic hydrocarbon ring or a substituted or unsubstituted C2 to C60 heteroring.

In another embodiment, R35 and R36 are the same as or different from each other, and each independently a substituted or unsubstituted C1 to C40 alkyl group; or a substituted or unsubstituted C6 to C40 aryl group, or adjacent groups may bond to each other to form a substituted or unsubstituted C6 to C40 aromatic hydrocarbon ring or a substituted or unsubstituted C2 to C40 heteroring.

In another embodiment, R35 and R36 are the same as or different from each other, and each independently a C1 to C40 alkyl group; or a C6 to C40 aryl group, or adjacent groups may bond to each other to form a C6 to C40 aromatic hydrocarbon ring.

In another embodiment, R35 and R36 are the same as or different from each other, and each independently a methyl group; or a phenyl group, or adjacent groups may bond to each other to form a spirobifluorene ring.

In one embodiment of the present application, R31 to R34 are the same as or different from each other, and each independently selected from the group consisting of hydrogen; deuterium; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group.

In another embodiment, R31 to R34 may be hydrogen.

In one embodiment of the present application, R, R' and R" are the same as or different from each other, and may be each independently hydrogen; a substituted or unsubstituted C1 to C40 alkyl group; or a substituted or unsubstituted C6 to C40 aryl group.

In another embodiment, R, R' and R" are the same as or different from each other, and may be each independently a substituted or unsubstituted C1 to C20 alkyl group; or a substituted or unsubstituted C6 to C20 aryl group.

In another embodiment, R, R' and R" are the same as or different from each other, and may be each independently a C1 to C20 alkyl group; or a C6 to C20 aryl group.

In another embodiment, R, R' and R" are the same as or different from each other, and may be each independently a C6 to C20 monocyclic aryl group.

In another embodiment, R, R' and R" may be a phenyl group.

In the heterocyclic compound provided in one embodiment of the present application, Chemical Formula 1 is represented by any one of the following compounds.

1

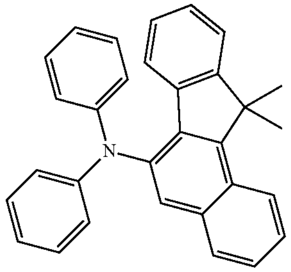

2

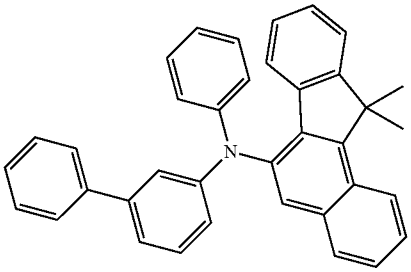

3

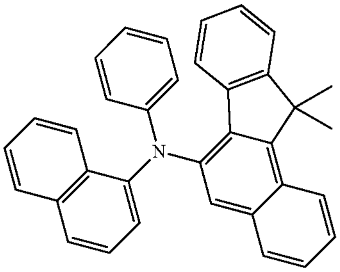

4

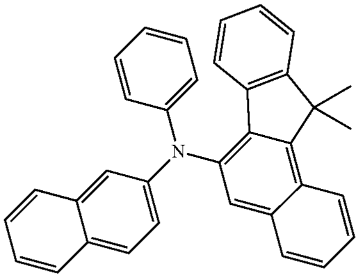

5

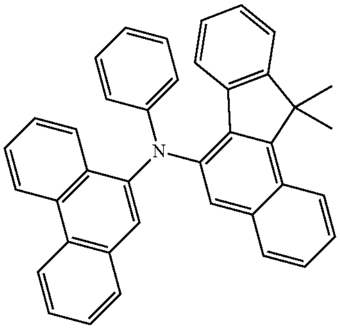

-continued
6
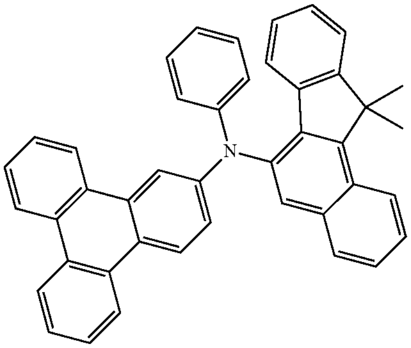
7
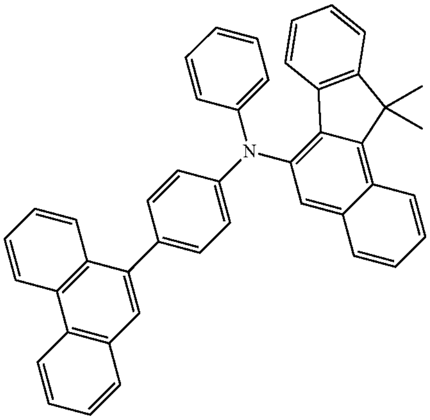
8
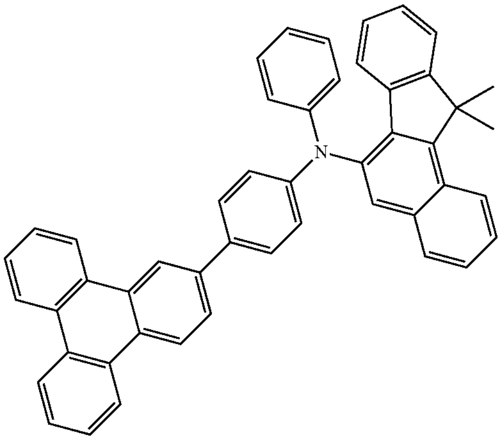
-continued
9
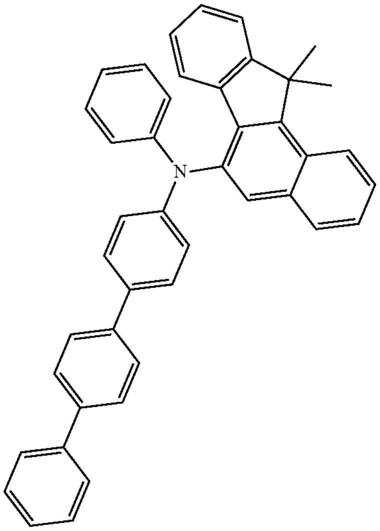
10
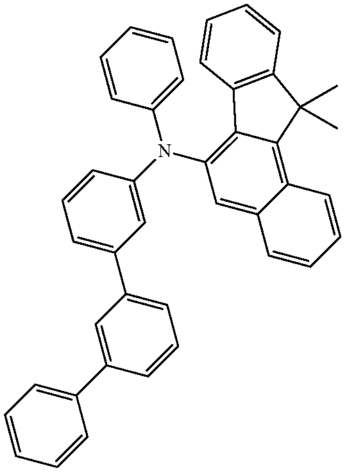
11
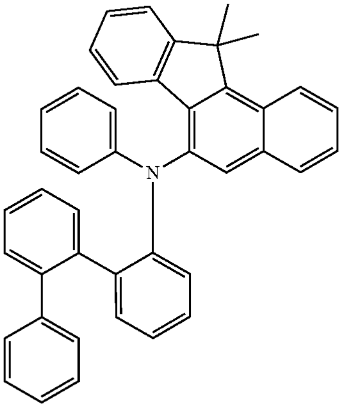

-continued
12
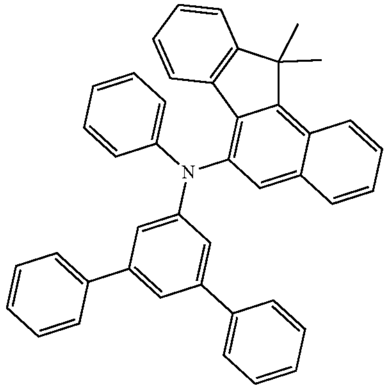
13
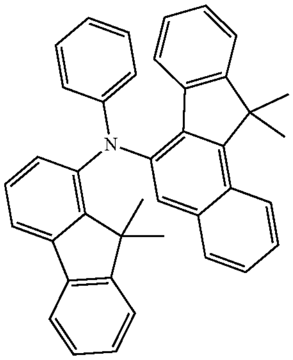
14
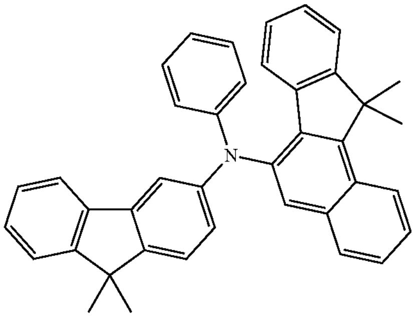
15
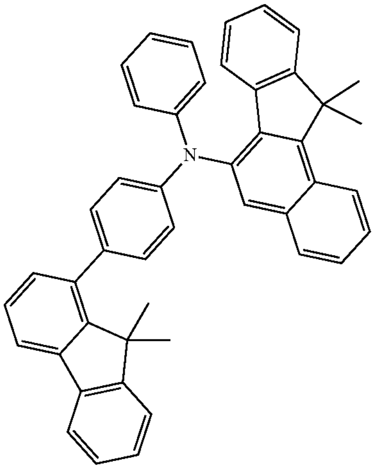
-continued
16
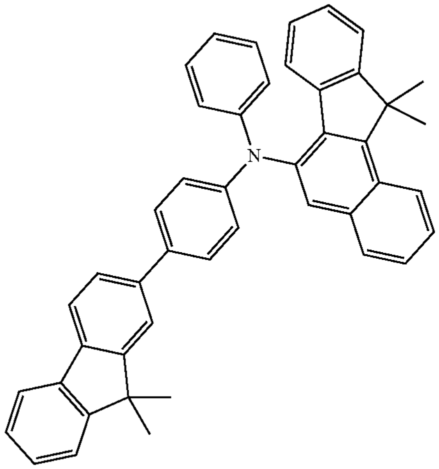
17
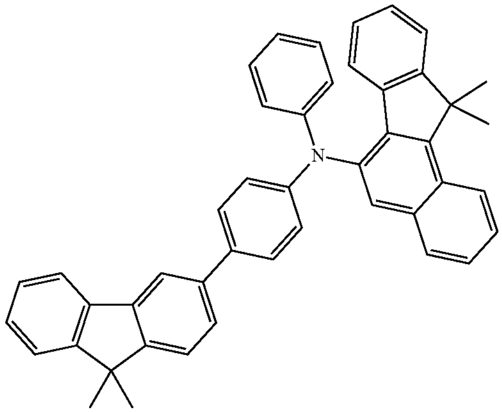
18
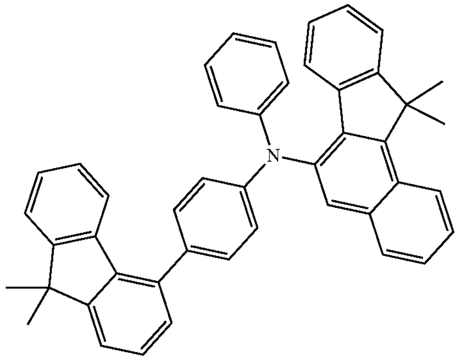

-continued
19
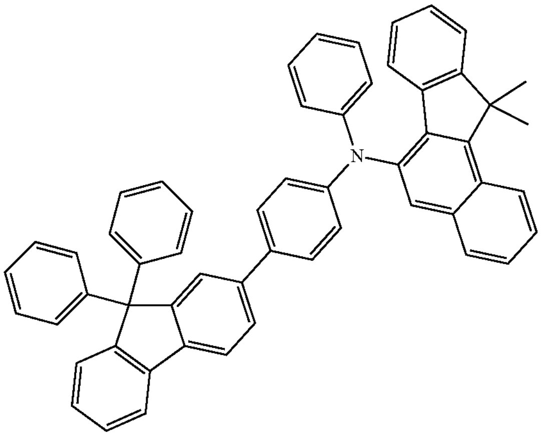
20
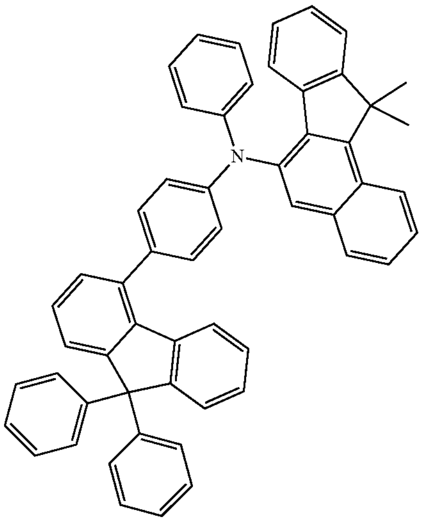
21
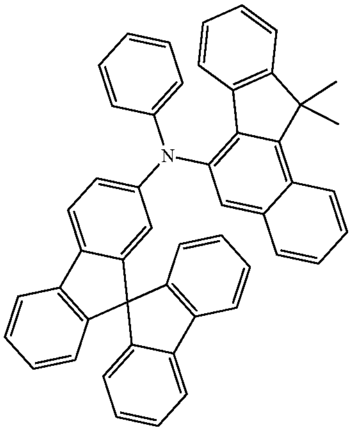
-continued
22
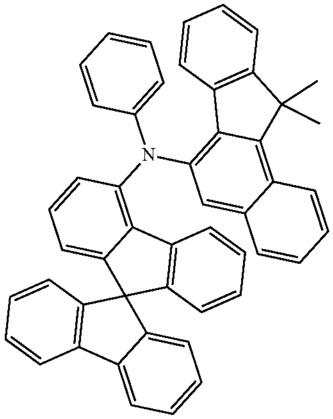
23
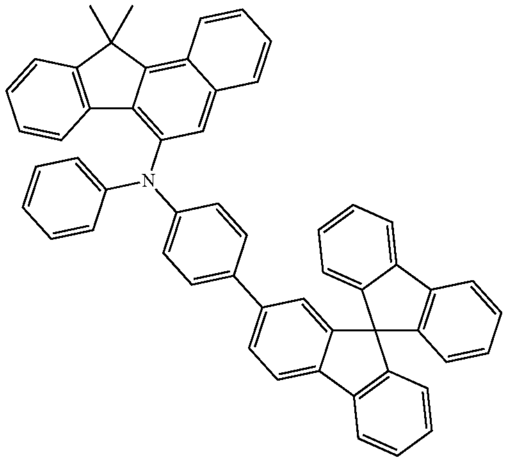
24
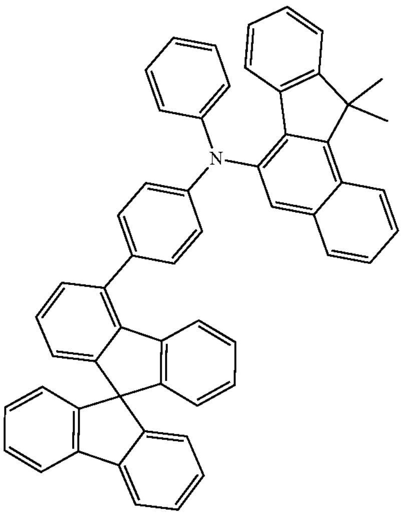

25
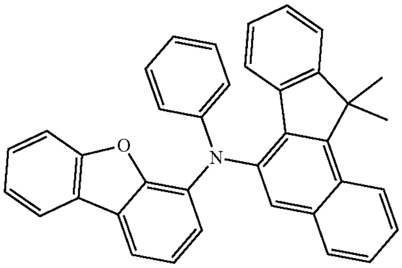
26
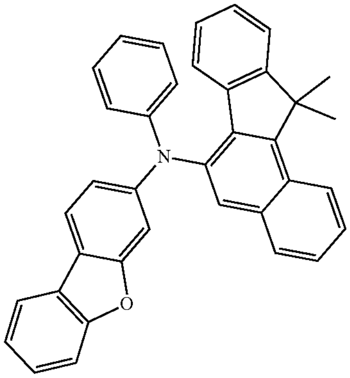
27
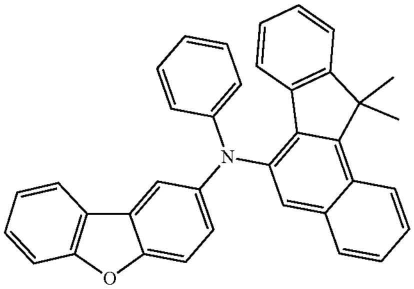
28
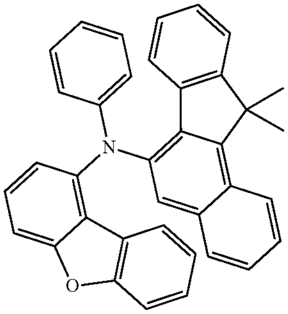
29
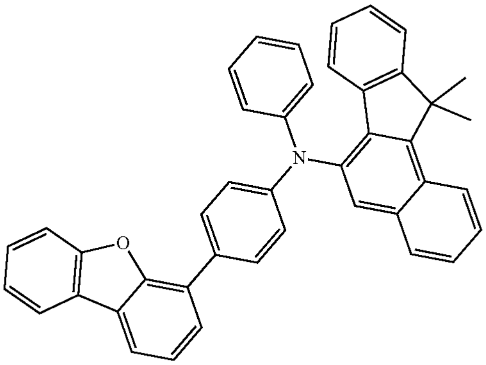
30
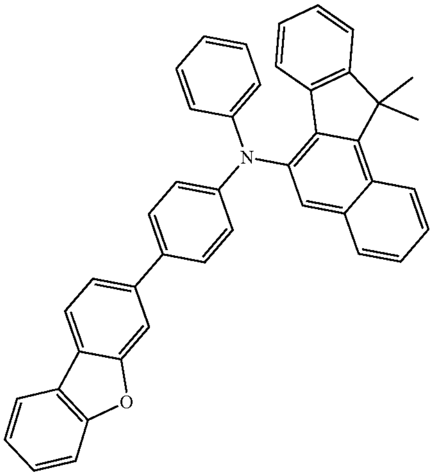
31
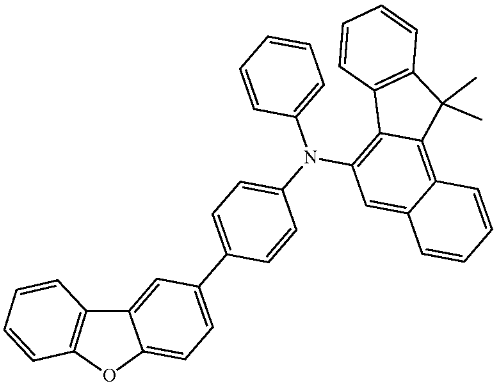
32
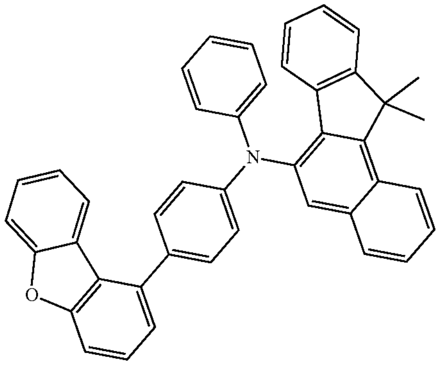
33
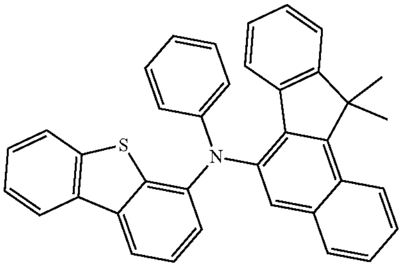

-continued
34
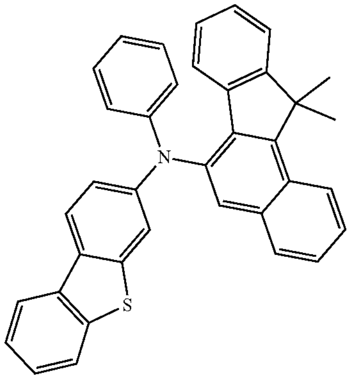
35
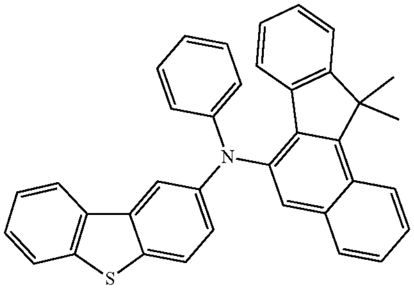
36
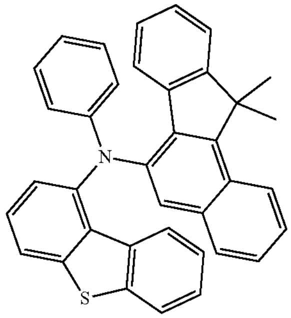
37
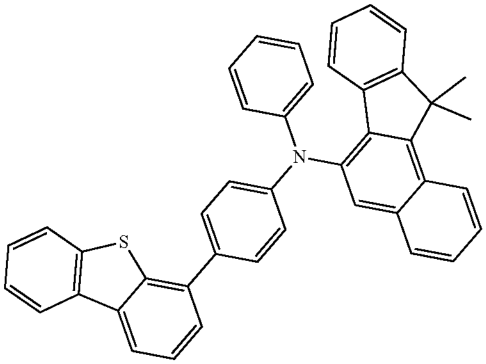
-continued
38
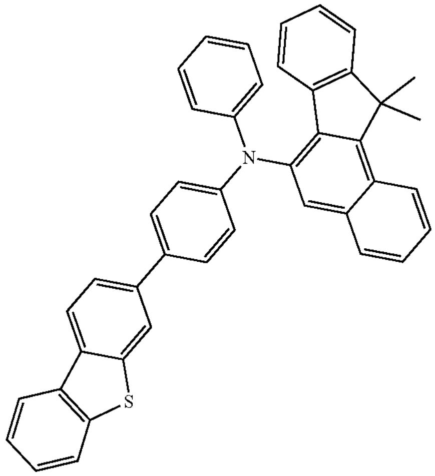
39
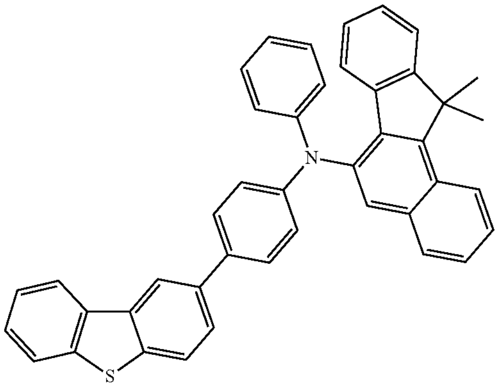
40
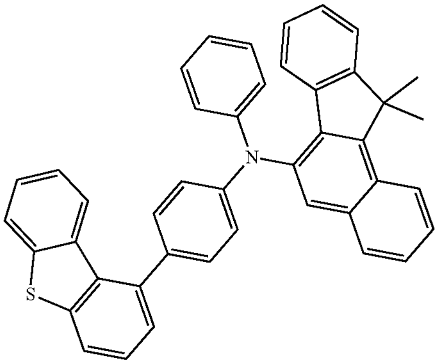
41
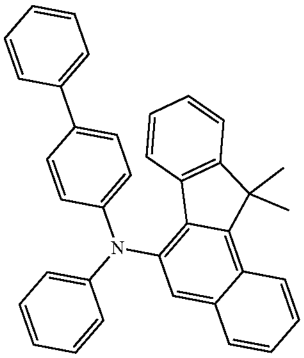

-continued
42
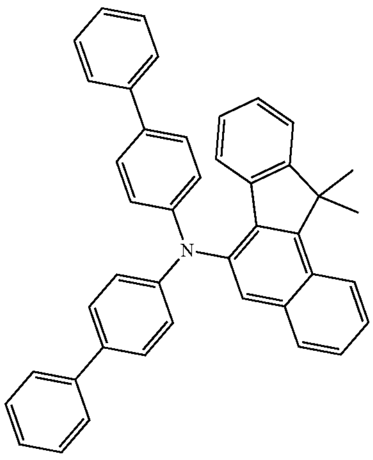
43
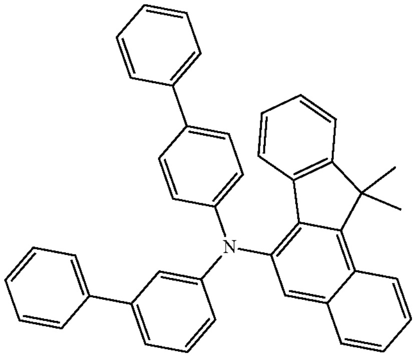
44
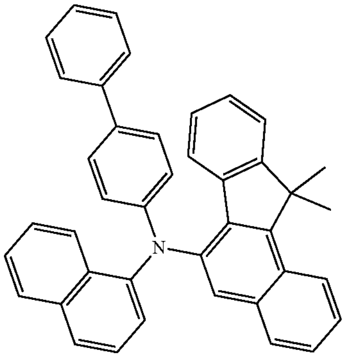
45
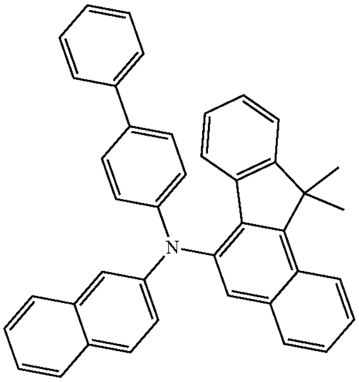
-continued
46
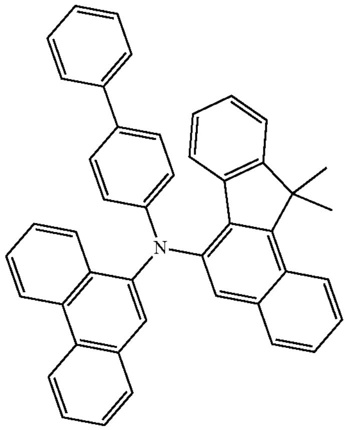
47
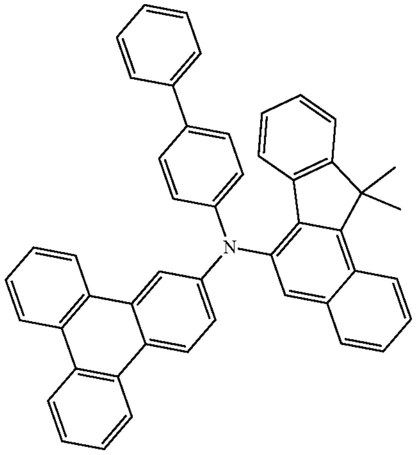
48
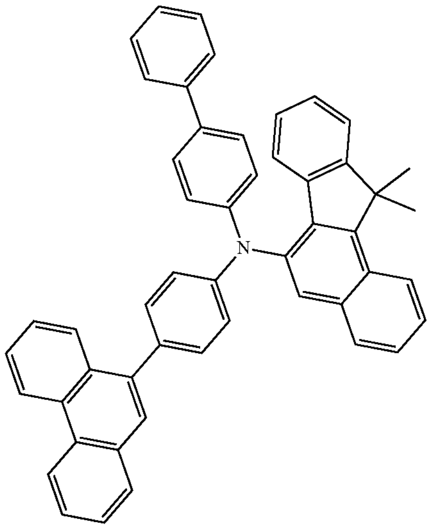

-continued
49
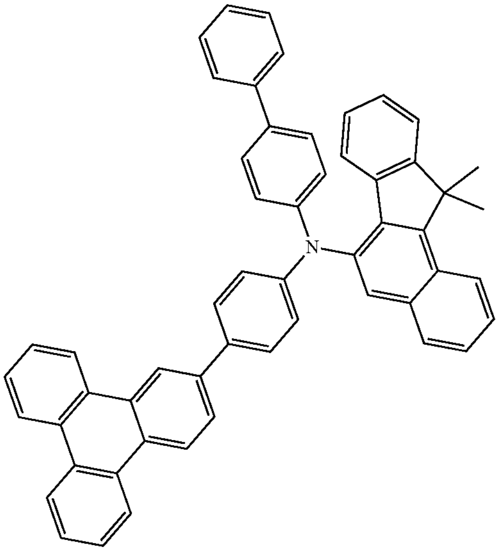
50
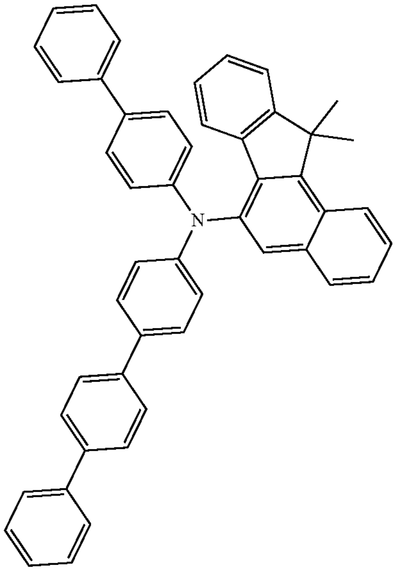
-continued
51
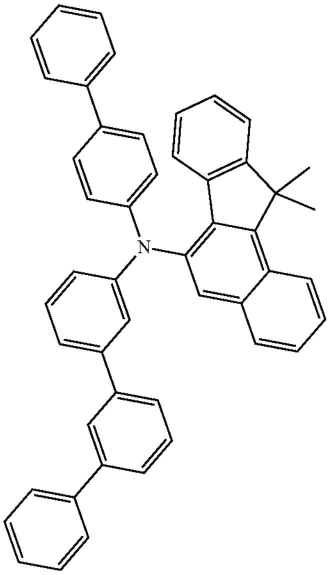
52
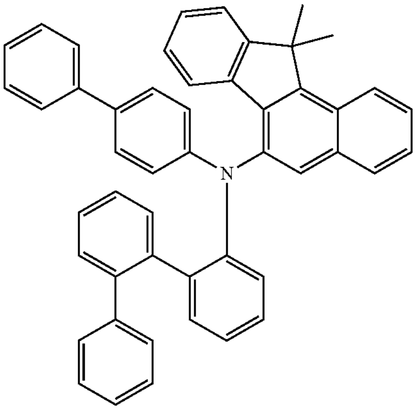
53
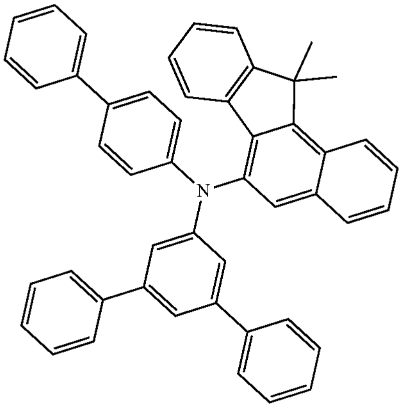

-continued
54
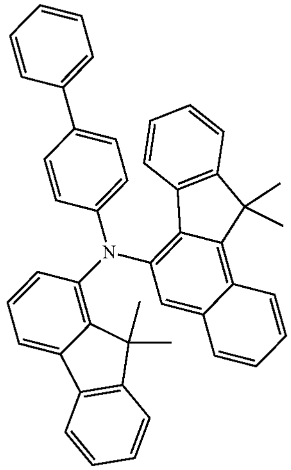
55
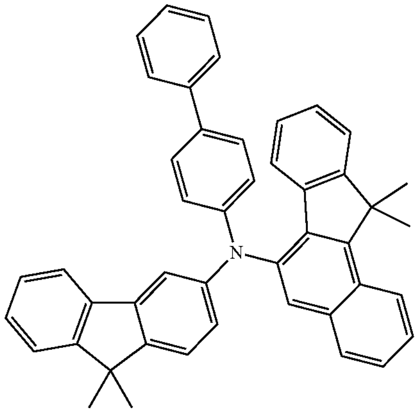
56
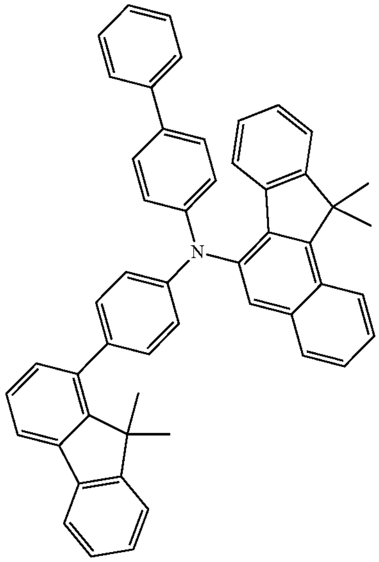
-continued
57
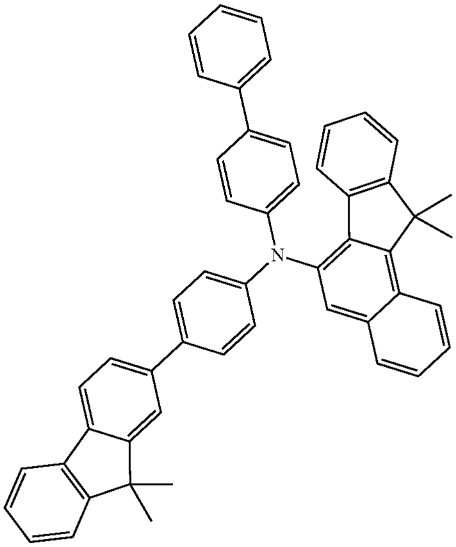
58
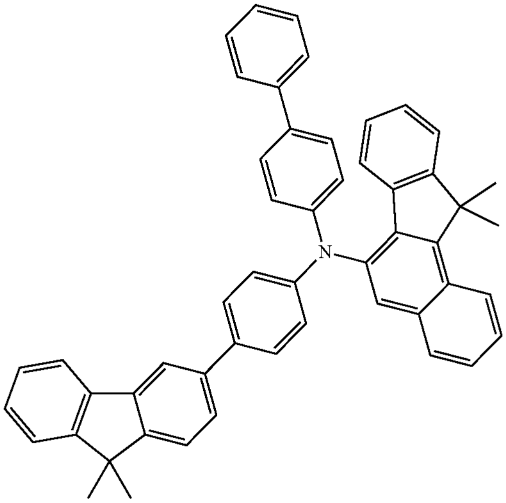
59
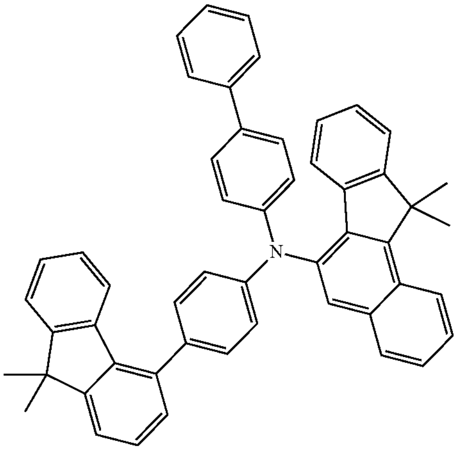

60
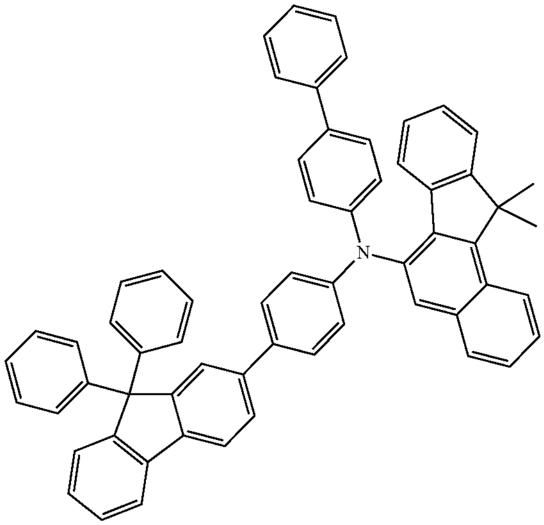
61
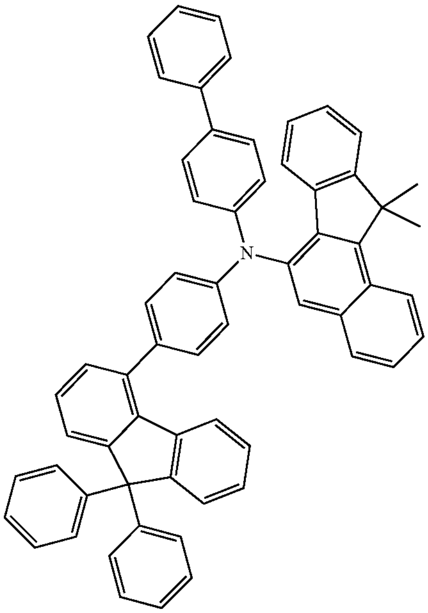
62
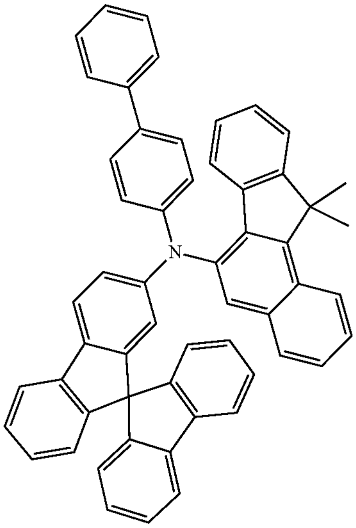
63
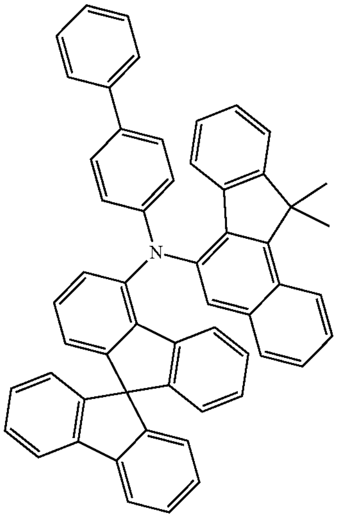
64
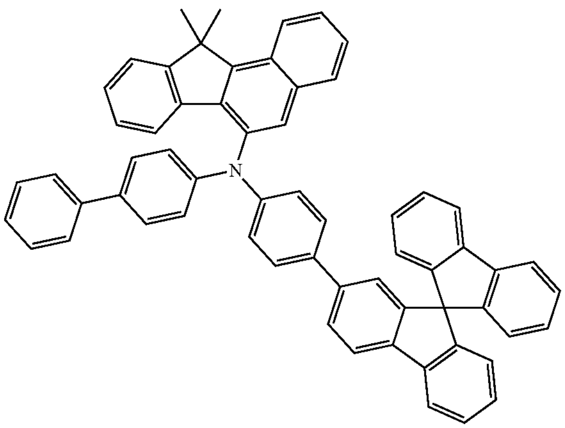

-continued
65
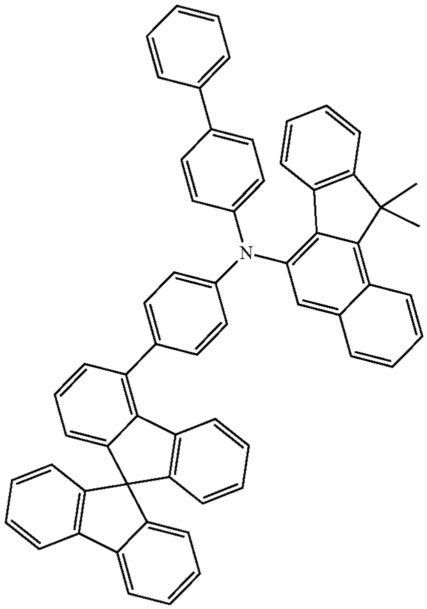
66
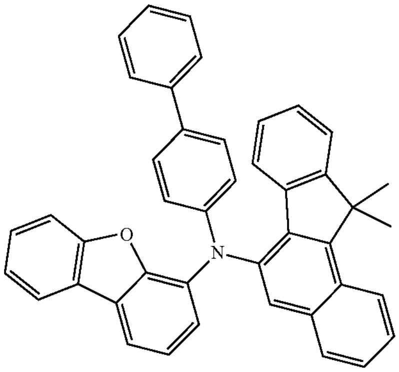
67
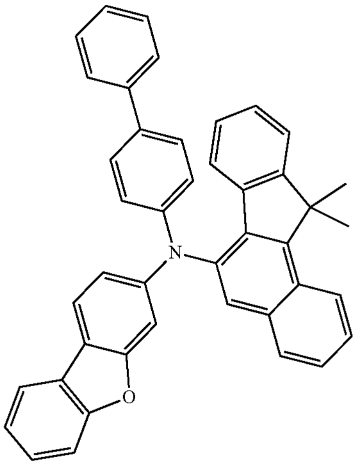
-continued
68
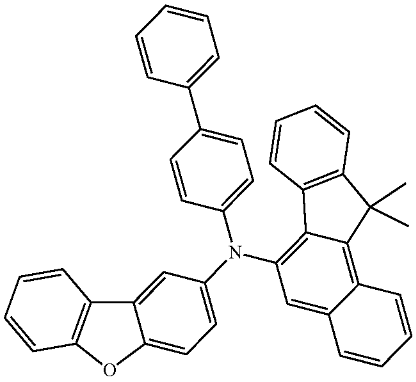
69
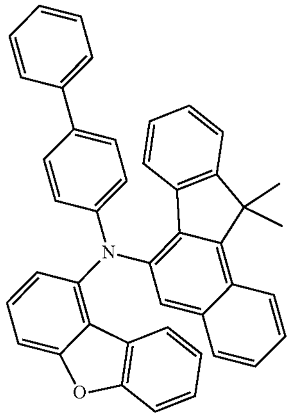
70
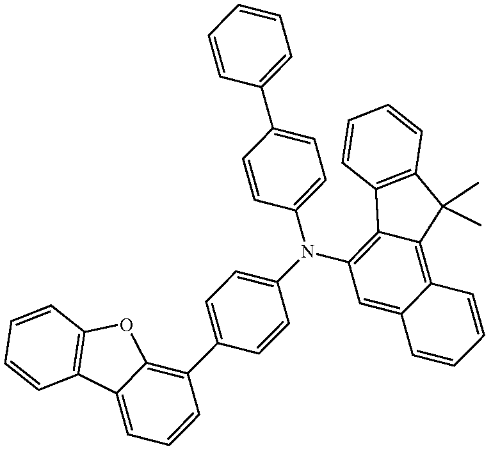

-continued
71
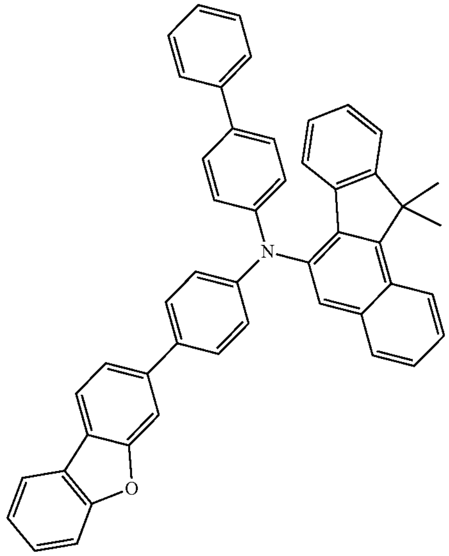
72
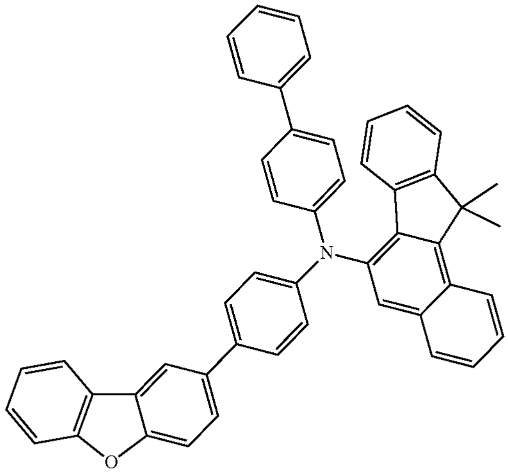
73
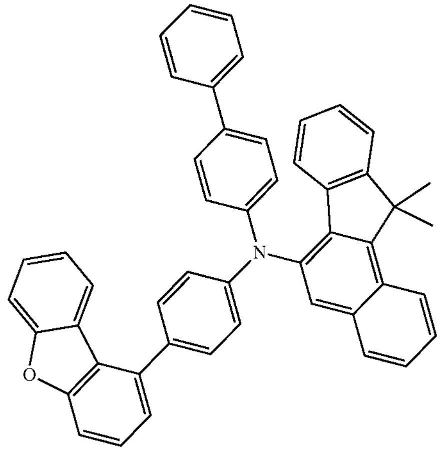
-continued
74
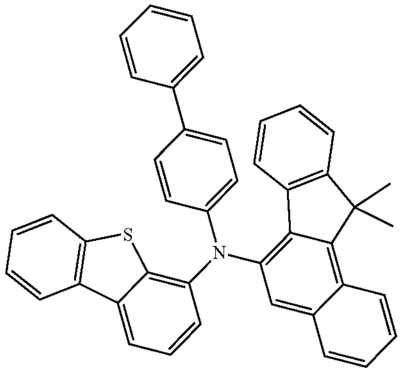
75
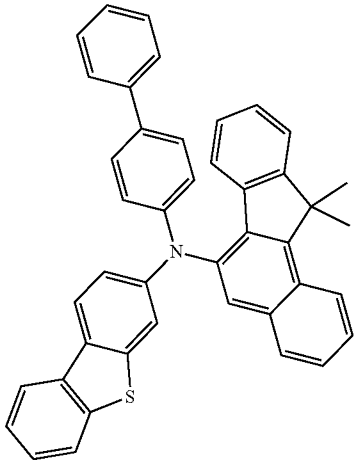
76
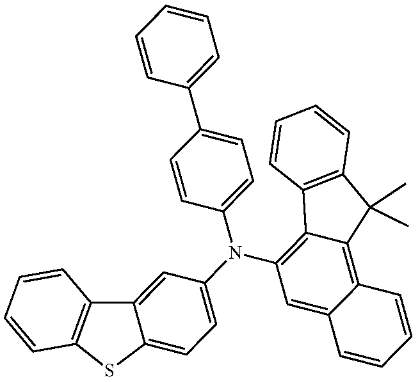
77
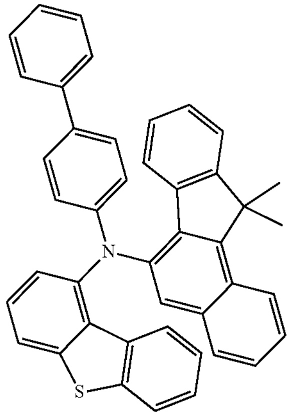

-continued
78
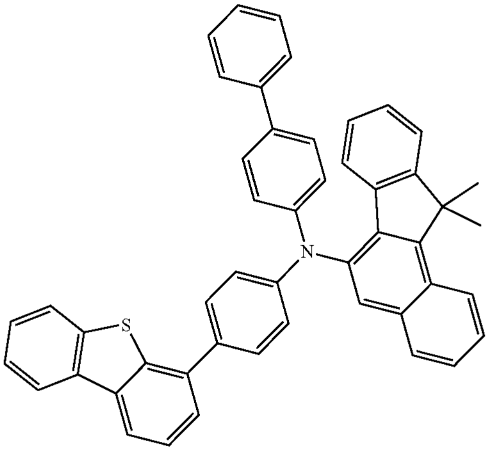
79
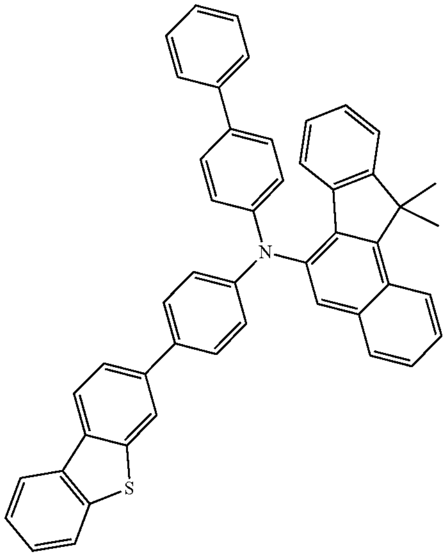
80
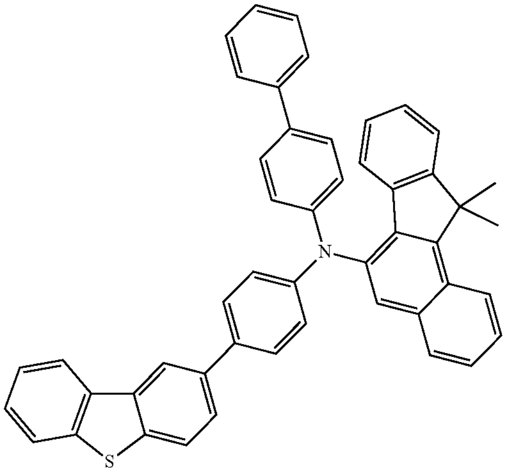
-continued
81
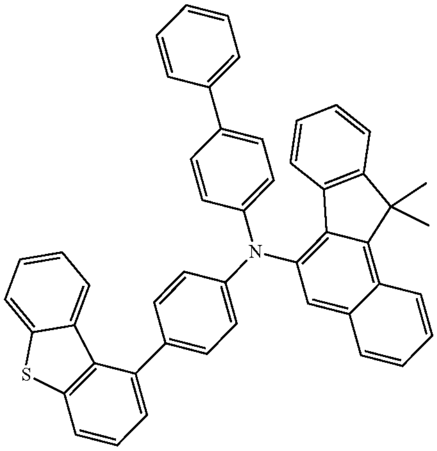
82
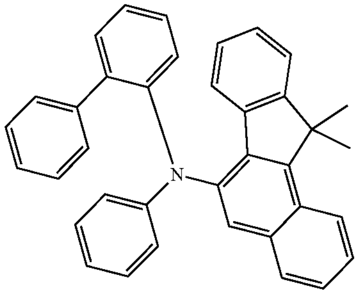
83
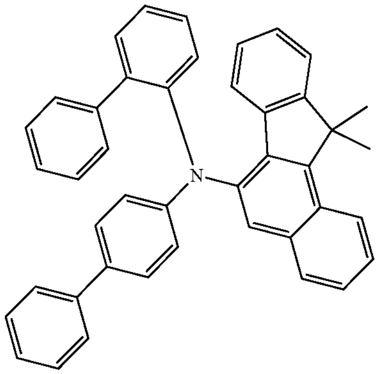
84
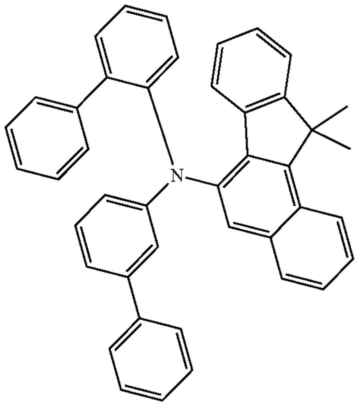

-continued
85
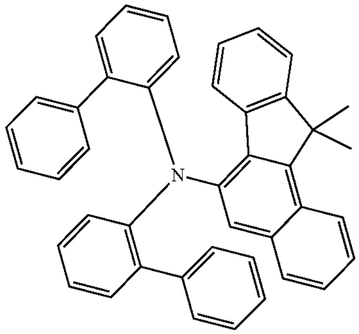
86
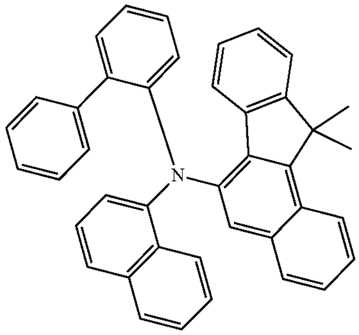
87
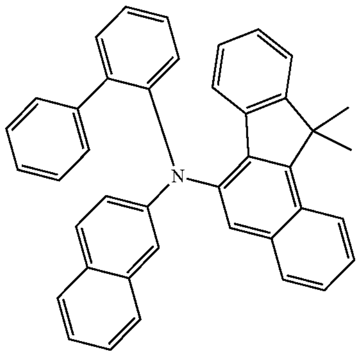
88
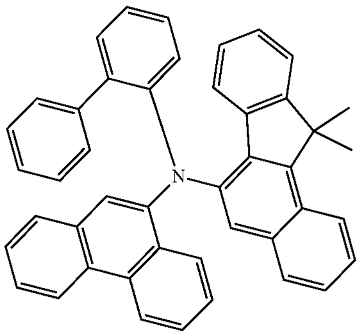
89
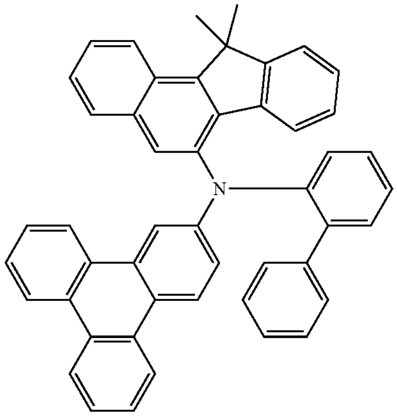
90
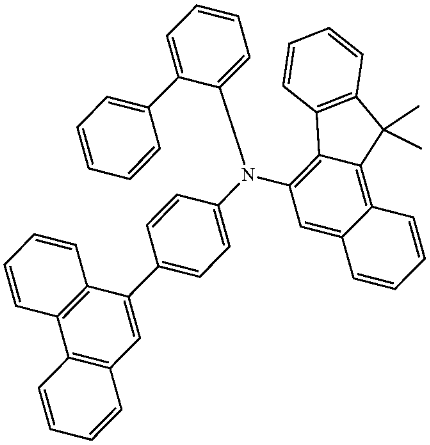
91
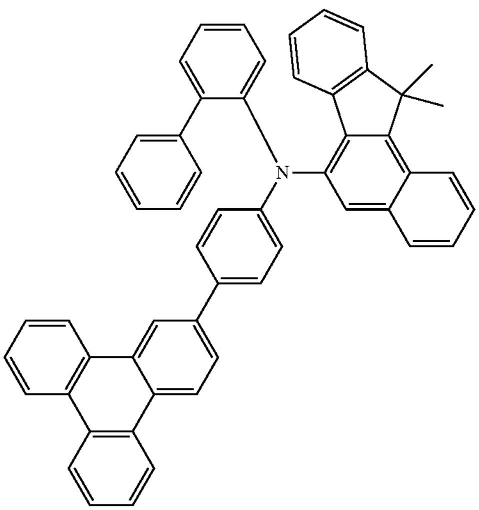

92
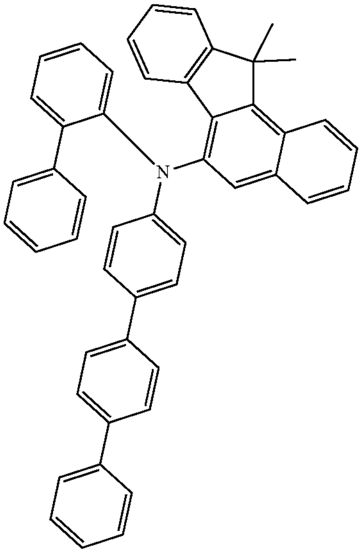
93
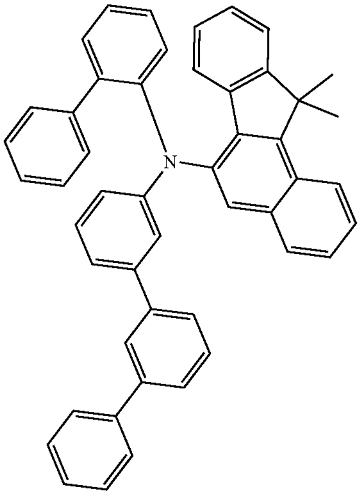
94
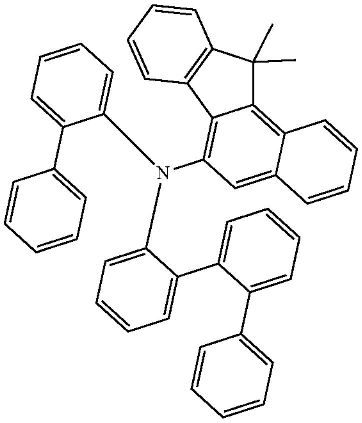
95
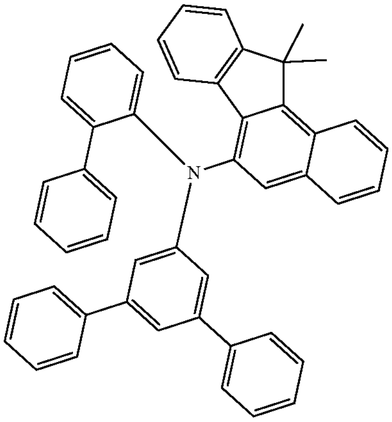
96
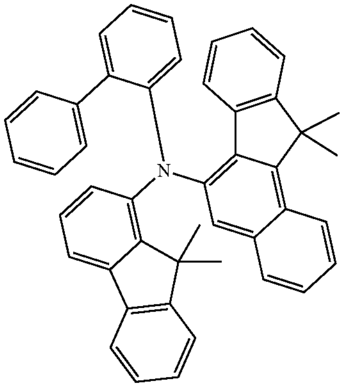
97
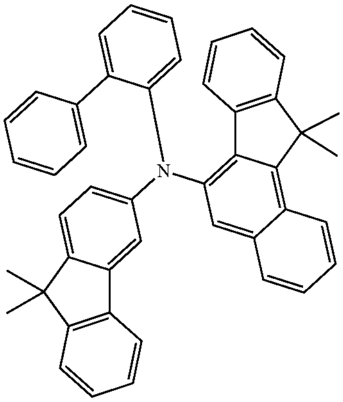

-continued
98
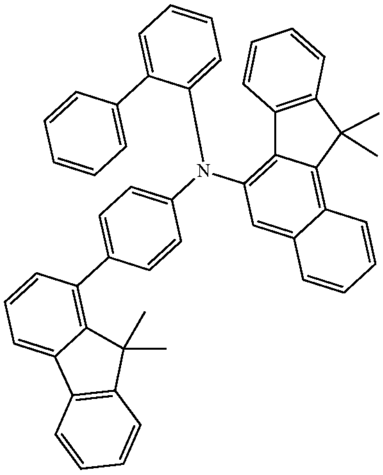
99
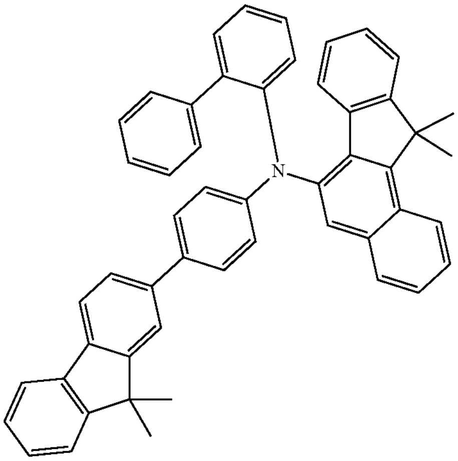
100
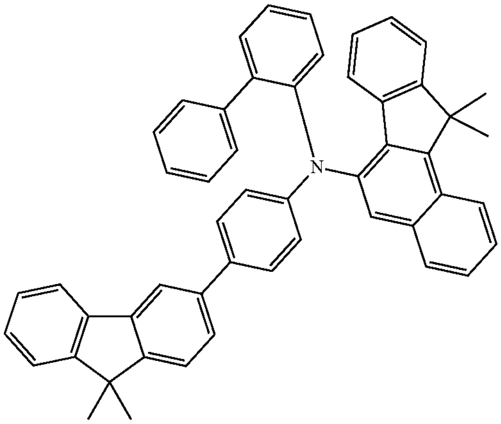
-continued
101
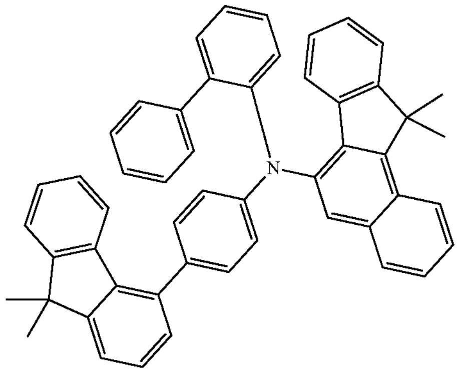
102
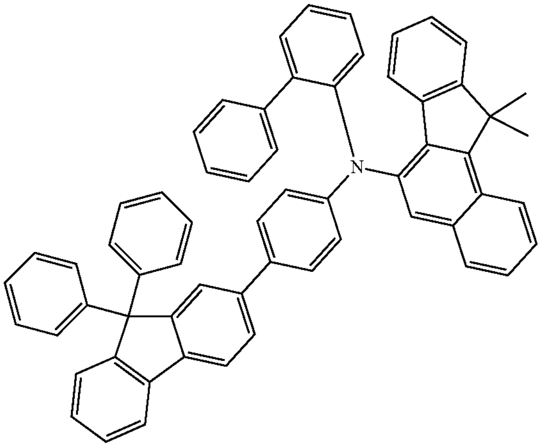
103
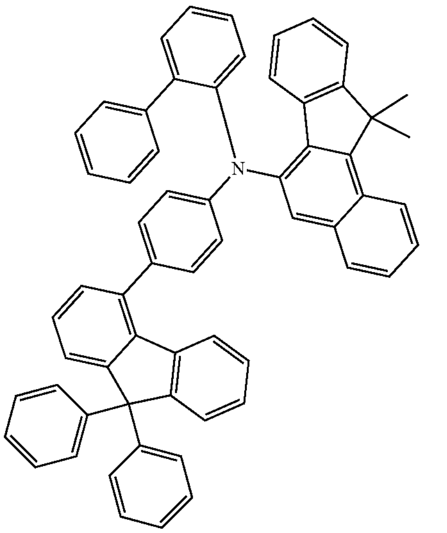

-continued
104
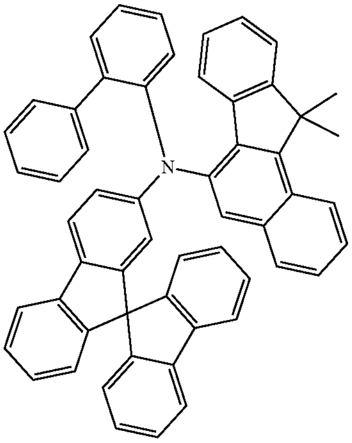
105
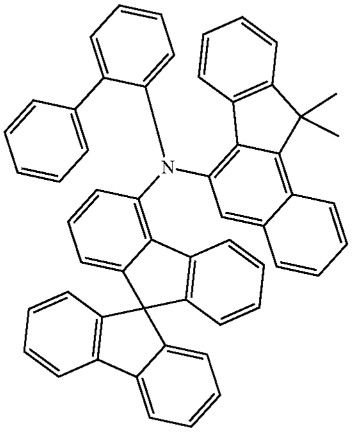
106
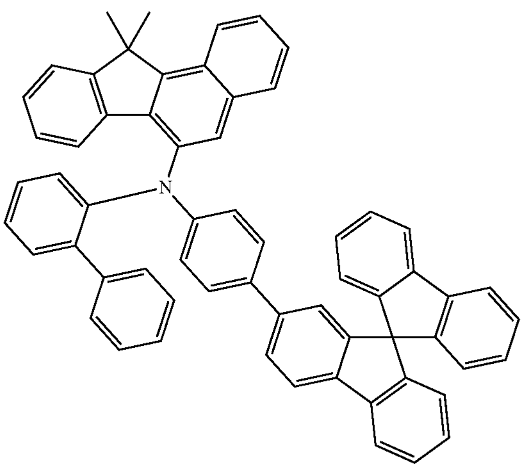
-continued
107
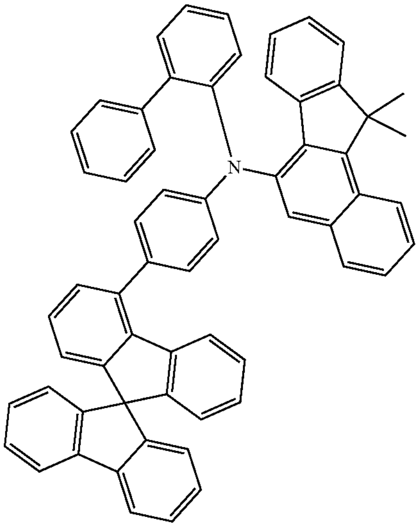
108
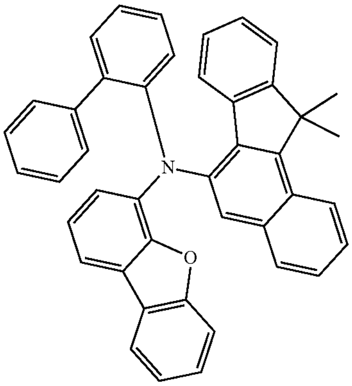
109
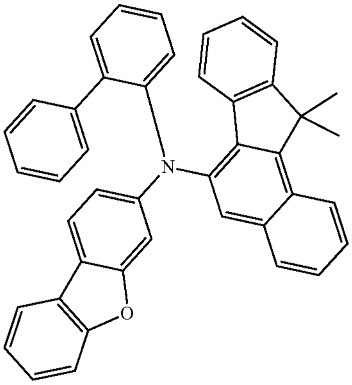

-continued
110
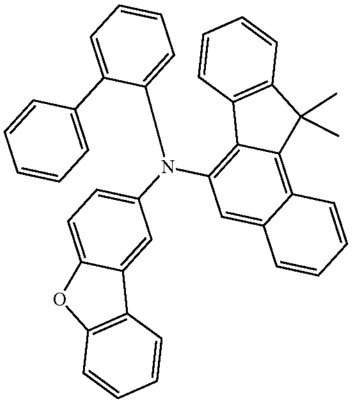
111
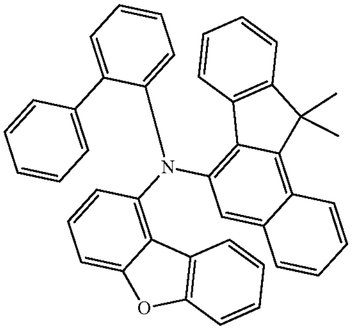
112
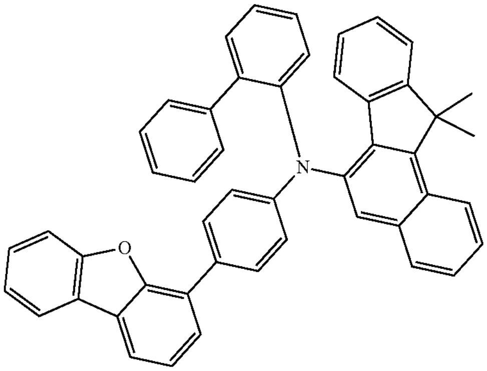
113
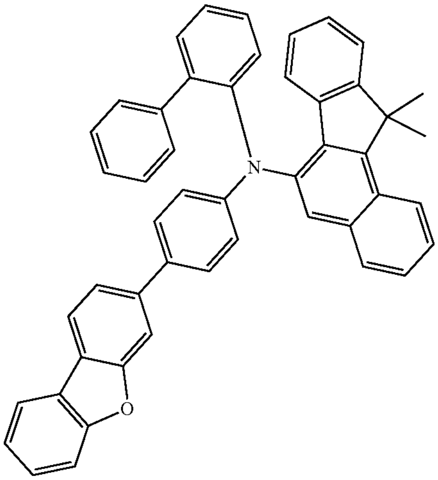
-continued
114
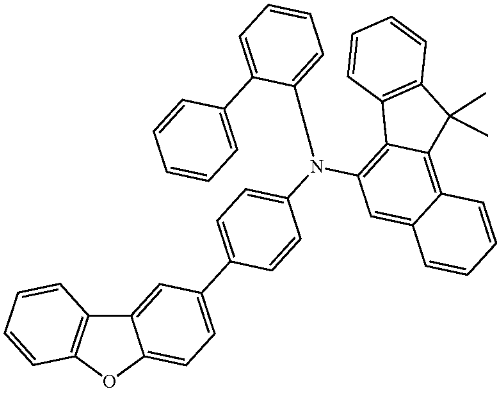
115
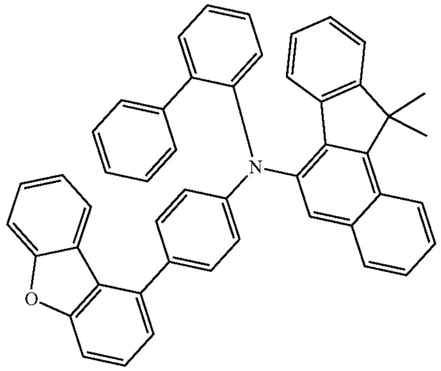
116
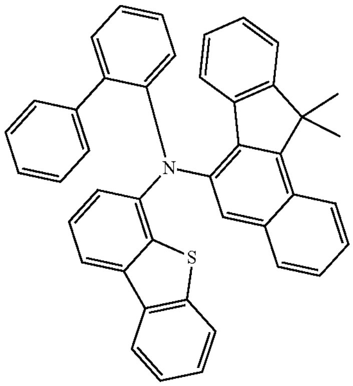
117
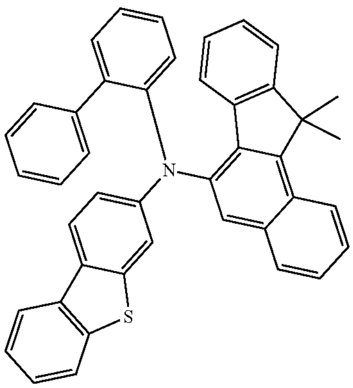

-continued
118
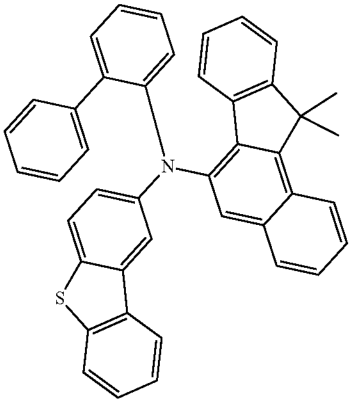
119
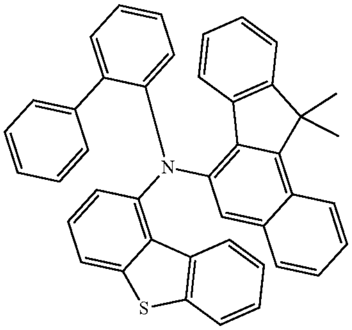
120
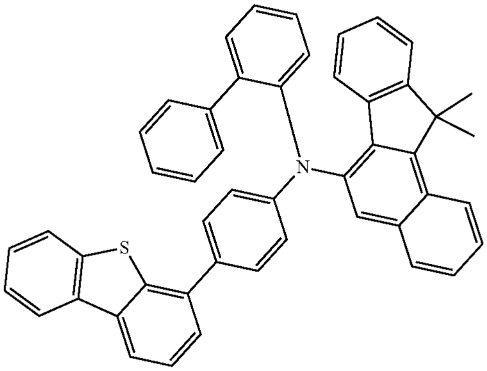
121
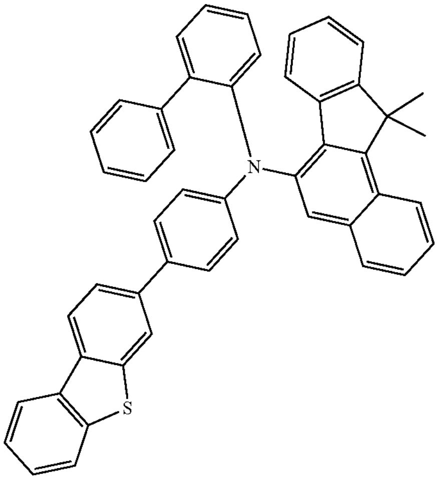
-continued
122
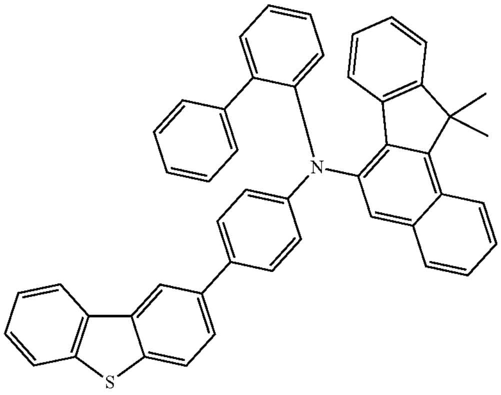
123
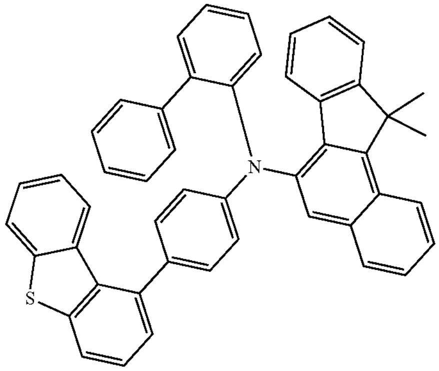
124
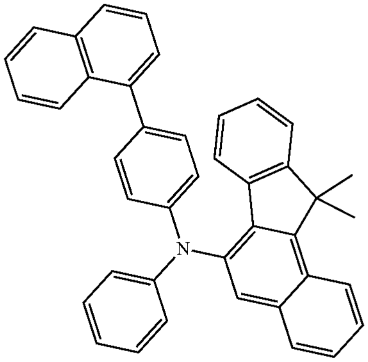
125
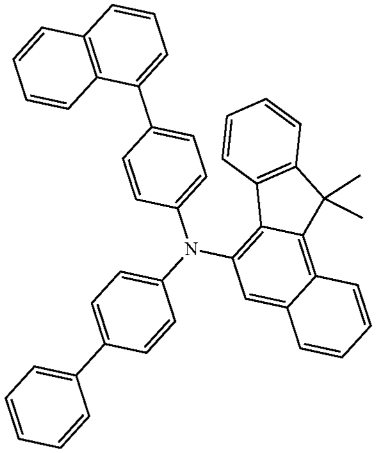

-continued
126
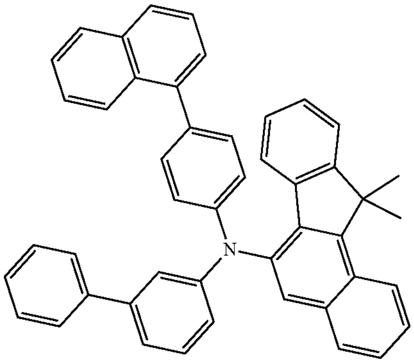
127
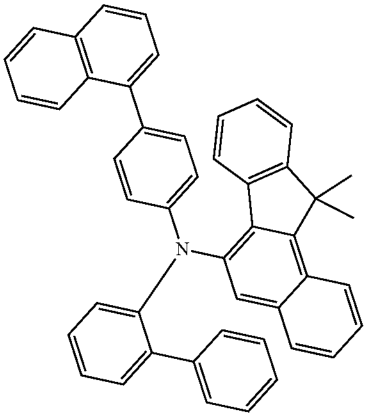
128
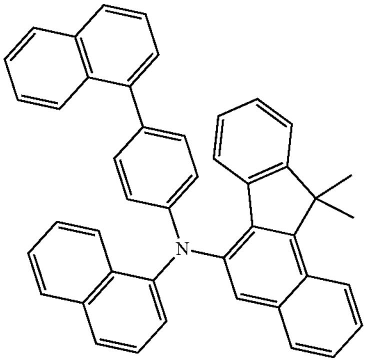
129
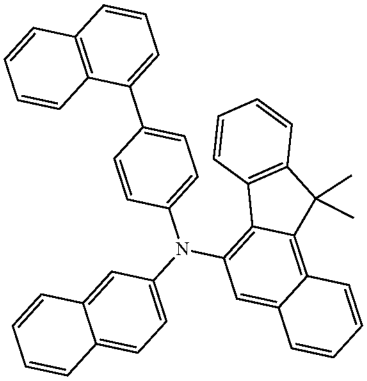
-continued
130
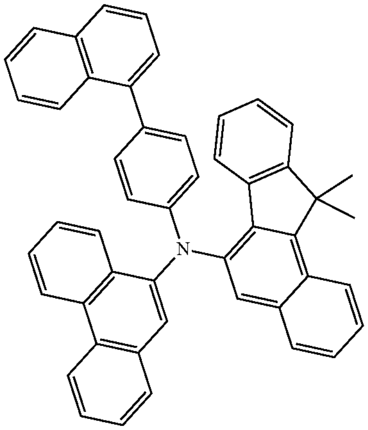
131
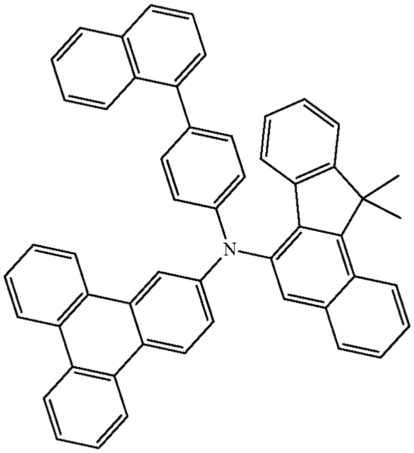
132
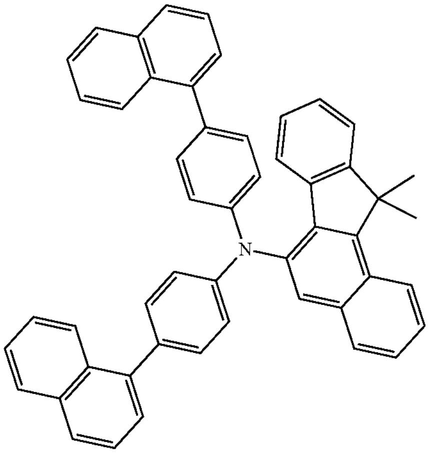

-continued
133
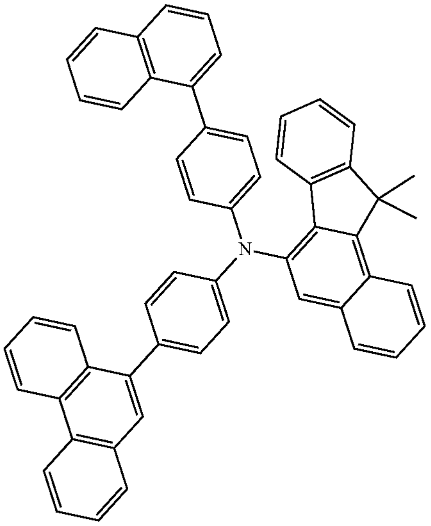
134
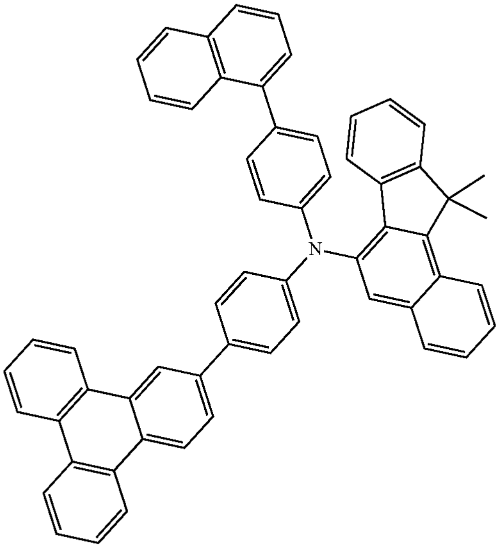
135
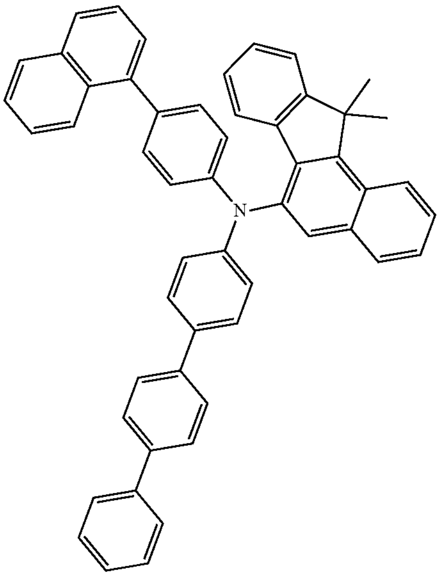
-continued
136
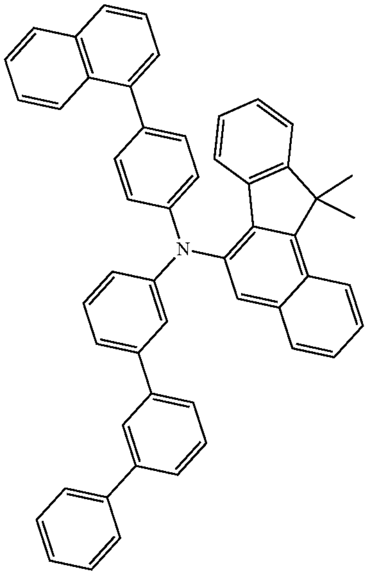
137
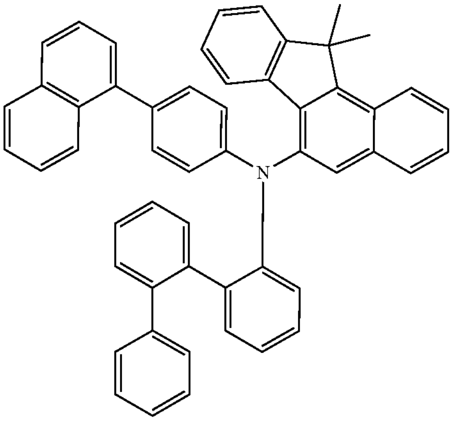
138
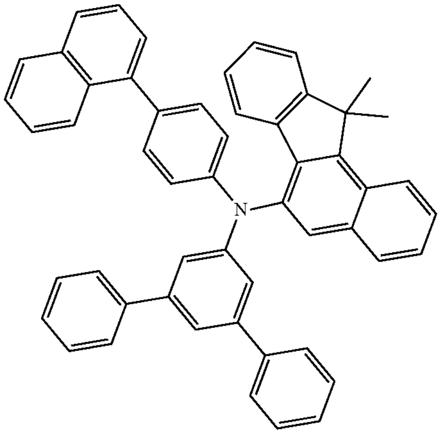

-continued
139
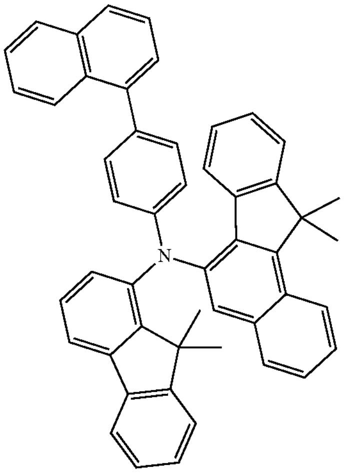
140
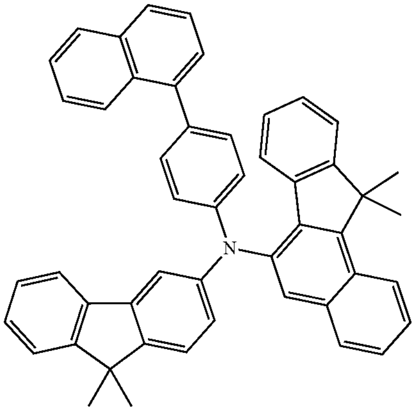
141
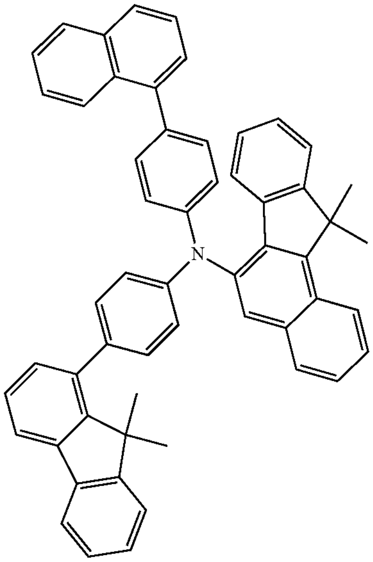
-continued
142
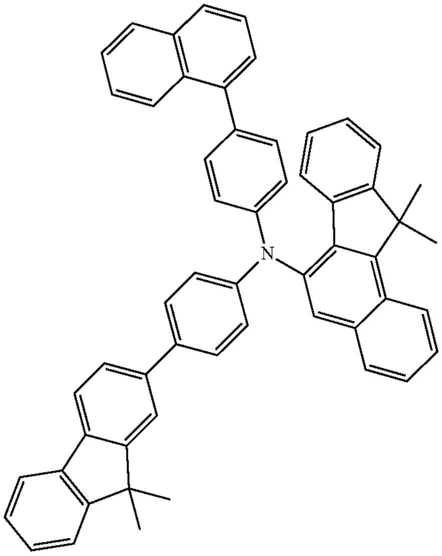
143
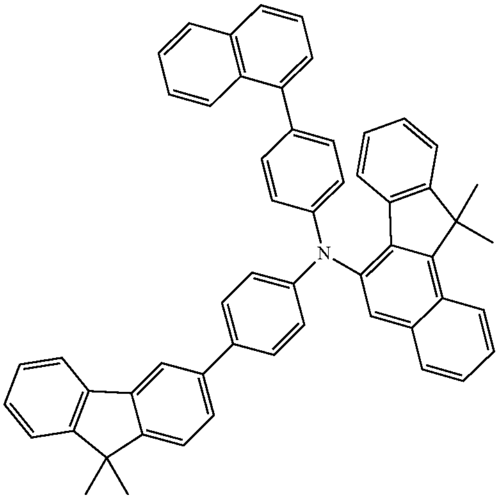
144
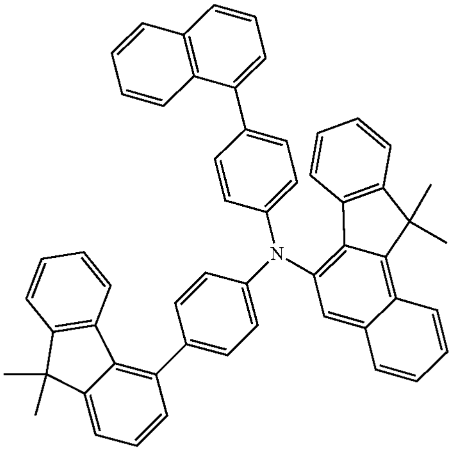

-continued
145
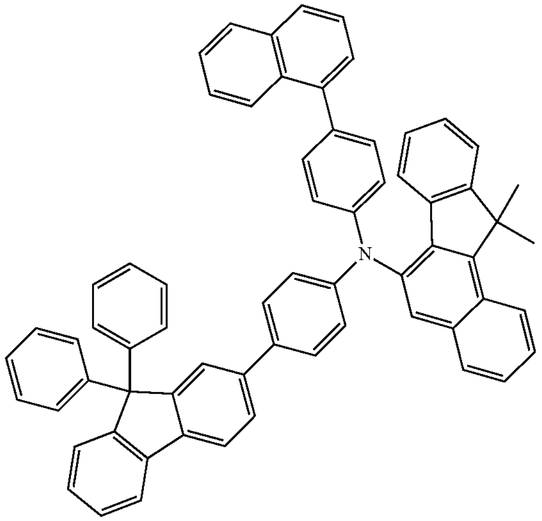
146
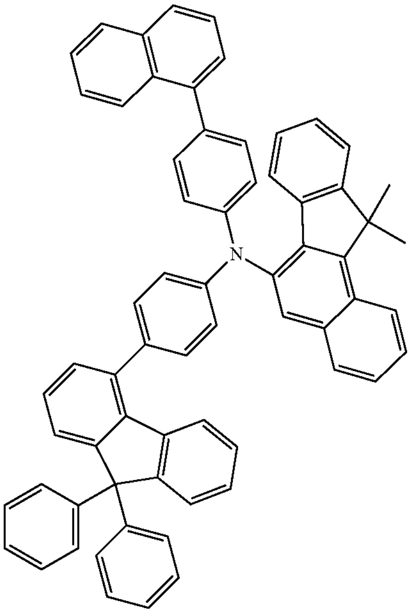
-continued
147
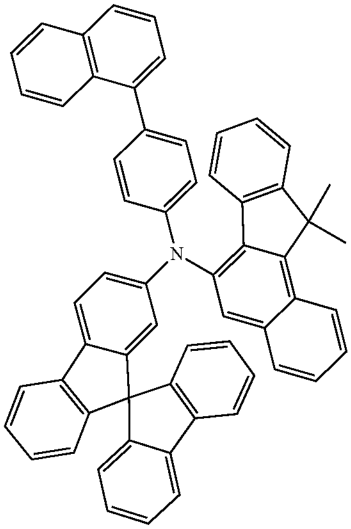
148
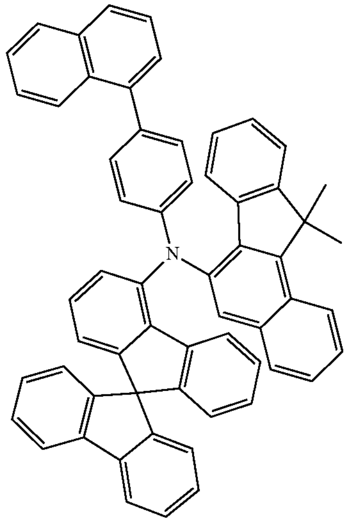
149
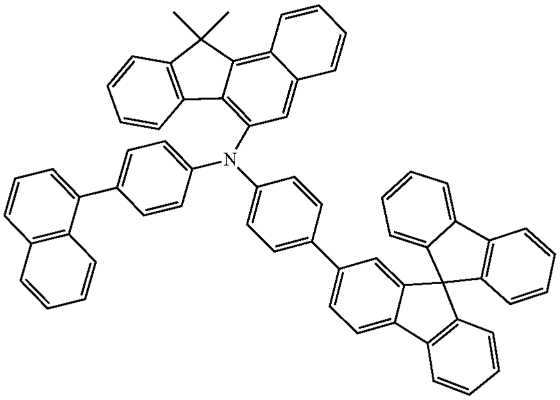

-continued
150
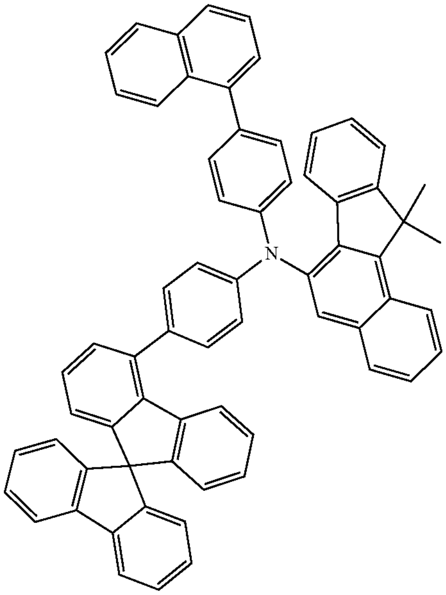
151
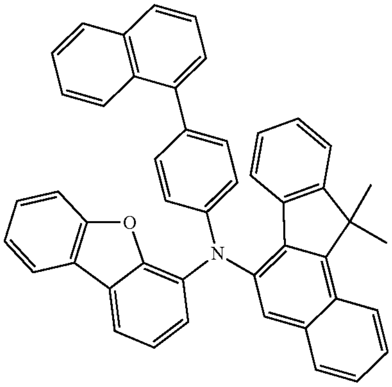
152
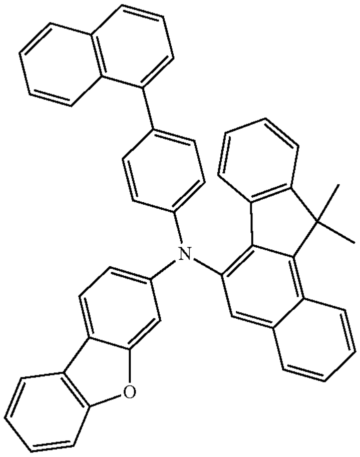
-continued
153
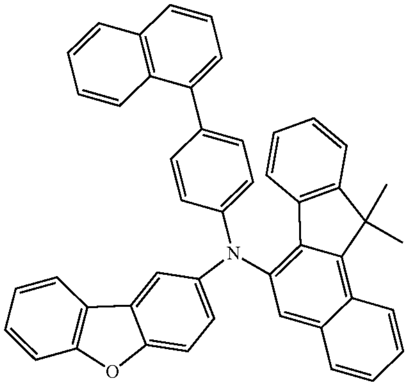
154
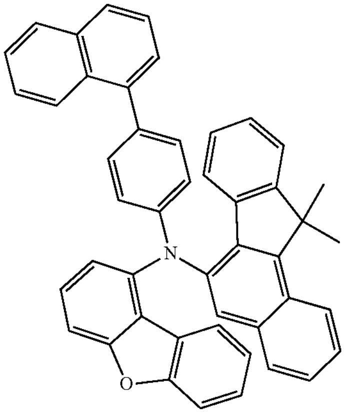
155
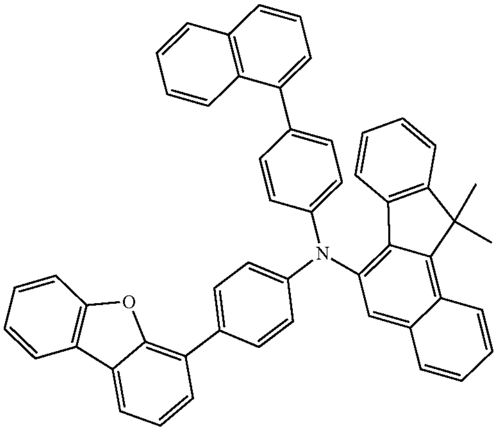

-continued
156
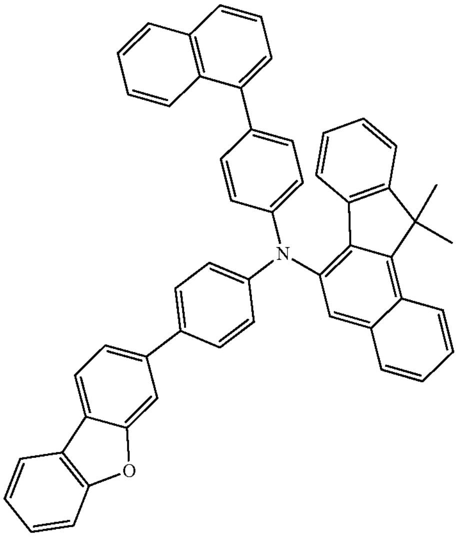
157
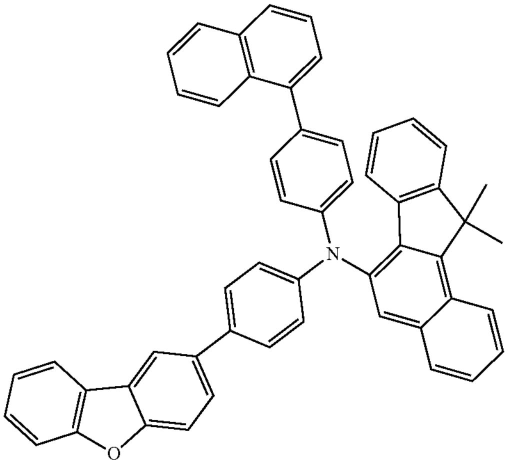
158
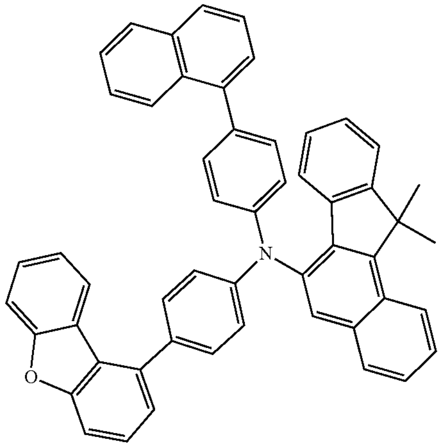
-continued
159
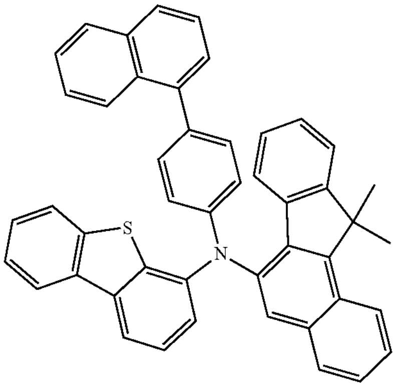
160
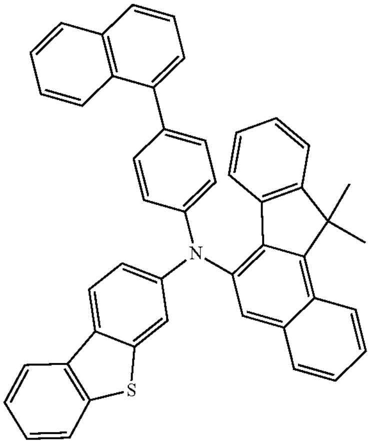
161
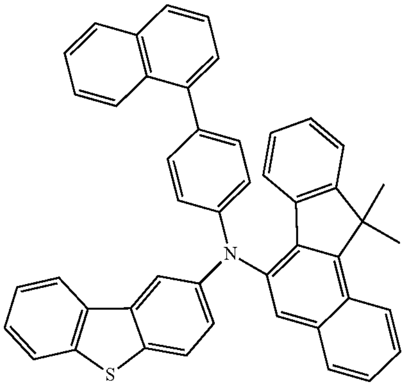
162
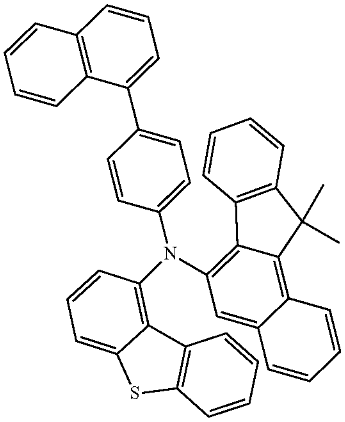

-continued
163
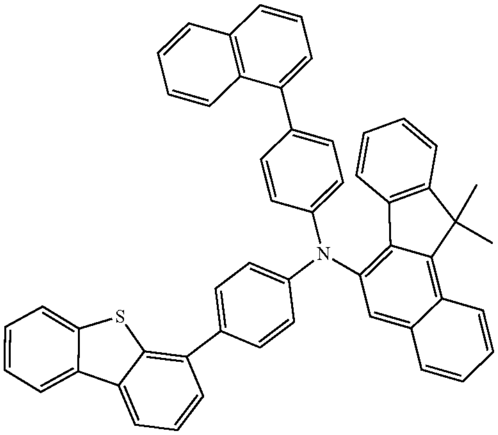
164
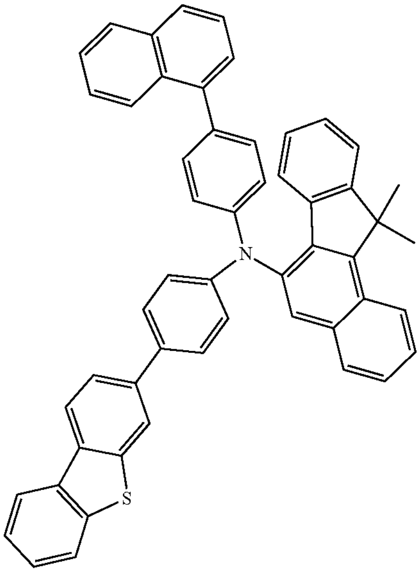
165
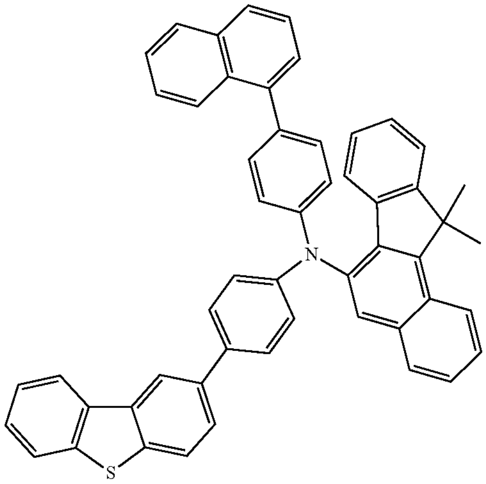
-continued
166
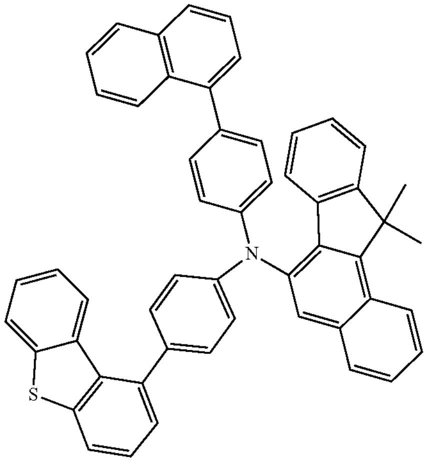
167
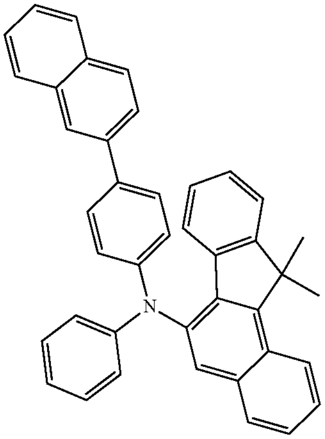
168
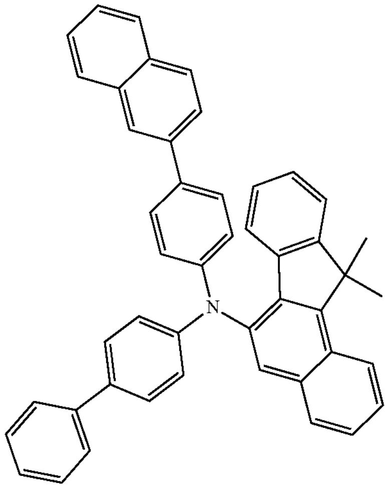

169
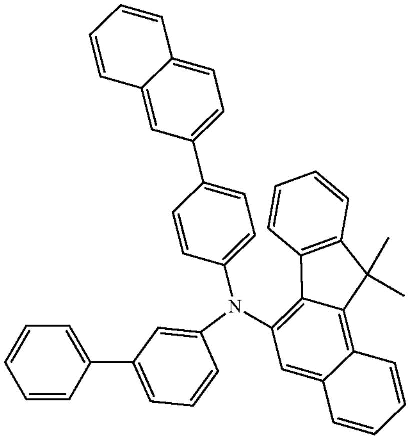
170
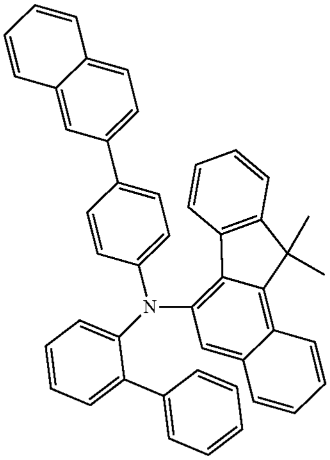
171
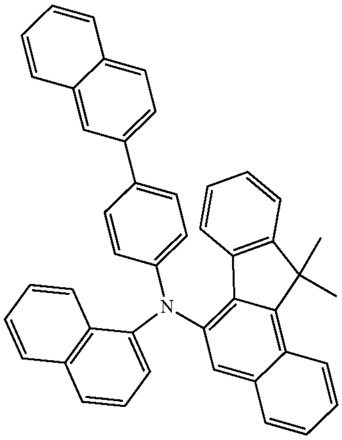
172
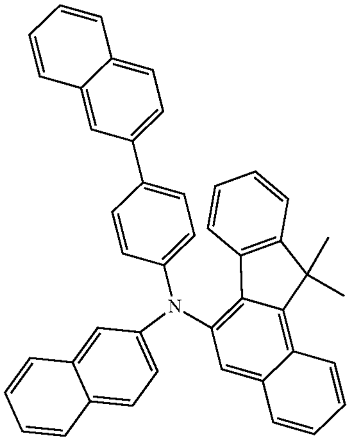
173
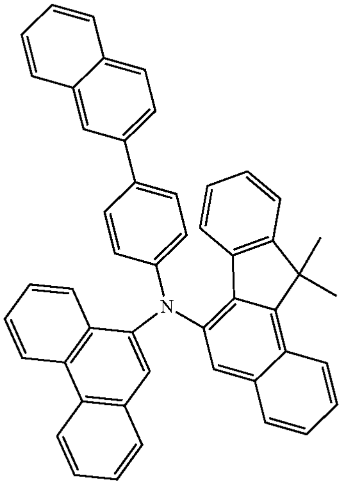
174
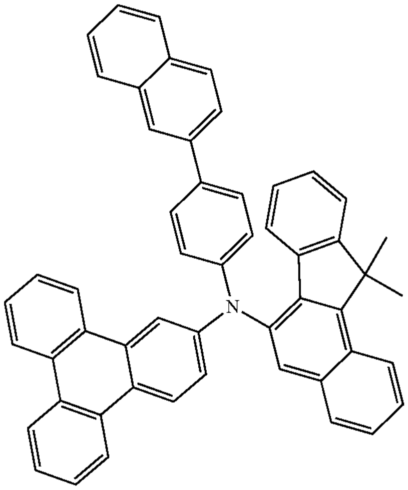

-continued
175
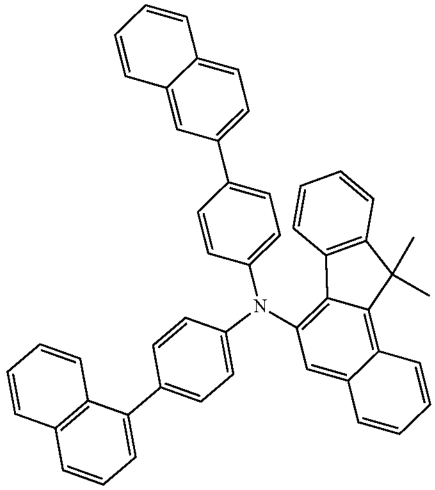
176
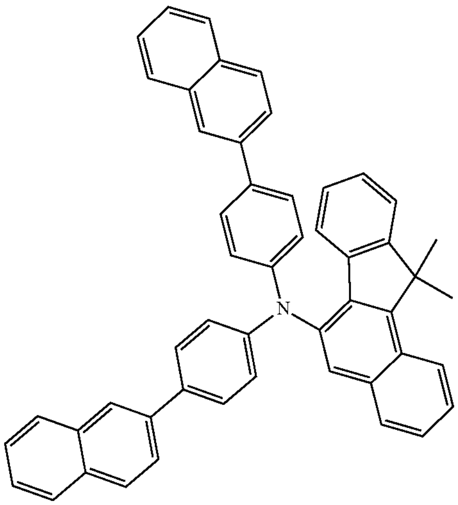
177
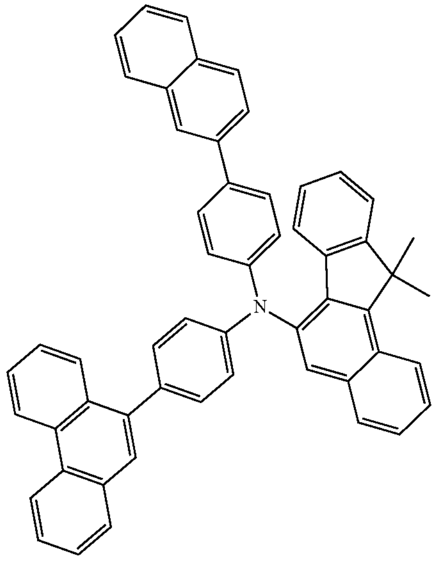
-continued
178
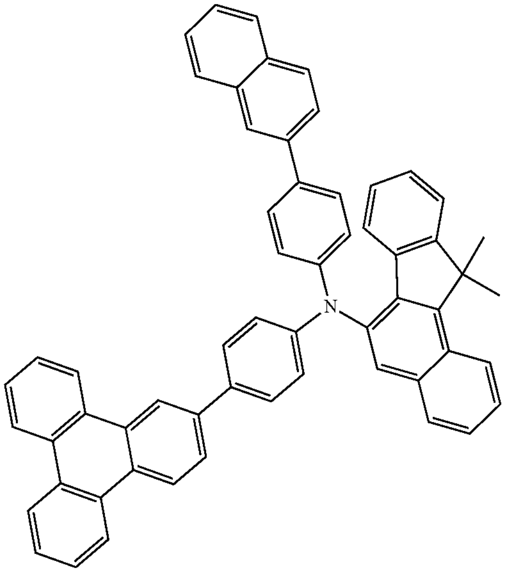
179
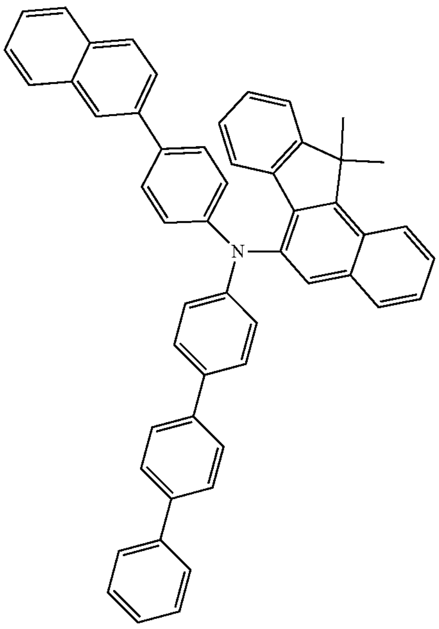

-continued
180
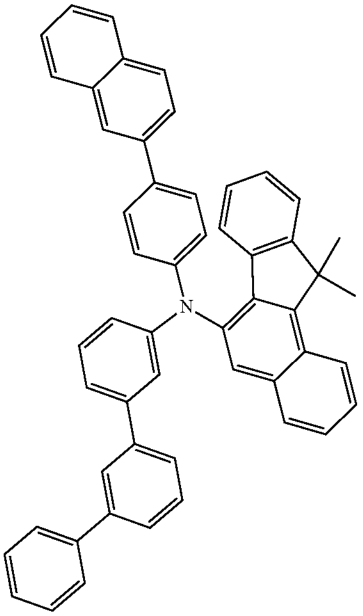
181
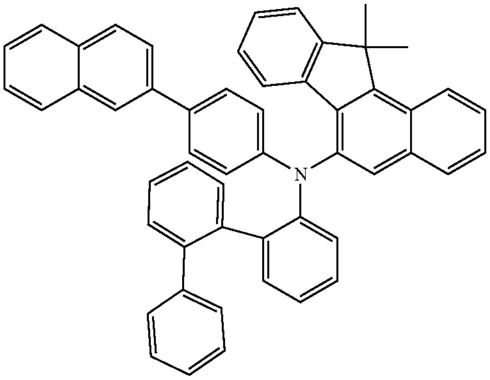
182
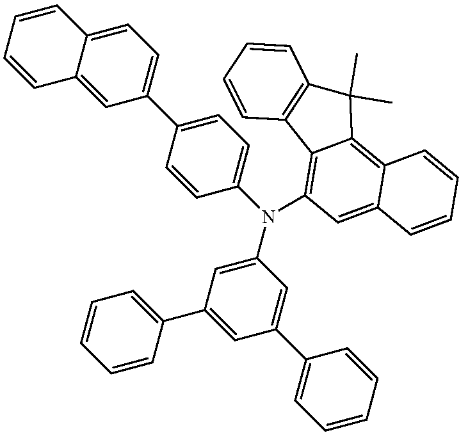
-continued
183
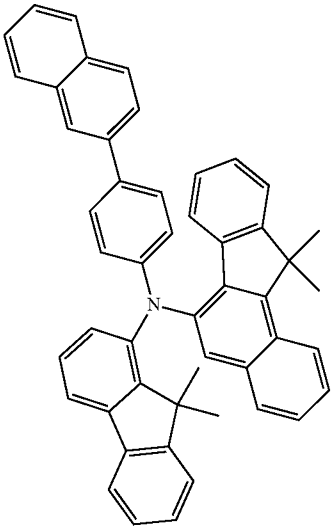
184
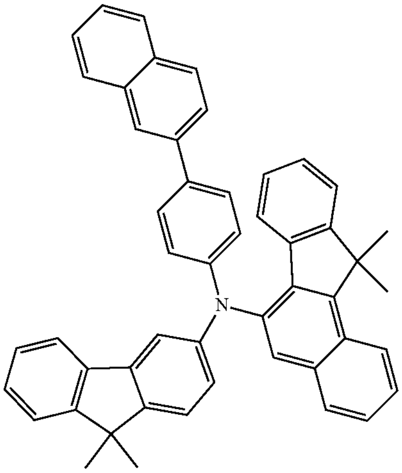
185
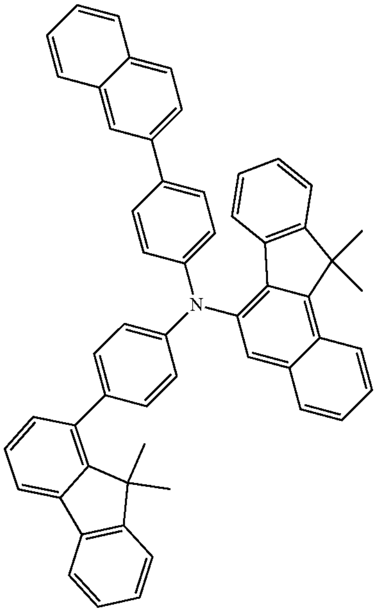

-continued
186
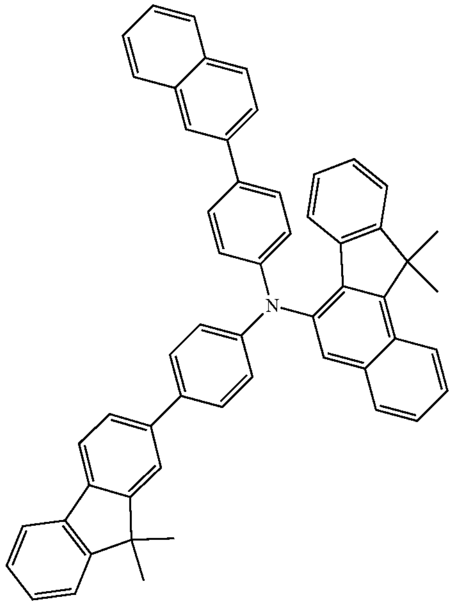
188
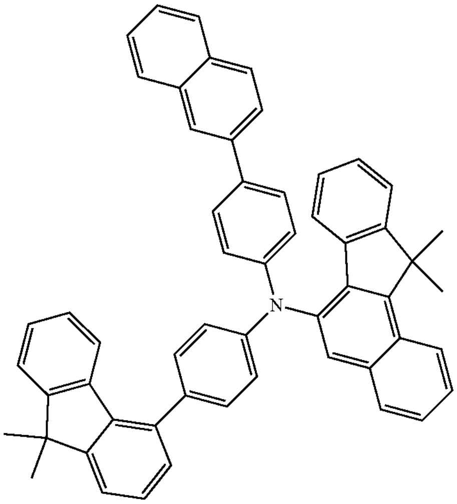
187
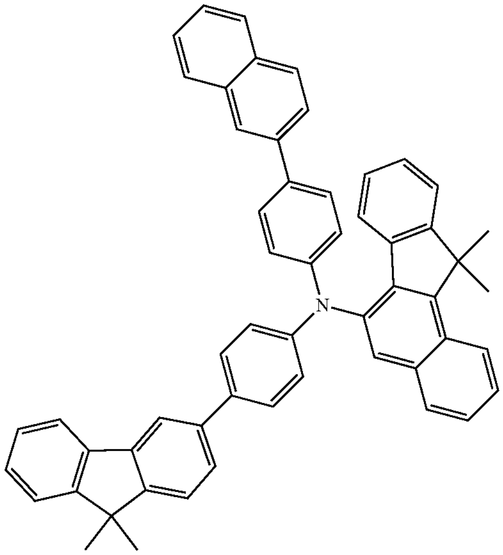
189
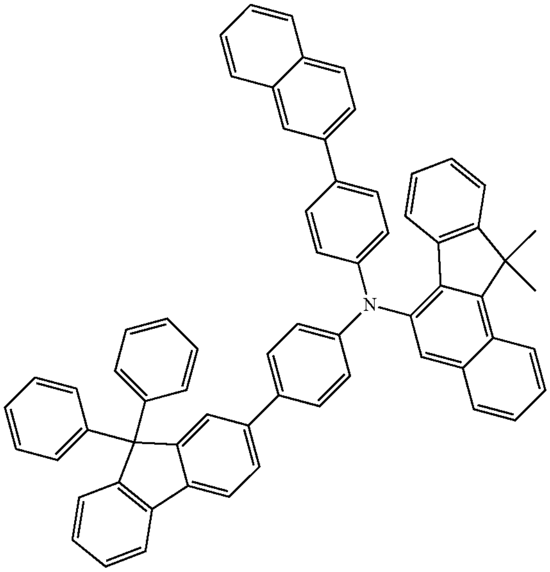

-continued
190
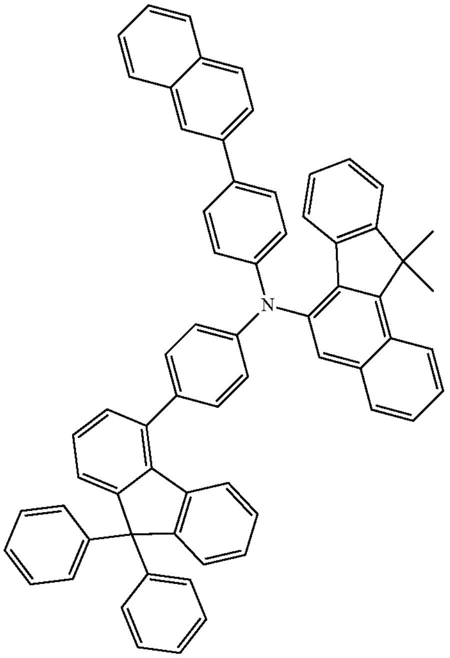
191
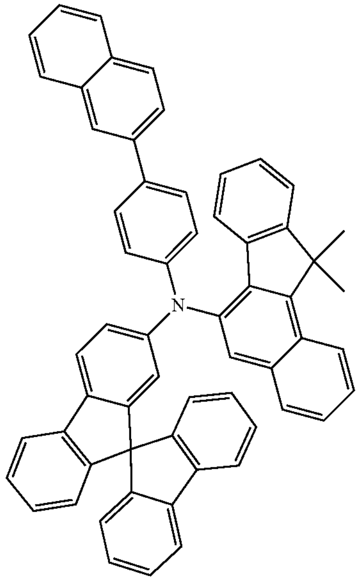
-continued
192
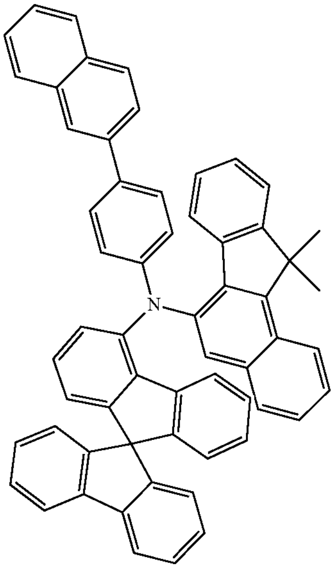
193
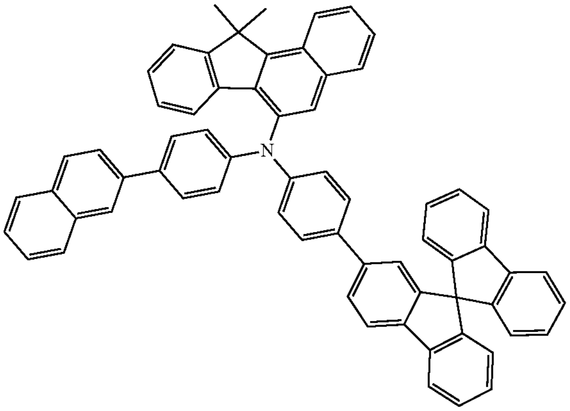
194
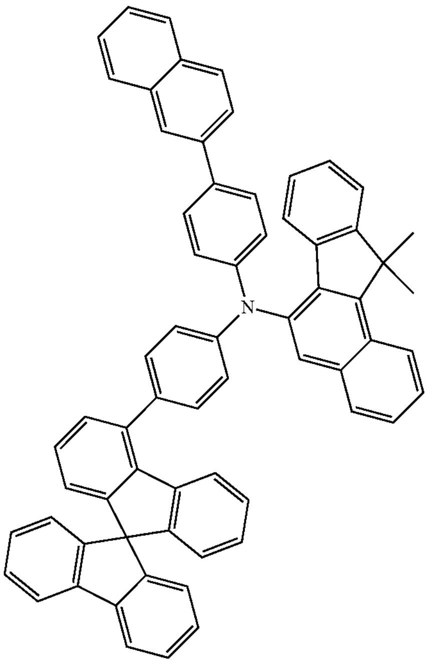

-continued
195
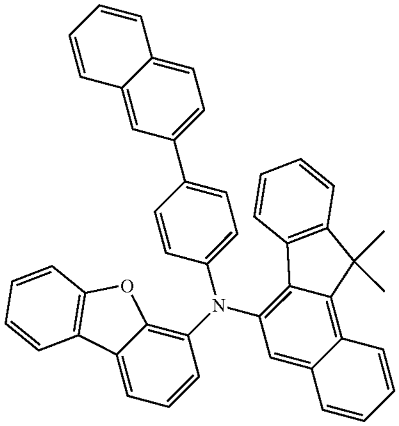
196
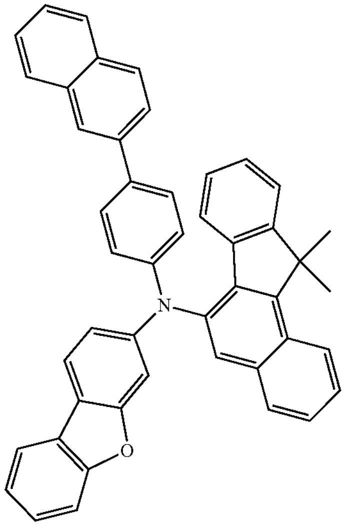
197
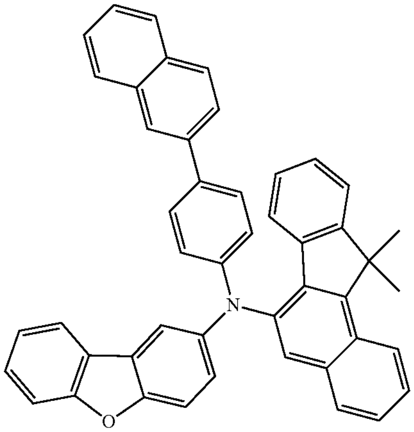
-continued
198
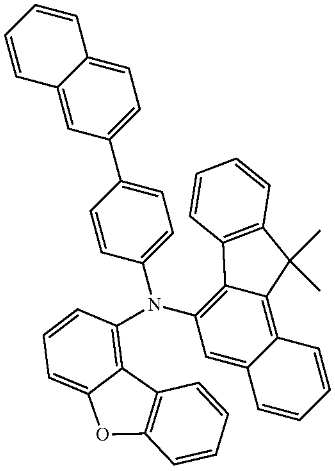
199
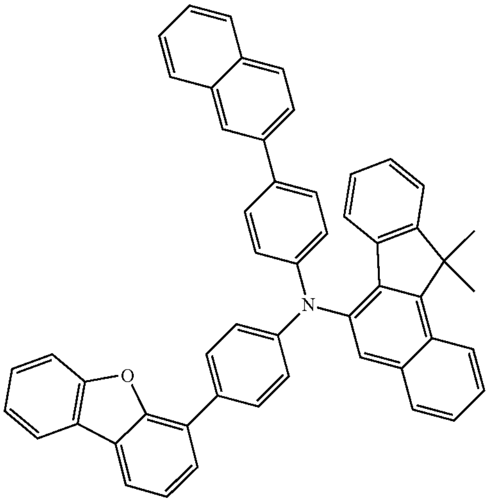
200
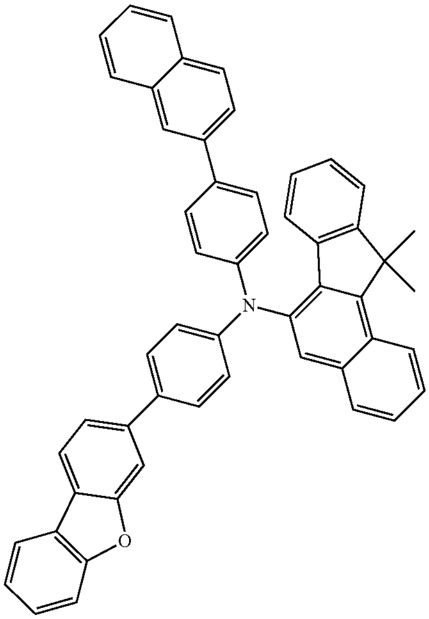

-continued
201
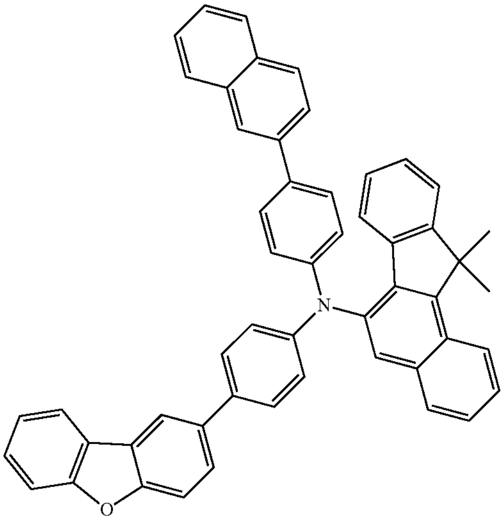
202
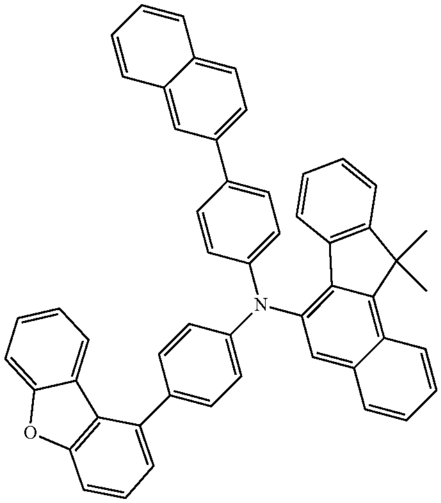
203
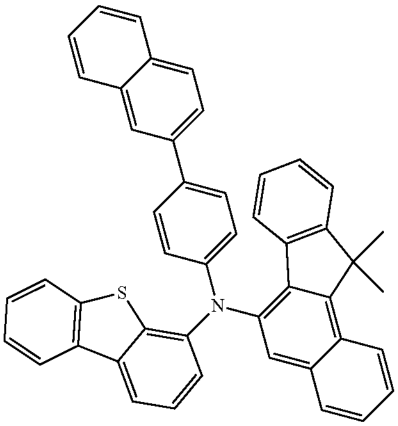
-continued
204
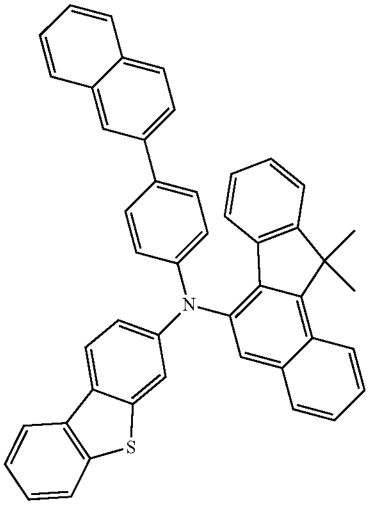
205
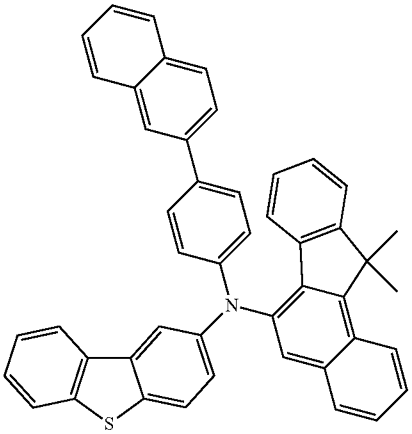
206
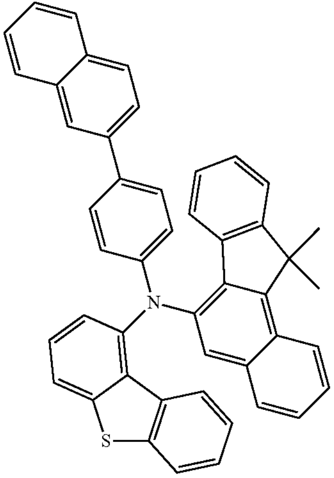

-continued
207
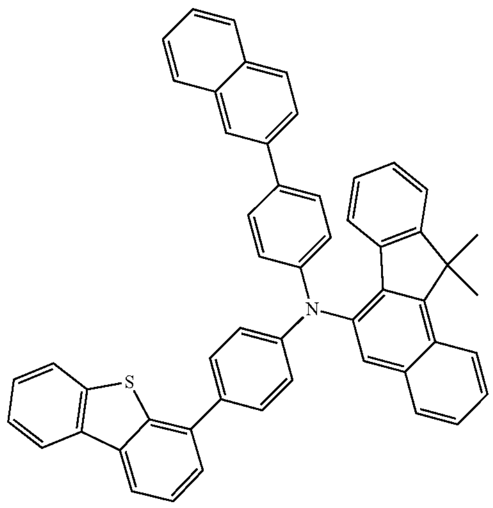
208
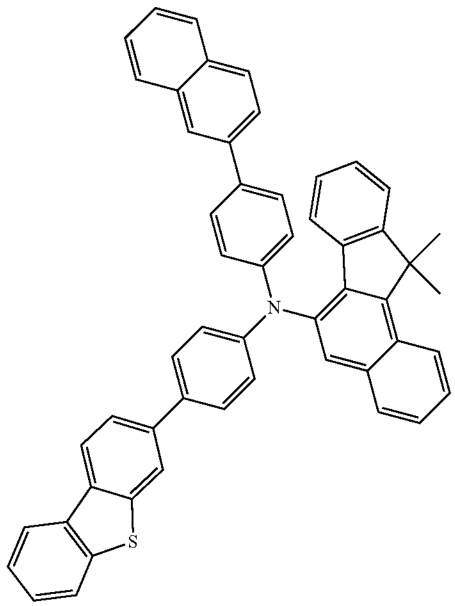
209
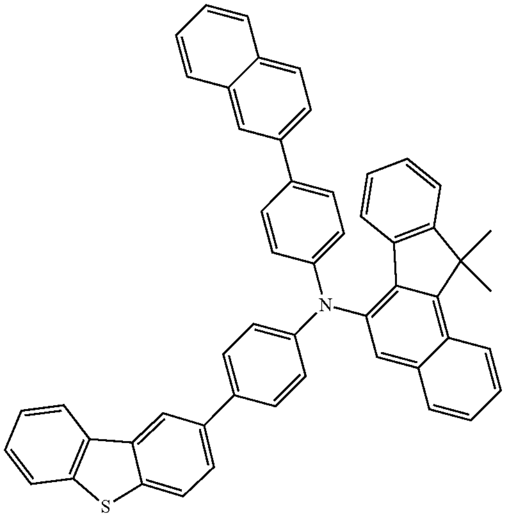
-continued
210
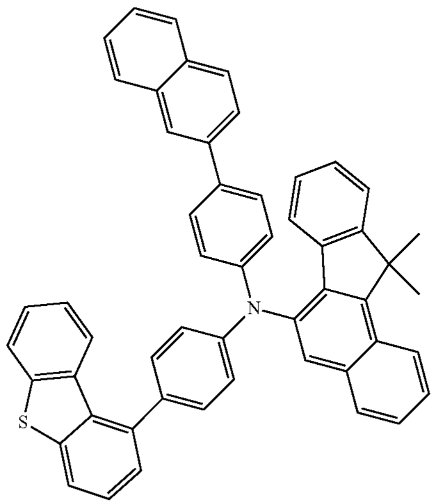
211
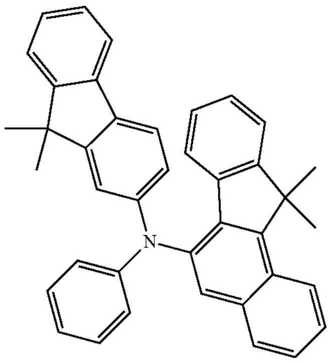
212
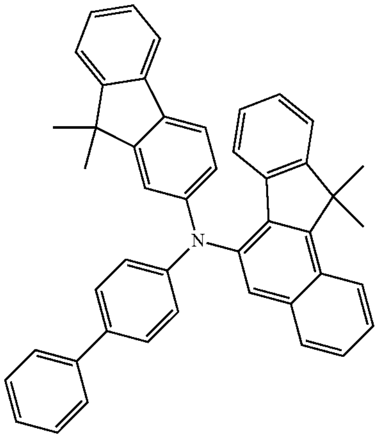

-continued
213
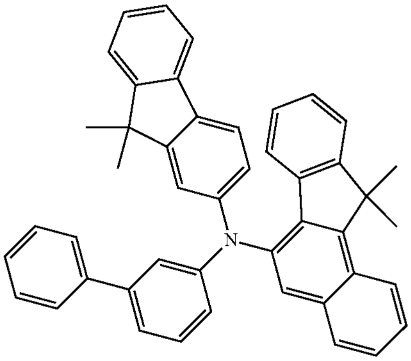
214
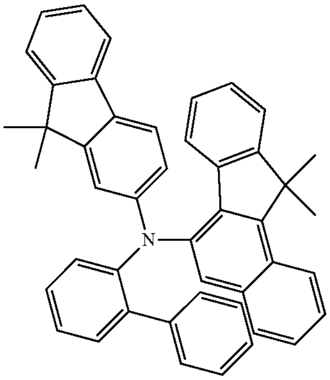
215
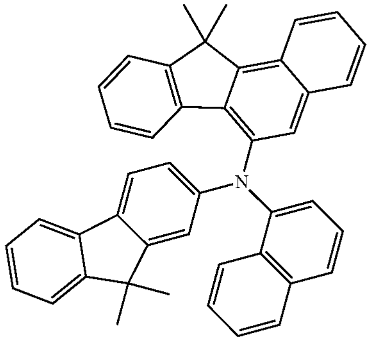
216
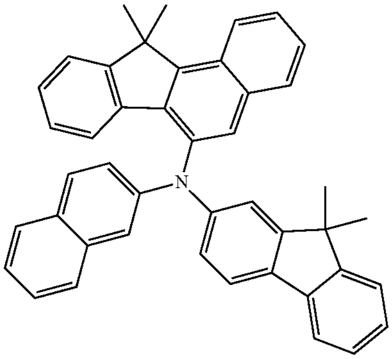
-continued
217
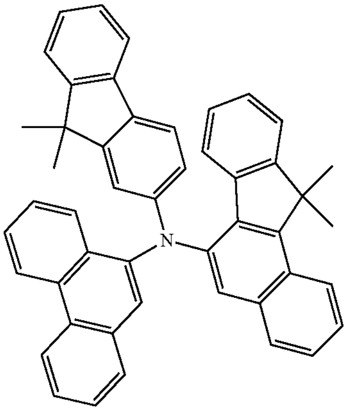
218
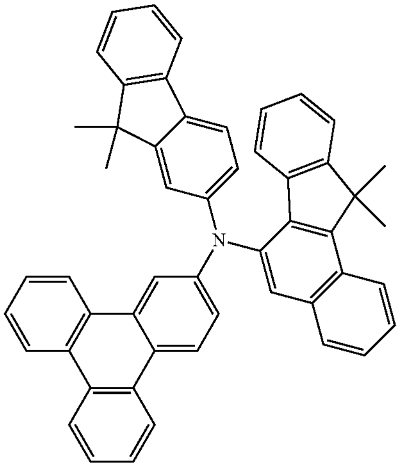
219
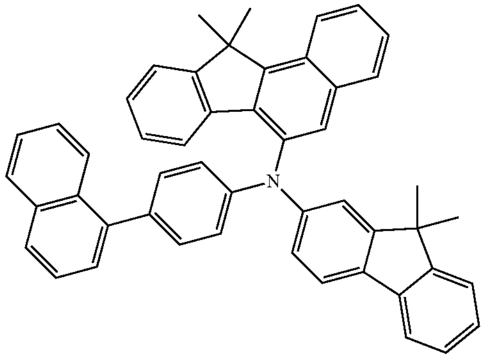
220
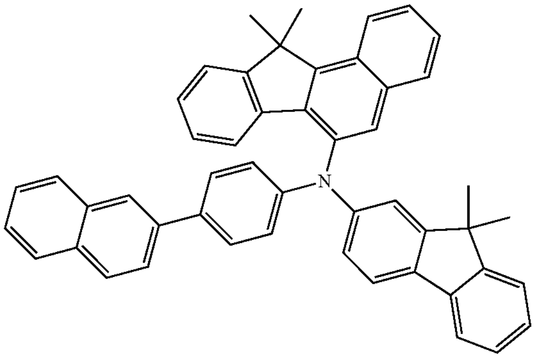

-continued
221
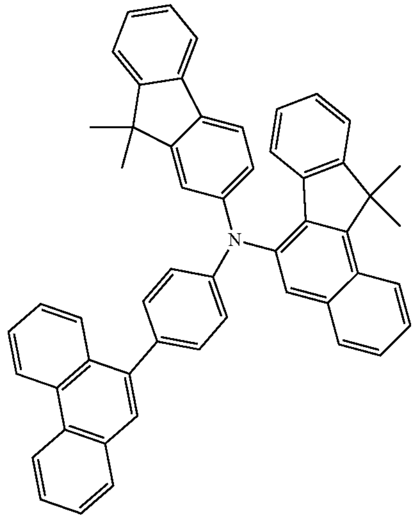
222
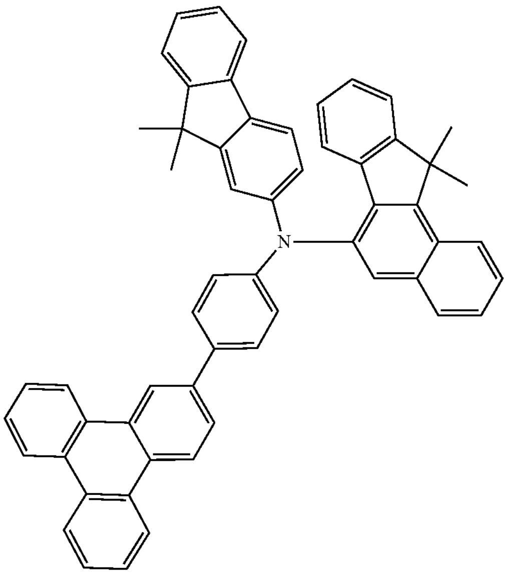
223
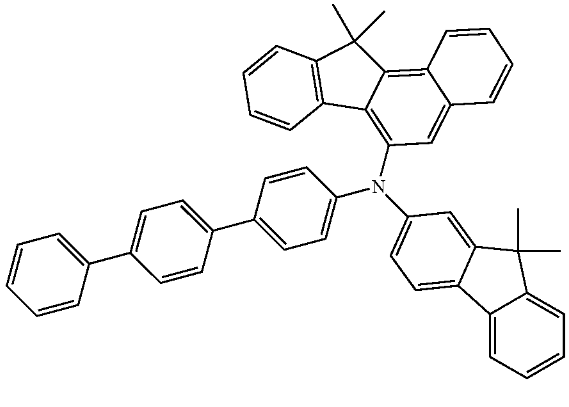
-continued
224
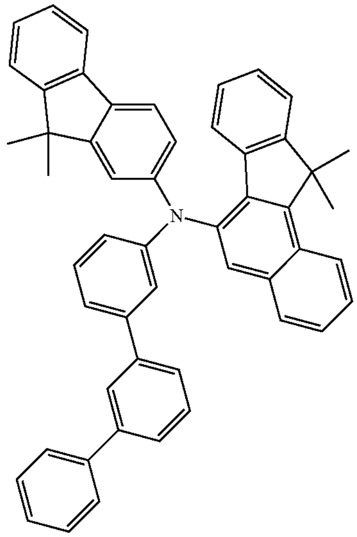
225
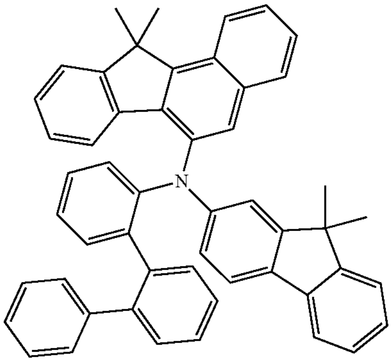
226
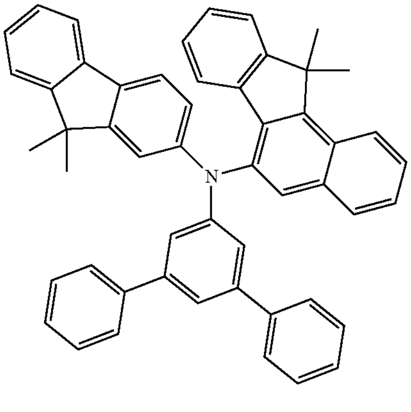

-continued
227
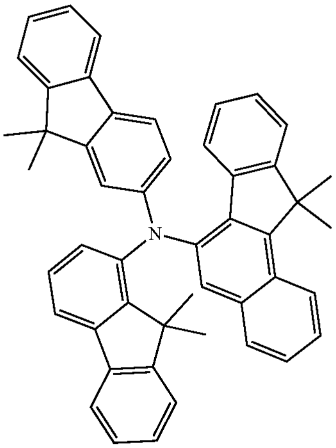
228
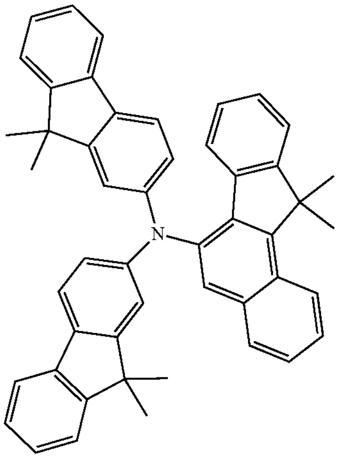
229
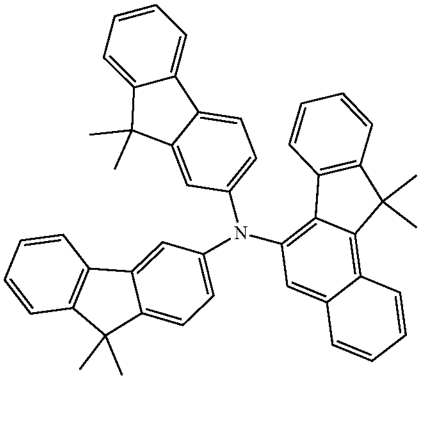
-continued
230
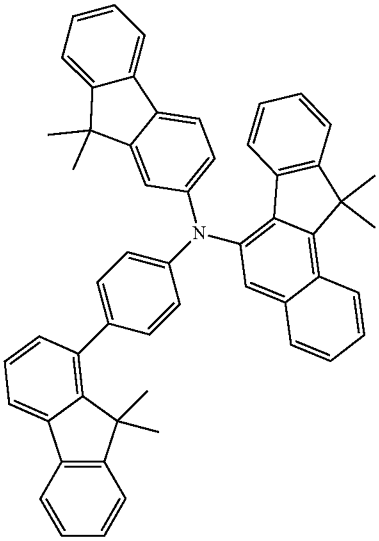
231
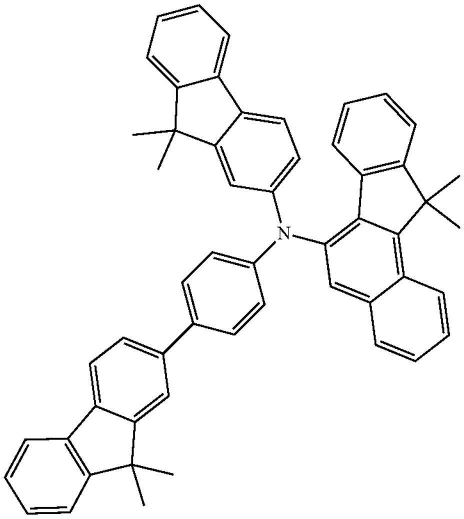
232
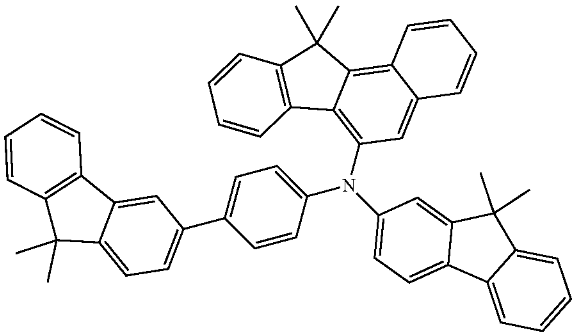

-continued
233
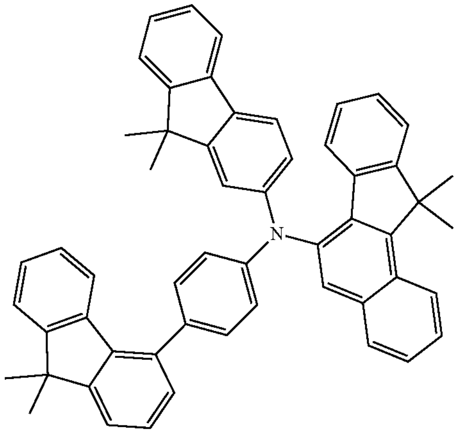
234
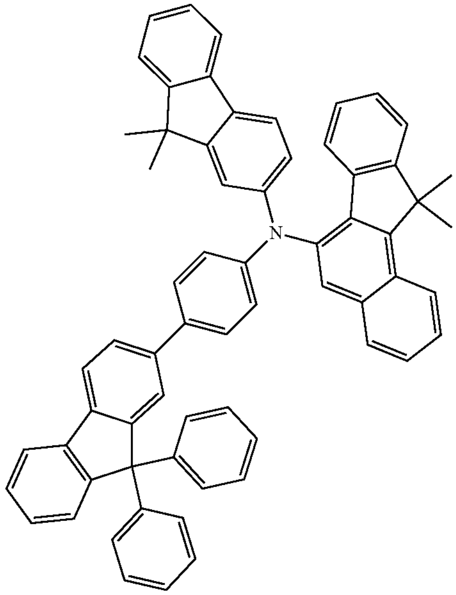
235
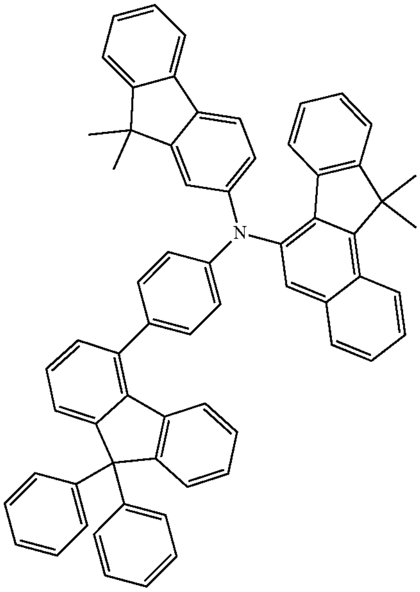
-continued
236
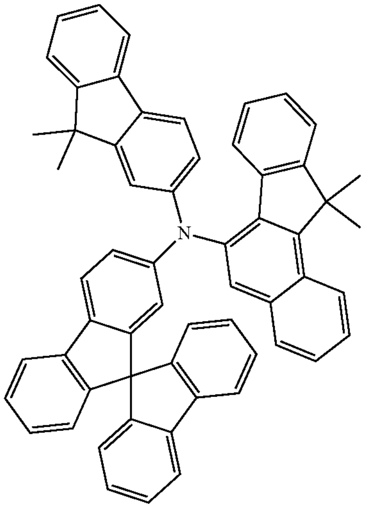
237
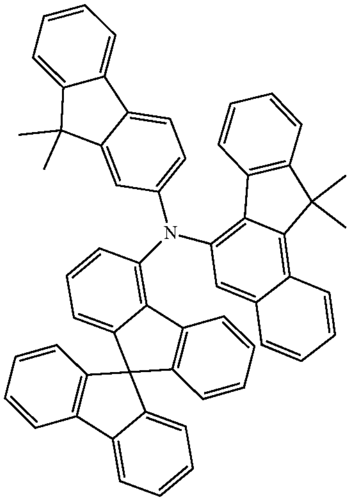
238
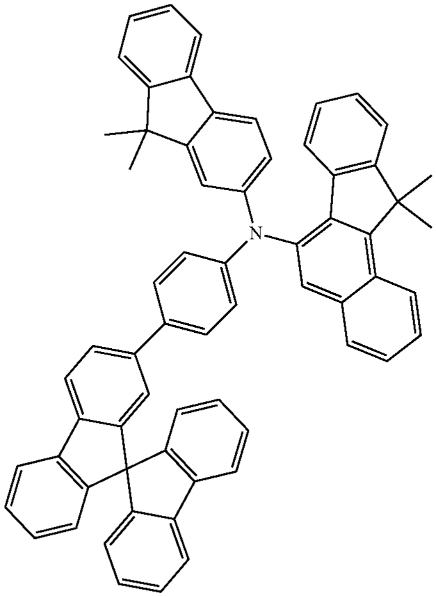

-continued
239
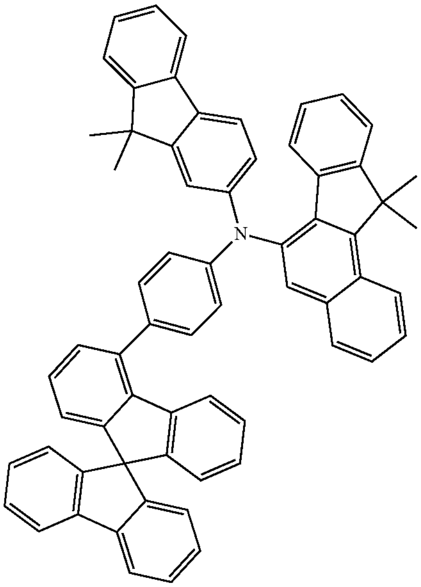
240
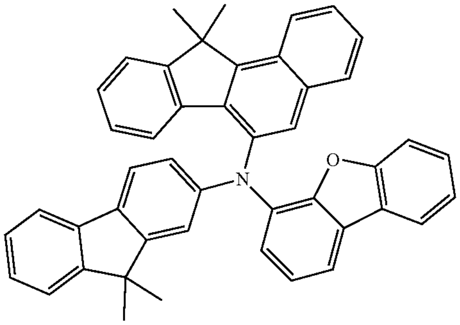
241
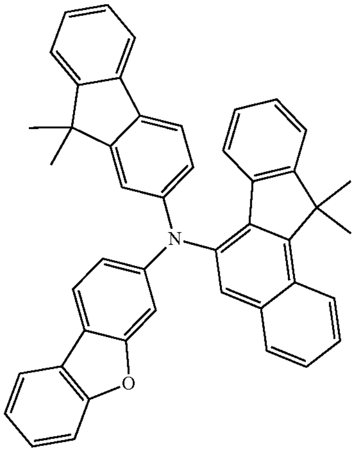
-continued
242
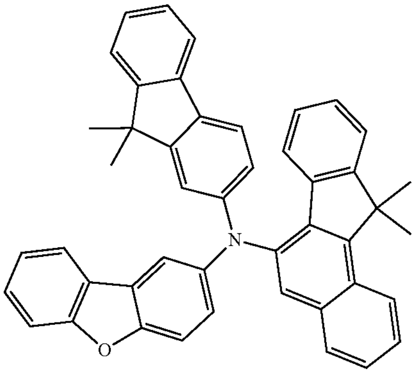
243
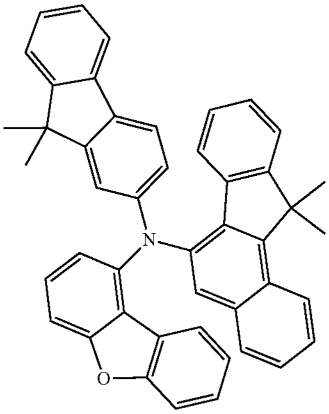
244
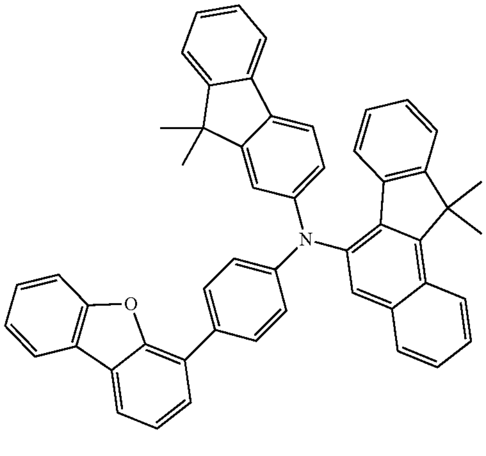

-continued
245
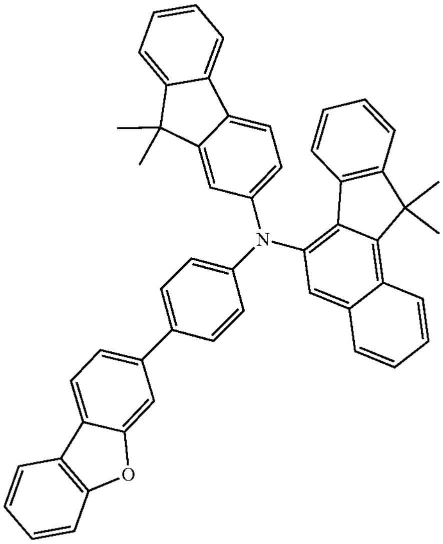
246
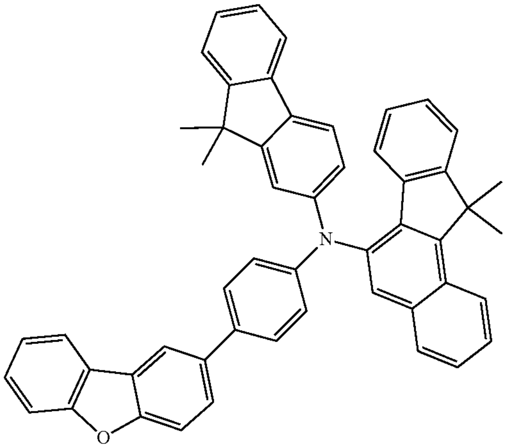
247
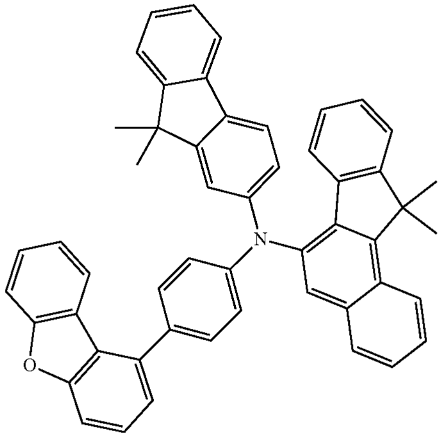
-continued
248
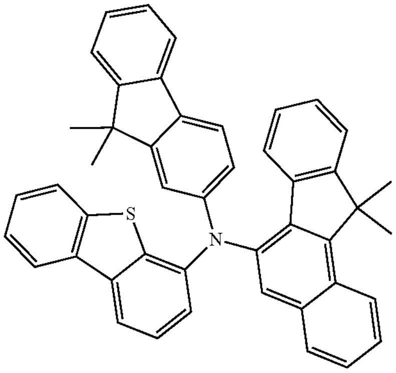
249
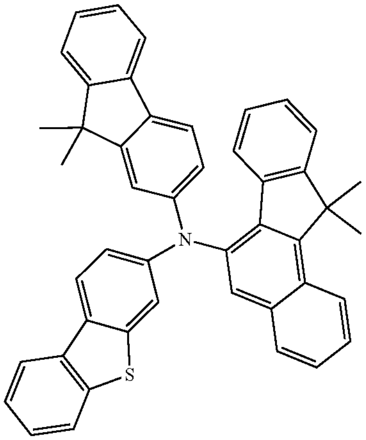
250
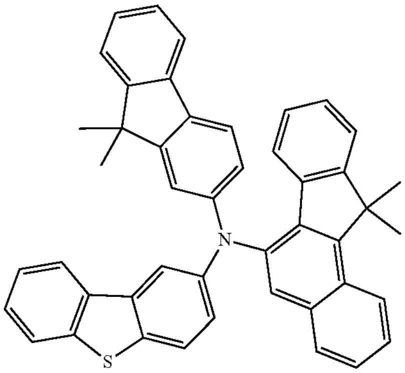
251
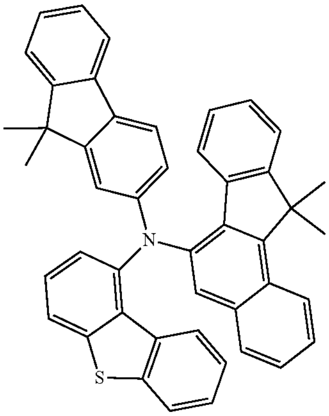

-continued
252
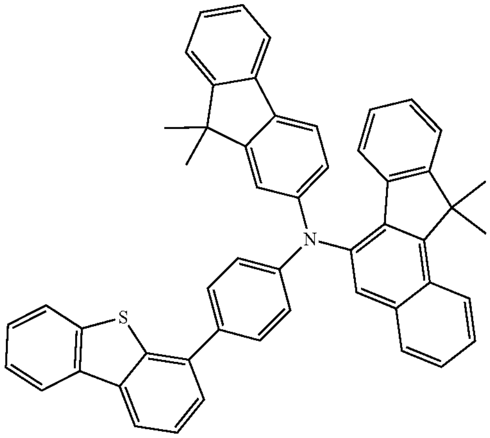
253
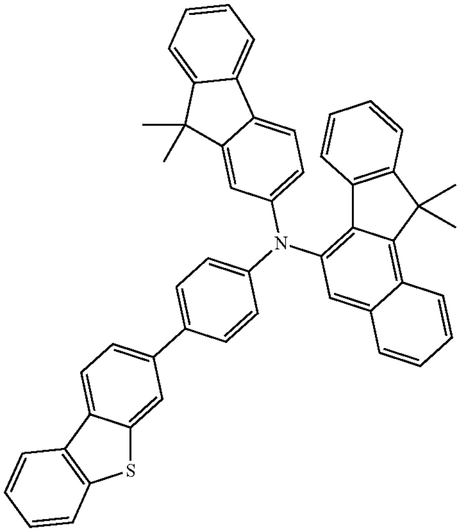
254
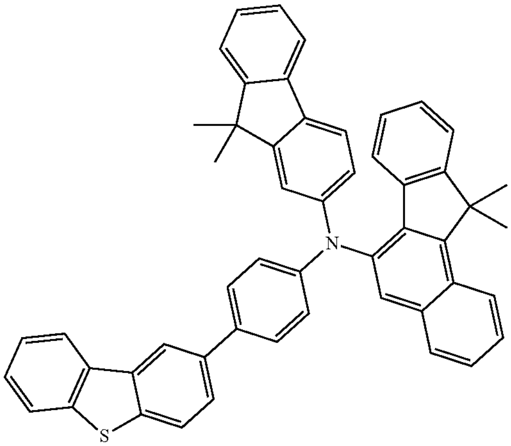
-continued
255
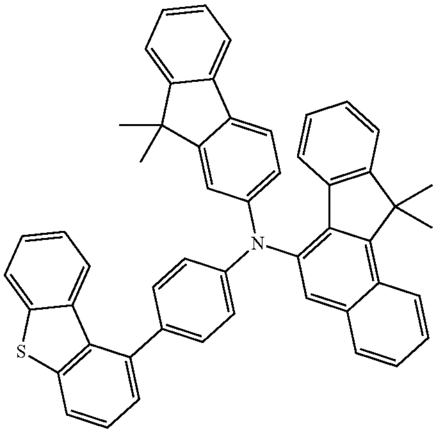
256
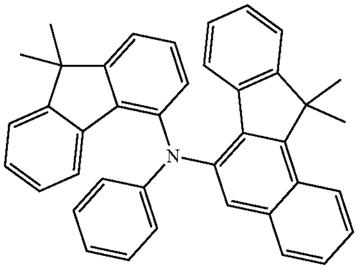
257
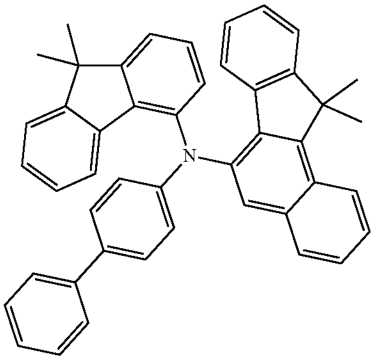
258
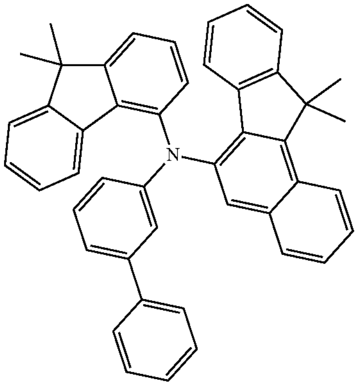

-continued
259
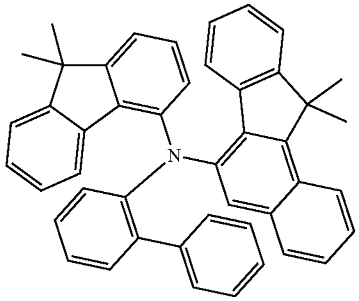
260
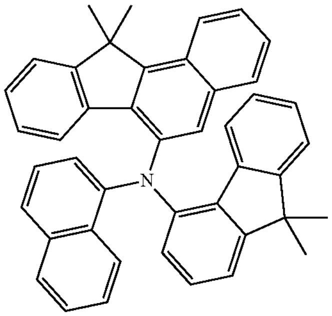
261
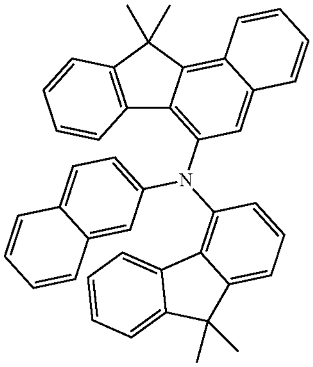
262
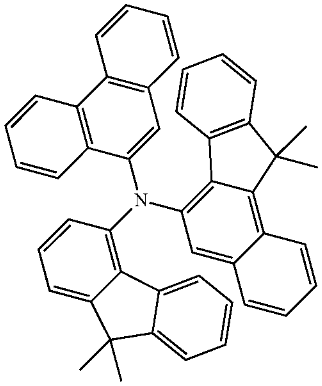
-continued
263
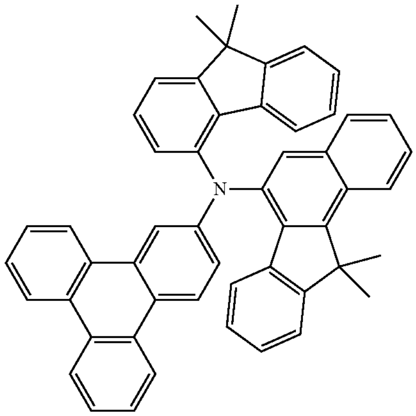
264
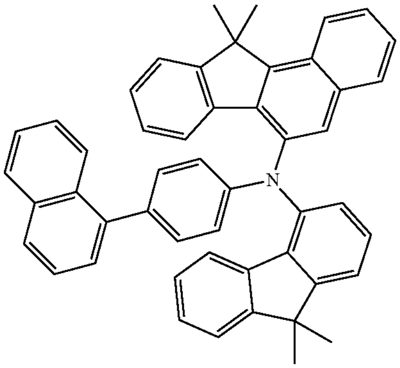
265
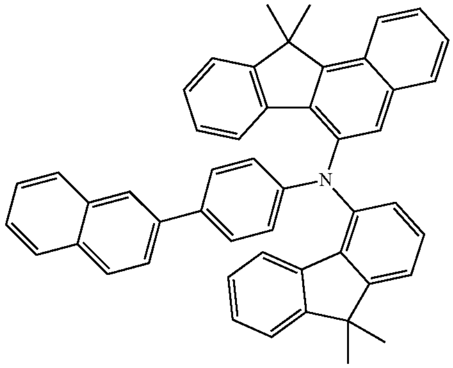
266
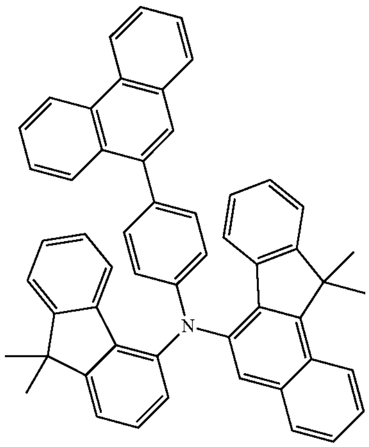

-continued
267
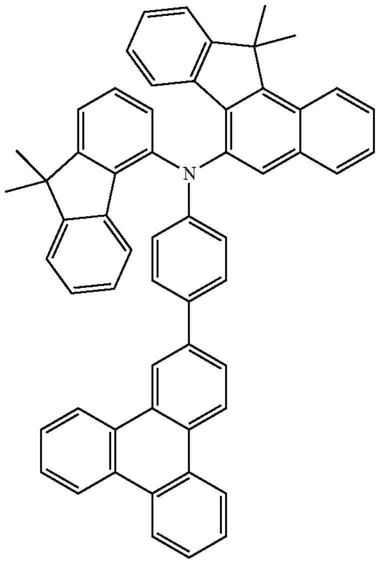
268
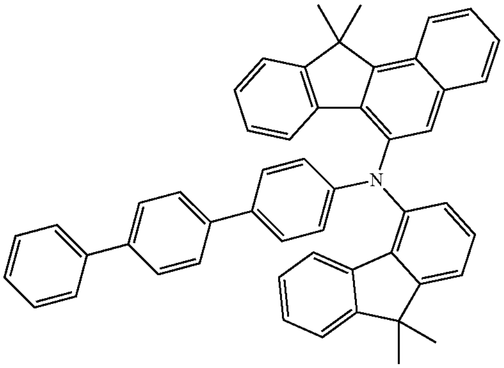
269
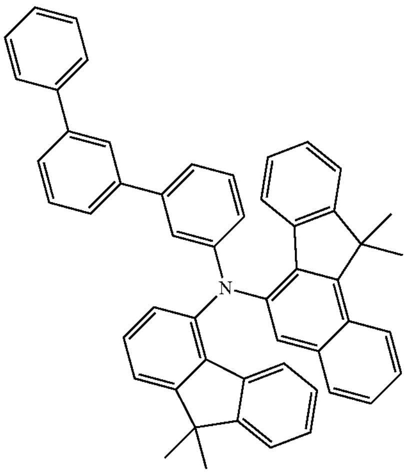
-continued
270
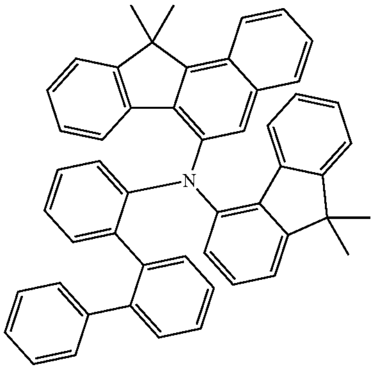
271
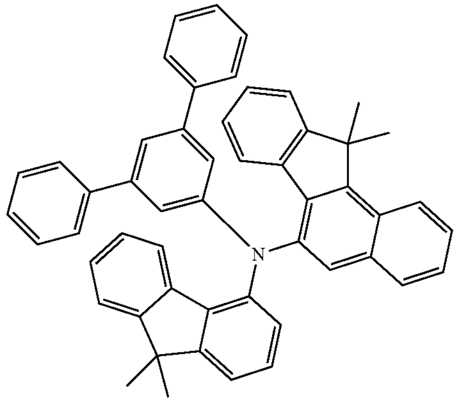
272
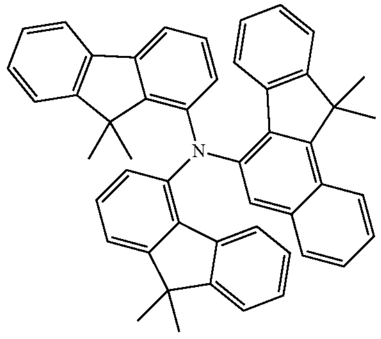
273
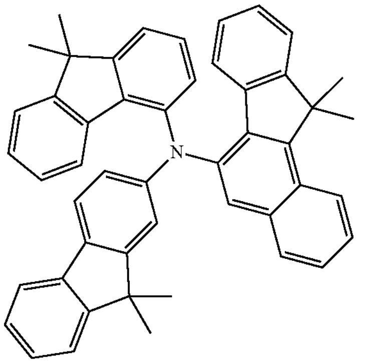

-continued
274
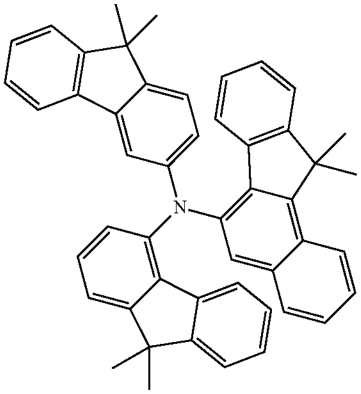
275
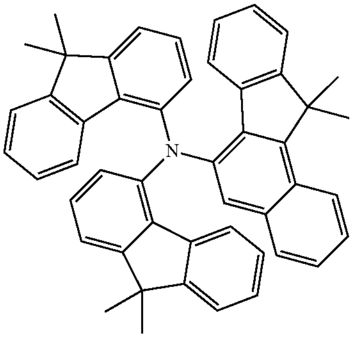
276
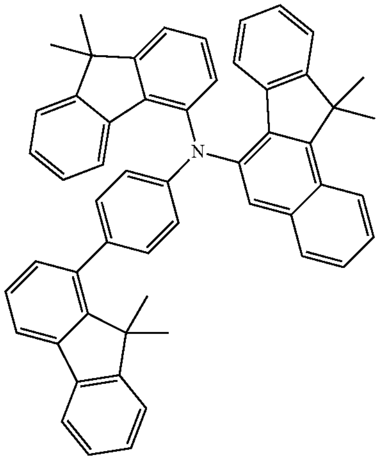
277
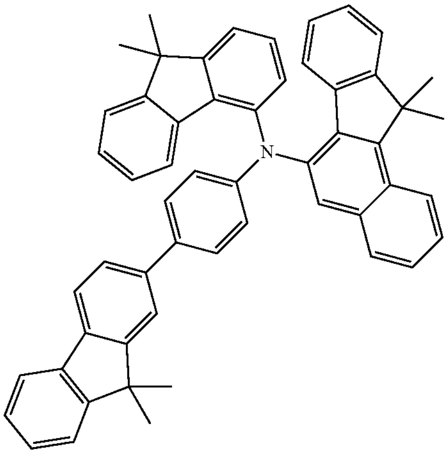
-continued
278
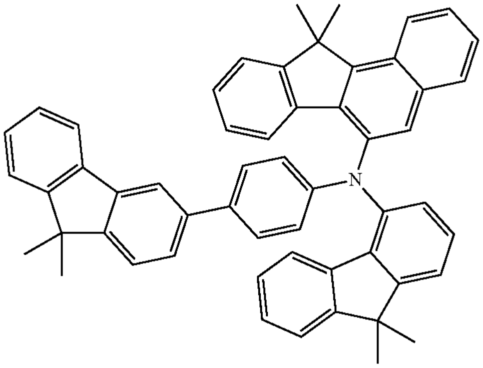
279
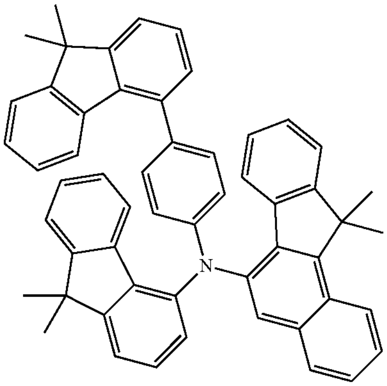
280
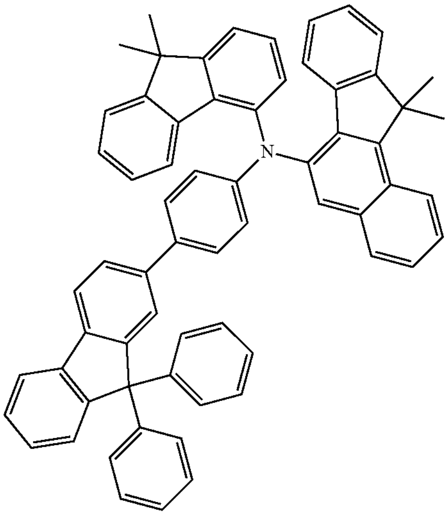

-continued
281
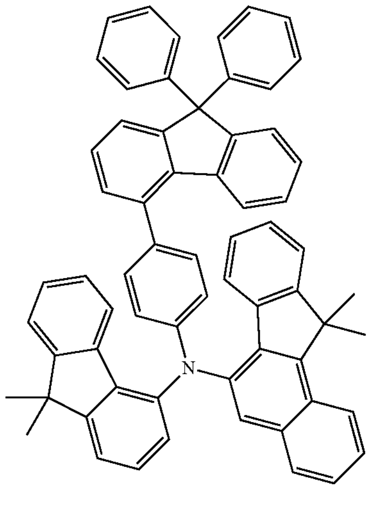
282
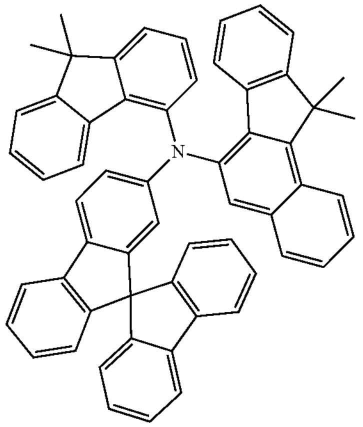
283
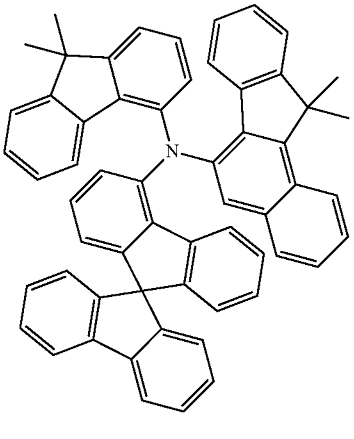
-continued
284
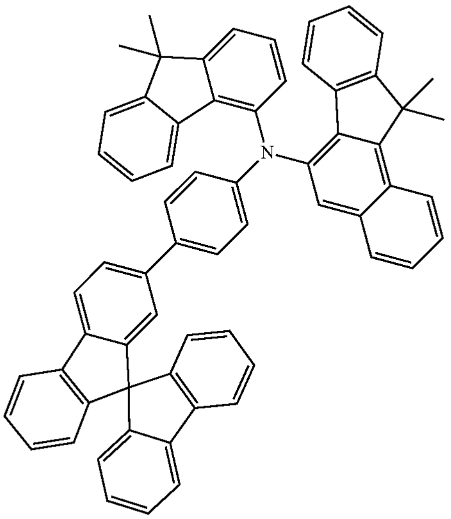
285
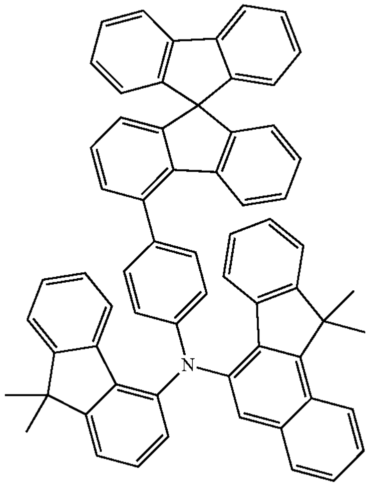
286
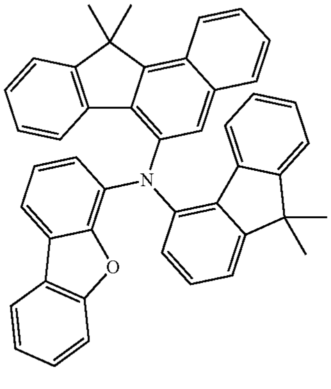

-continued
287
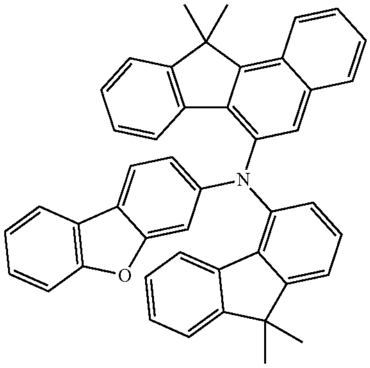
288
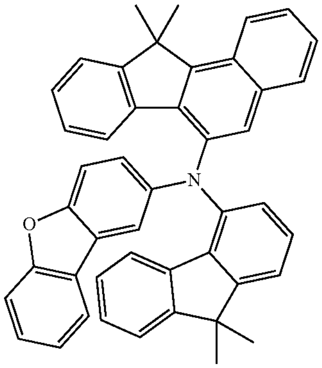
289
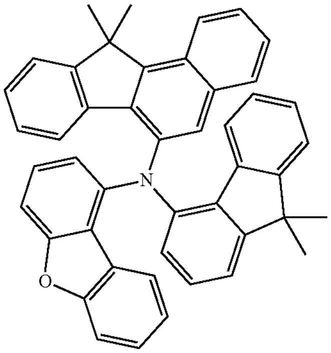
290
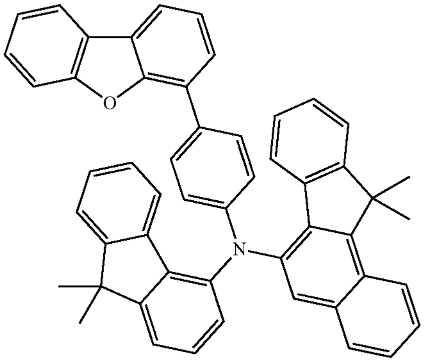
-continued
291
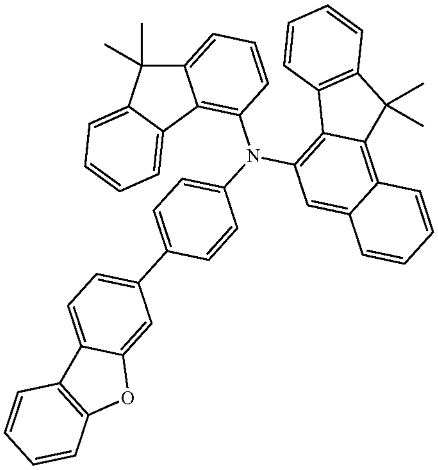
292
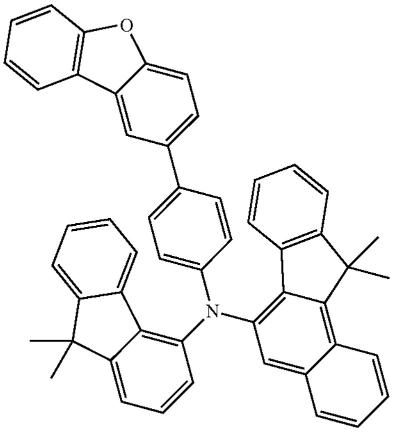
293
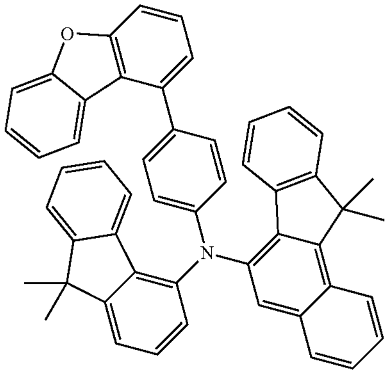
294
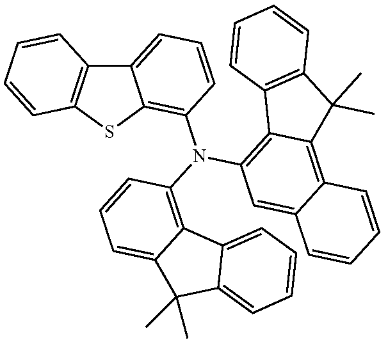

-continued
295
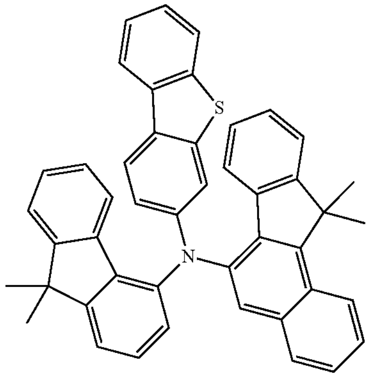
296
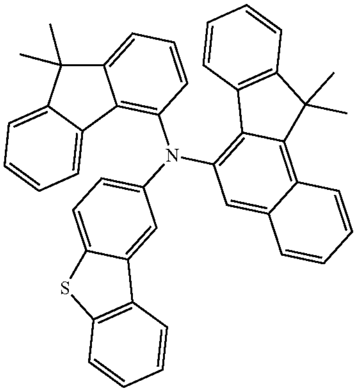
297
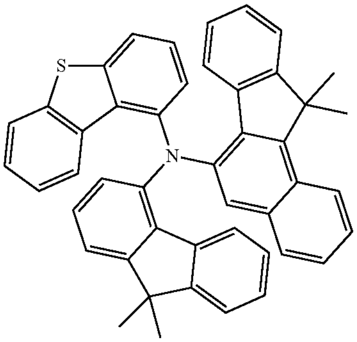
298
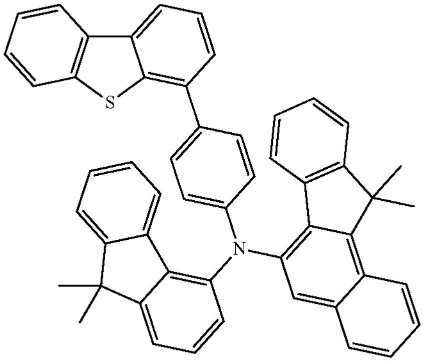
-continued
299
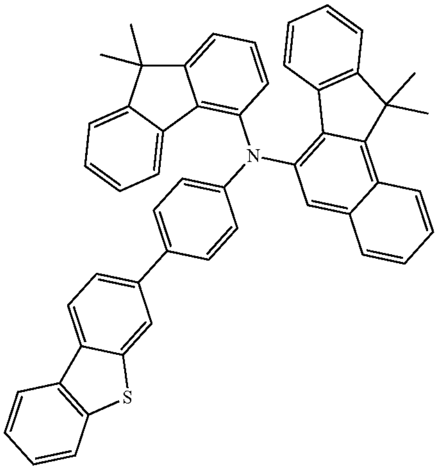
300
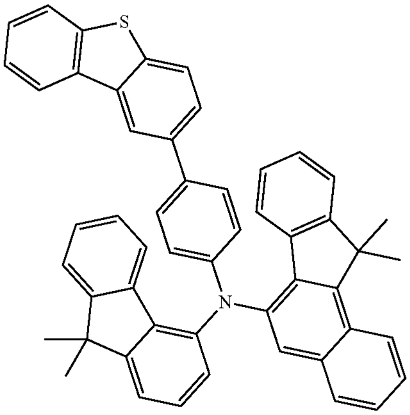
301
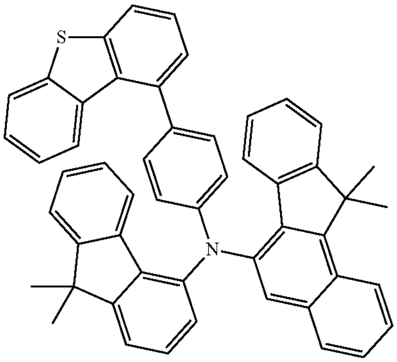
302
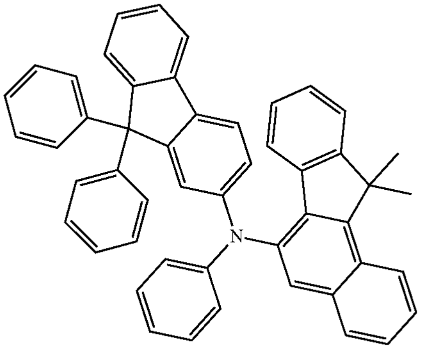

-continued
303
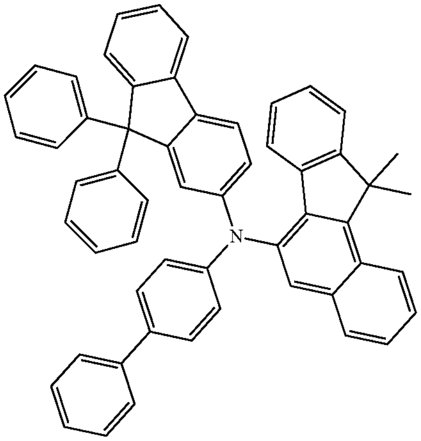
304
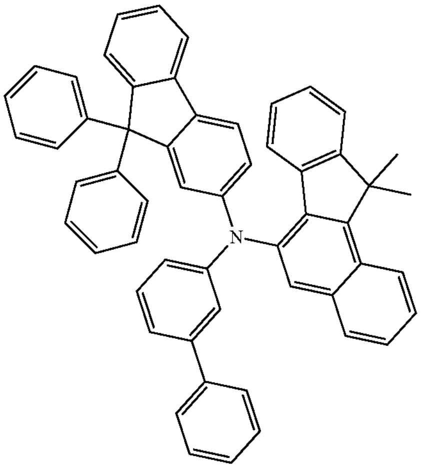
305
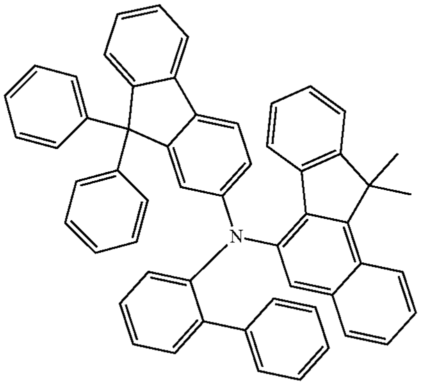
-continued
306
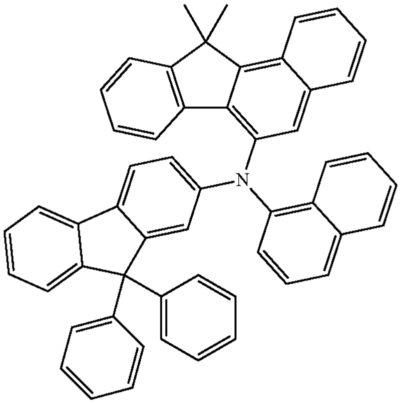
307
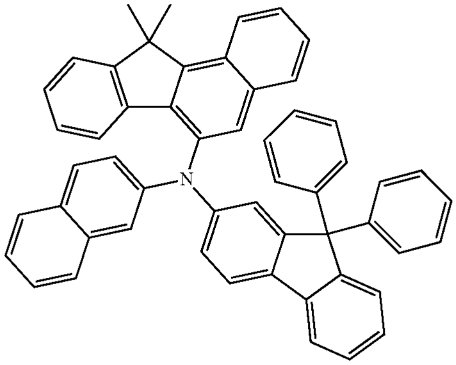
308
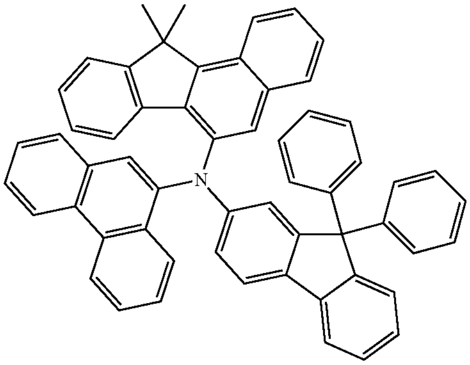
309
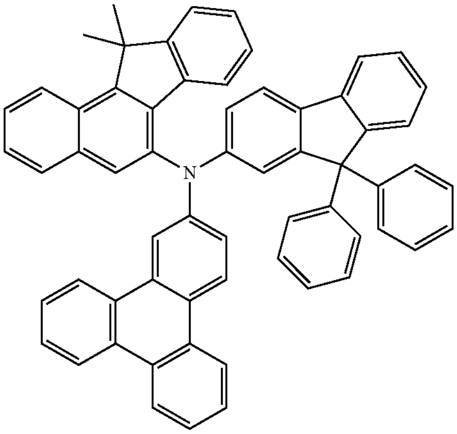

-continued
310
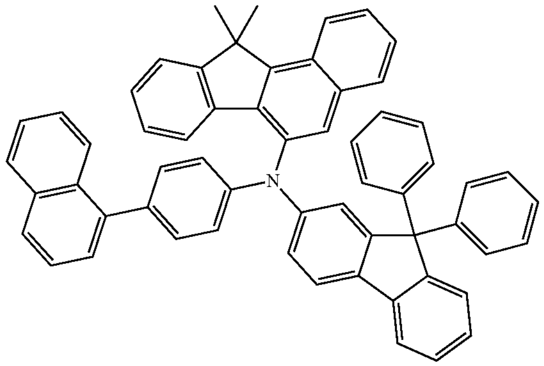
311
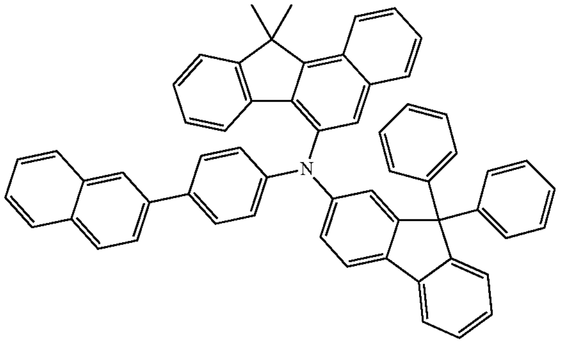
312
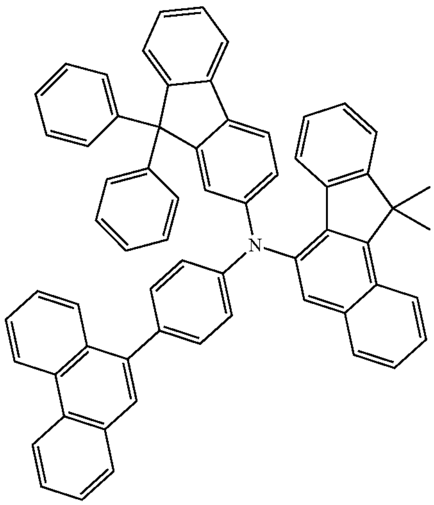
-continued
313
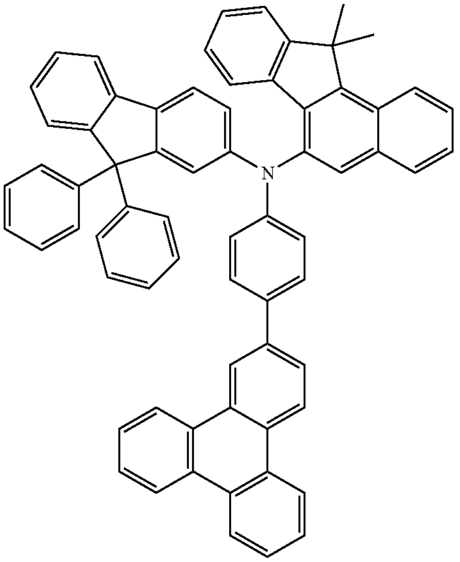
314
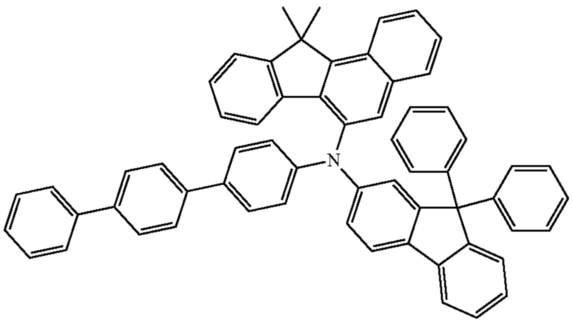
315
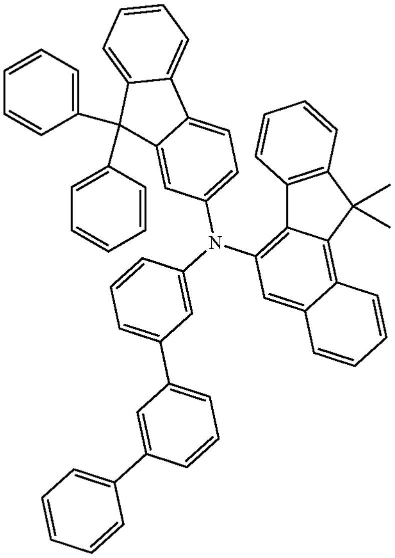

-continued
316
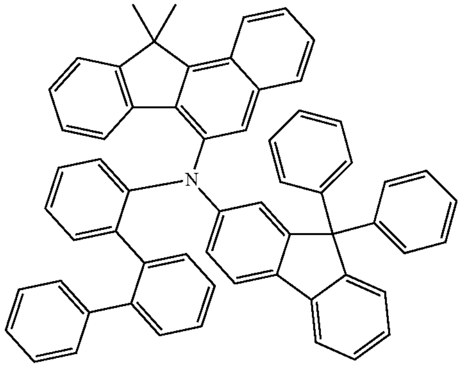
317
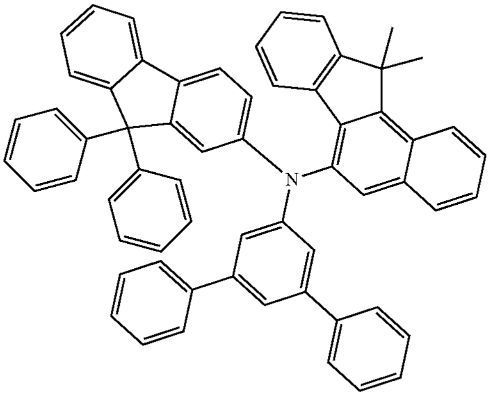
318
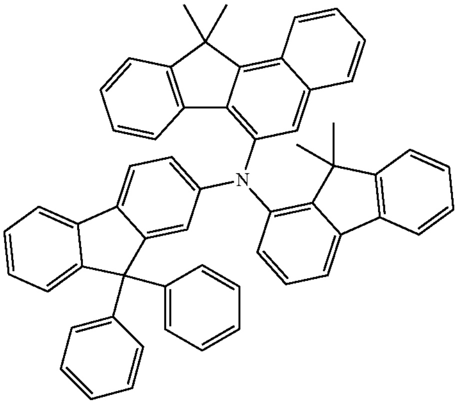
319
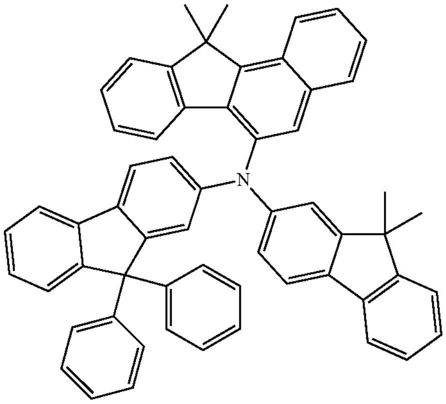
-continued
320
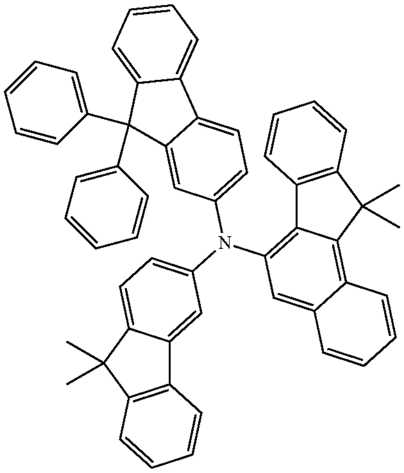
321
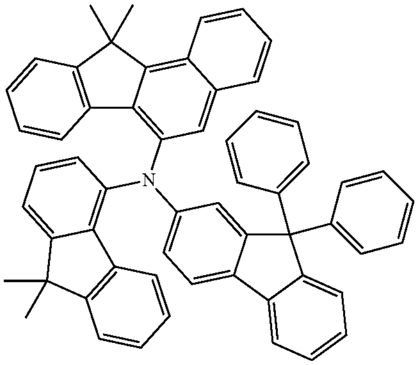
322
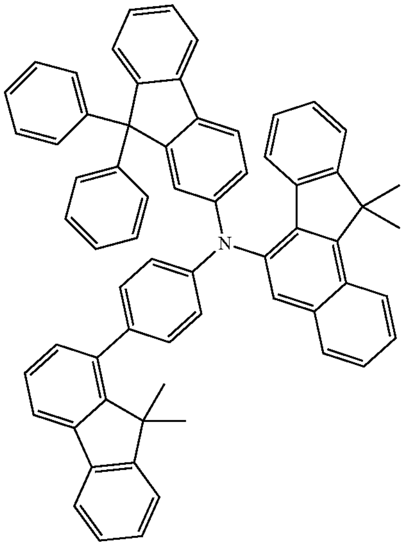

-continued
323
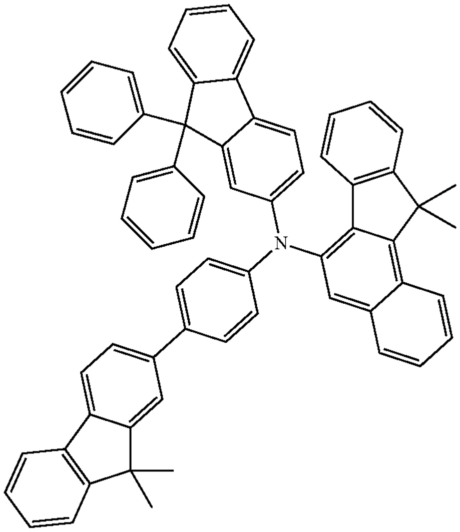
324
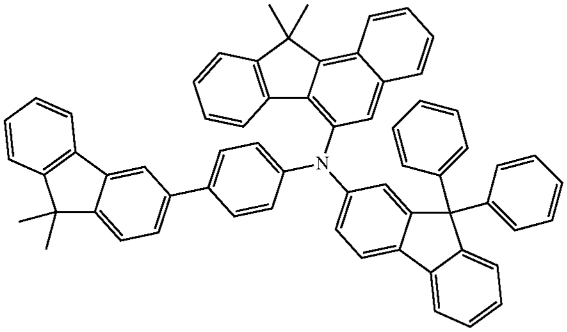
325
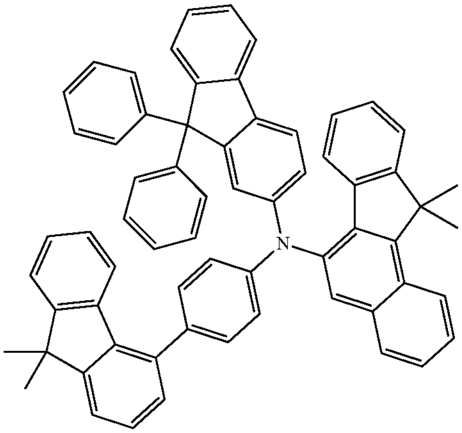
-continued
326
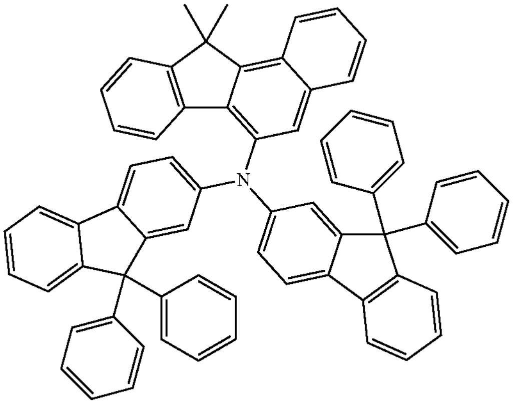
327
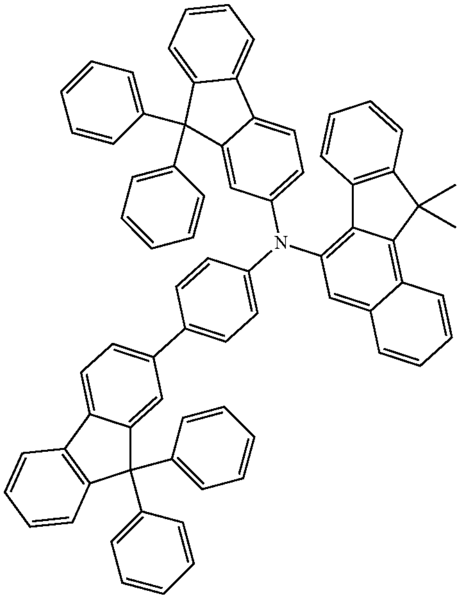
328
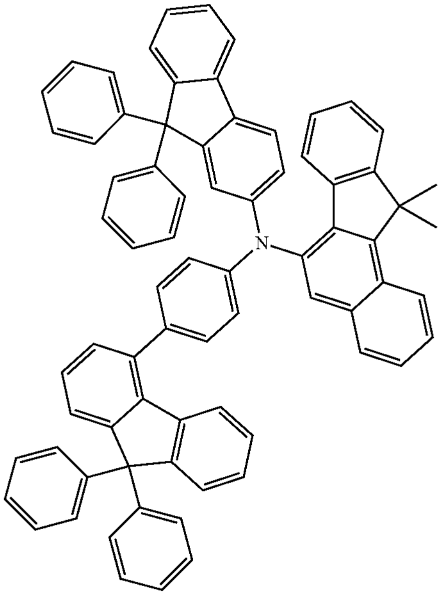

-continued
329
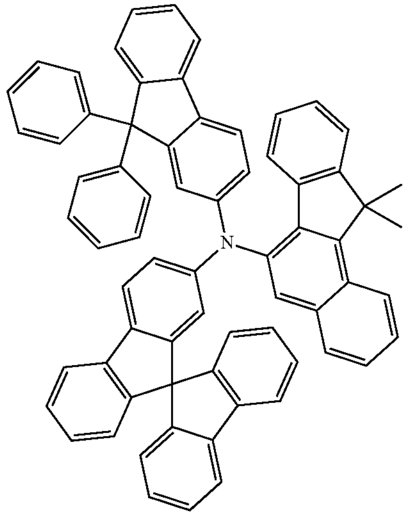
330
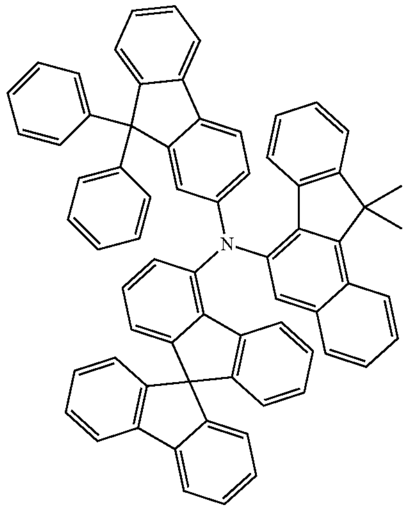
331
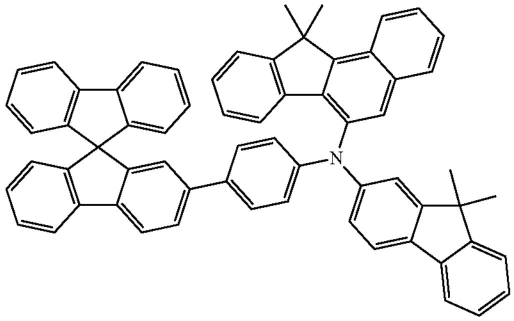
-continued
332
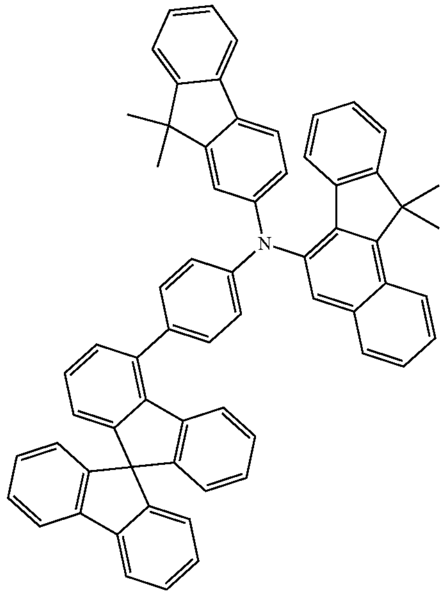
333
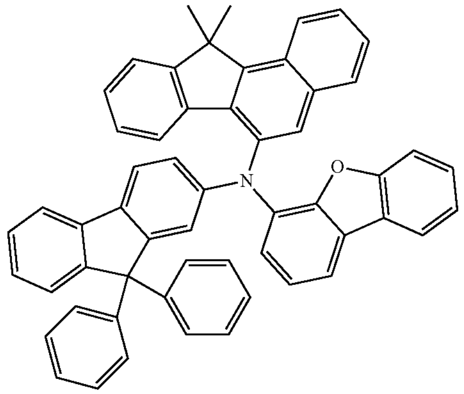
334
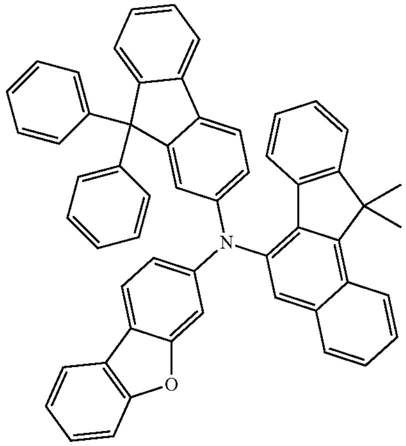

-continued
335
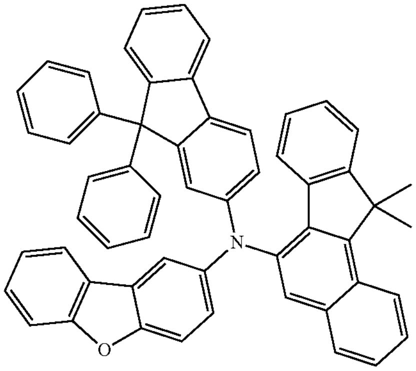
336
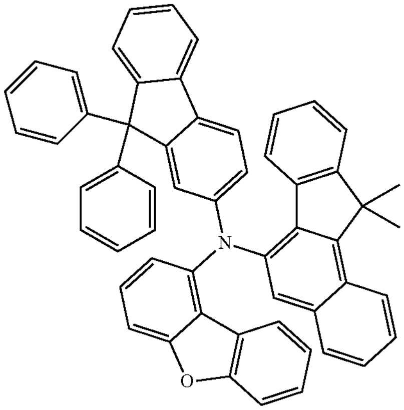
337
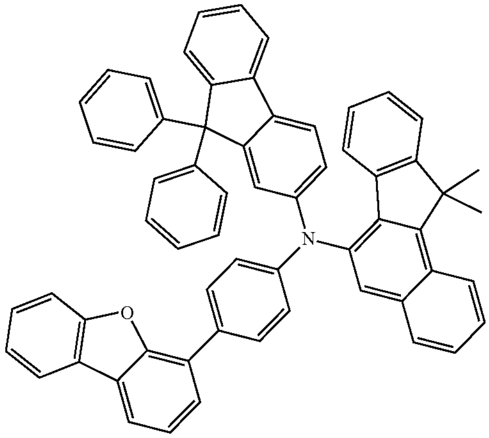
-continued
338
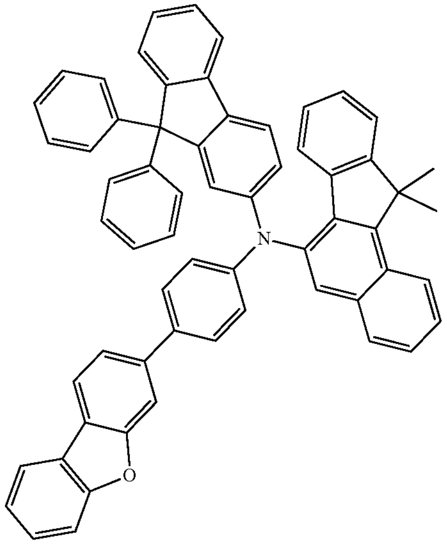
339
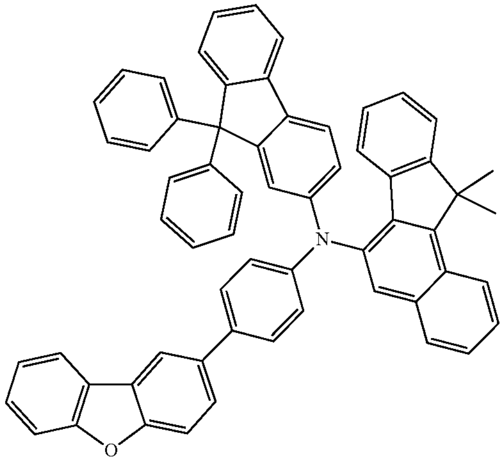
340
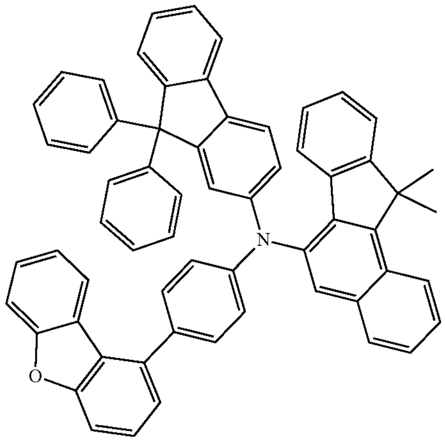

-continued
341
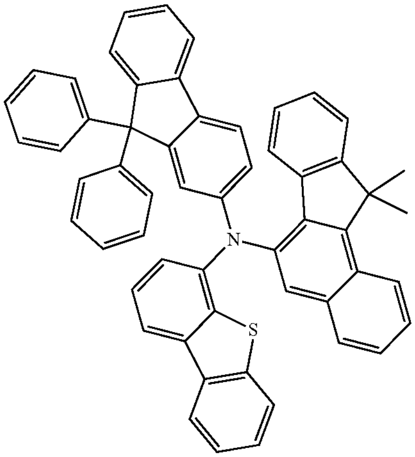
342
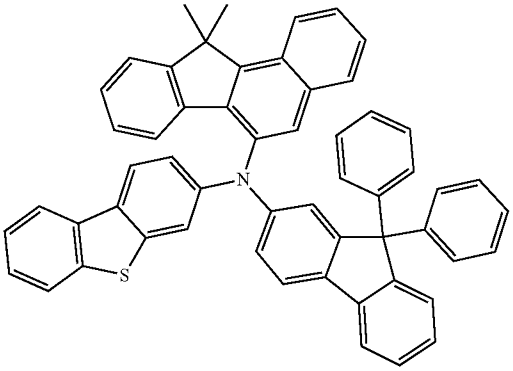
343
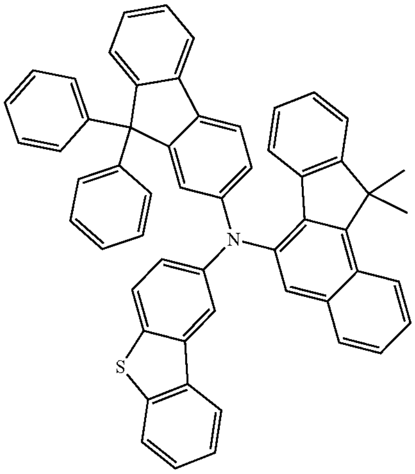
-continued
344
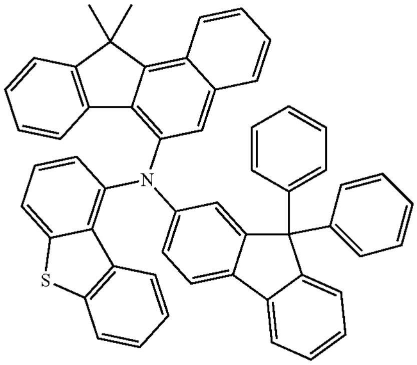
345
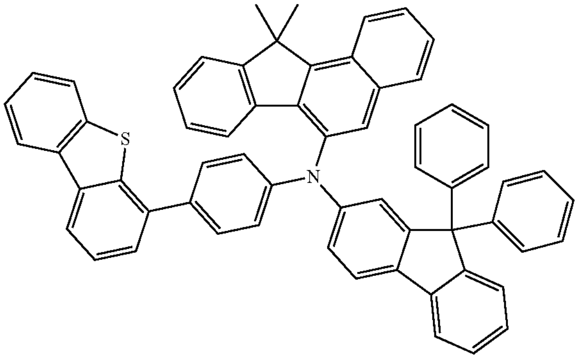
346
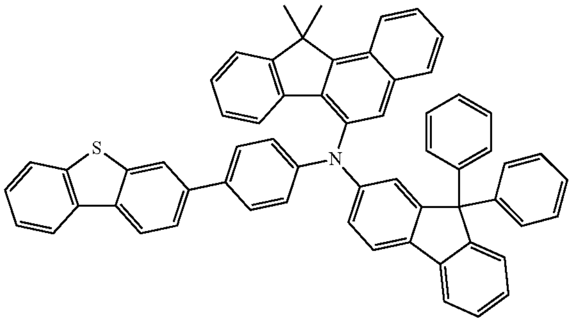
347
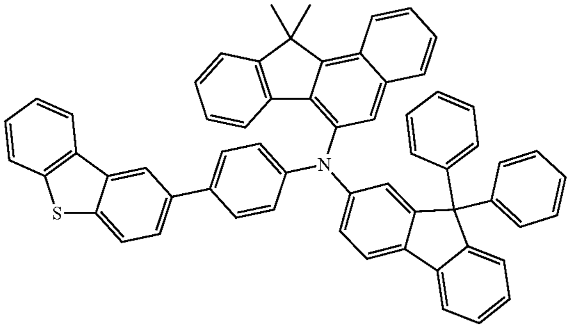

-continued
348
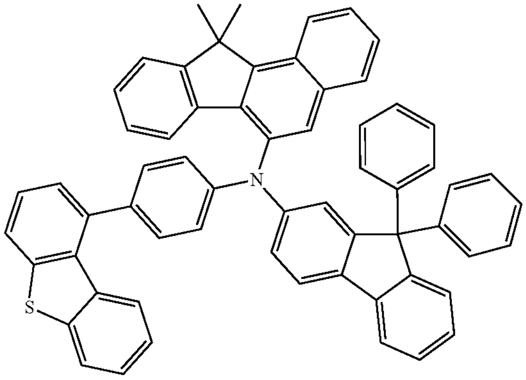
349
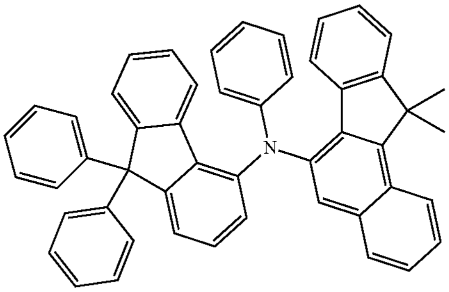
350
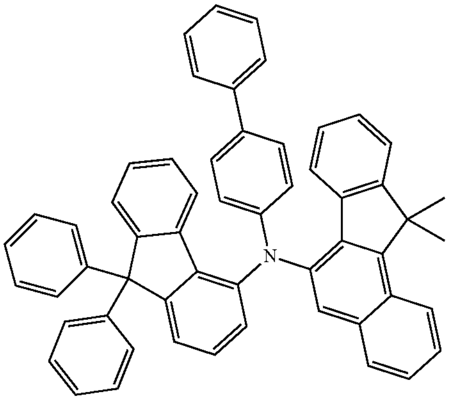
351
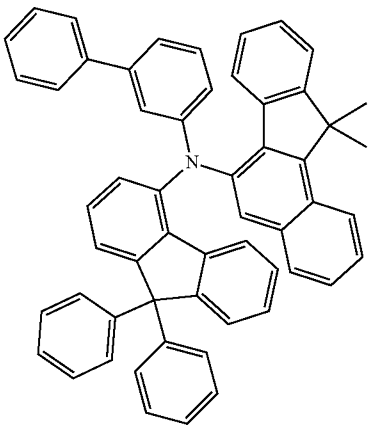
-continued
352
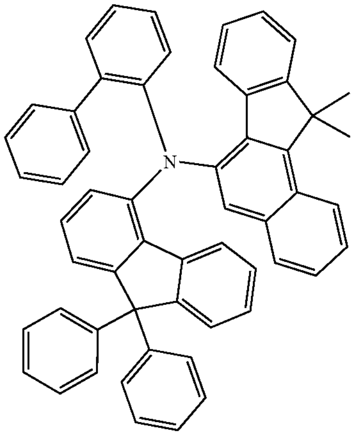
353
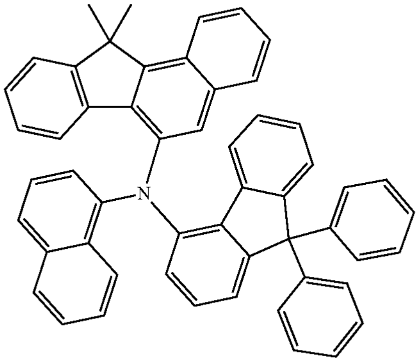
354
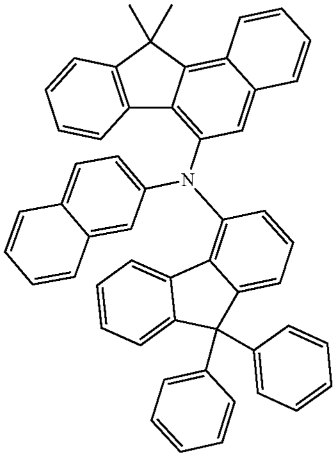
355
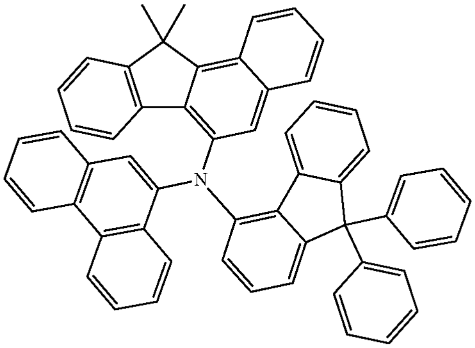

-continued
356
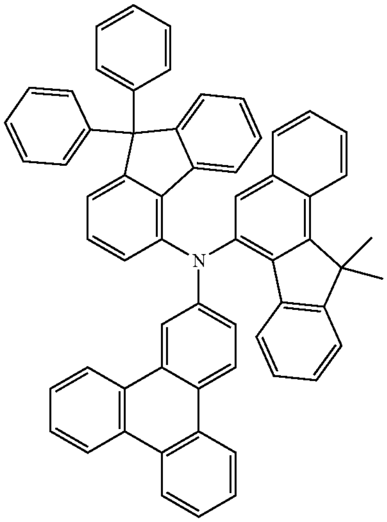
357
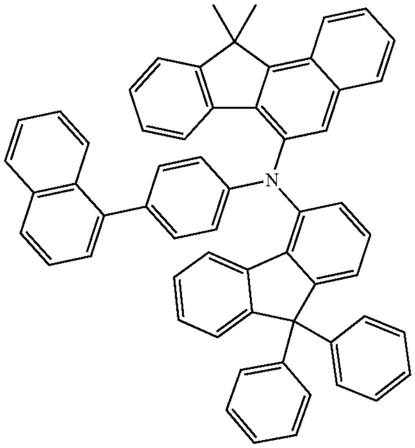
358
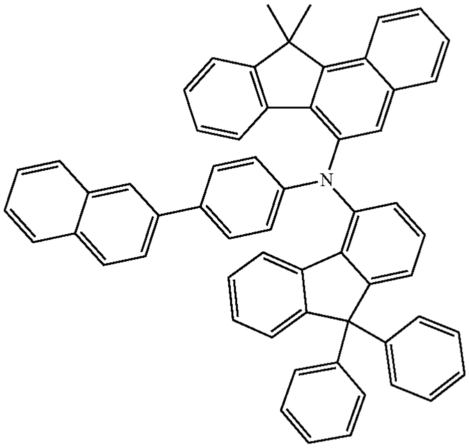
-continued
359
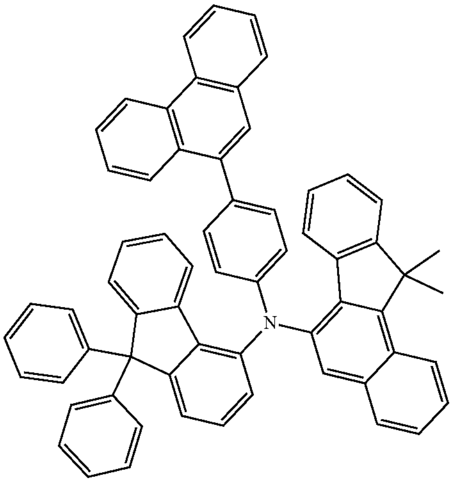
360
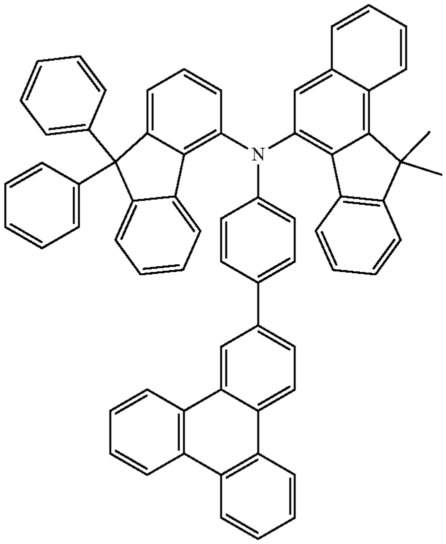
361
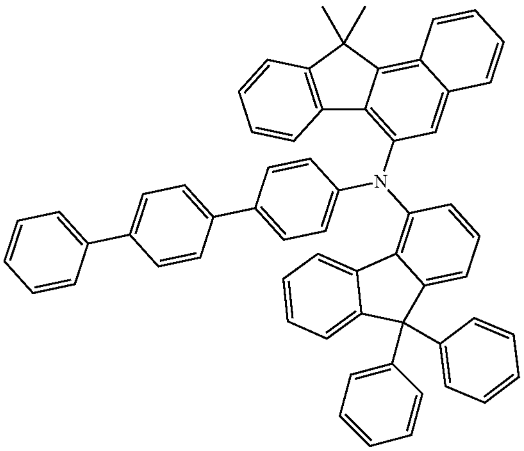

362
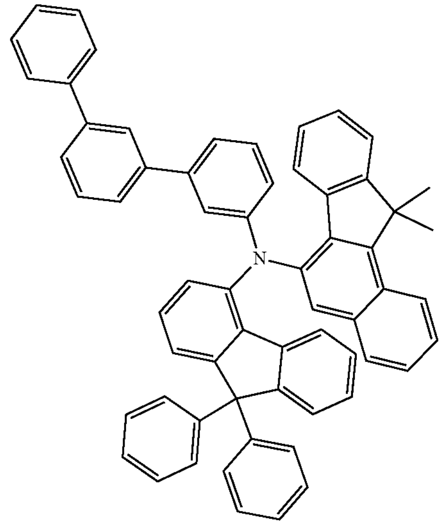
363
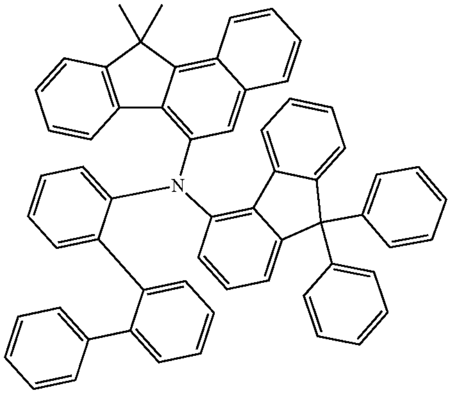
364
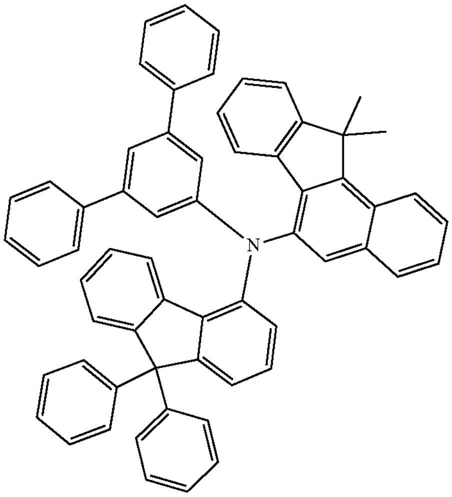
365
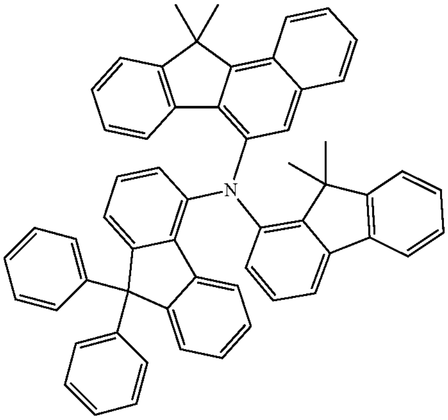
366
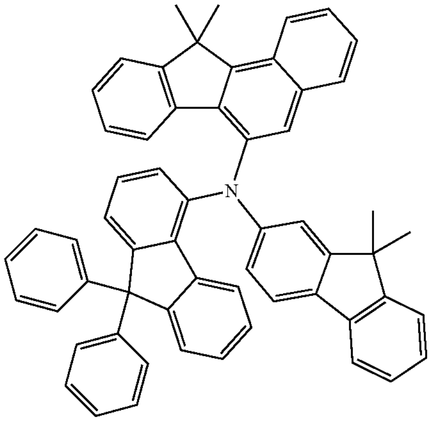
367
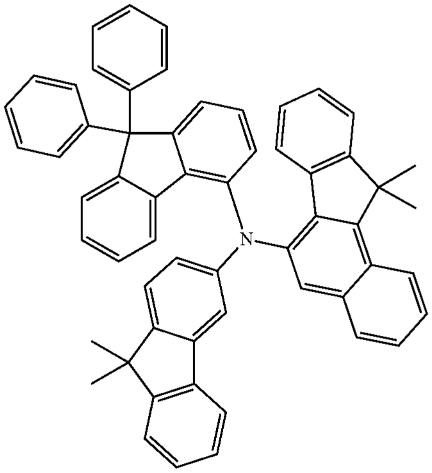

-continued
368
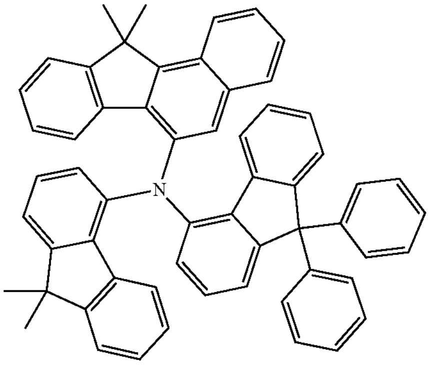
369
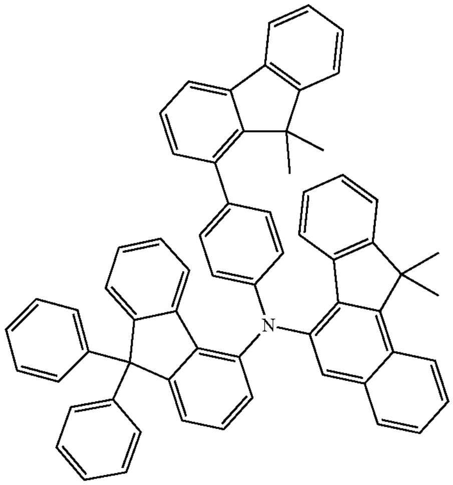
370
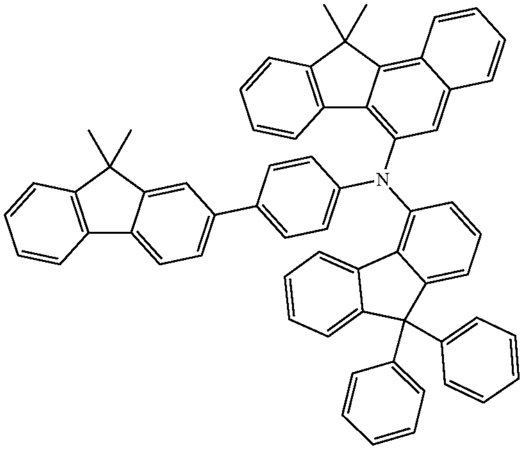
-continued
371
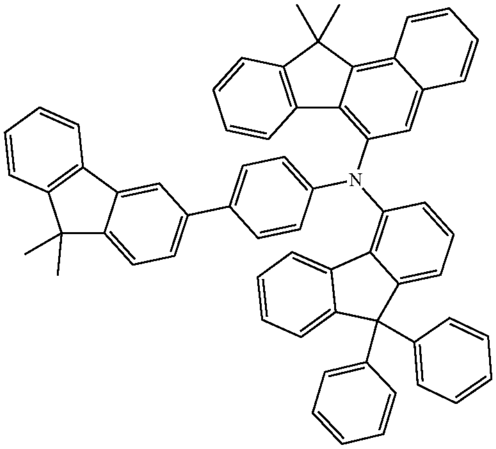
372
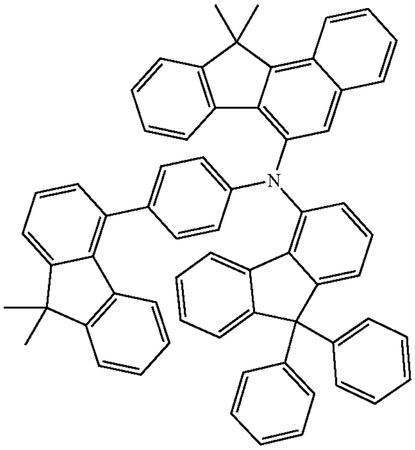
373
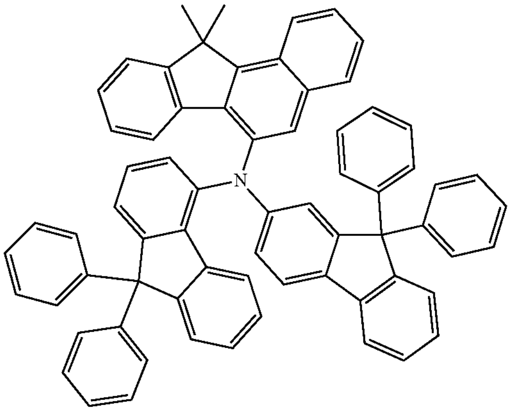

-continued
374
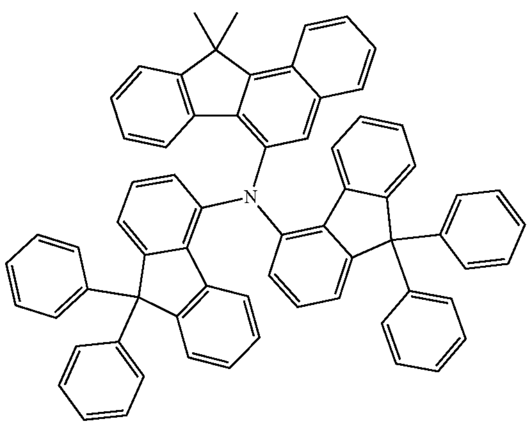
375
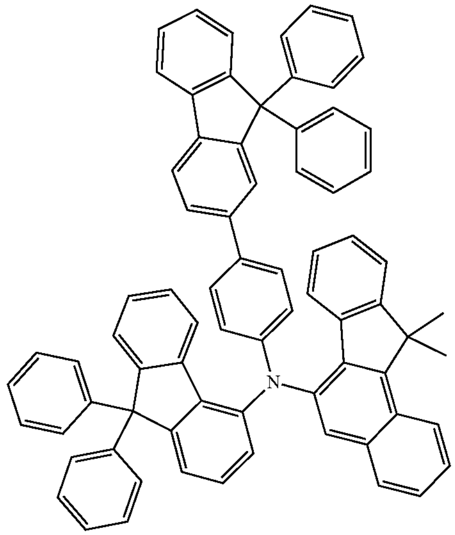
376
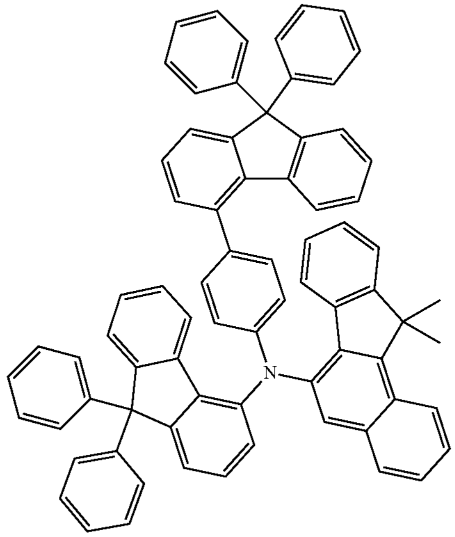
-continued
377
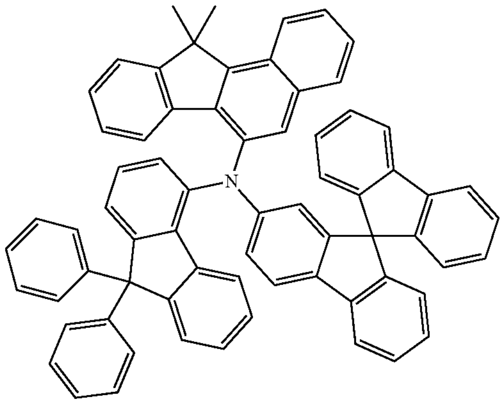
378
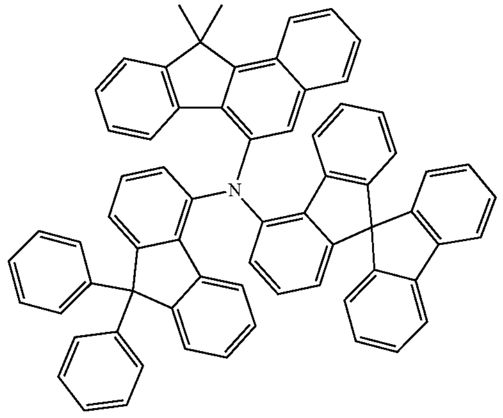
379
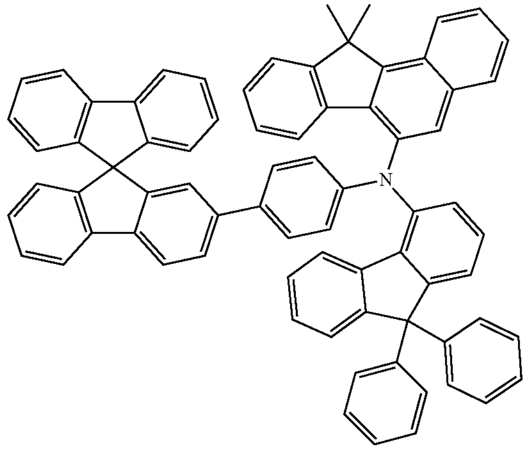

-continued
380
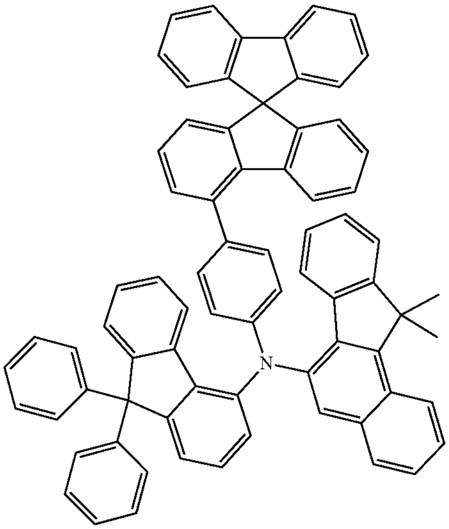
381
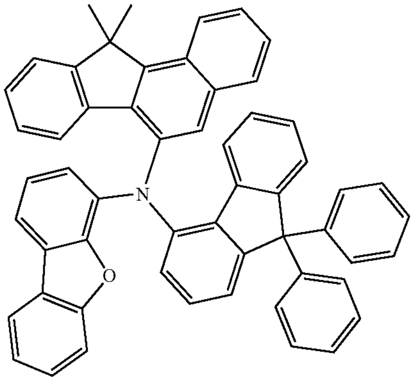
382
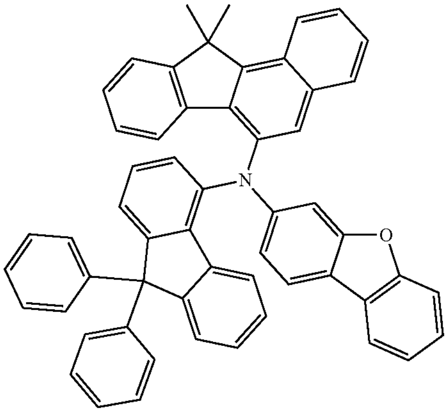
-continued
383
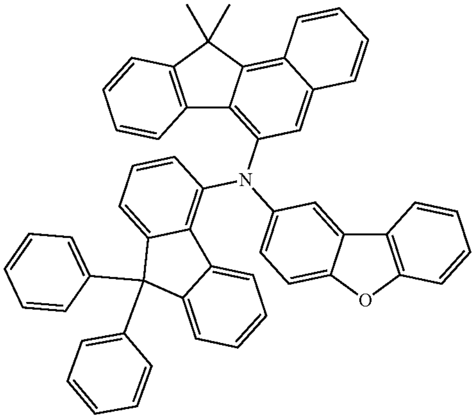
384
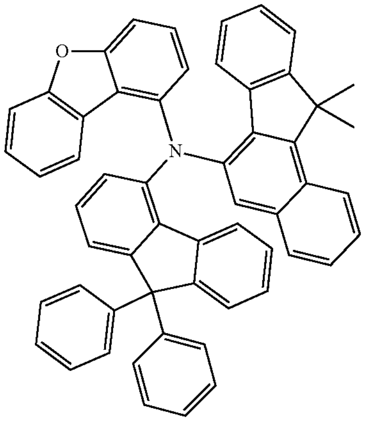
385
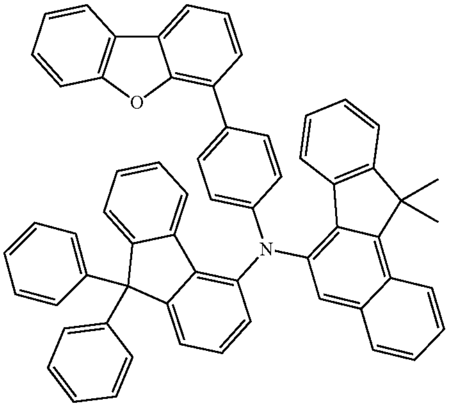

386
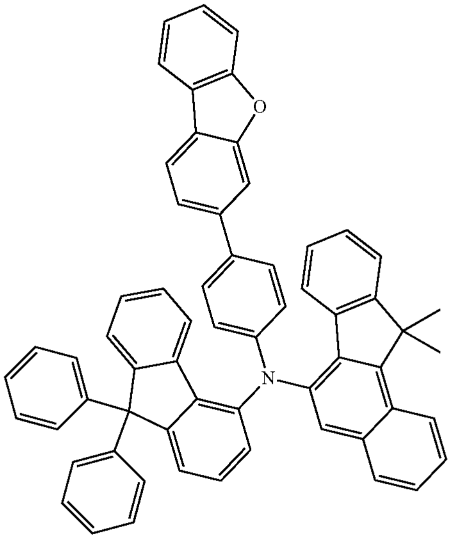
387
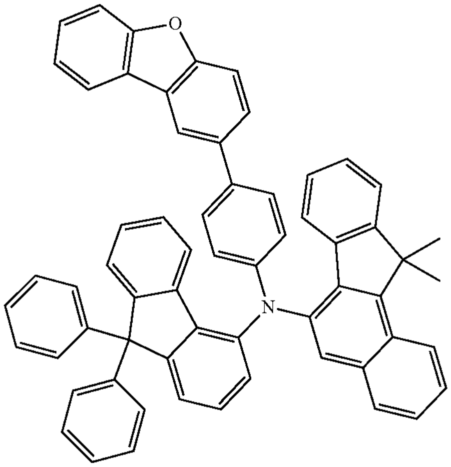
388
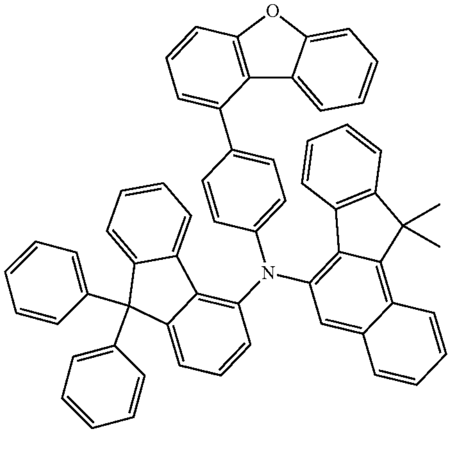
389
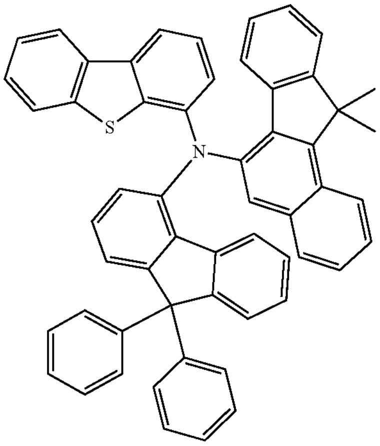
390
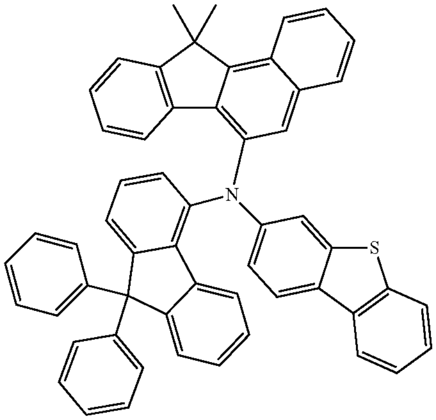
391
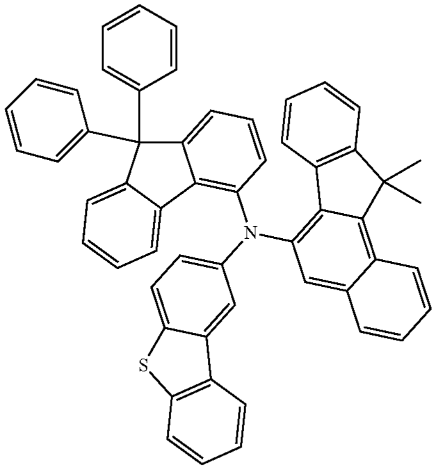

-continued
392
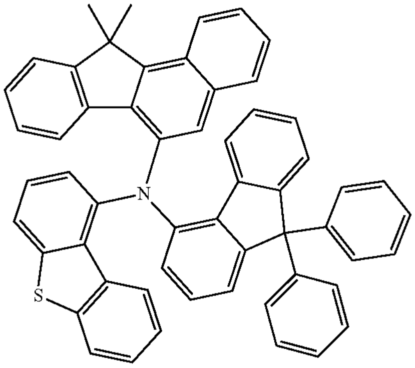
393
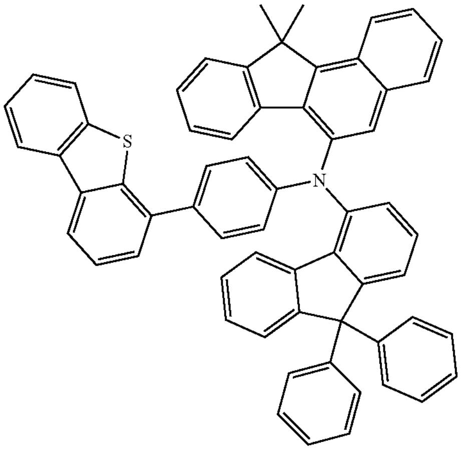
394
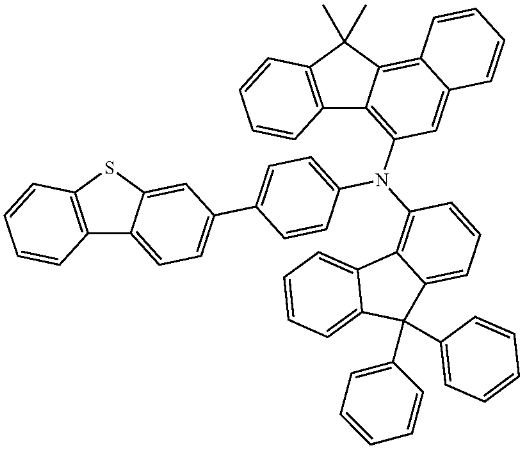
-continued
395
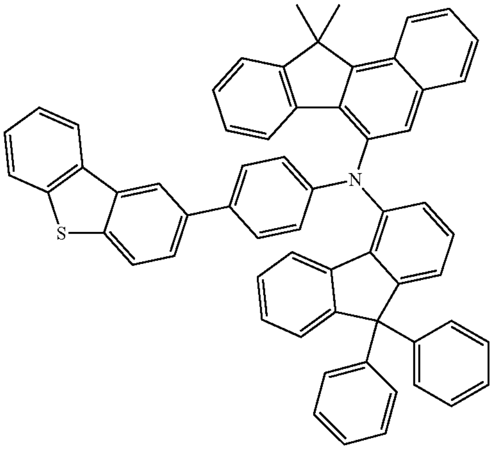
396
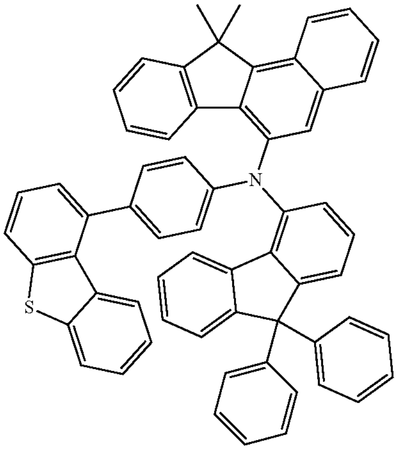
397
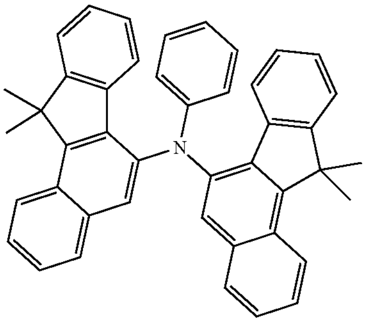

-continued
398
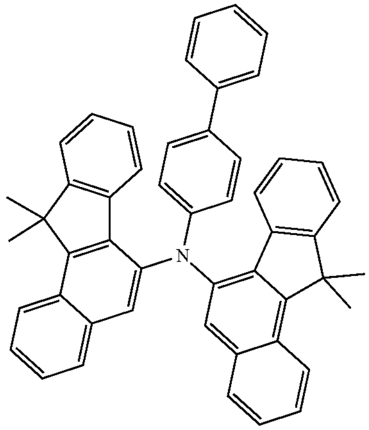
399
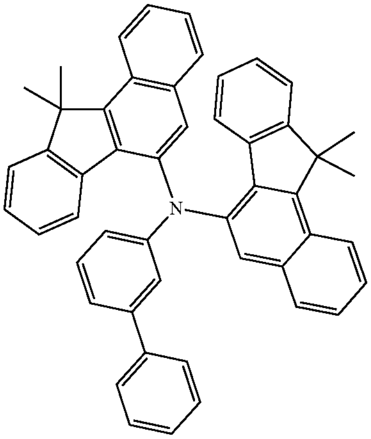
400
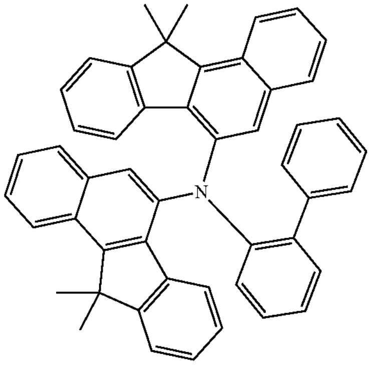
401
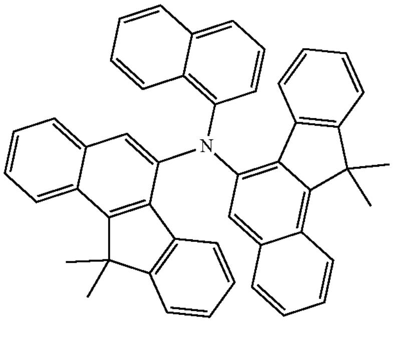
-continued
402
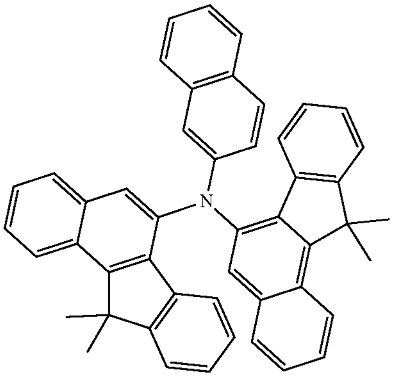
403
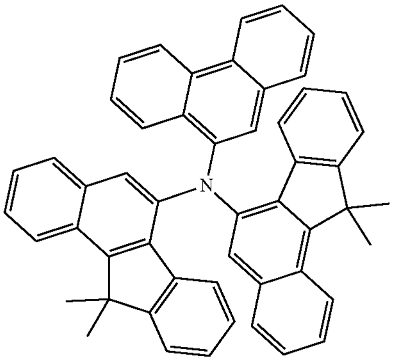
404
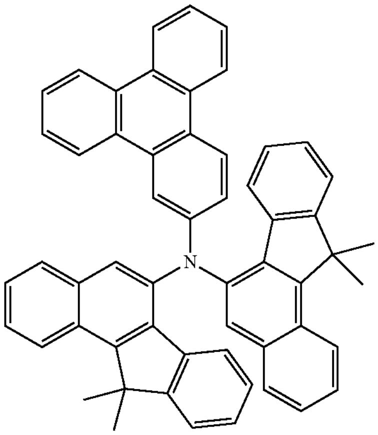
405
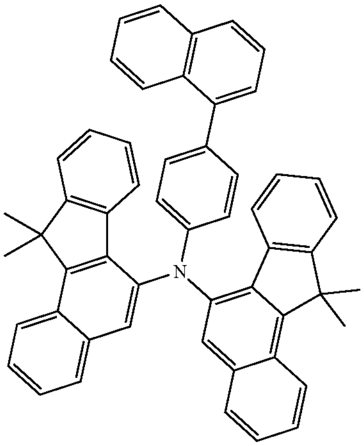

-continued
406
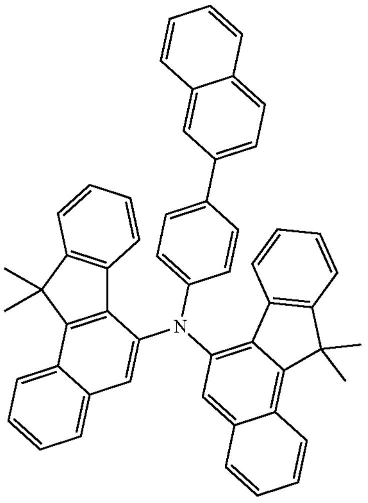
407
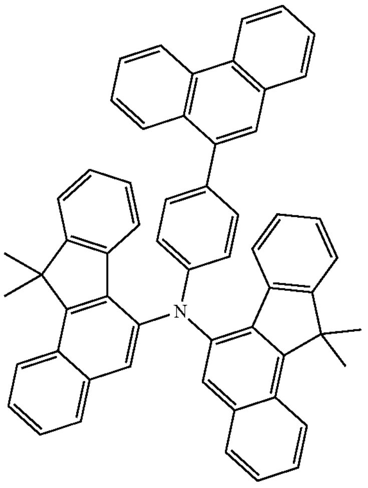
408
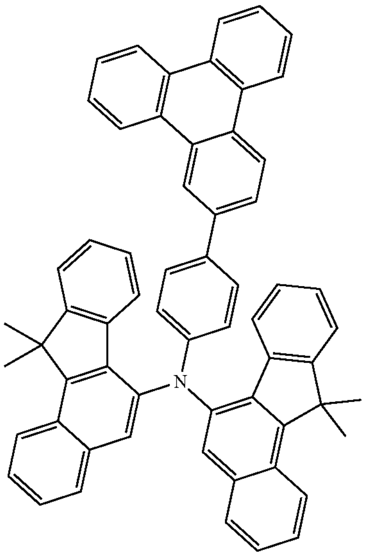
-continued
409
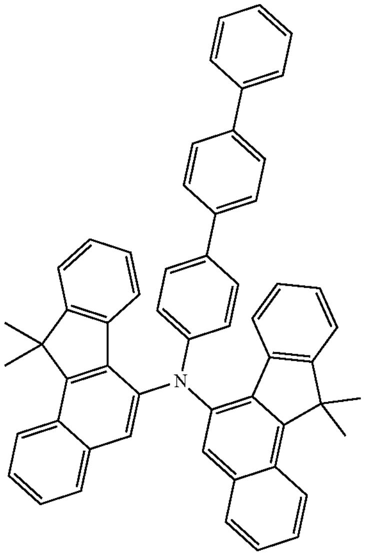
410
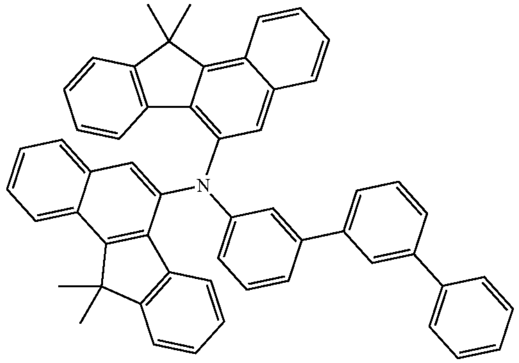
411
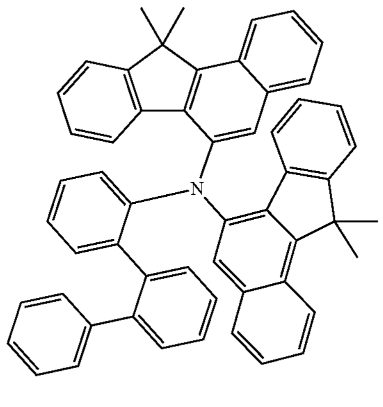

412
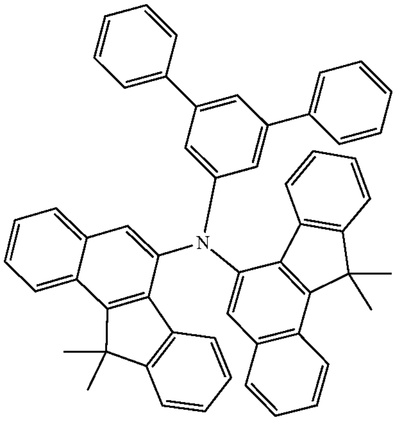
413
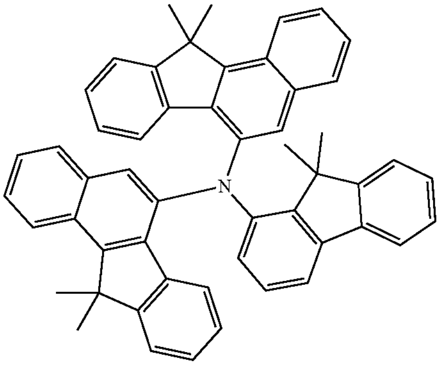
414
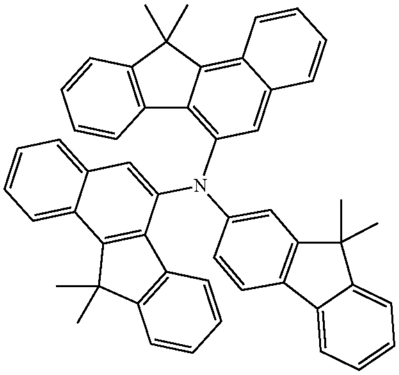
415
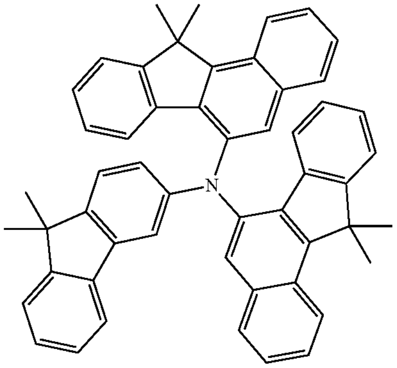
416
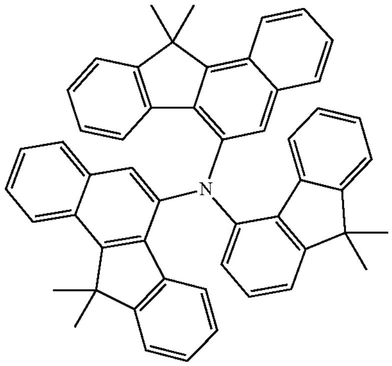
417
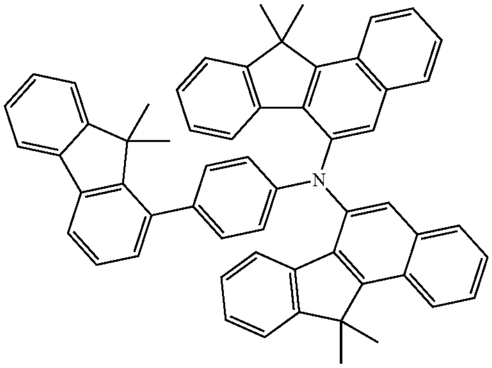
418
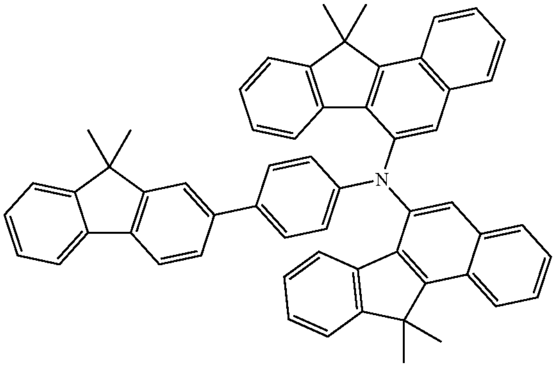
419
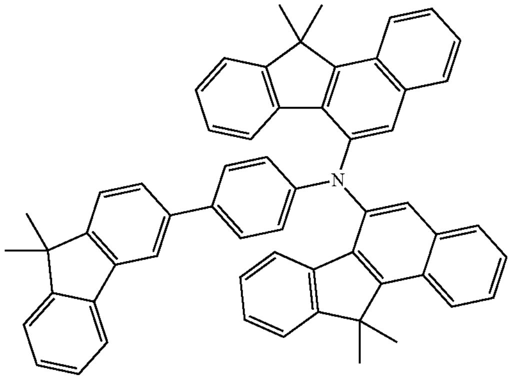

-continued
420
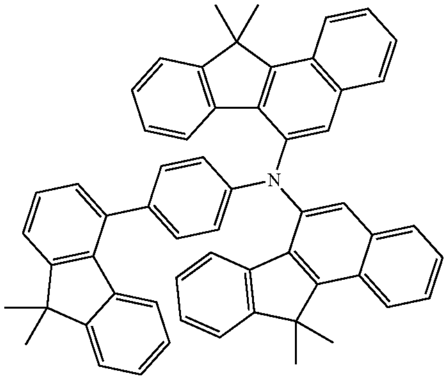
421
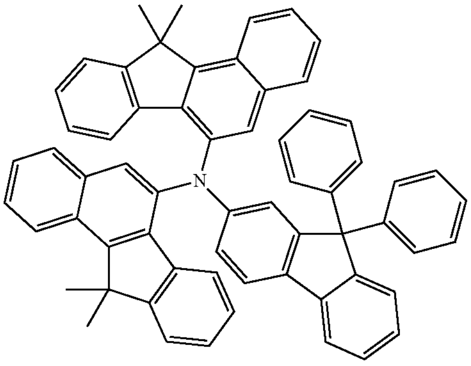
422
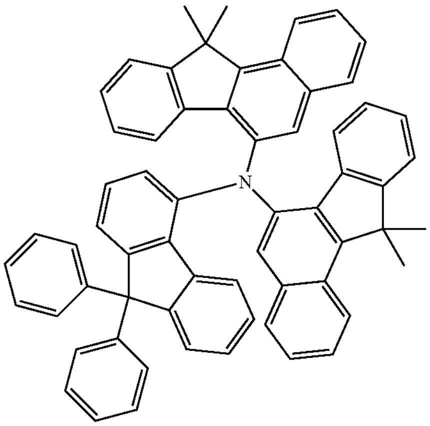
-continued
423
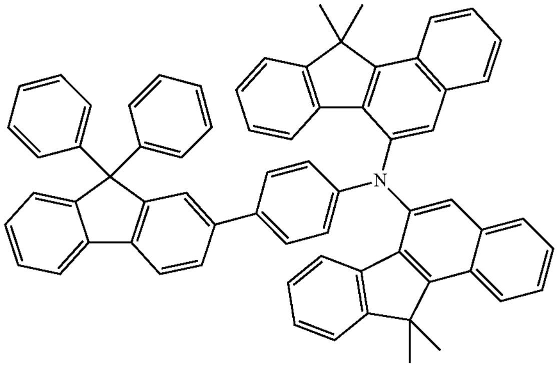
424
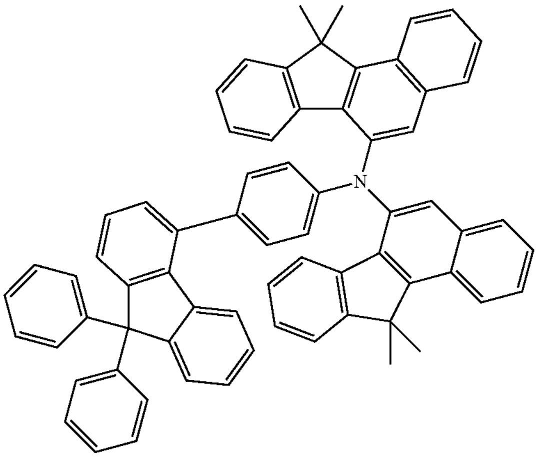
425
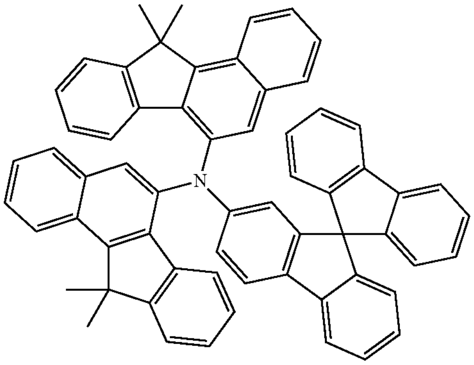
426
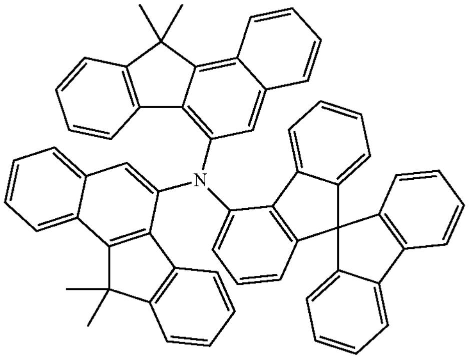

-continued
427
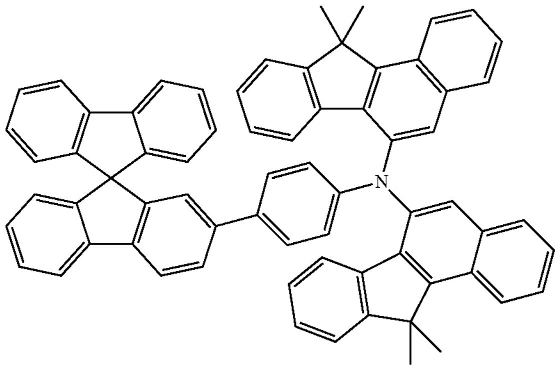
428
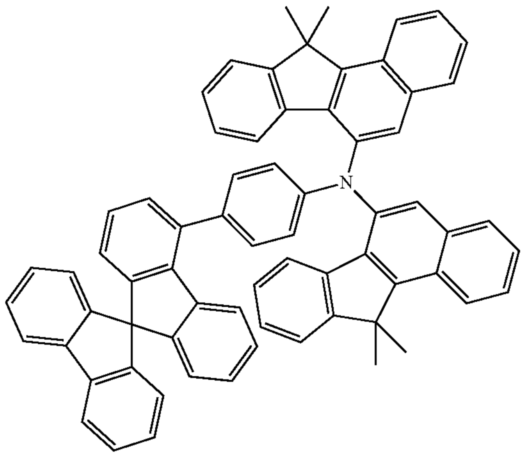
429
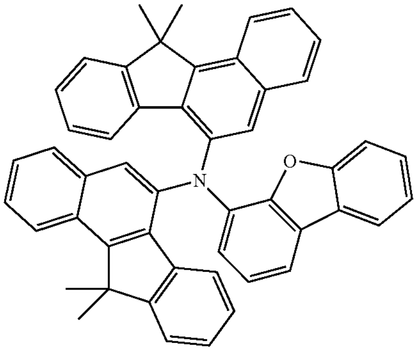
430
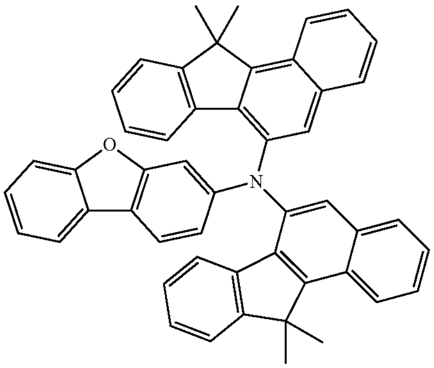
-continued
431
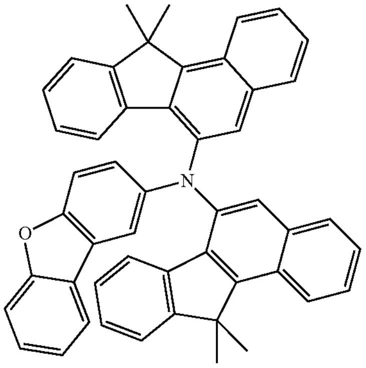
432
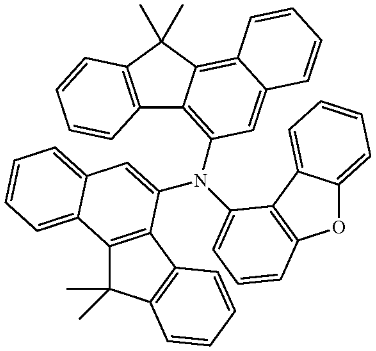
433
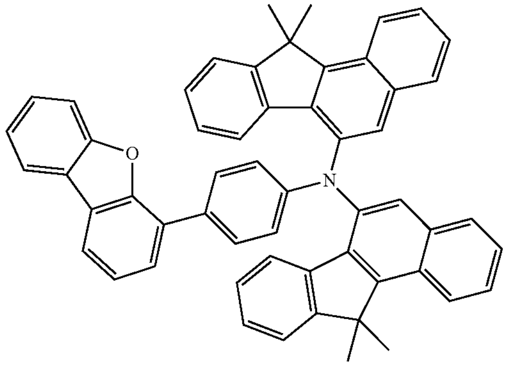
434
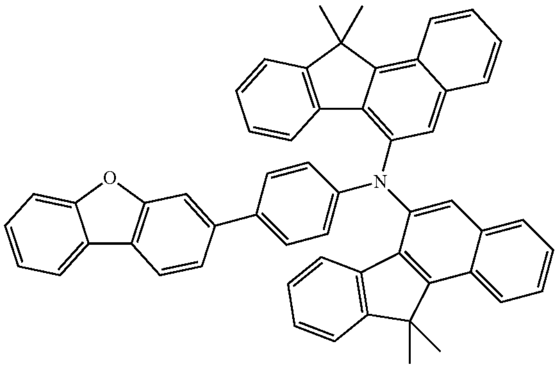

-continued
435
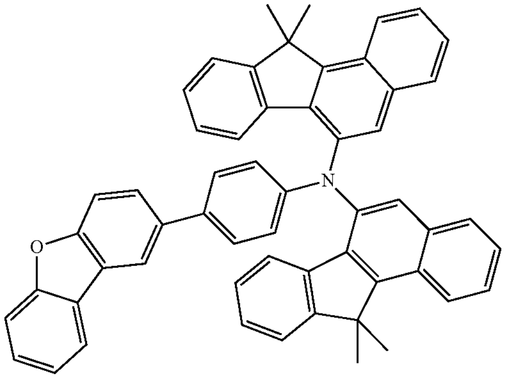
436
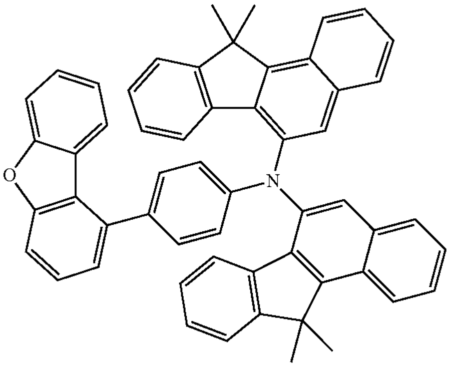
437
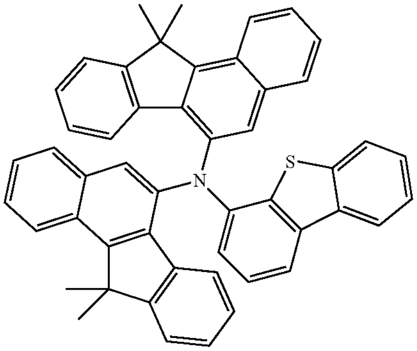
438
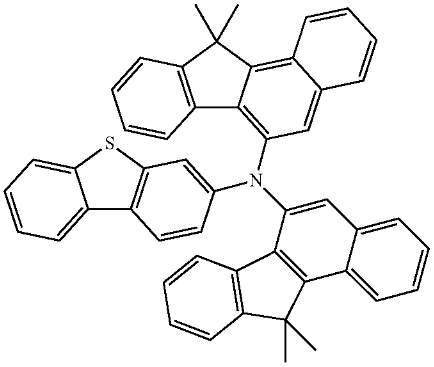
-continued
439
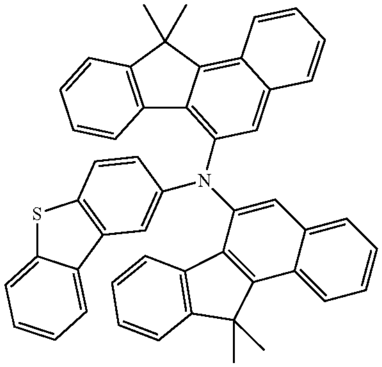
440
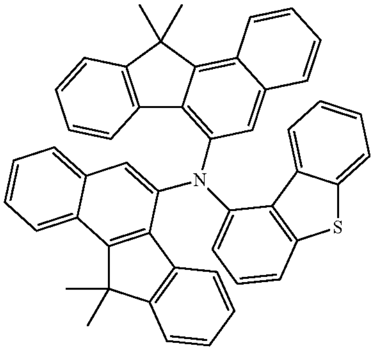
441
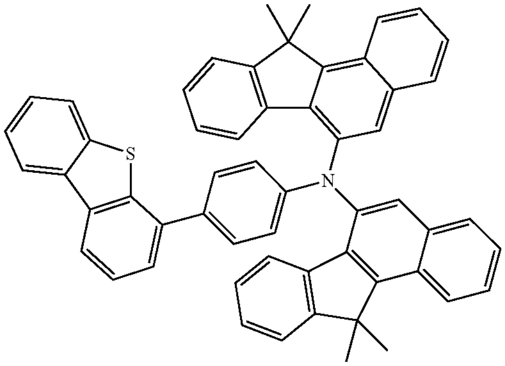
442
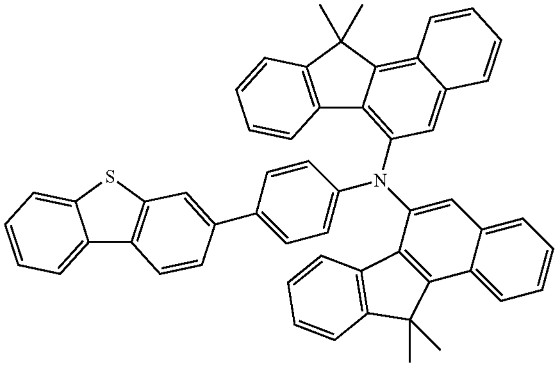

-continued
443
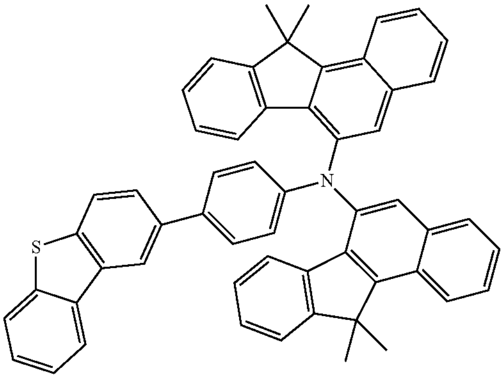
444
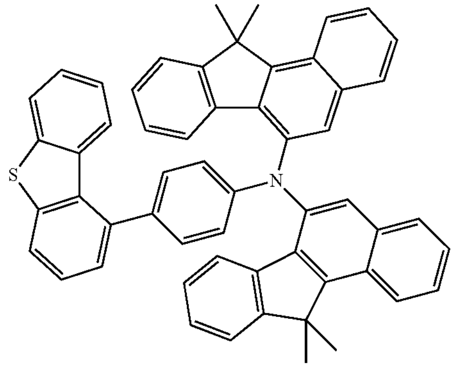
445
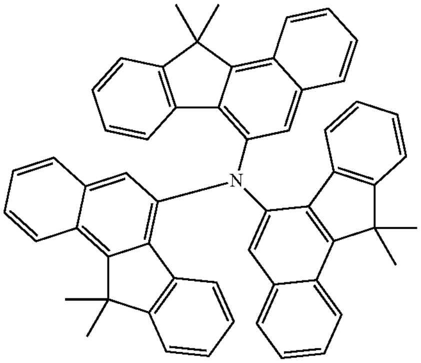
446
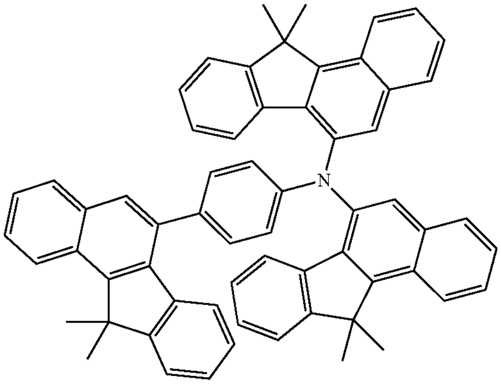
-continued
447
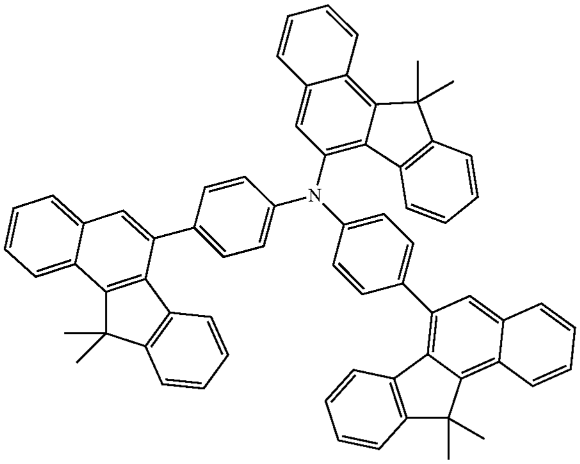
448
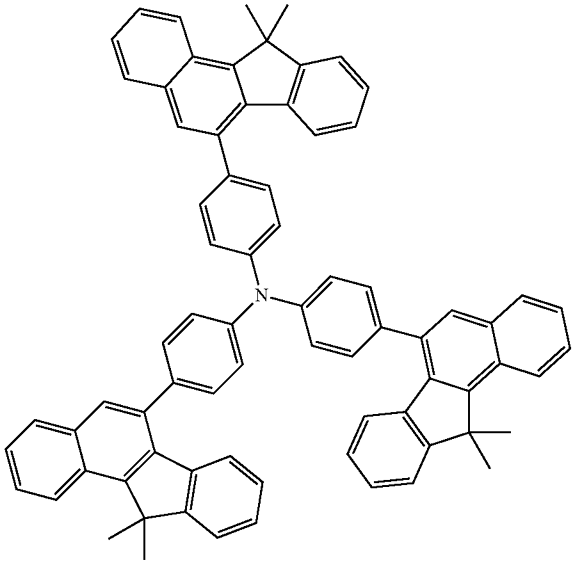
449
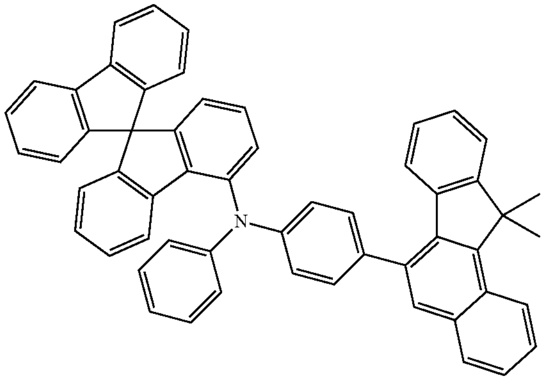

-continued
450
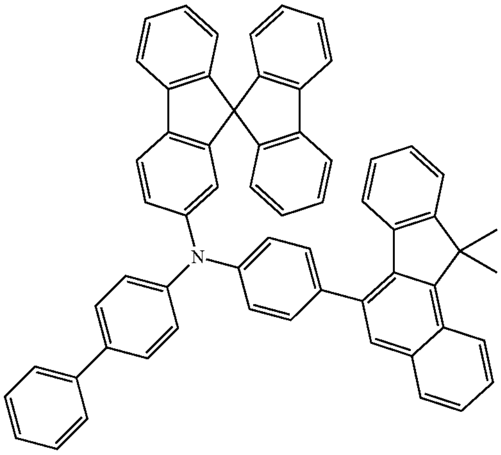
451
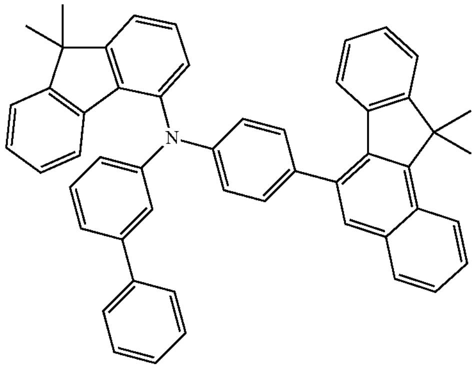
452
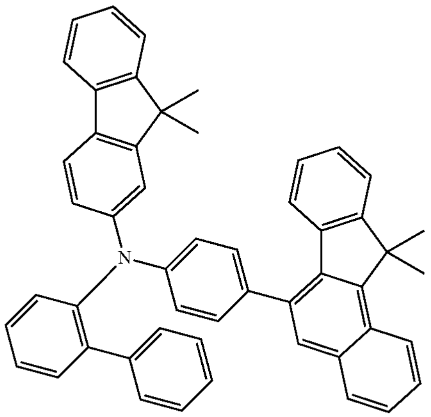
-continued
453
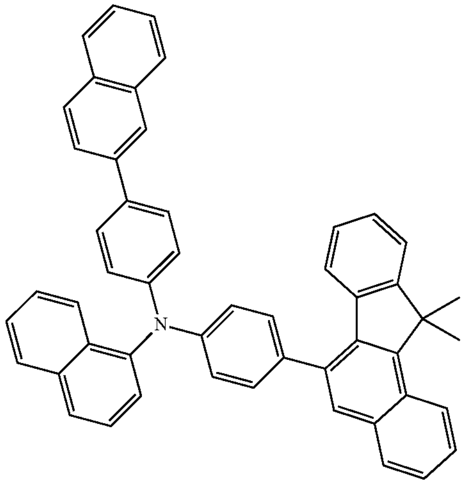
454
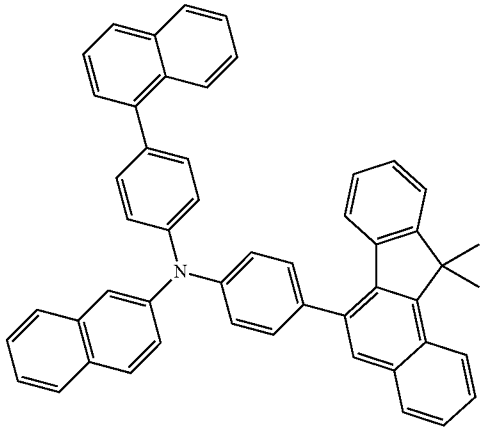
455
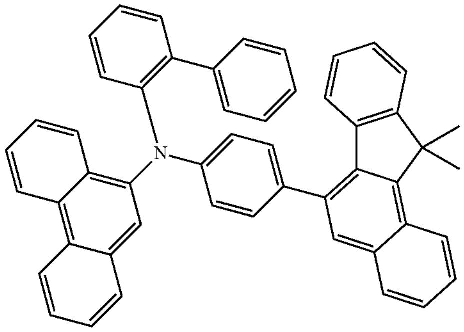

-continued
456
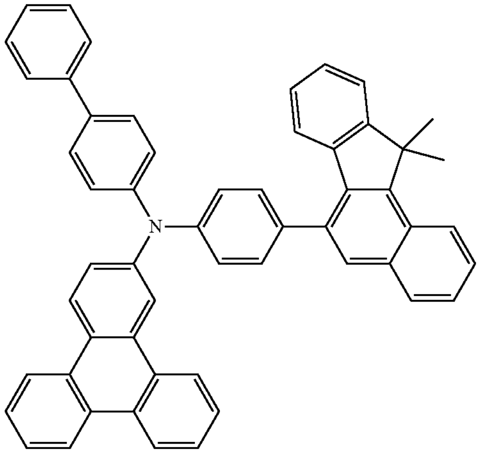
457
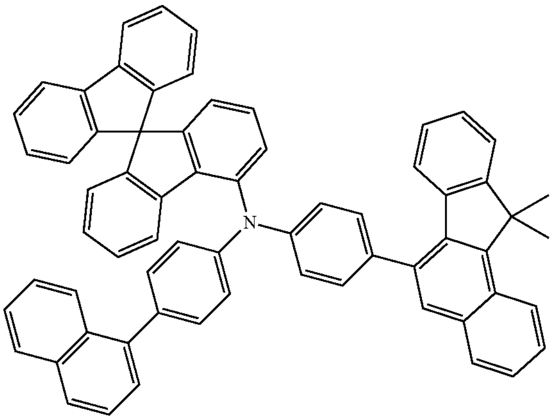
458
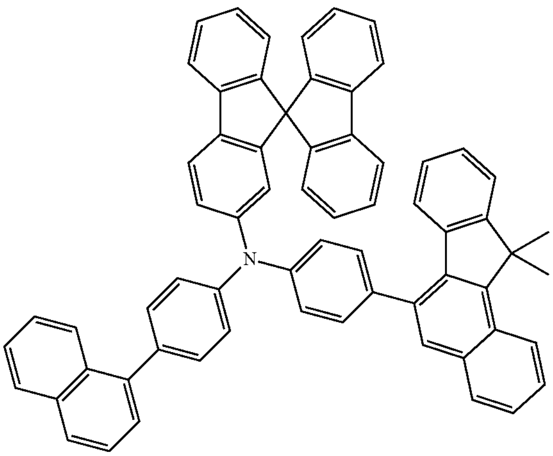
-continued
459
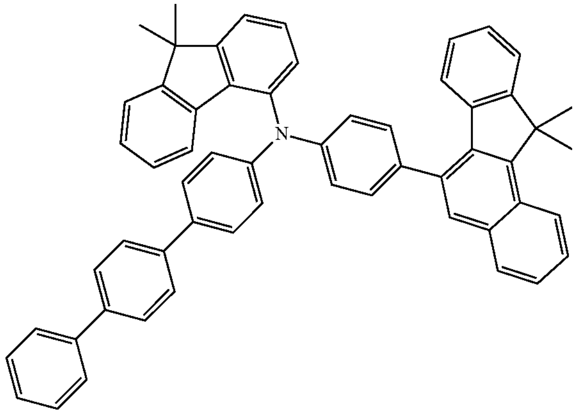
460
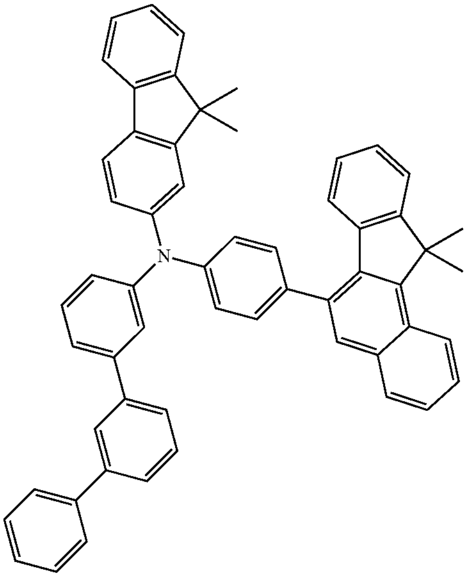
461
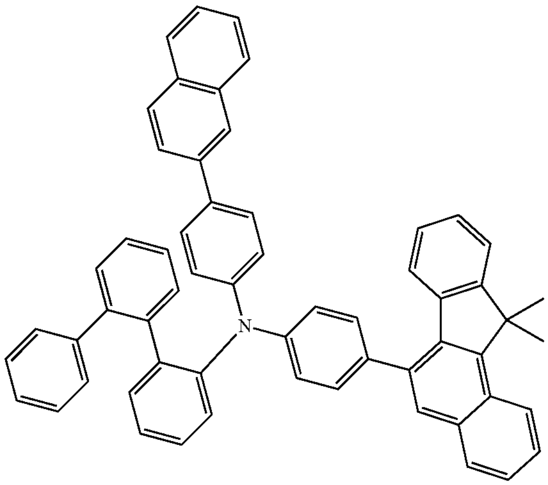

-continued
462
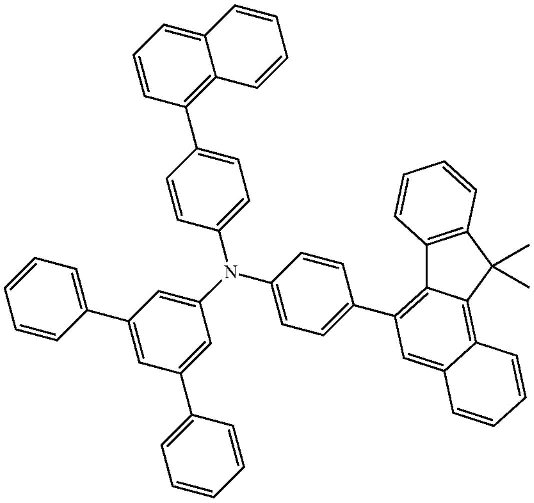
463
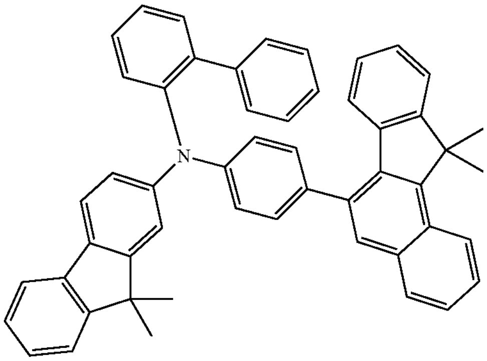
464
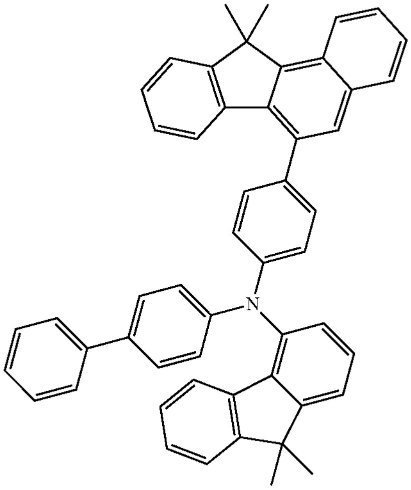
-continued
465
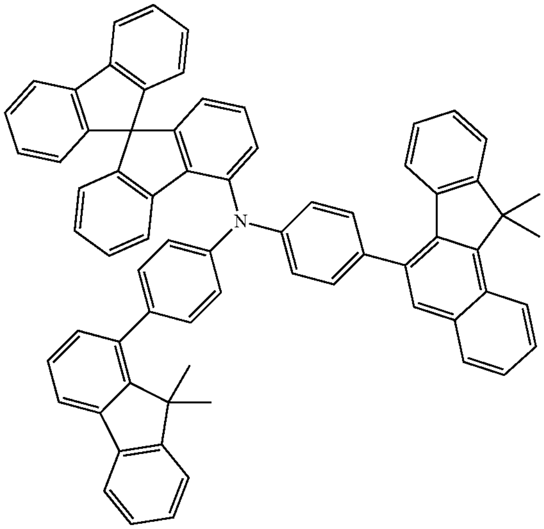
466
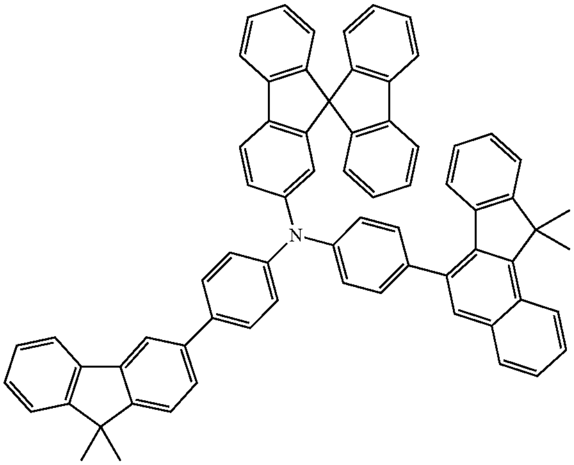
467
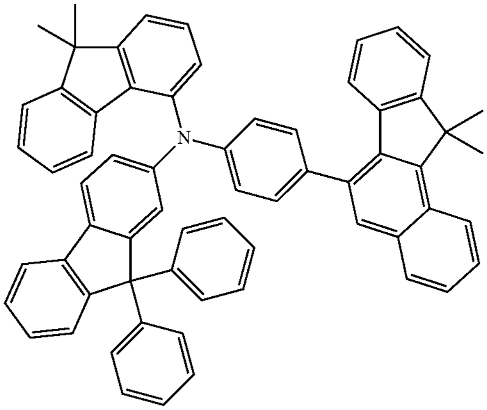

-continued
468
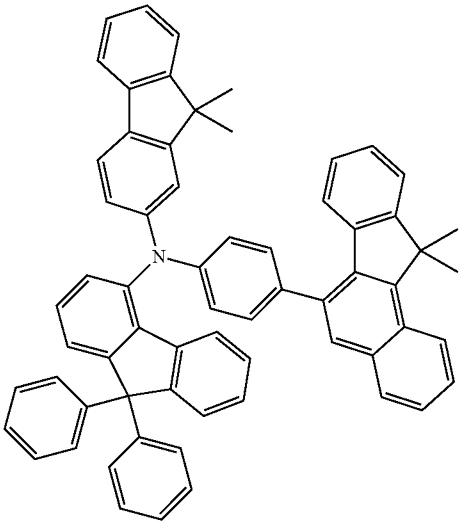
469
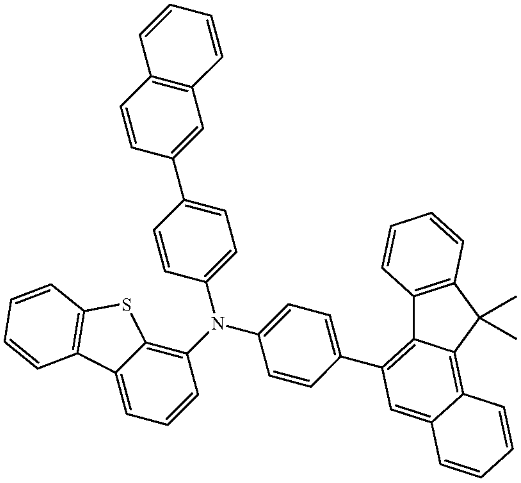
470
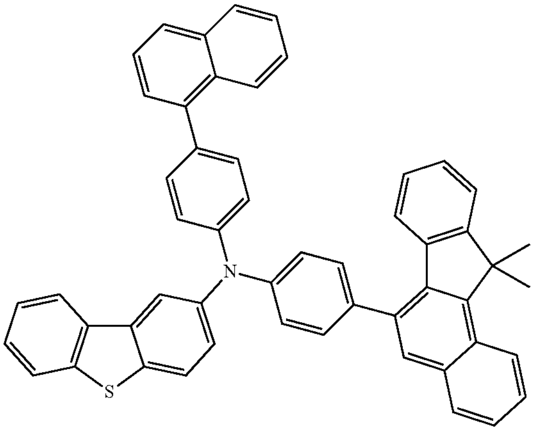
-continued
471
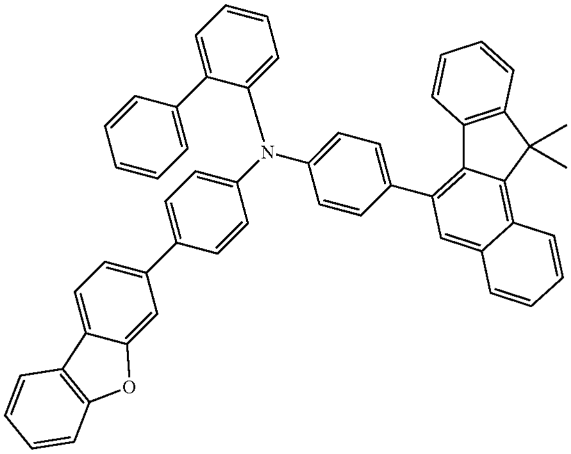
472
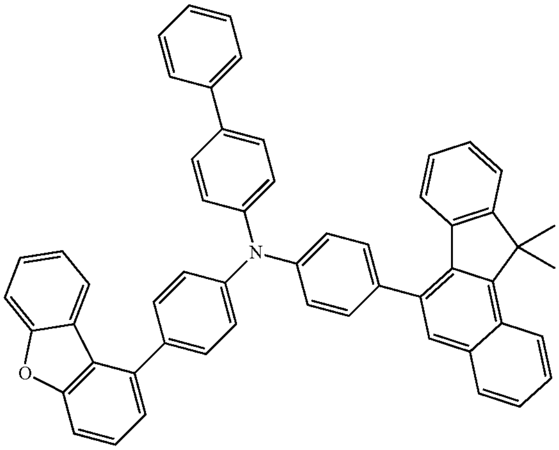
473
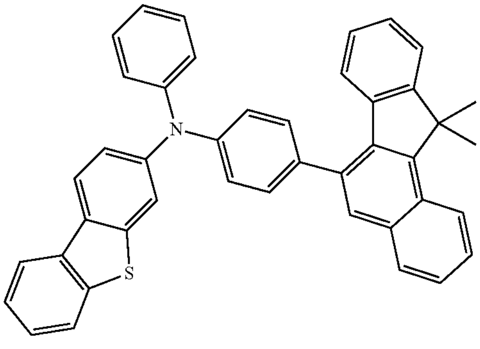

-continued
474
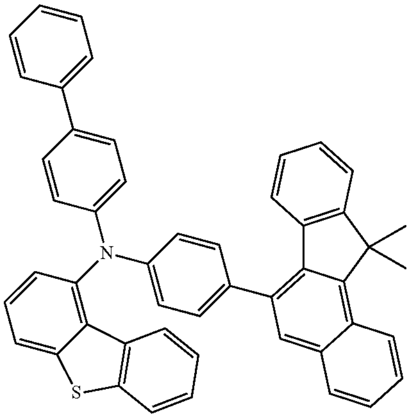
475
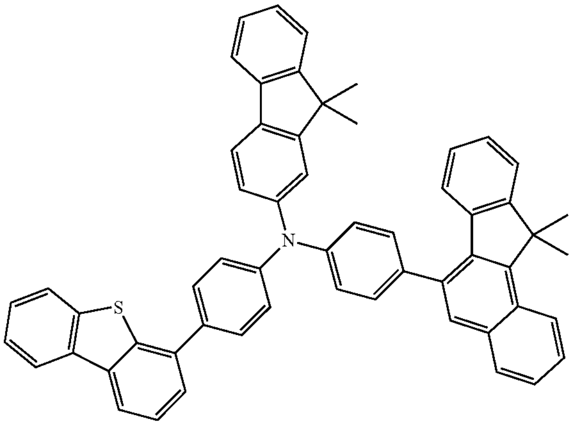
476
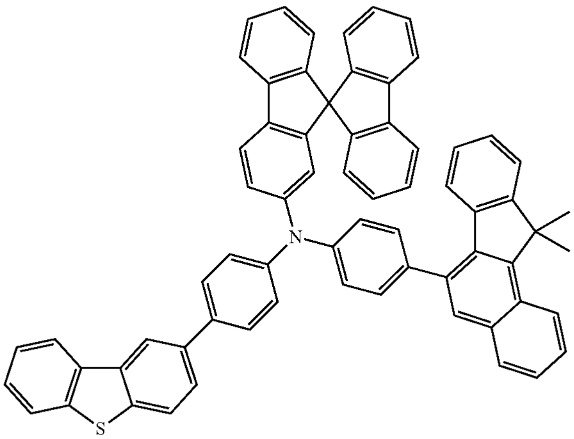
-continued
477
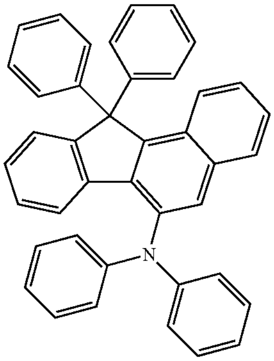
478
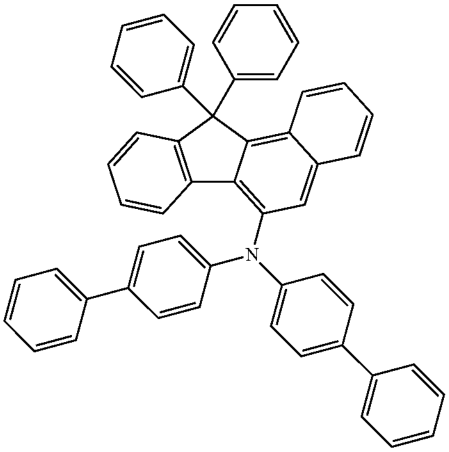
479
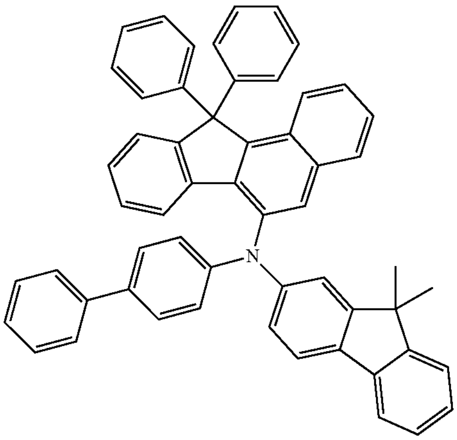

-continued
480
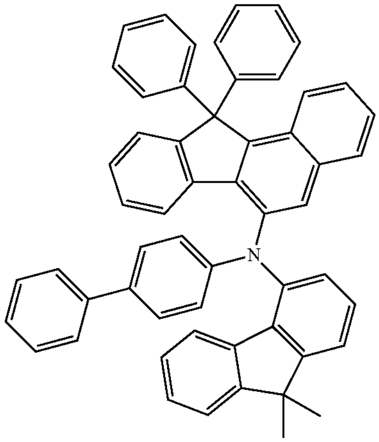
481
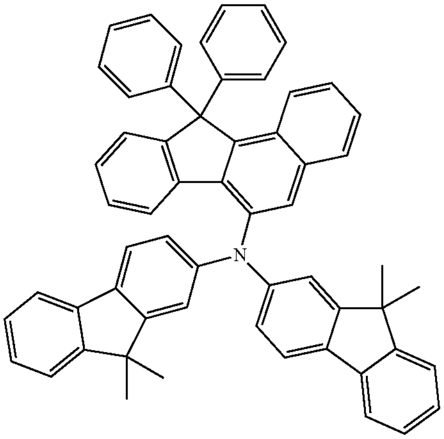
482
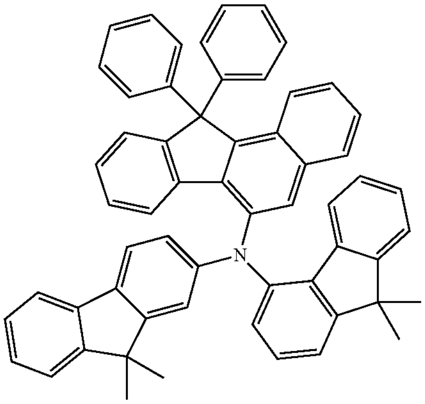
483
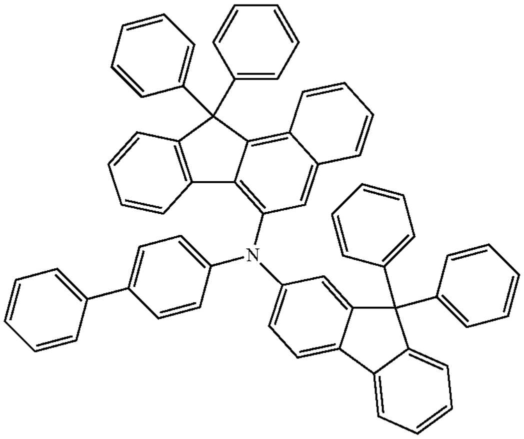
484
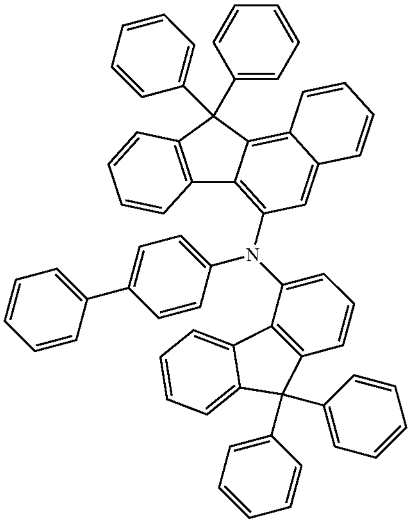
485
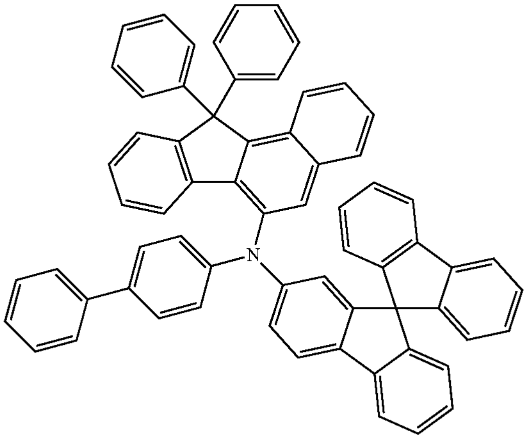

486
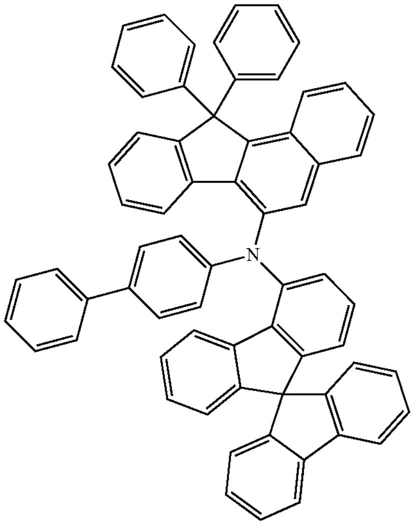
487
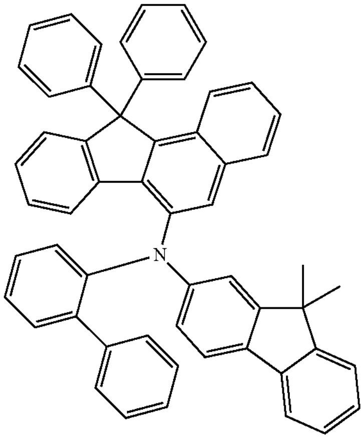
488
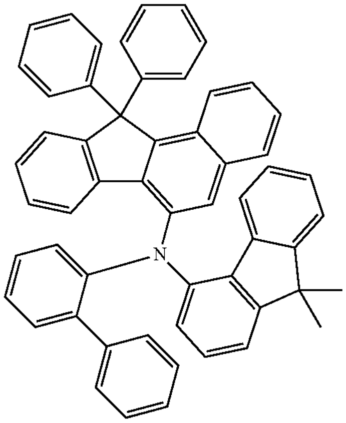
489
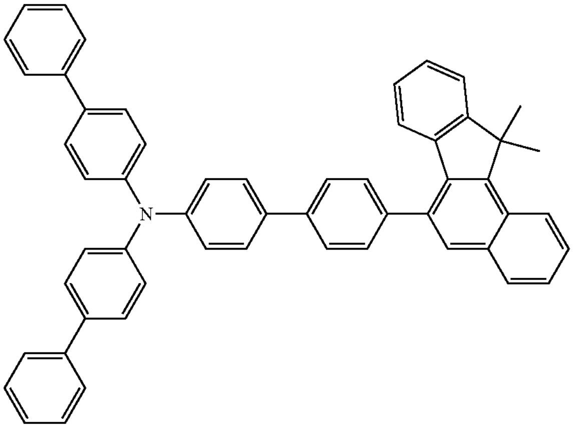
490
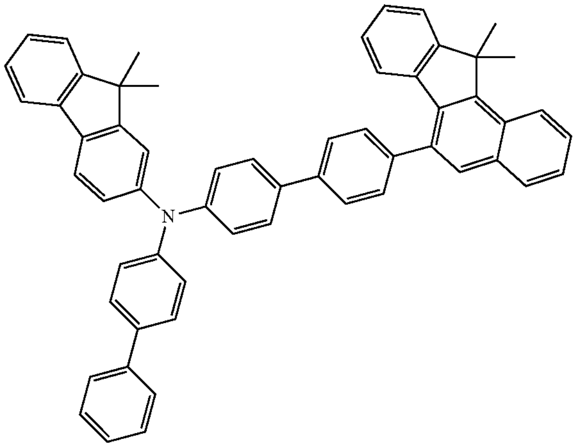
491
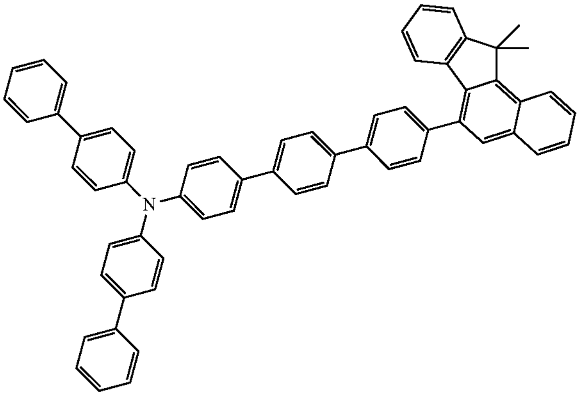

492
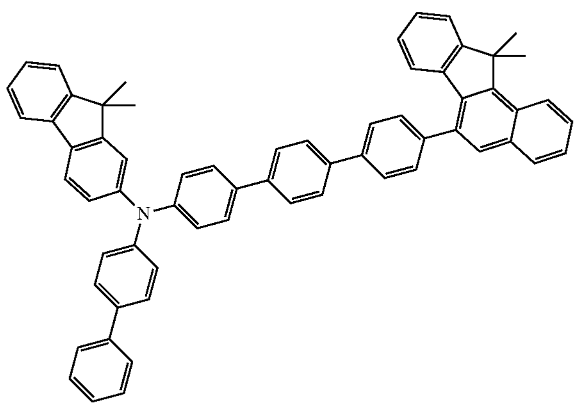
493
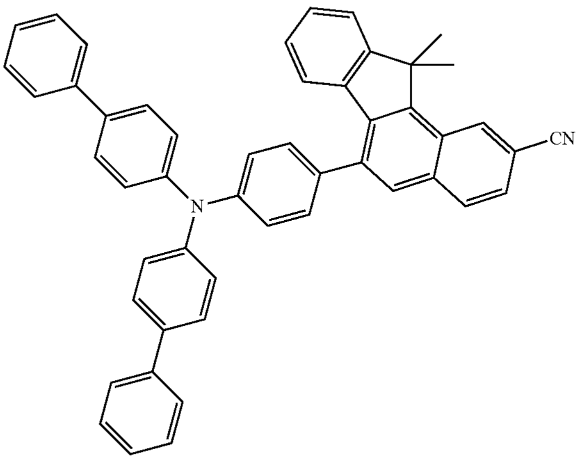
494
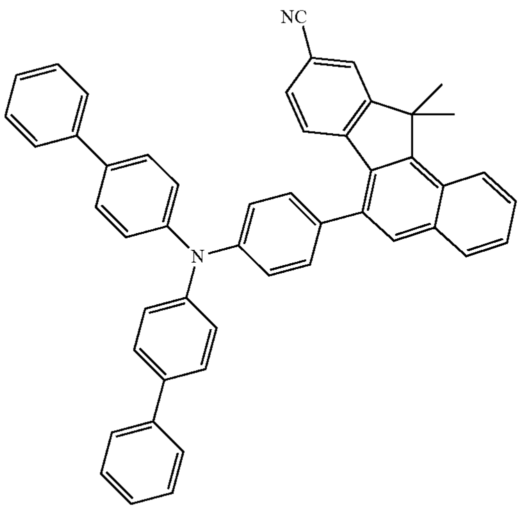
495
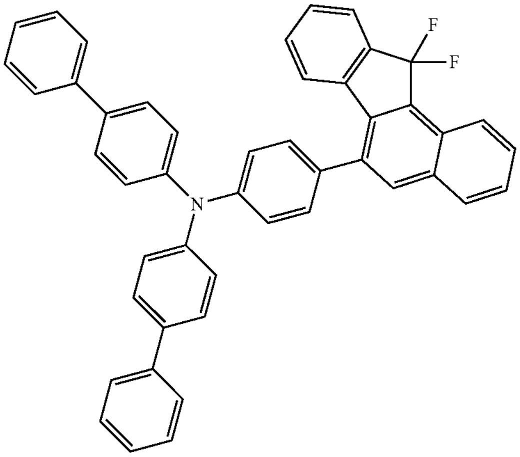
496
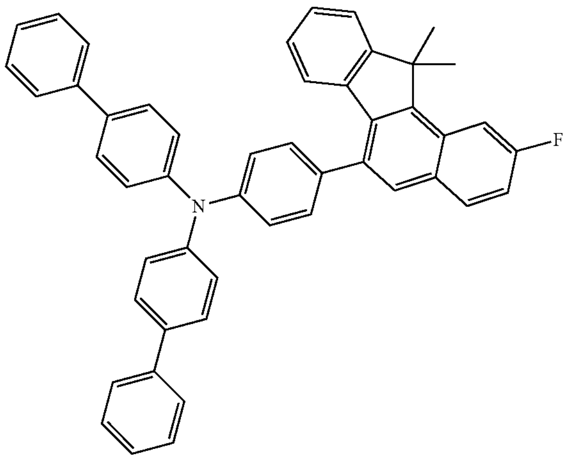
497
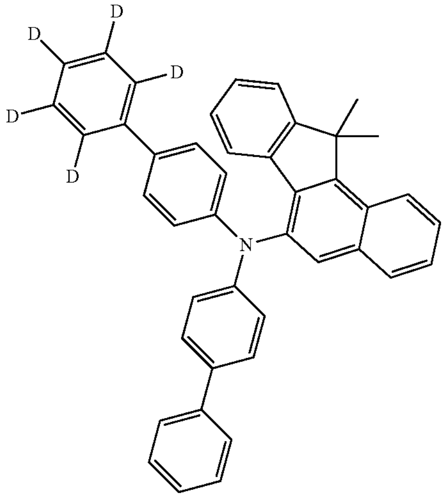

-continued

498

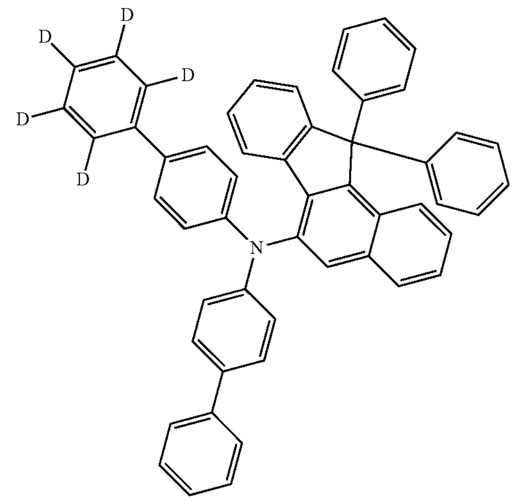

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg) and thereby has superior thermal stability. Such an increase in the thermal stability becomes an important factor in providing driving stability to a device.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific descriptions on the heterocyclic compound represented by Chemical Formula 1 are the same as the descriptions provided above.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

The organic light emitting device of the present disclosure may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer comprises an electron injection layer or an electron transfer layer, and the electron injection layer or the electron transfer layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises a hole blocking layer, and the hole blocking layer may comprise the heterocyclic compound.

In another organic light emitting device, the organic material layer comprises an electron blocking layer, and the electron blocking layer may comprise the heterocyclic compound.

In one embodiment of the present application, the organic material layer comprises a hole injection layer, and the hole injection layer may comprise the heterocyclic compound.

In one embodiment of the present application, the organic material layer comprises a hole transfer layer, and the hole transfer layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIG. 1 to FIG. 4 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

The organic material layer comprising Chemical Formula 1 may further comprise other materials as necessary.

In addition, the organic light emitting device according to one embodiment of the present application comprises an anode, a cathode, and two or more stacks provided between the anode and the cathode, the two or more stacks each independently comprise a light emitting layer, a charge generation layer is included between the two or more stacks, and the charge generation layer comprises the compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer and the like described above.

As the organic light emitting device according to one embodiment of the present application, an organic light emitting device having a 2-stack tandem structure is schematically illustrated in FIG. 4.

Herein, the first electron blocking layer, the first hole blocking layer, the second hole blocking layer and the like described in FIG. 4 may not be included in some cases.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

[Preparation Example 1] Preparation of Compound 1

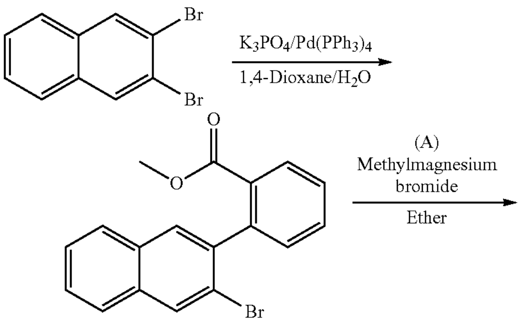

1-1

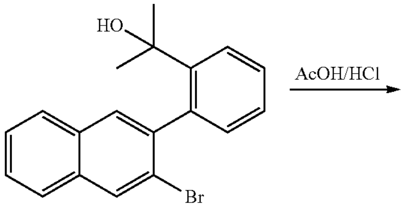

1-2

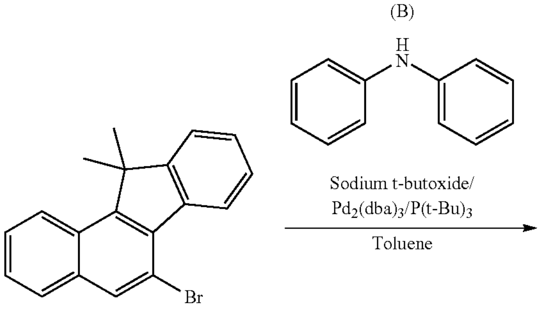

1-3

-continued

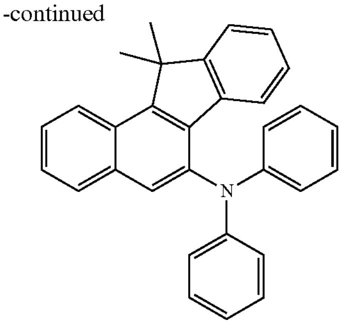

1

Preparation of Compound 1-2

Compound 1-1 (15 g, 0.044 mol, 1 eq.) was dissolved in ether (200 ml), and methylmagnesium bromide (A) (15.7 g, 0.131 mol, 3 eq.) (3 M in ether solution) was slowly dropped thereto at 0° C. After slowly raising the temperature, the result was stirred for 4 hours at 40° C. After terminating the reaction by introducing water thereto, the result was extracted using MC and water. Then, moisture was removed therefrom using $MgSO_4$. The result was separated using a silica gel column to obtain Compound 1-2 (13 g) in a 87% yield.

Preparation of Compound 1-3

Acetic acid (100 ml) and HCl (10 ml) were introduced to Compound 1-2 (13 g, 0.038 mol, 1 eq.), and the result was stirred for 3 hours at 140° C. After terminating the reaction by introducing water thereto, the result was extracted using MC and water. Then, moisture was removed therefrom using $MgSO_4$. The result was separated using a silica gel column to obtain Compound 1-3 (10 g) in a 81% yield.

Preparation of Compound 1

Compound 1-3 (10 g, 0.03 mol, 1 eq.), diphenylamine (B) (6.3 g, 0.037 mol, 1.2 eq.), NaOt-Bu (8.9 g, 0.092 mol, 3 eq.), $Pd_2(dba)_3$ (0.28 g, 0.0003 mol, 0.01 eq.) and $P(t\text{-}Bu)_3$ (0.12 g, 0.006 mol, 0.02 eq.) were introduced to toluene (100 ml), and the result was stirred for 6 hours at 90° C. After terminating the reaction by introducing water thereto, the result was extracted using MC and water. Then, moisture was removed therefrom using $MgSO_4$. The result was separated using a silica gel column to obtain Compound 1-1 (8.5 g) in a 66% yield.

Compounds were synthesized in the same manner as in Preparation Example 1 except that Intermediate A of the following Table 1 was used instead of methylmagnesium bromide (A), and Intermediate B of the following Table 1 was used instead of diphenylamine (B).

TABLE 1

| Compound No. | Intermediate A | Intermediate B | Yield |
|---|---|---|---|
| 9 | —MgBr | 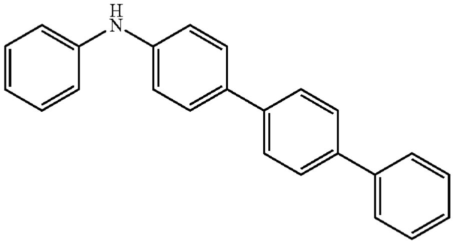 [SMILES: c1ccc(Nc2ccc(-c3ccc(-c4ccccc4)cc3)cc2)cc1] | 58% |

TABLE 1-continued
| Compound No. | Intermediate A | Intermediate B | Yield |
|---|---|---|---|
| 25 | —MgBr | 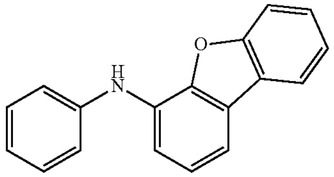 [SMILES: c1ccc(Nc2cccc3c2oc2ccccc23)cc1] | 62% |
| 42 | —MgBr | 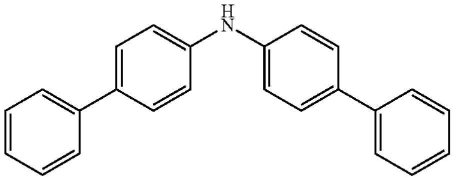 [SMILES: c1ccc(-c2ccc(Nc3ccc(-c4ccccc4)cc3)cc2)cc1] | 60% |
| 53 | —MgBr | 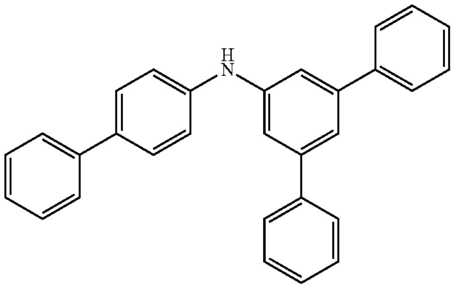 [SMILES: c1ccc(-c2ccc(Nc3cc(-c4ccccc4)cc(-c4ccccc4)c3)cc2)cc1] | 51% |
| 62 | —MgBr | 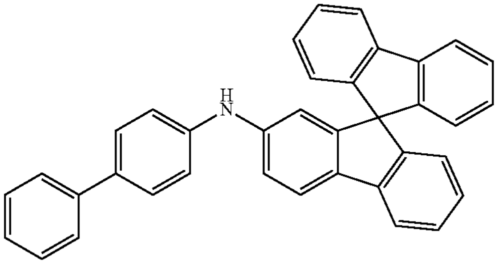 [SMILES: c1ccc(-c2ccc(Nc3ccc4c(c3)C3(c5ccccc5-c5ccccc53)c3ccccc3-4)cc2)cc1] | 66% |
| 63 | —MgBr | 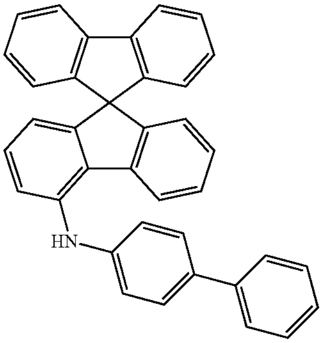 [SMILES: c1ccc(-c2ccc(Nc3cccc4c3-c3ccccc3C43c4ccccc4-c4ccccc43)cc2)cc1] | 53% |

TABLE 1-continued
| Compound No. | Intermediate A | Intermediate B | Yield |
| --- | --- | --- | --- |
| 89 | —MgBr | 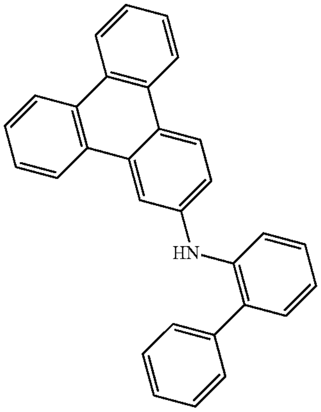 [SMILES: c1ccc(-c2ccccc2Nc2ccc3c4ccccc4c4ccccc4c3c2)cc1] | 63% |
| 104 | —MgBr | 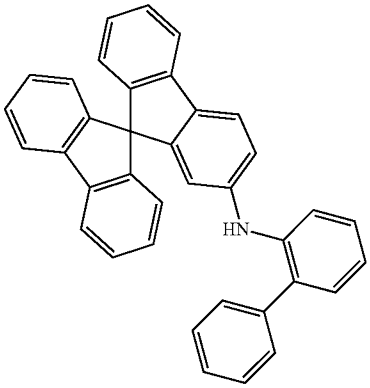 [SMILES: c1ccc(-c2ccccc2Nc2ccc3c(c2)C2(c4ccccc4-c4ccccc42)c2ccccc2-3)cc1] | 65% |
| 105 | —MgBr | 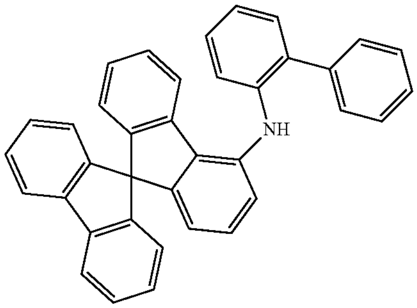 [SMILES: c1ccc(-c2ccccc2Nc2cccc3c2-c2ccccc2C32c3ccccc3-c3ccccc32)cc1] | 71% |

TABLE 1-continued
| Compound No. | Intermediate A | Intermediate B | Yield |
|---|---|---|---|
| 132 | —MgBr | 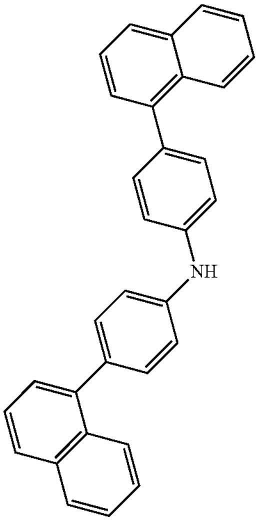 [SMILES: c1ccc2c(-c3ccc(Nc4ccc(-c5cccc6ccccc56)cc4)cc3)cccc2c1] | 68% |
| 225 | —MgBr | 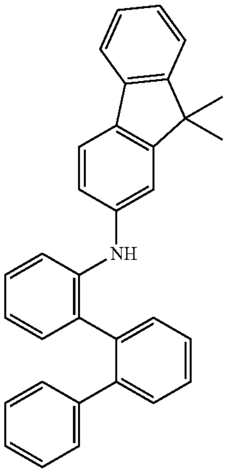 [SMILES: CC1(C)c2ccccc2-c2ccc(Nc3ccccc3-c3ccccc3-c3ccccc3)cc21] | 51% |
| 282 | —MgBr | 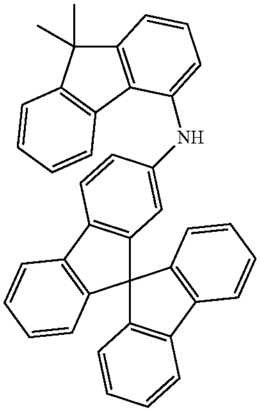 [SMILES: CC1(C)c2ccccc2-c2c(Nc3ccc4c(c3)C3(c5ccccc5-c5ccccc53)c3ccccc3-4)cccc21] | 70% |

TABLE 1-continued
| Compound No. | Intermediate A | Intermediate B | Yield |
|---|---|---|---|
| 321 | —MgBr | 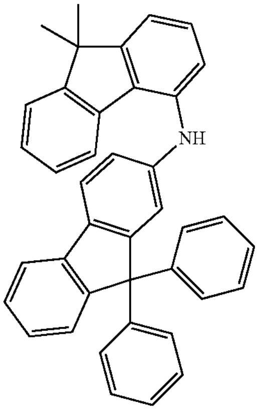 [SMILES: CC1(C)c2ccccc2-c2c(Nc3ccc4c(c3)C(c3ccccc3)(c3ccccc3)c3ccccc3-4)cccc21] | 66% |
| 350 | —MgBr | 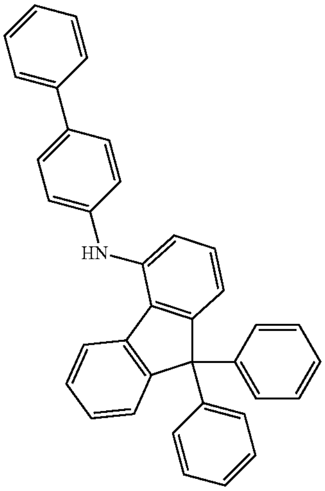 [SMILES: c1ccc(-c2ccc(Nc3cccc4c3-c3ccccc3C4(c3ccccc3)c3ccccc3)cc2)cc1] | 52% |
| 352 | —MgBr | 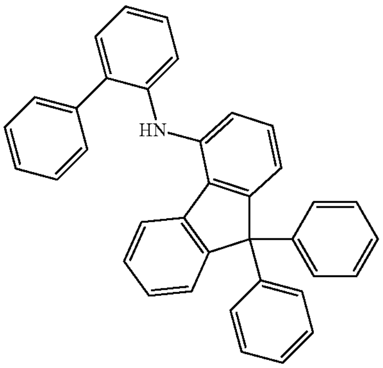 [SMILES: c1ccc(-c2ccccc2Nc2cccc3c2-c2ccccc2C3(c2ccccc2)c2ccccc2)cc1] | 68% |

TABLE 1-continued
| Compound No. | Intermediate A | Intermediate B | Yield |
|---|---|---|---|
| 478 | 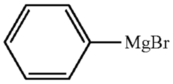 | 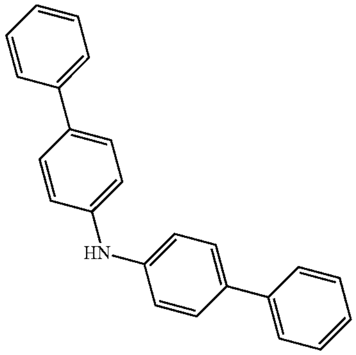 [SMILES: c1ccc(-c2ccc(Nc3ccc(-c4ccccc4)cc3)cc2)cc1] | 60% |
| 479 | 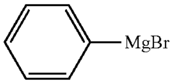 | 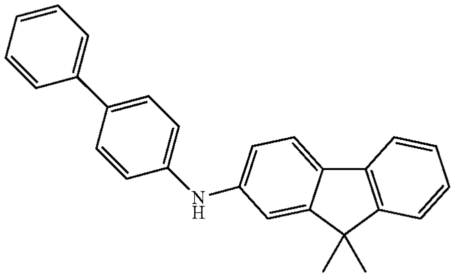 [SMILES: CC1(C)c2ccccc2-c2ccc(Nc3ccc(-c4ccccc4)cc3)cc21] | 51% |
| 487 | 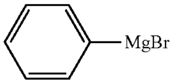 | 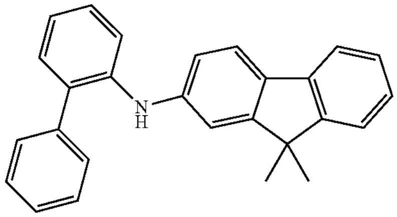 [SMILES: CC1(C)c2ccccc2-c2ccc(Nc3ccccc3-c3ccccc3)cc21] | 63% |
| 488 | 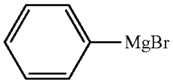 | 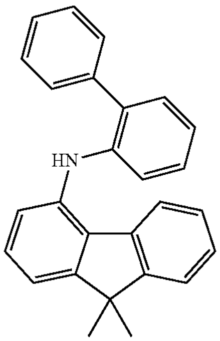 [SMILES: CC1(C)c2ccccc2-c2c(Nc3ccccc3-c3ccccc3)cccc21] | 59% |

Compounds other than the compounds described in Preparation Example 1 and Table 1 were also prepared in the same manner as the compounds described in Preparation Example 1 and Table 1, and the synthesis identification results are shown in the following Table 2 and Table 3.

Table 2 shows measurement values of $^1$H NMR ($CDCl_3$, 200 Mz), and Table 3 shows measurement values of FD-mass spectrometry (FD-MS: field desorption mass spectrometry).

TABLE 2

| Compound | $^1$H NMR ($CDCl_3$, 200 Mz) |
|---|---|
| 1 | δ = 8.06(2H, m), 7.82(1H, d), 7.61(1H, d), 7.43(2H, m), 7.31(1H, t), 7.20(5H, m), 6.81(2H, m), 6.70(1H, s), 6.63(4H, m), 1.85(6H, s) |
| 9 | δ = 8.06(2H, m), 7.82(1H, d), 7.61(1H, d), 7.52~7.41(9H, m), 7.31(1H, t), 7.25(7H, m), 6.81(1H, t), 6.69(5H, m), 1.85(6H, s) |
| 25 | δ = 8.06(2H, m), 7.89(1H, d), 7.82(1H, d), 7.61(2H, dd), 7.43~7.20(9H, m), 7.07(1H, t), 6.81(1H, t), 6.70(1H, s), 6.63(2H, d), 6.39(1H, d), 1.85(6H, s) |
| 42 | δ = 8.06(2H, m), 7.82(1H, d), 7.61(1H, d), 7.52~7.41(16H, m), 7.31(1H, t), 7.24(1H, t), 6.69(5H, m), 1.85(6H, s) |
| 53 | δ = 8.06(2H, m), 7.82(1H, d), 7.61(1H, d), 7.52~7.41(19H, m), 7.31(1H, t), 7.24(1H, t), 7.06(1H, s), 6.85(2H, s), 6.70(3H, m), 1.85(6H, s) |
| 62 | δ = 8.06(2H, m), 7.75(4H, m), 7.61~7.16(22H, m), 6.75(1H, s), 6.70(3H, m), 6.58(1H, d), 1.85(6H, s) |
| 63 | δ = 8.06(2H, m), 7.75(4H, m), 7.61~7.16(21H, m), 7.03(1H, t), 6.90(1H, d), 6.70(3H, m), 6.58(1H, d), 1.85(6H, s) |
| 89 | δ = 8.93(2H, m), 8.12(5H, m), 7.82(6H, m), 7.61(7H, m), 7.46~7.02(6H, m), 6.87(1H, t), 6.70(2H, m), 1.85(6H, s) |
| 104 | δ = 8.06(2H, m), 7.75(4H, m), 7.61~7.08(22H, m), 6.87(1H, t), 6.70(3H, m), 6.58(1H, d), 1.85(6H, s) |
| 105 | δ = 8.06(2H, m), 7.75(4H, m), 7.61~7.08(22H, m), 6.87(2H, m), 6.70(2H, m), 6.58(1H, d), 1.85(6H, s) |
| 132 | δ = 8.55(2H, d), 8.42(2H, d), 8.04(6H, m), 7.82(1H, d), 7.55(11H, m), 7.43(2H, m), 7.31(2H, m), 6.70(5H, m), 1.85(6H, s) |
| 225 | δ = 8.06(2H, m), 7.82(6H, m), 7.61~7.16(16H, m), 6.87(1H, t), 6.70(3H, m), 6.58(1H, d), 1.85(6H, s), 1.72(6H, s) |
| 282 | δ = 8.06(2H, m), 7.87(5H, m), 7.55(4H, m), 7.31~7.16(14H, m), 7.03(1H, t), 6.91(1H, m), 6.75(1H, s), 6.70(1H, s), 6.58(2H, d), 1.85(6H, s), 1.72(6H, s) |
| 321 | δ = 8.06(2H, m), 7.82(2H, dd), 7.61~7.28(25H, m), 7.11(4H, m), 7.06 (1H, m), 6.85(2H, s), 6.75(1H, s), 6.70(1H, s), 6.58(1H, d), 1.85(6H, s) |
| 350 | δ = 8.06(2H, m), 7.82(2H, dd), 7.61(1H, d), 7.51~7.26(20H, m), 7.11(5H, m), 6.91(1H, d), 6.70(3H, m), 6.58(1H, d), 1.85(6H, s) |
| 352 | δ = 8.06(2H, m), 7.82(2H, dd), 7.61(1H, d), 7.51~7.08(25H, m), 6.87(2H, m), 6.69(2H, m), 6.58(1H, d), 1.85(6H, s) |
| 478 | δ = 8.06(2H, m), 7.82(1H, d), 7.61(1H, d), 7.51~7.08(24H, m), 7.11(4H, m), 6.69(5H, m) |
| 479 | δ = 8.06(2H, m), 7.82(2H, dd), 7.61(1H, d), 7.51~7.24(21H, m), 7.11(4H, m), 6.75(1H, s), 6.70(3H, m), 6.58(1H, d), 1.85(6H, s) |
| 487 | δ = 8.06(2H, m), 7.82(2H, dd), 7.55~7.08(26H, m), 6.87(1H, t) 6.75(1H, s), 6.70(2H, m), 6.58(1H, d), 1.85(6H, s) |
| 488 | δ = 8.06(2H, m), 7.82(2H, dd), 7.55~7.08(26H, m), 6.91(2H, m), 6.70(2H, m), 6.58(1H, d), 1.85(6H, s) |

TABLE 3

| Compound | FD-MS | Compound | FD-MS |
|---|---|---|---|
| 1 | m/z = 411.54 (C31H25N = 411.20) | 9 | m/z = 563.73 (C43H33N = 563.26) |
| 25 | m/z = 501.62 (C37H27NO = 501.21) | 42 | m/z = 563.73 (C43H33N = 563.26) |
| 53 | m/z = 639.82 (C49H37N = 639.29) | 62 | m/z = 725.92 (C56H39N = 725.31) |
| 63 | m/z = 725.92 (C56H39N = 725.31) | 89 | m/z = 637.81 (C49H35N = 637.28) |

TABLE 3-continued

| Compound | FD-MS | Compound | FD-MS |
|---|---|---|---|
| 104 | m/z = 725.92 (C56H39N = 725.31) | 105 | m/z = 725.92 (C56H39N = 725.31) |
| 132 | m/z = 663.85 (C51H37N = 663.29) | 225 | m/z = 679.89 (C52H41N = 679.32) |
| 282 | m/z = 765.34 (C59H43N = 765.98) | 321 | m/z = 768.00 (C59H45N = 767.36) |
| 350 | m/z = 727.93 (C56H41N = 727.32) | 352 | m/z = 727.93 (C56H41N = 727.32) |
| 478 | m/z = 687.87 (C53H37N = 687.29) | 479 | m/z = 727.93 (C56H41N = 727.32) |
| 487 | m/z = 727.93 (C56H41N = 727.32) | 488 | m/z = 727.93 (C56H41N = 727.32) |

EXPERIMENTAL EXAMPLE

Experimental Example 1

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, the ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

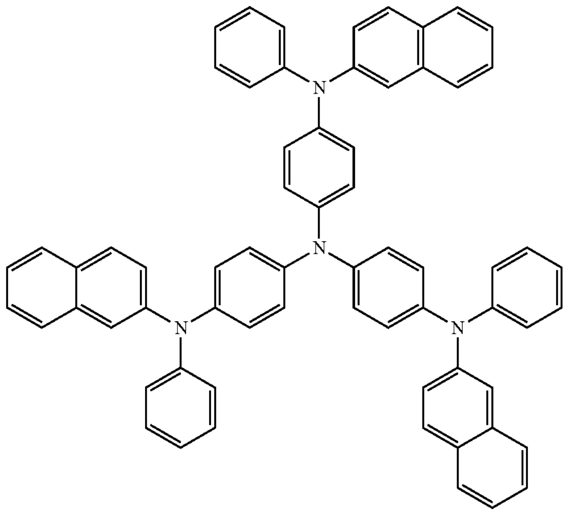

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

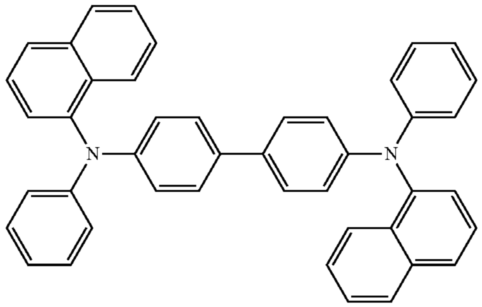

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

H1

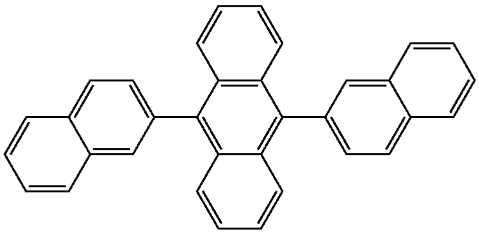

D1

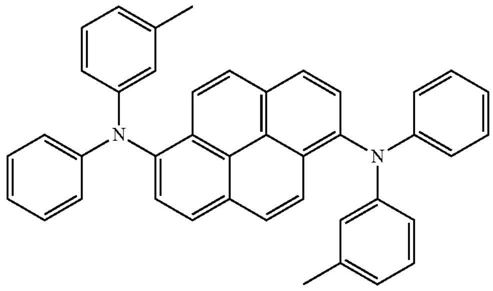

Subsequently, a compound of the following Structural Formula E1 was deposited to a thickness of 300 Å as an electron transfer layer.

E1

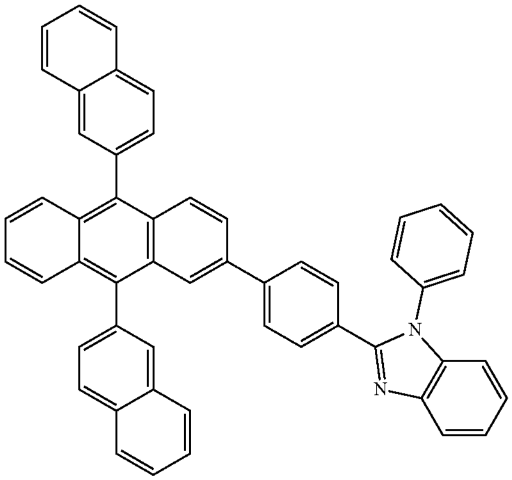

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-8}$ torr to $10^{-6}$ torr by each material to be used in the OLED manufacture.

Organic electroluminescent devices were manufactured in the same manner as in Experimental Example 1 except that compounds shown in the following Table 4 were used instead of NPB used when forming the hole transfer layer in Experimental Example 1.

For each of the organic light emitting devices manufactured as above, electroluminescent (EL) properties were measured using M7000 manufactured by McScience Inc., and with the measurement results, T95 was measured when standard luminance was 700 cd/m$^2$ through a lifetime measurement system (M6000) manufactured by McScience Inc. Results of measuring driving voltage, light emission efficiency, color coordinate (CIE) and lifetime of the blue organic light emitting devices manufactured according to the present disclosure are as shown in the following Table 4.

TABLE 4

| | Compound | Driving Voltage (V) | Light Emission Efficiency (cd/A) | CIE (x, y) | Lifetime (T95) |
|---|---|---|---|---|---|
| Example 1 | 1 | 5.70 | 6.79 | (0.134, 0.100) | 57 |
| Example 2 | 9 | 4.92 | 6.72 | (0.134, 0.100) | 56 |
| Example 3 | 25 | 4.96 | 6.78 | (0.134, 0.100) | 64 |
| Example 4 | 42 | 4.72 | 6.88 | (0.134, 0.100) | 63 |
| Example 5 | 53 | 4.84 | 6.89 | (0.134, 0.101) | 58 |
| Example 6 | 62 | 4.76 | 6.75 | (0.134, 0.100) | 60 |
| Example 7 | 63 | 4.68 | 6.84 | (0.134, 0.100) | 61 |
| Example 8 | 89 | 4.70 | 6.84 | (0.134, 0.101) | 66 |
| Example 9 | 104 | 4.77 | 6.70 | (0.134, 0.100) | 61 |
| Example 10 | 105 | 4.80 | 6.76 | (0.134, 0.101) | 64 |
| Example 11 | 132 | 4.83 | 6.82 | (0.134, 0.100) | 62 |
| Example 12 | 225 | 4.84 | 6.81 | (0.134, 0.100) | 66 |
| Example 13 | 282 | 4.72 | 6.70 | (0.134, 0.101) | 61 |
| Example 14 | 321 | 4.72 | 6.73 | (0.134, 0.101) | 66 |
| Example 15 | 350 | 4.85 | 6.84 | (0.134, 0.100) | 62 |
| Example 16 | 352 | 4.81 | 6.90 | (0.134, 0.100) | 64 |
| Example 17 | 478 | 4.76 | 6.61 | (0.134, 0.101) | 63 |
| Example 18 | 479 | 4.81 | 6.72 | (0.134, 0.100) | 61 |

TABLE 4-continued

| | Compound | Driving Voltage (V) | Light Emission Efficiency (cd/A) | CIE (x, y) | Lifetime (T95) |
|---|---|---|---|---|---|
| Example 19 | 487 | 4.73 | 6.74 | (0.134, 0.101) | 64 |
| Example 20 | 488 | 4.75 | 6.88 | (0.134, 0.100) | 63 |
| Comparative Example 1 | NPB | 5.14 | 6.06 | (0.134, 0.100) | 49 |
| Comparative Example 2 | HT1 | 5.10 | 6.08 | (0.134, 0.100) | 50 |
| Comparative Example 3 | HT2 | 5.11 | 6.12 | (0.134, 0.100) | 51 |
| Comparative Example 4 | HT3 | 5.07 | 6.00 | (0.134, 0.101) | 50 |
| Comparative Example 5 | HT4 | 5.08 | 6.02 | (0.134, 0.101) | 48 |
| Comparative Example 6 | HT5 | 5.12 | 6.06 | (0.134, 0.101) | 47 |

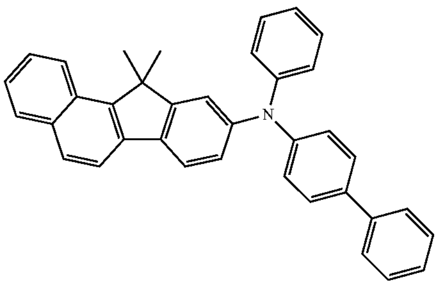

HT1

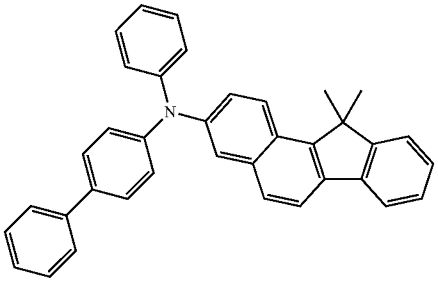

HT2

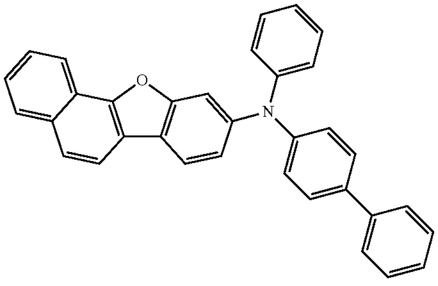

HT3

TABLE 4-continued

| Compound | Driving Voltage (V) | Light Emission Efficiency (cd/A) | CIE (x, y) | Lifetime (T95) |
|---|---|---|---|---|

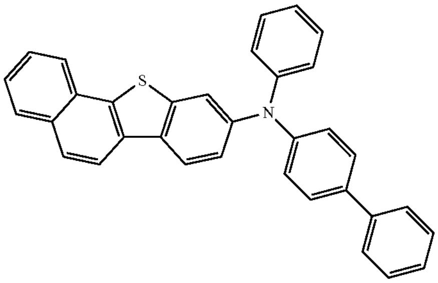

HT4

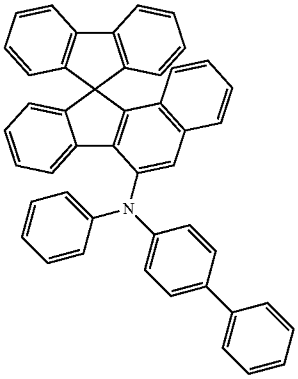

HT5

As seen from the results of Table 4, the organic light emitting device using the hole transfer layer material of the blue organic light emitting device of the present disclosure had lower driving voltage, and significantly improved light emission efficiency and lifetime compared to Comparative Example 1.

When comparing Comparative Example 1 of Table 4 with the compounds of the present disclosure, having an arylamine group is similar, but there is a difference in that the fluorene group is substituted. The fluorene group having a substituent suppresses pi-pi stacking of the aromatic ring, which increases a driving voltage of the organic light emitting device and thereby prevents decline in the device properties.

Accordingly, it is considered that the compound of the present disclosure using such a derivative brings excellence in all aspects of driving, efficiency and lifetime by enhancing hole transfer properties or stability.

Experimental Example 2

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, the ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

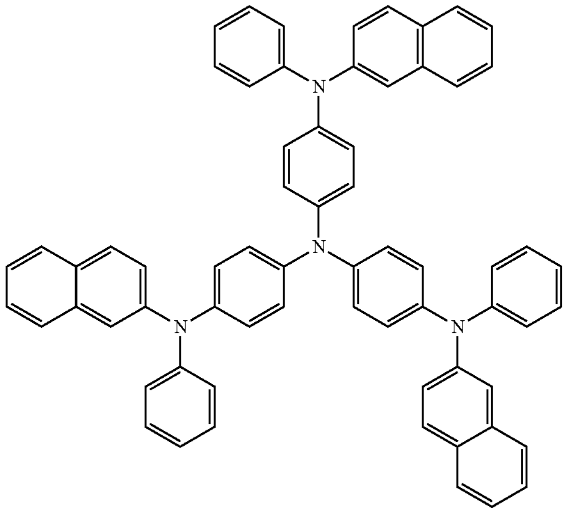

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

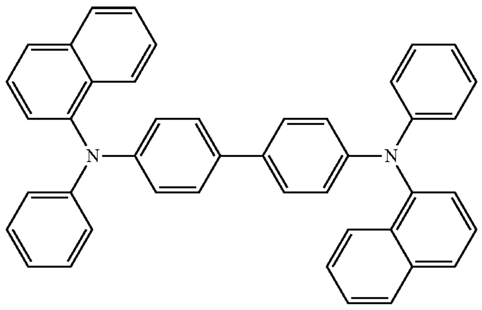

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

H1

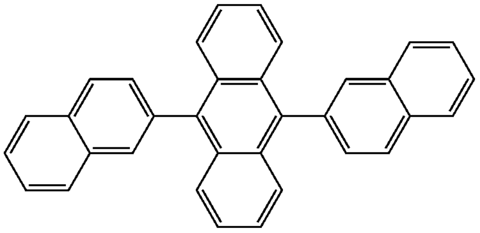

D1

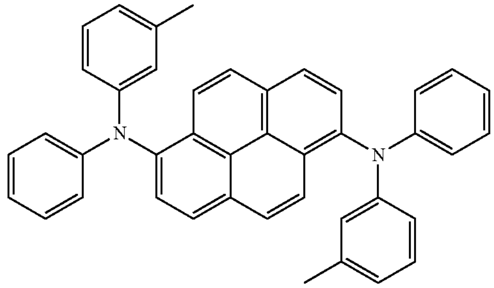

Subsequently, a compound of the following Structural Formula E1 was deposited to a thickness of 300 Å as an electron transfer layer.

E1

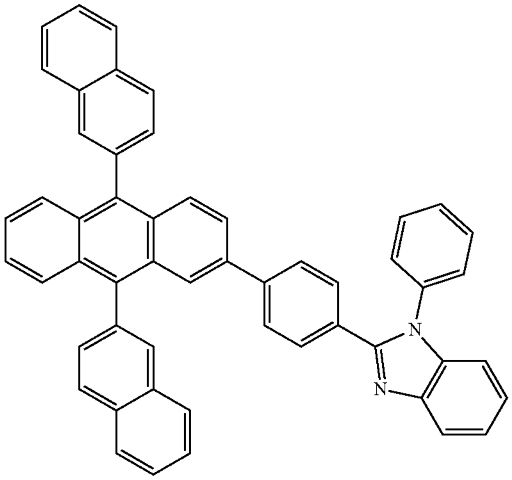

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Organic electroluminescent devices were manufactured in the same manner as in Example 2 except that, after forming the hole transfer layer NPB to a thickness of 250 Å, an electron blocking layer was formed on the hole transfer layer using compounds shown in the following Table 5 to a thickness of 50 Å. Results of measuring driving voltage, light emission efficiency, color coordinate (CIE) and lifetime of the blue organic light emitting devices manufactured according to the present disclosure are as shown in the following Table 5.

TABLE 5

| | Compound | Driving Voltage (V) | Light Emission Efficiency (cd/A) | CIE (x, y) | Lifetime (T95) |
|---|---|---|---|---|---|
| Example 21 | 1 | 5.13 | 5.99 | (0.134, 0.100) | 53 |
| Example 22 | 9 | 5.11 | 6.18 | (0.134, 0.101) | 60 |
| Example 23 | 25 | 5.07 | 6.21 | (0.134, 0.100) | 58 |
| Example 24 | 42 | 5.05 | 6.33 | (0.134, 0.100) | 57 |
| Example 25 | 53 | 4.98 | 6.25 | (0.134, 0.101) | 52 |
| Example 26 | 62 | 4.97 | 6.23 | (0.134, 0.100) | 57 |
| Example 27 | 63 | 4.93 | 6.14 | (0.134, 0.100) | 52 |
| Example 28 | 89 | 5.07 | 6.28 | (0.134, 0.100) | 56 |
| Example 29 | 104 | 4.94 | 6.25 | (0.134, 0.101) | 55 |
| Example 30 | 105 | 4.88 | 6.29 | (0.134, 0.100) | 59 |
| Example 31 | 132 | 4.93 | 6.35 | (0.134, 0.100) | 54 |
| Example 32 | 225 | 4.90 | 6.31 | (0.134, 0.100) | 59 |
| Example 33 | 282 | 4.87 | 6.28 | (0.134, 0.101) | 53 |
| Example 34 | 321 | 4.94 | 6.28 | (0.134, 0.101) | 54 |
| Example 35 | 350 | 4.91 | 6.33 | (0.134, 0.100) | 55 |
| Example 36 | 352 | 5.02 | 6.36 | (0.134, 0.100) | 58 |
| Example 37 | 478 | 5.03 | 6.36 | (0.134, 0.101) | 60 |
| Example 38 | 479 | 4.95 | 6.40 | (0.134, 0.101) | 55 |
| Example 39 | 487 | 4.93 | 6.30 | (0.134, 0.100) | 58 |
| Example 40 | 488 | 4.98 | 6.31 | (0.134, 0.100) | 56 |
| Comparative Example 7 | NPB | 5.27 | 5.88 | (0.134, 0.100) | 48 |
| Comparative Example 8 | HT1 | 5.23 | 5.90 | (0.134, 0.101) | 47 |
| Comparative Example 9 | HT2 | 5.25 | 5.87 | (0.134, 0.101) | 46 |
| Comparative Example 10 | HT3 | 5.33 | 5.80 | (0.134, 0.100) | 48 |
| Comparative Example 11 | HT4 | 5.30 | 5.81 | (0.134, 0.100) | 48 |
| Comparative Example 12 | HT5 | 5.31 | 5.88 | (0.134, 0.100) | 49 |

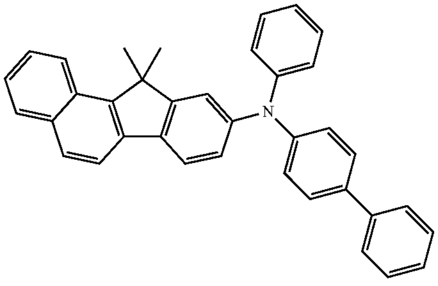

HT1

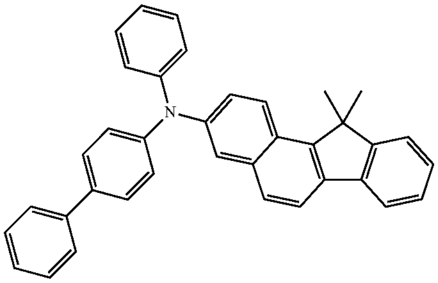

HT2

TABLE 5-continued

| Compound | Driving Voltage (V) | Light Emission Efficiency (cd/A) | CIE (x, y) | Lifetime (T95) |
|---|---|---|---|---|

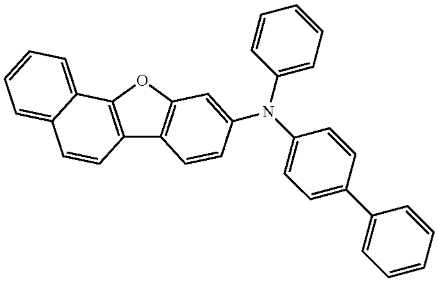

HT3

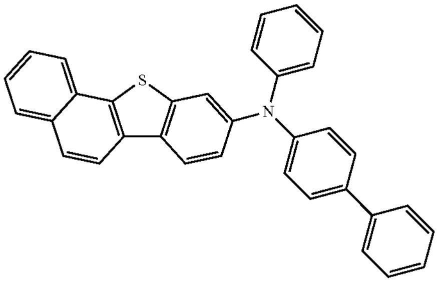

HT4

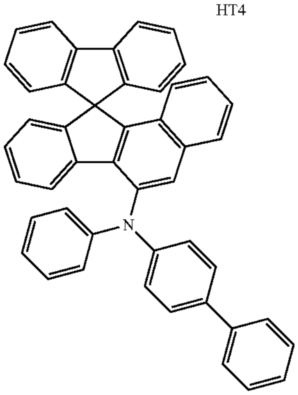

HT5

As seen from the results of Table 5, the organic light emitting device using the electron blocking layer material of the blue organic light emitting device of the present disclosure had lower driving voltage and significantly improved light emission efficiency and lifetime compared to Comparative Examples 7 to 12. When electrons pass through a hole transfer layer and reach an anode without binding in a light emitting layer, efficiency and lifetime decrease in an OLED. When using a compound having a high HOMO level as an electron blocking layer in order to prevent such a phenomenon, the electrons trying to pass through the light emitting layer and reach the anode are blocked by an energy barrier of the electron blocking layer. As a result, it is considered that holes and the electrons have increased probability to form excitons, and have increased possibility to be emitted as light in the light emitting layer, and the compound of the present disclosure brings excellence in all aspects of driving, efficiency and lifetime.

Particularly, it was identified that, when using the amine derivative in the compound of Chemical Formula 1 as the hole transfer layer, an unshared electron pair of the amine improved the flow of holes enhancing hole transfer capability of the hole transfer layer, and when used as the electron blocking layer, deterioration of the hole transfer material caused by electrons invading the hole transfer layer was able to be suppressed, and by combining the amine moiety with a substituent with enhanced hole properties, planarity of the amine derivative and the glass transition temperature increased, which increased thermal stability of the compound.

It was also identified that hole transfer capability was enhanced through adjusting band gap and T1 value, and molecular stability increased as well, and as a result, the device had lowered driving voltage, enhanced light efficiency, and lifetime properties of the device were enhanced due to thermal stability of the compound.

The invention claimed is:

1. A heterocyclic compound represented by the following Chemical Formula 1:

[Chemical Formula 1]

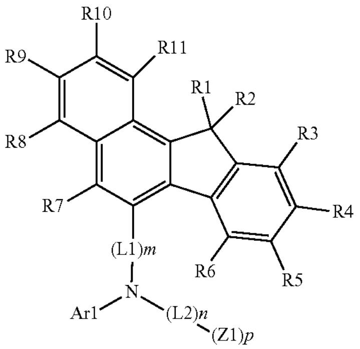

wherein, in Chemical Formula 1,

R1 and R2 are the same as or different from each other, and each independently a halogen group; a substituted or unsubstituted C1 to C60 alkyl group; or a substituted or unsubstituted C6 to C60 aryl group;

L1 and L2 are the same as or different from each other, and each independently a direct bond; a phenylene group; or a biphenylene group;

Ar1 is represented by any one of the following structural formulae:

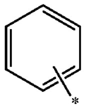
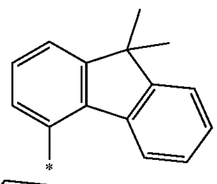
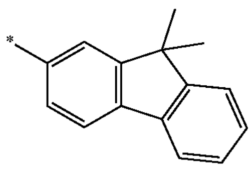
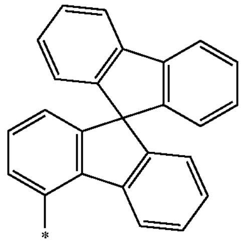
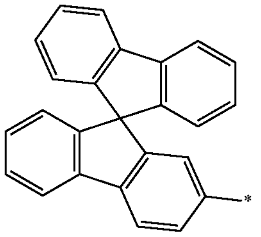

-continued

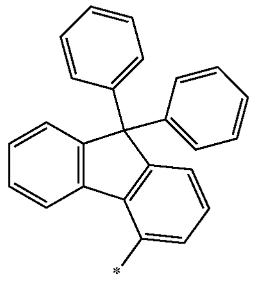
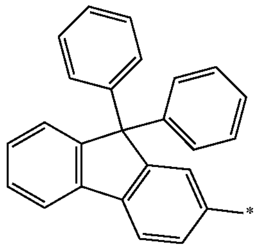
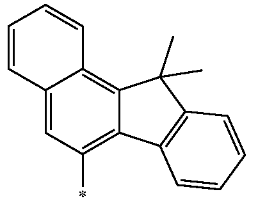
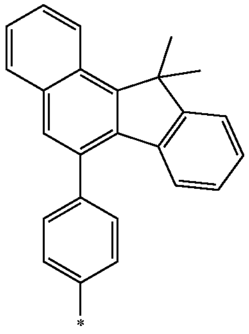
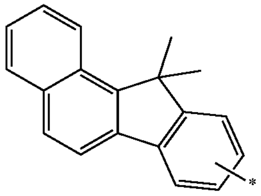

Z1 is a phenyl group substituted with deuterium; a phenanthrenyl group, a triphenylenyl group; a terphenyl group; a dimethylfluorenyl group; a diphenylfluorenyl group; a spirobifluorenyl group; a dimethyl-11H-benzo[a]fluorenyl group; a dibenzofuran group; or a dibenzothiophene group;

R3 to R11 are the same as or different from each other, and each independently selected from the group consisting of hydrogen; deuterium; a halogen group; and —CN;

wherein "substituted or unsubstituted" means being substituted with one or more substituents selected from the group consisting of C1 to C60 linear or branched alkyl; C6 to C60 monocyclic or polycyclic aryl; C2 to C60 monocyclic or polycyclic heteroaryl; —SiRR'R";

and —P(═O)RR'; or being unsubstituted,

R, R' and R" are the same as or different from each other, and each independently hydrogen; a substituted or unsubstituted C1 to C40 alkyl group; or a substituted or unsubstituted C6 to C40 aryl group; and m, n and p are an integer of 1 to 6, and when m, n and p are 2 or greater, two or more substituents in the parentheses are the same as or different from each other.

2. The heterocyclic compound of claim 1, wherein Chemical Formula 1 is represented by any one of the following Chemical Formula 2 to Chemical Formula 4:

[Chemical Formula 2]

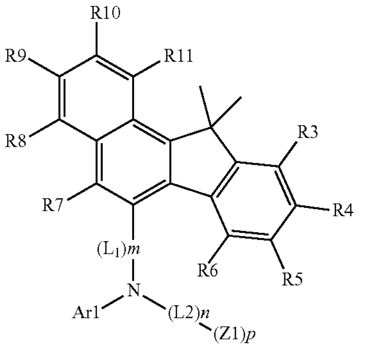

[Chemical Formula 3]

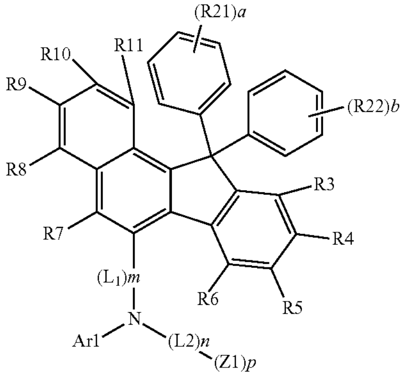

[Chemical Formula 4]

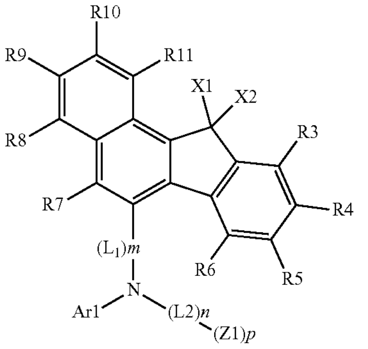

in Chemical Formulae 2 to 4,

R3 to R11, L1, L2, Z1, Ar1, m, n and p have the same definitions as in Chemical Formula 1;

X1 and X2 are the same as or different from each other, and each independently a halogen group;

R21 and R22 are the same as or different from each other, and each independently hydrogen; a substituted or unsubstituted C6 to C60 aryl group; or a substituted or unsubstituted C2 to C60 heteroaryl group; and a and b are each an integer of 1 to 6, and when a and b are 2 or greater, substituents in the parentheses are the same as or different from each other.

3. The heterocyclic compound of claim 1, wherein R3 to R11 are the same as or different from each other, and each independently hydrogen; a fluoro group (—F); or —CN.

4. The heterocyclic compound of claim 1, wherein Chemical Formula 1 is represented by any one of the following compounds:

5

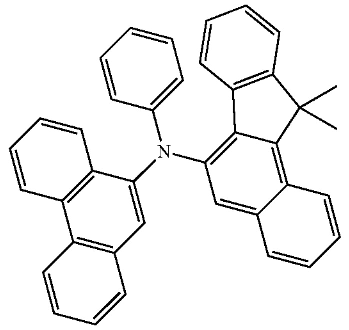

6

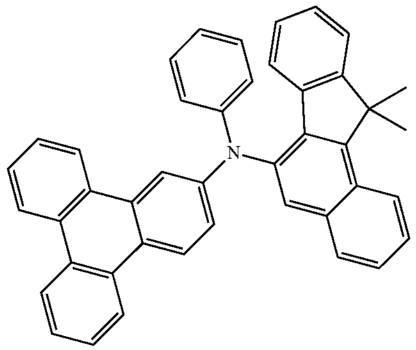

7

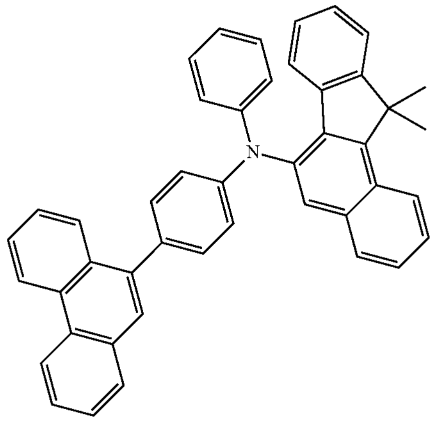

8

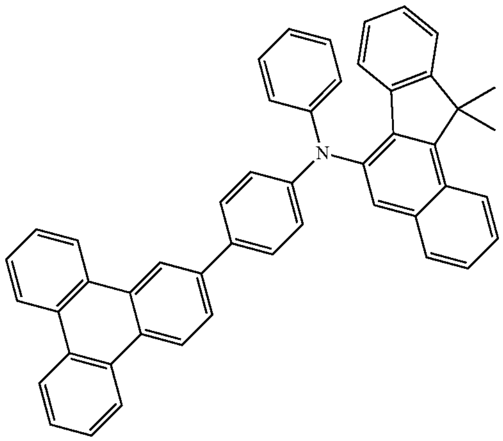

-continued
12
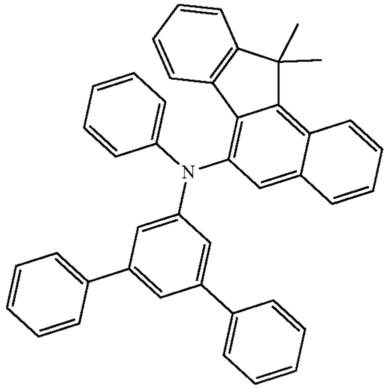
13
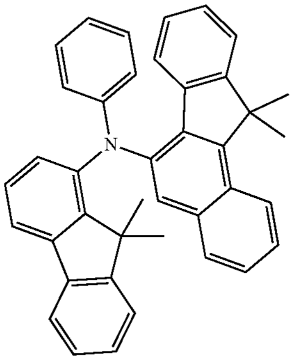
14
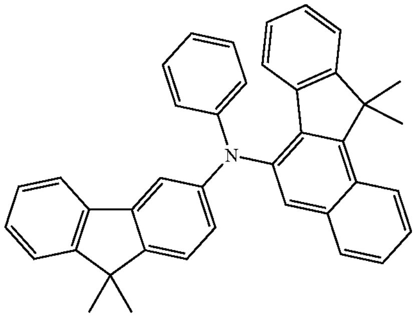
15
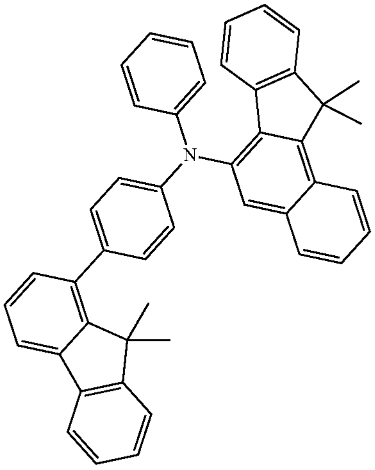
-continued
16
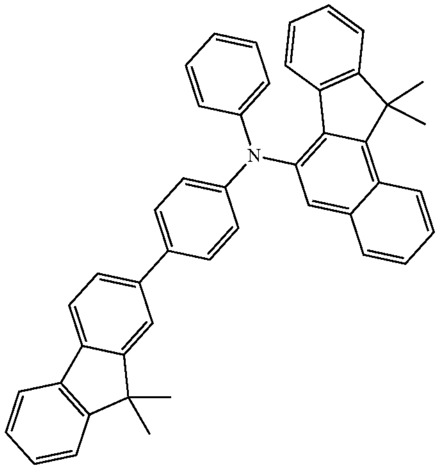
17
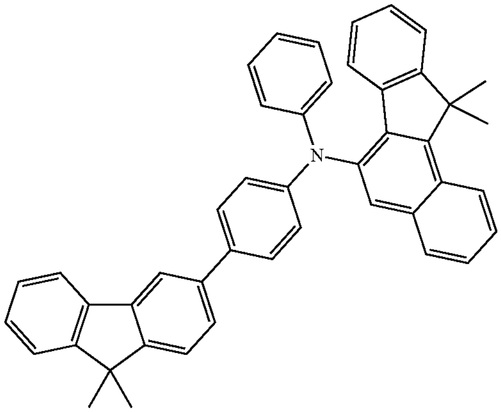
18
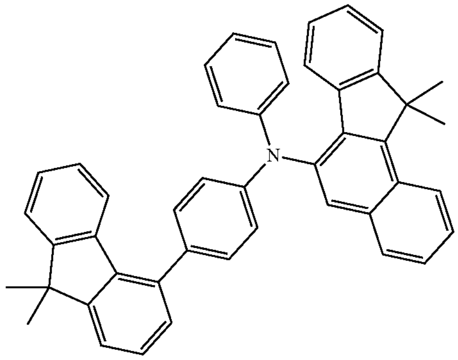

-continued
19
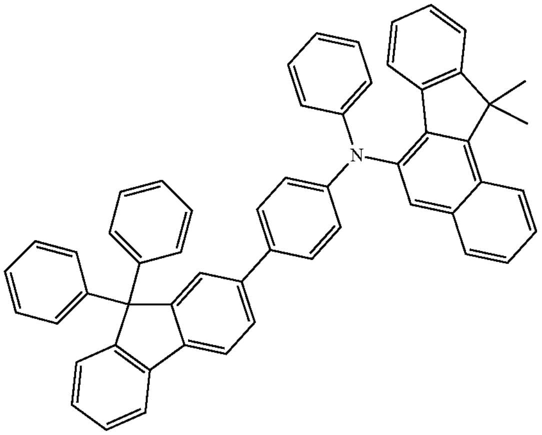
20
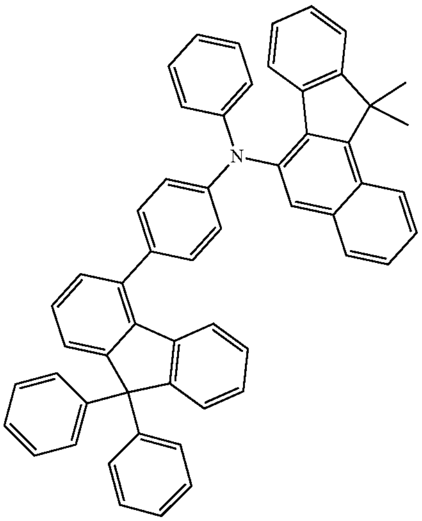
21
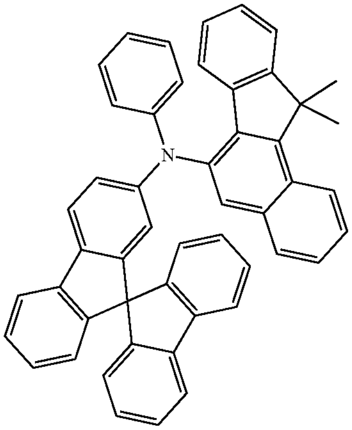
-continued
22
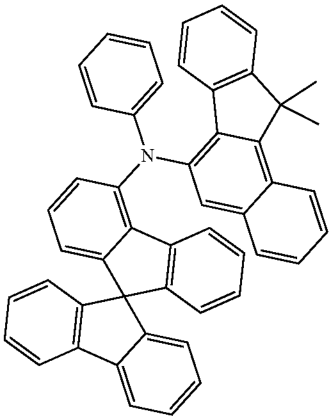
23
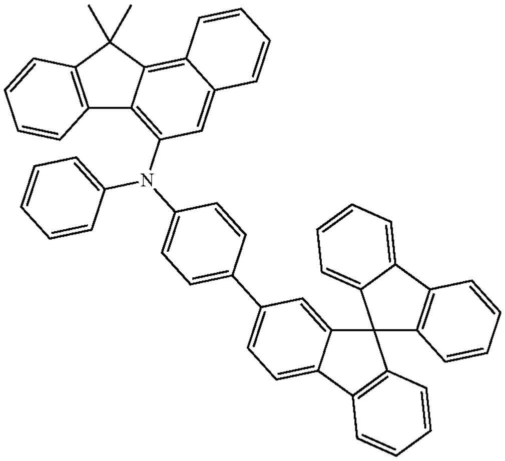
24
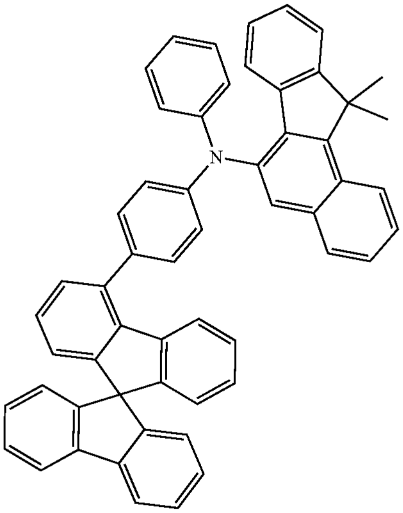

-continued
25
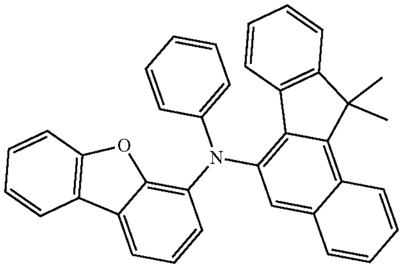
26
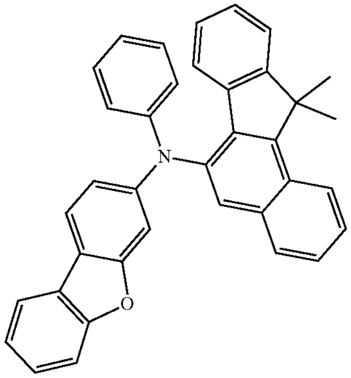
27
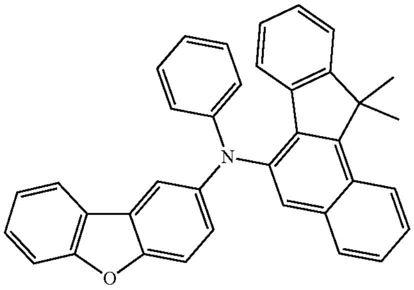
28
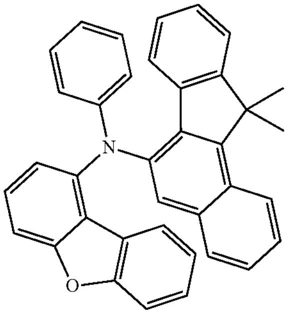
29
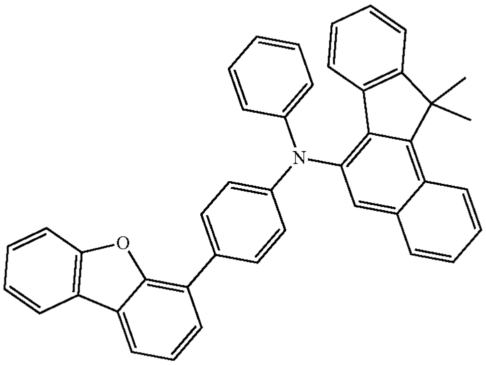
-continued
30
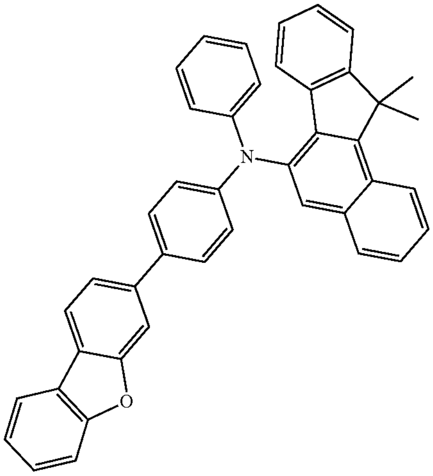
31
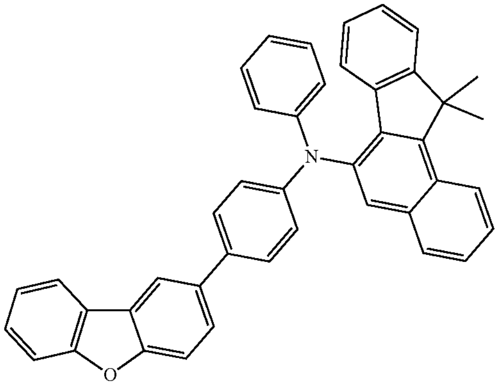
32
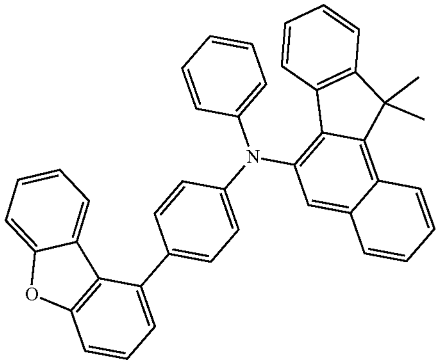
33
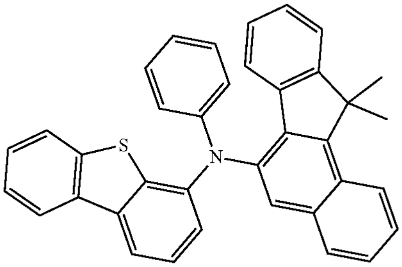

-continued
34
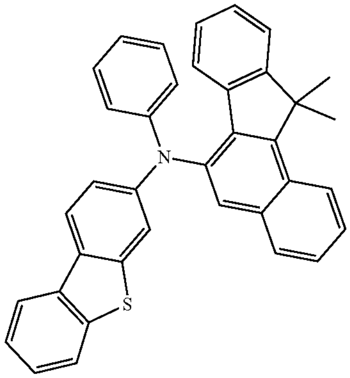
35
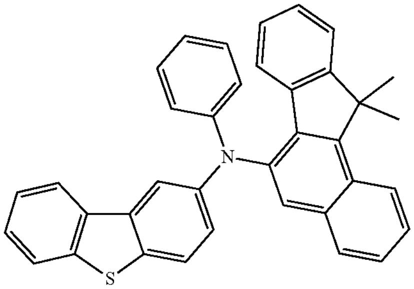
36
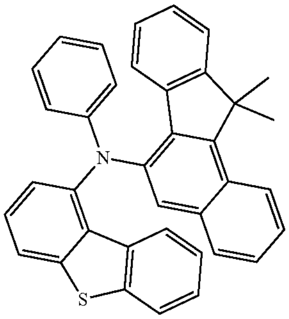
37
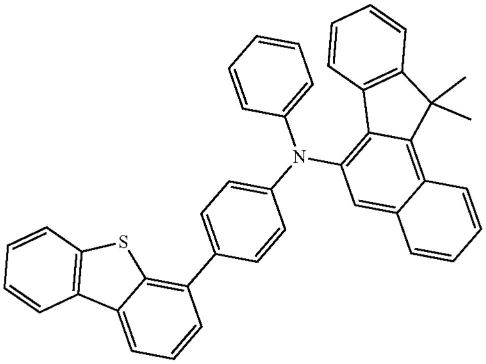
-continued
38
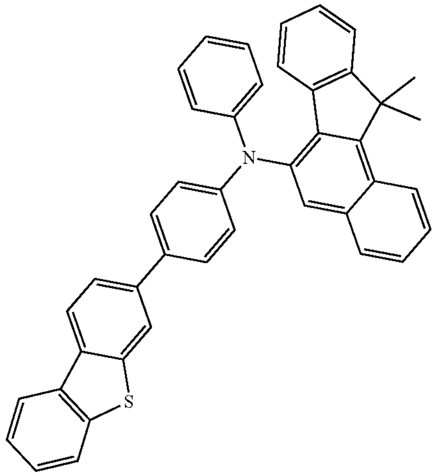
39
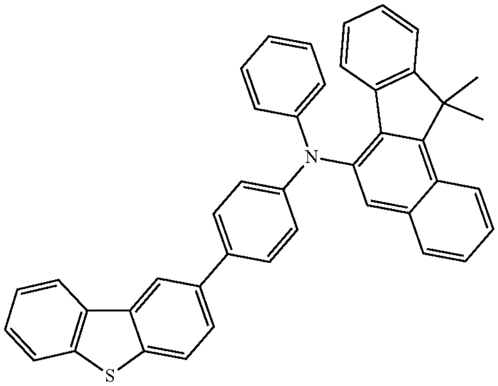
40
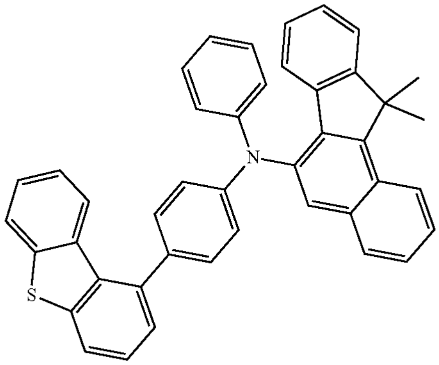

-continued
217
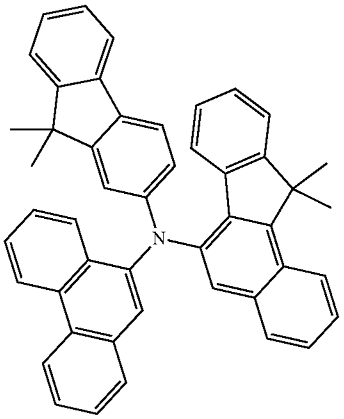
222
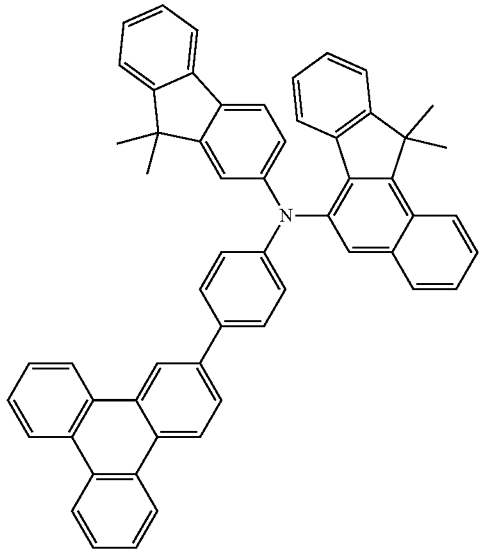
218
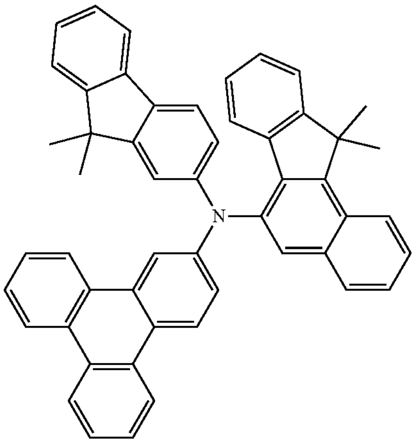
226
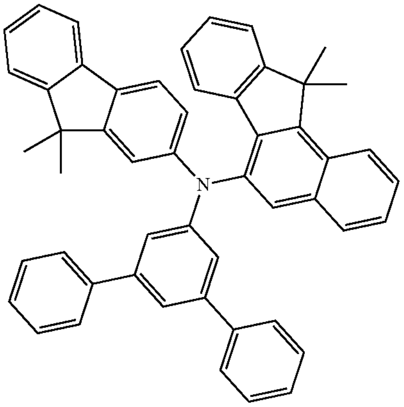
221
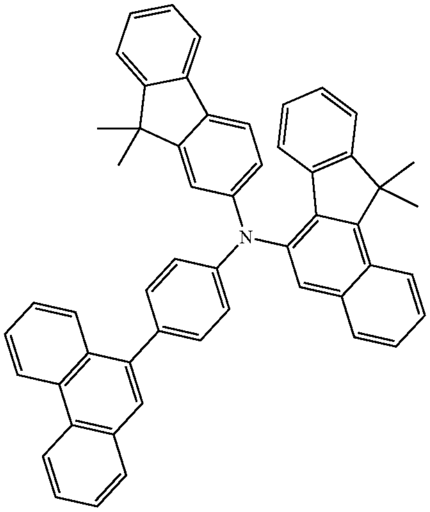
227
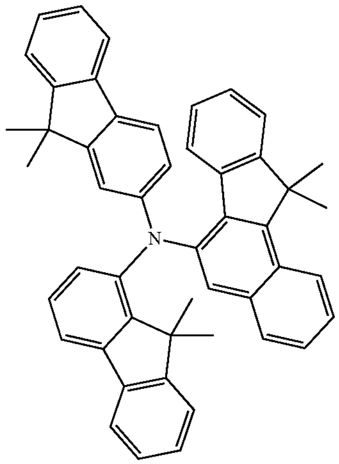

-continued
228
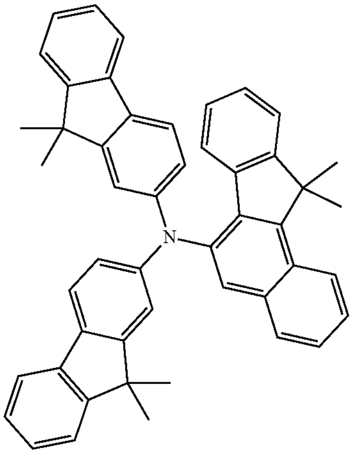
229
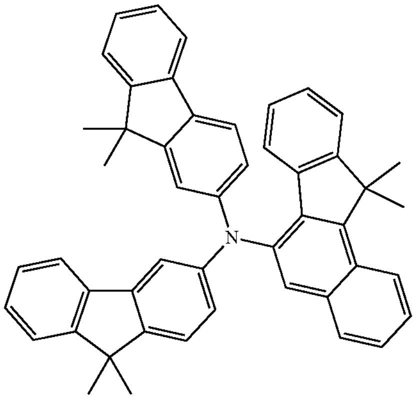
230
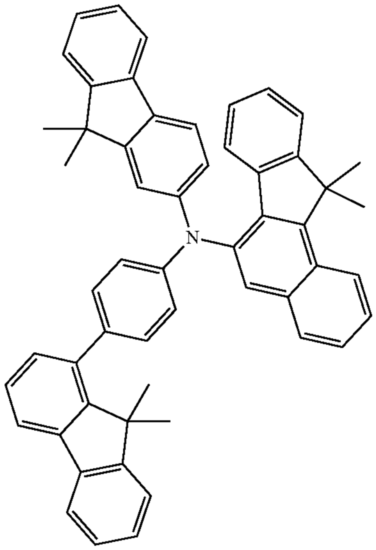
-continued
231
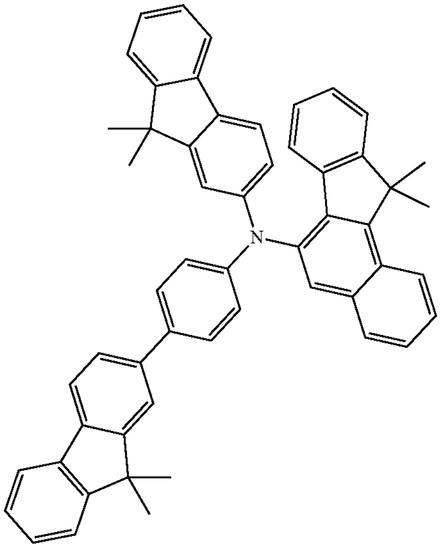
232
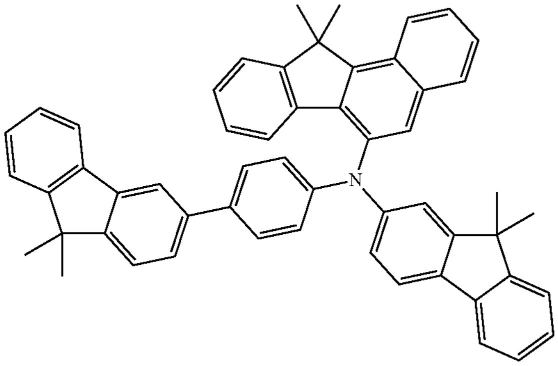
233
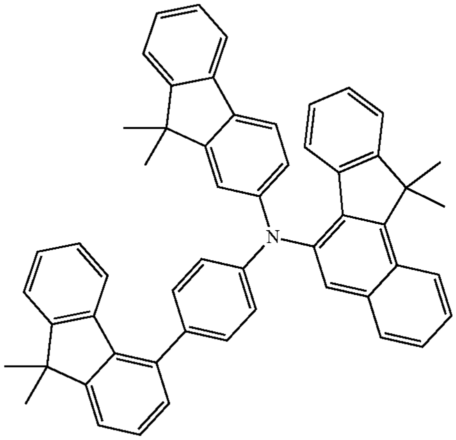

-continued
234
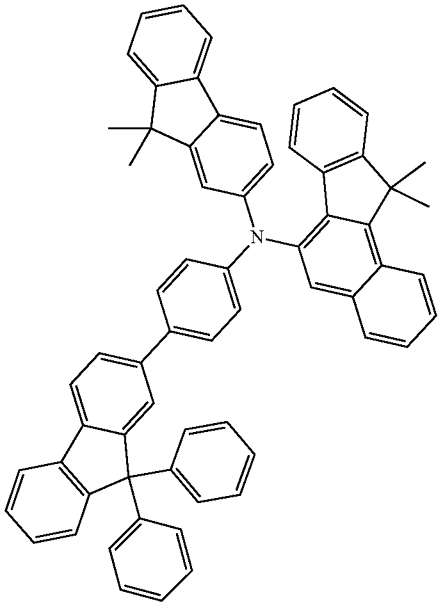
235
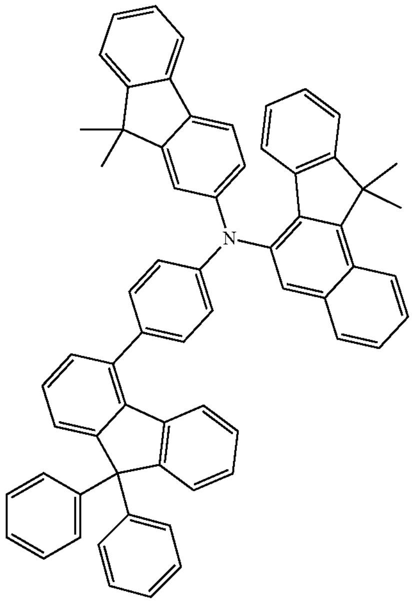
-continued
236
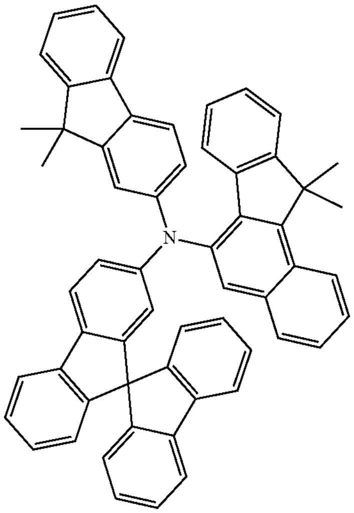
237
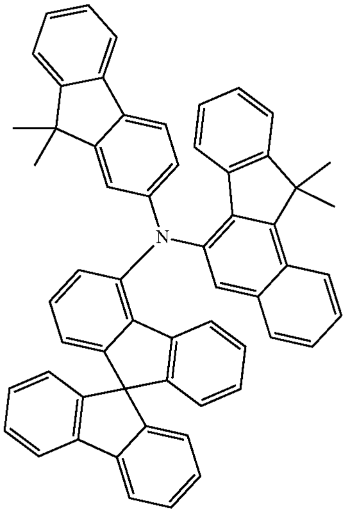
238
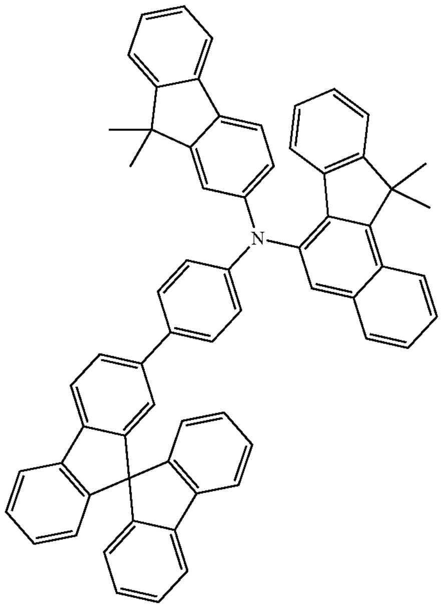

-continued
239
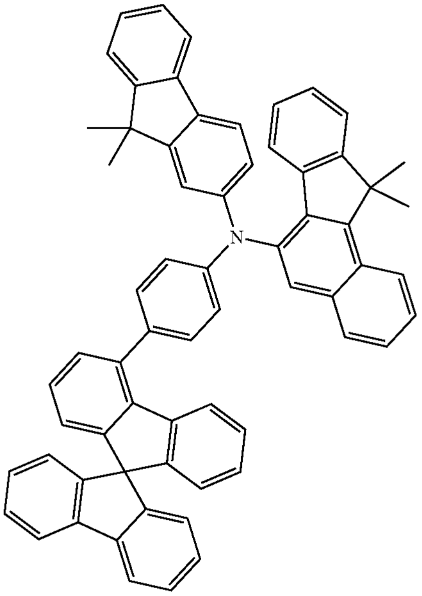
240
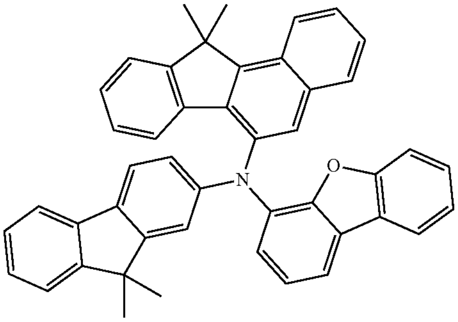
241
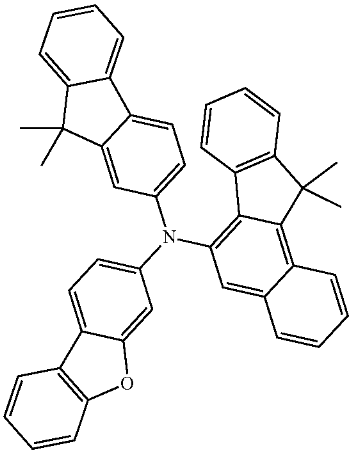
-continued
242
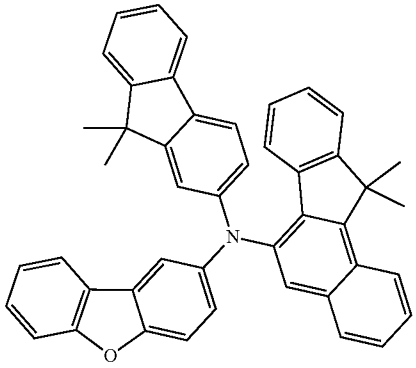
243
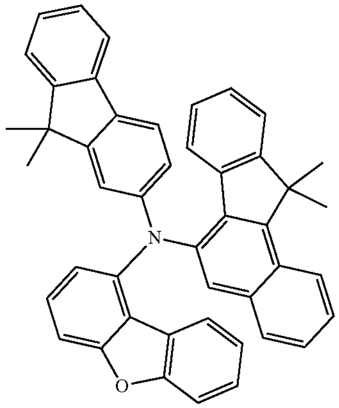
244
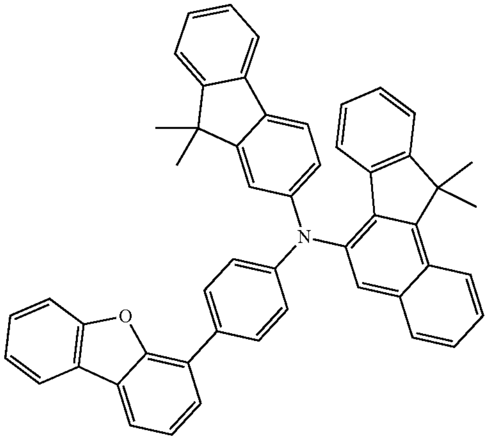

-continued
245
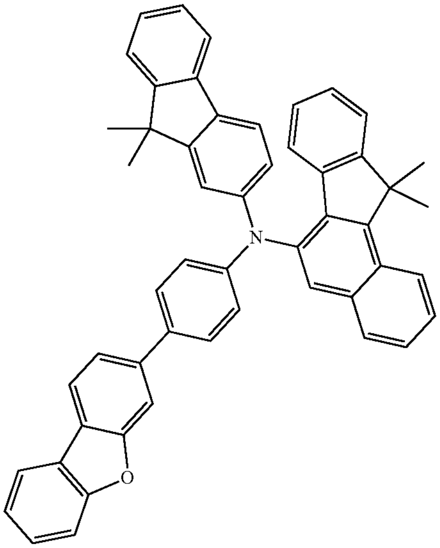
246
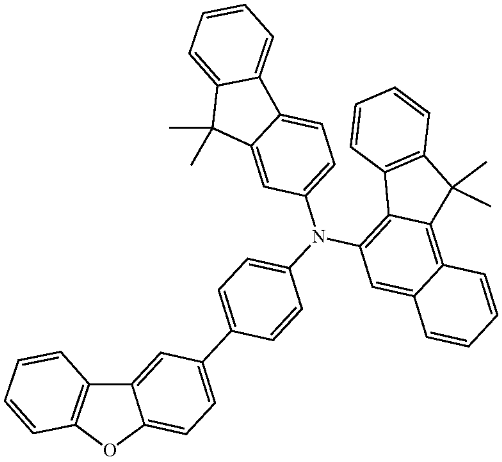
247
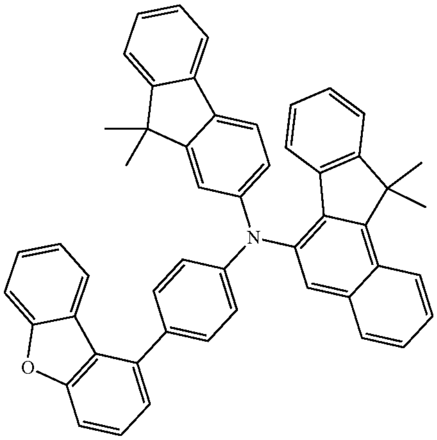
-continued
248
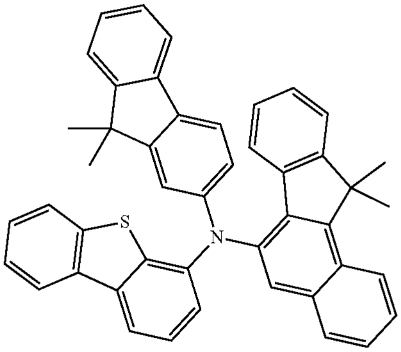
249
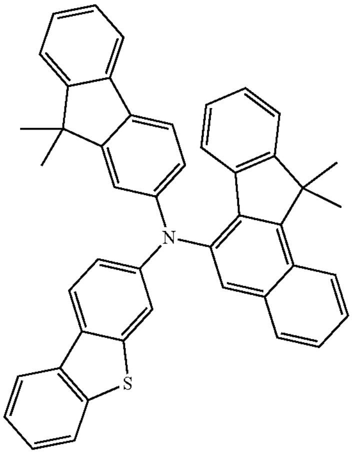
250
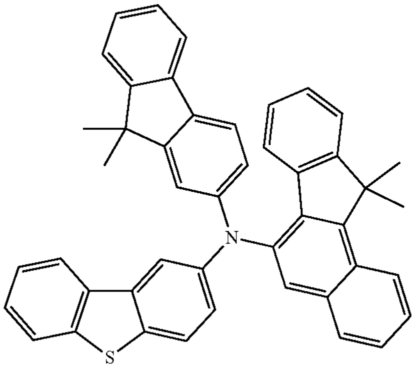
251
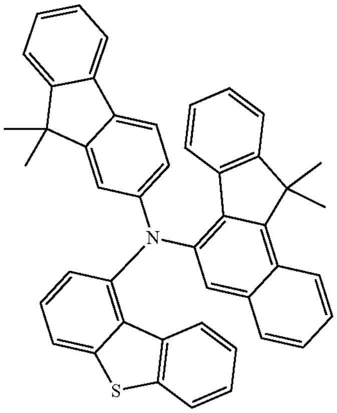

-continued
252
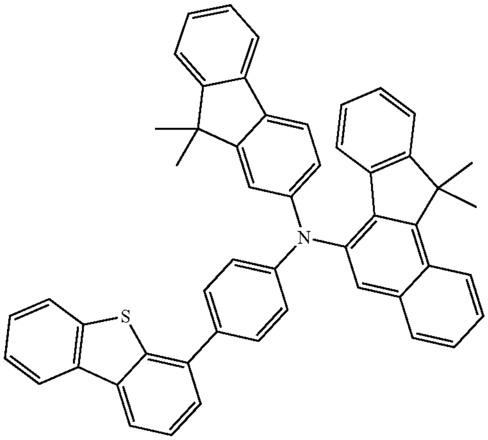
253
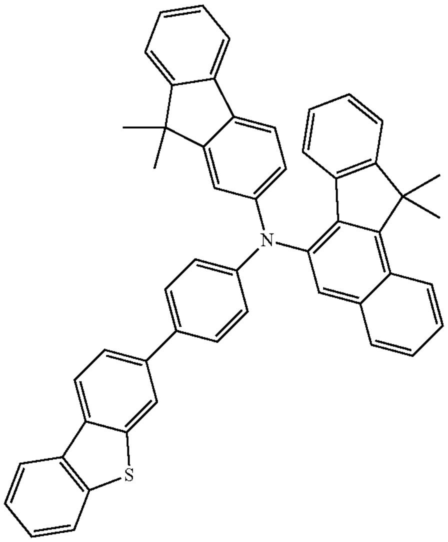
254
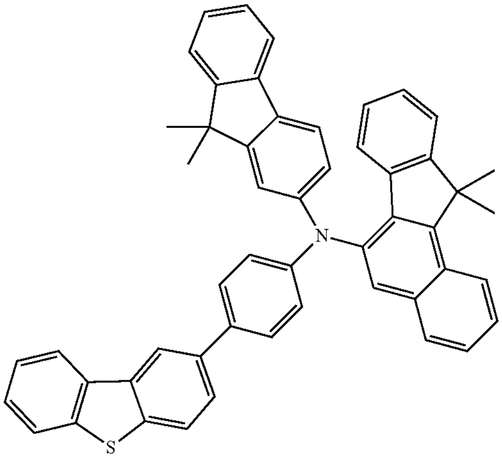
-continued
255
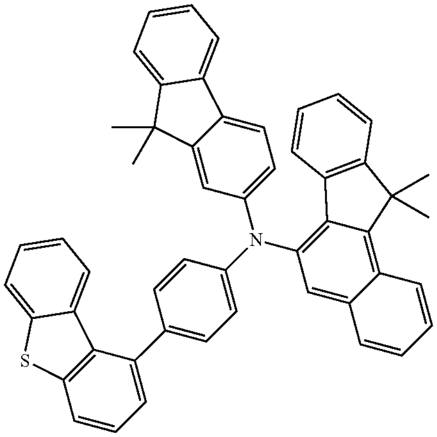
256
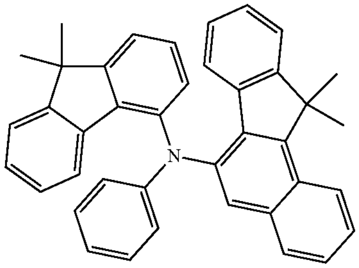
262
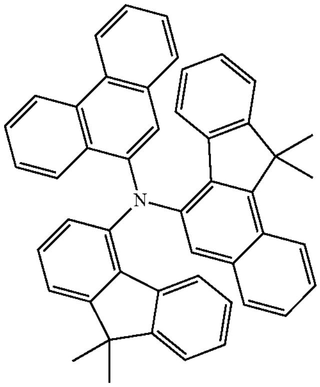
263
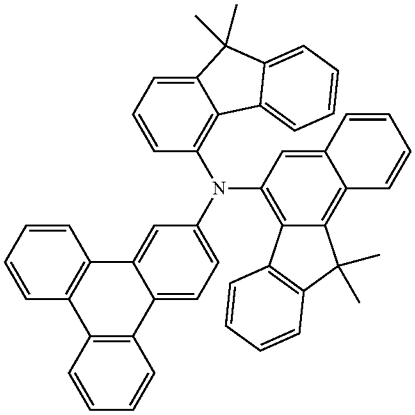

-continued
266
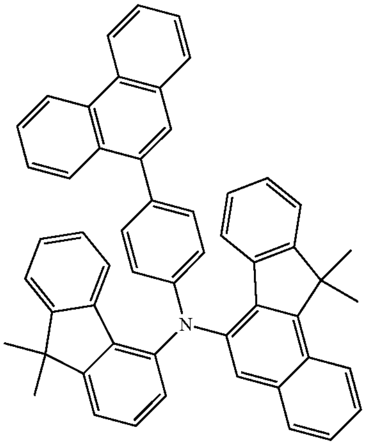
267
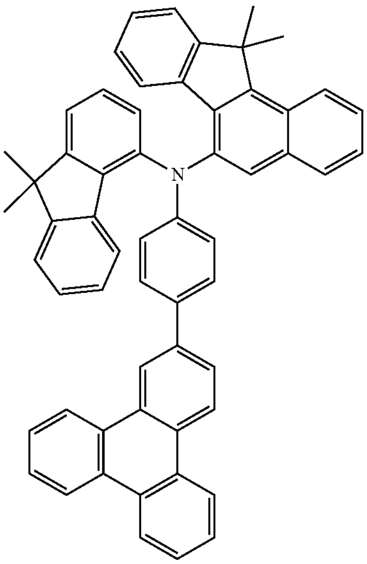
269
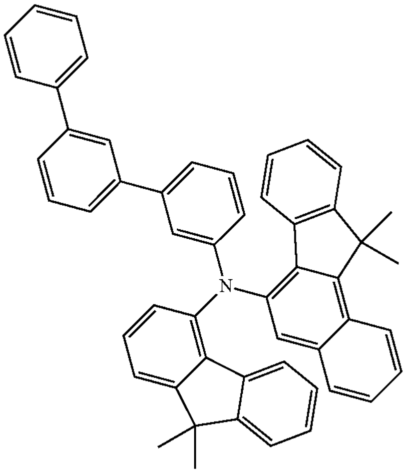
-continued
271
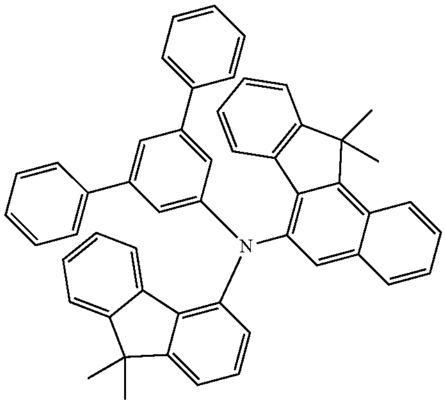
272
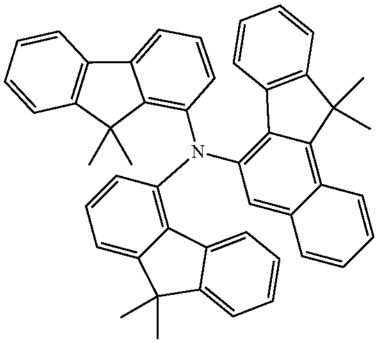
273
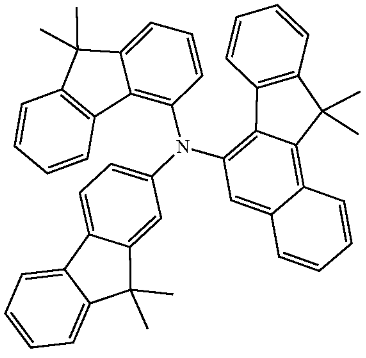
274
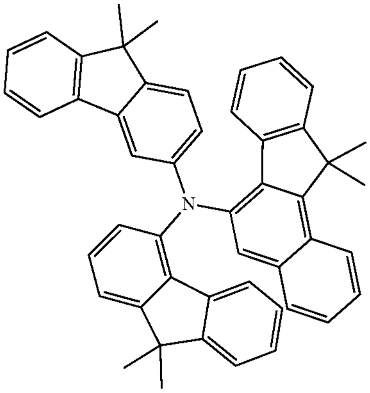

-continued
275
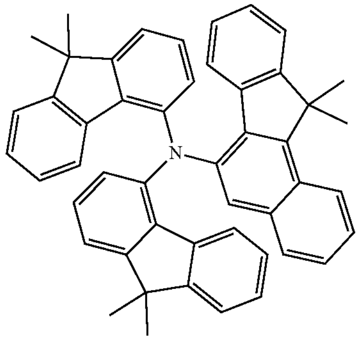
276
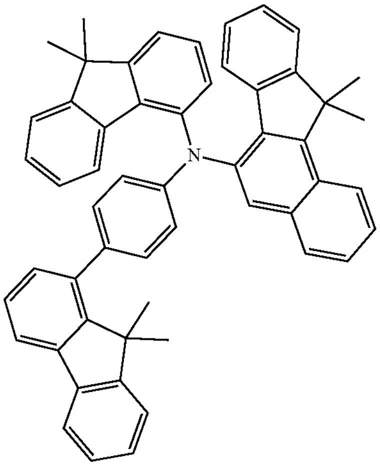
277
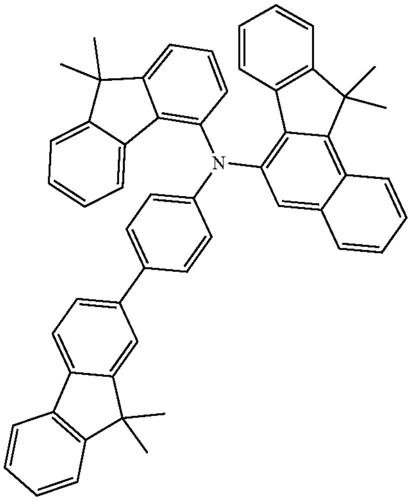
-continued
278
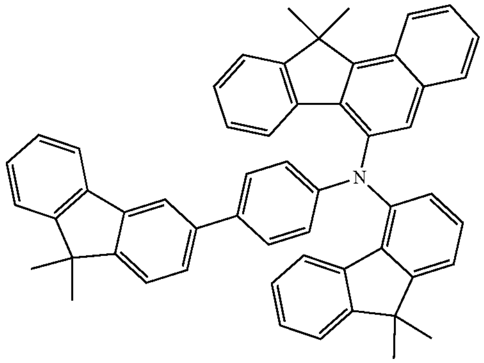
279
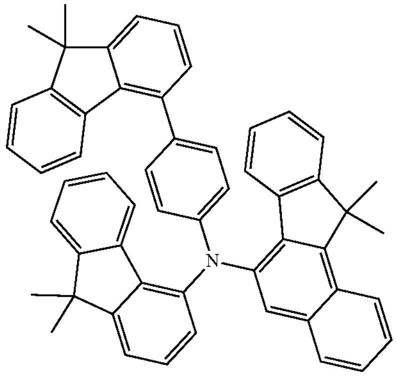
280
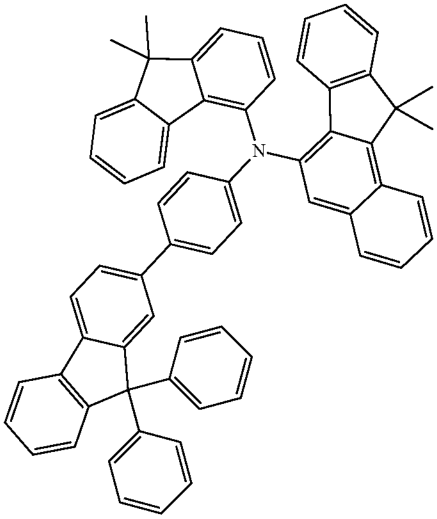

-continued
281
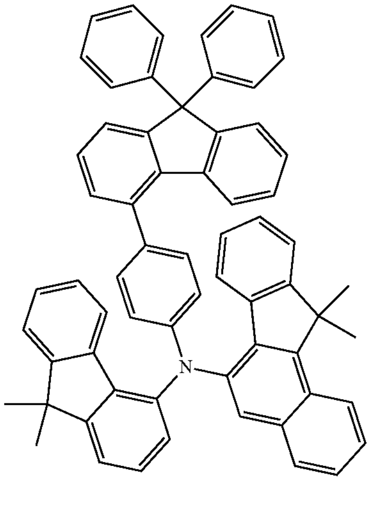
282
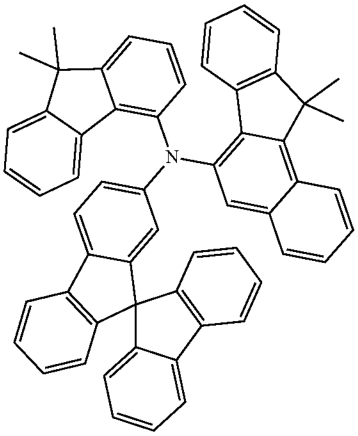
283
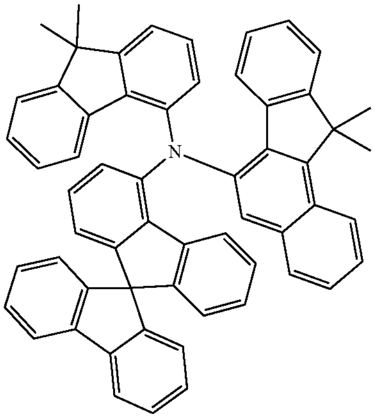
-continued
284
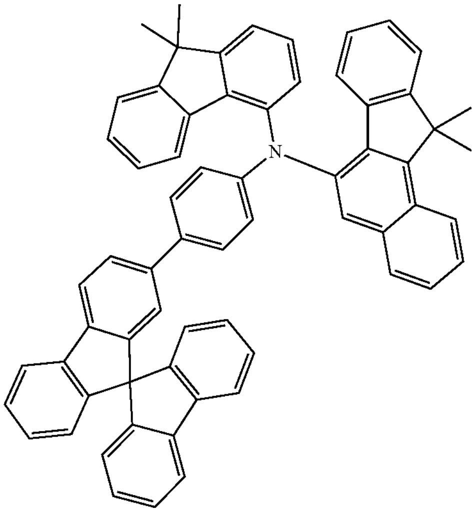
285
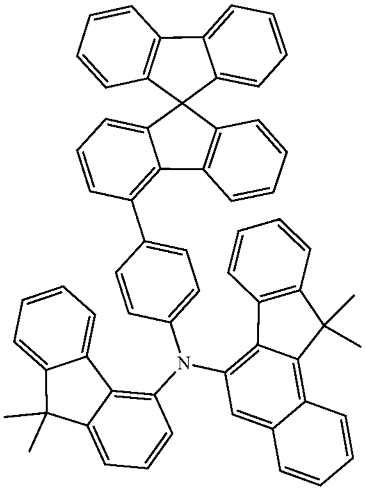
286
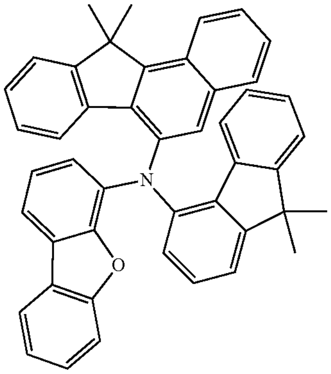

-continued
287
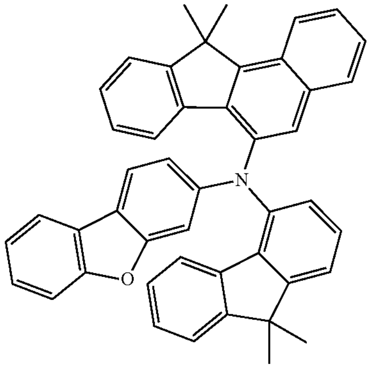
288
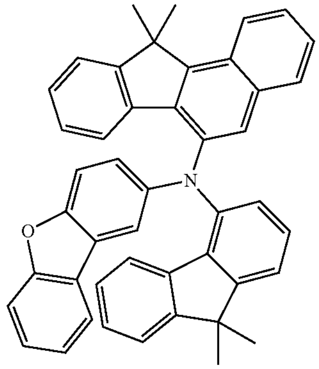
289
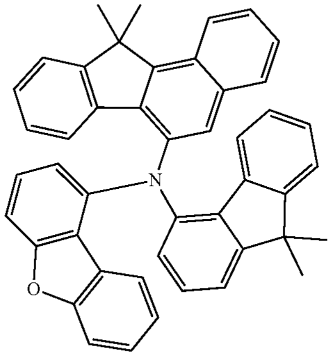
290
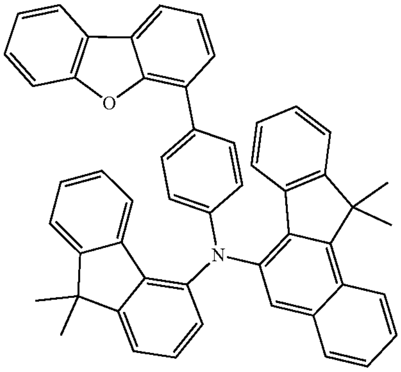
-continued
291
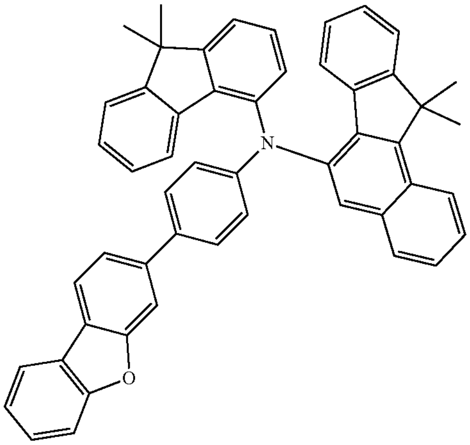
292
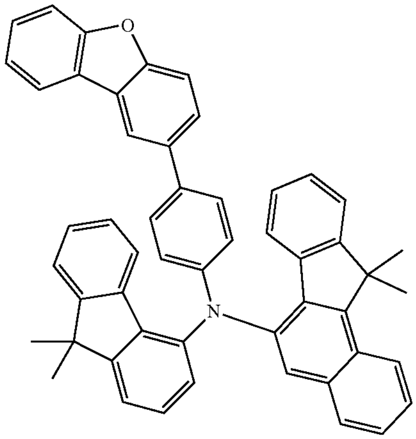
293
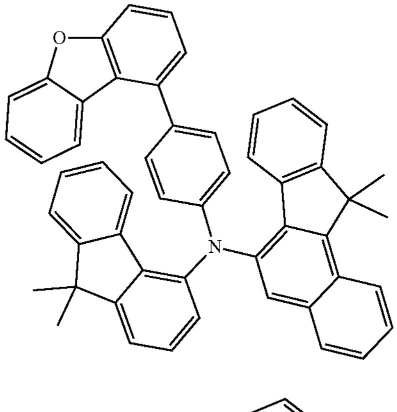
294
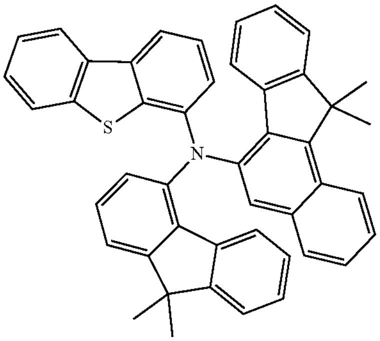

-continued
295
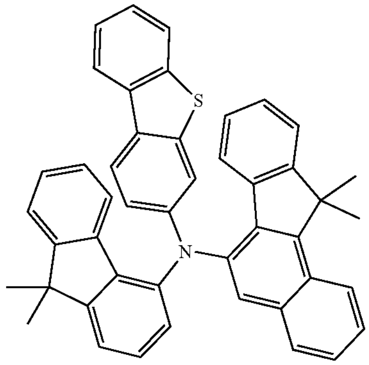
296
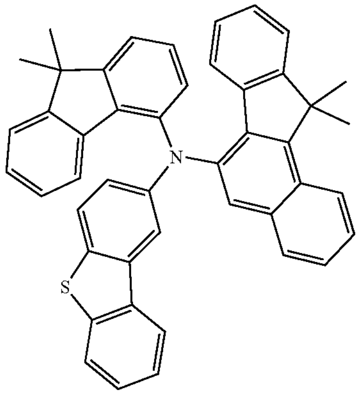
297
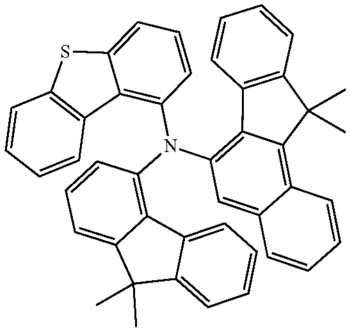
298
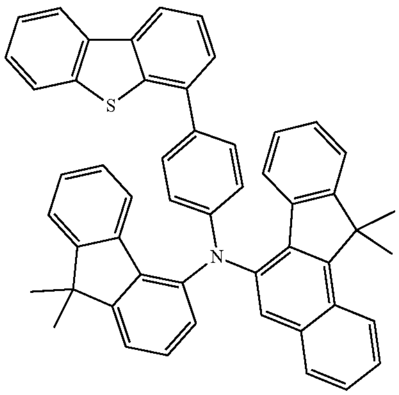
-continued
299
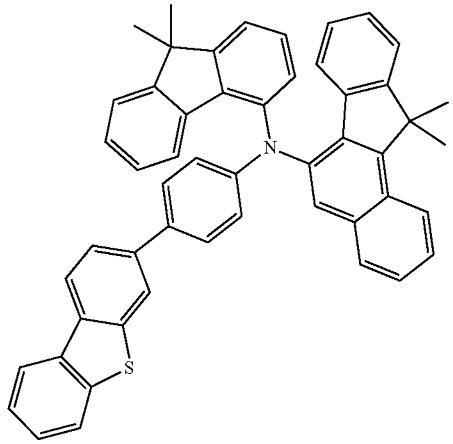
300
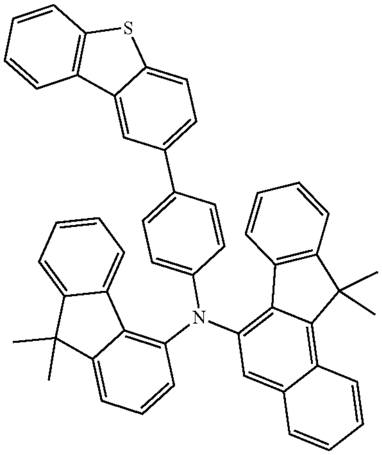
301
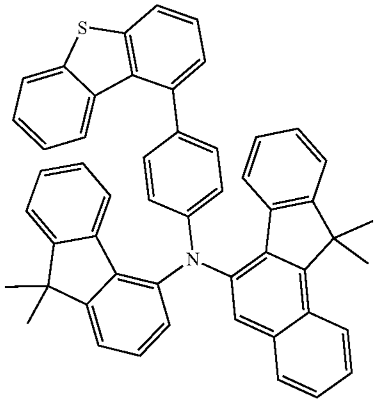

-continued
302
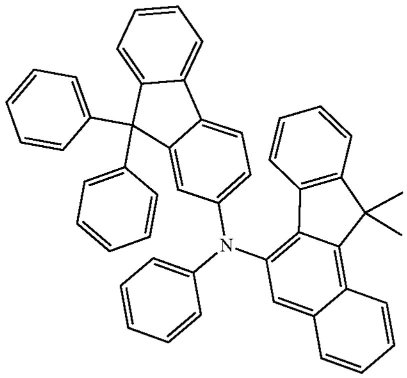
308
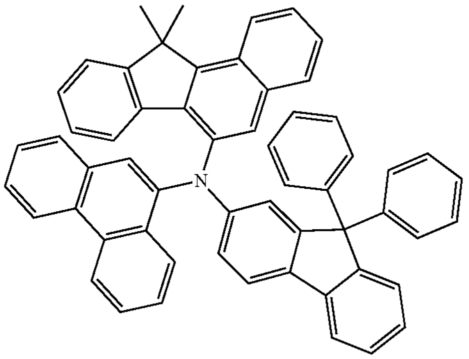
309
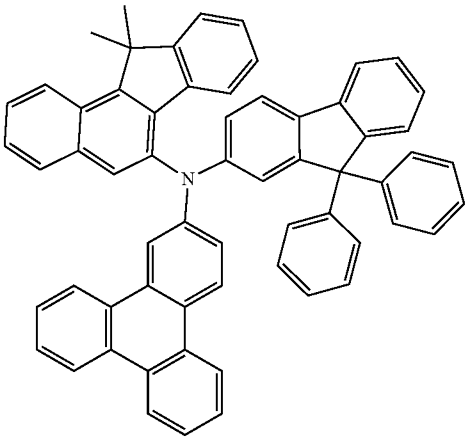
-continued
312
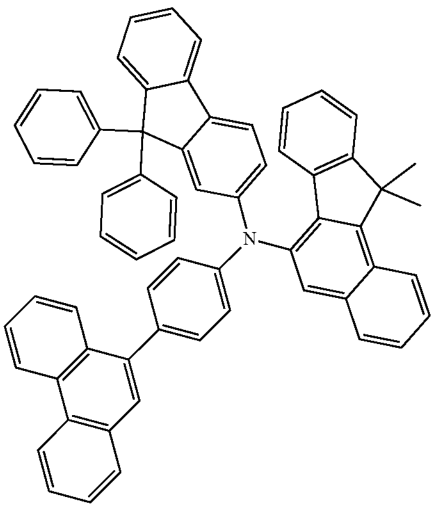
313
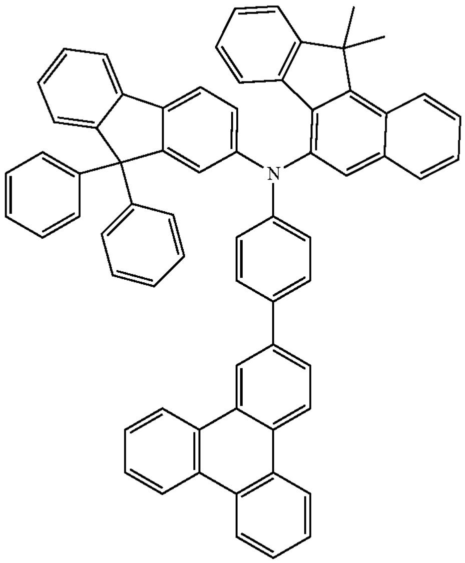
317
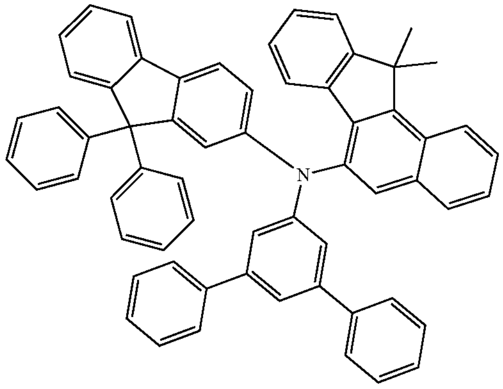

-continued
318
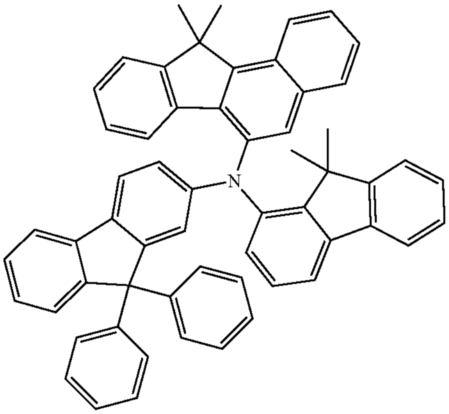
319
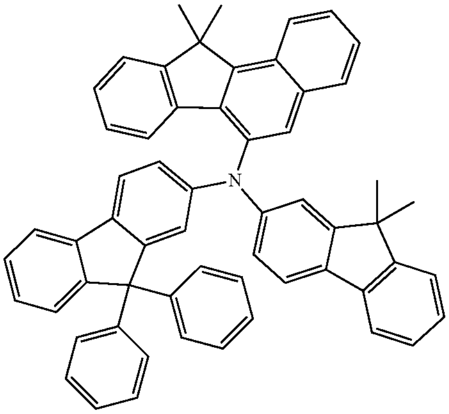
320
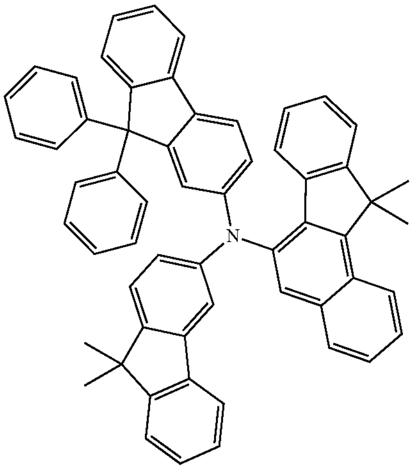
321
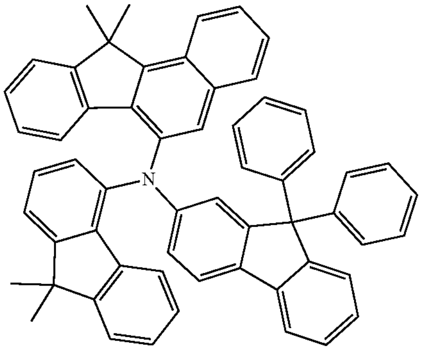
-continued
322
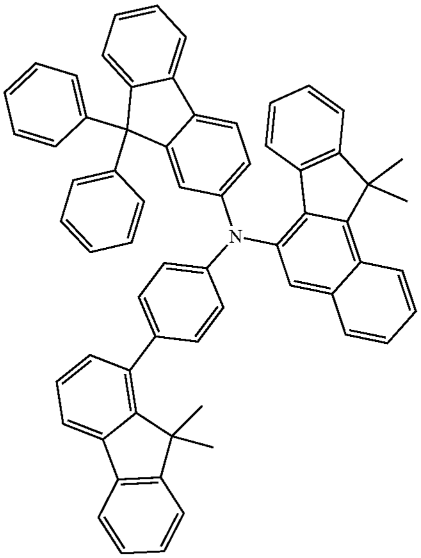
323
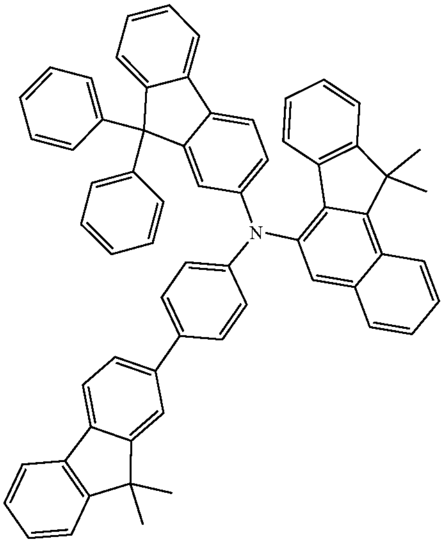
324
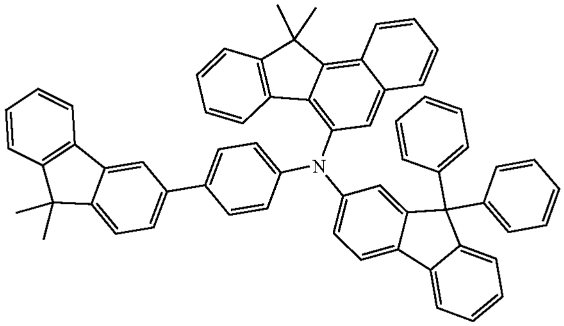

-continued
325
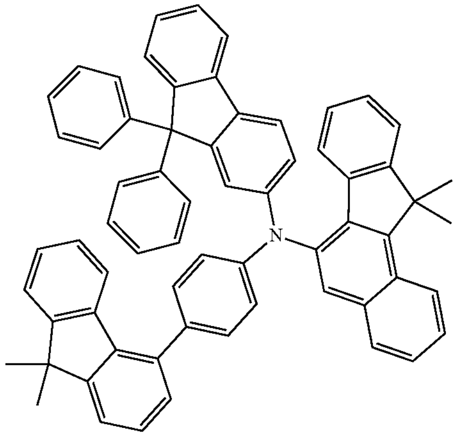
326
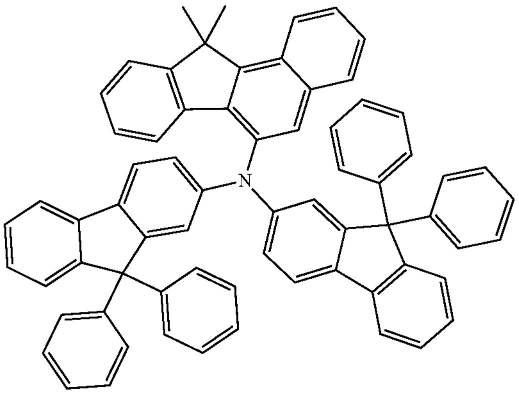
327
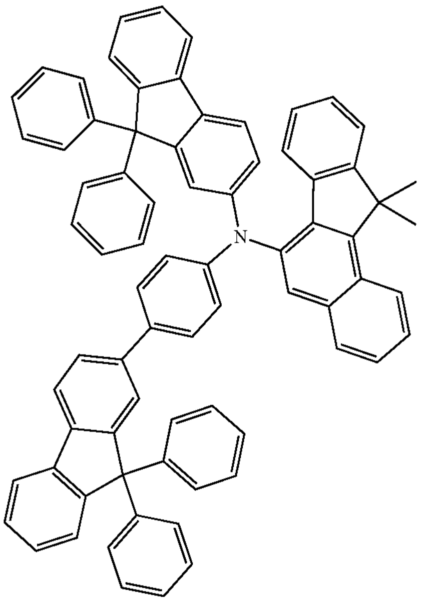
-continued
328
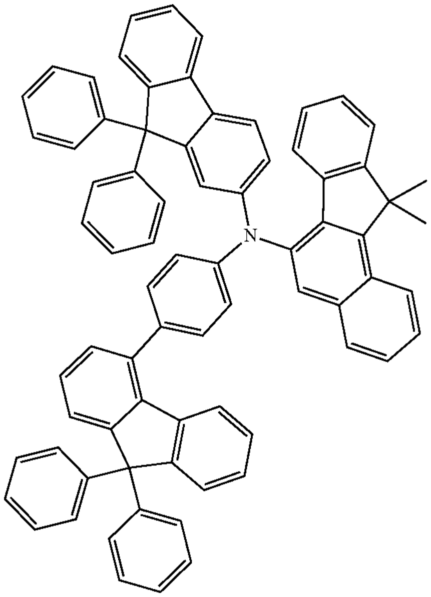
329
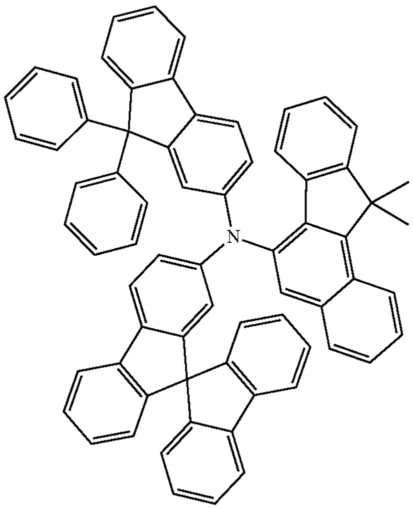
330
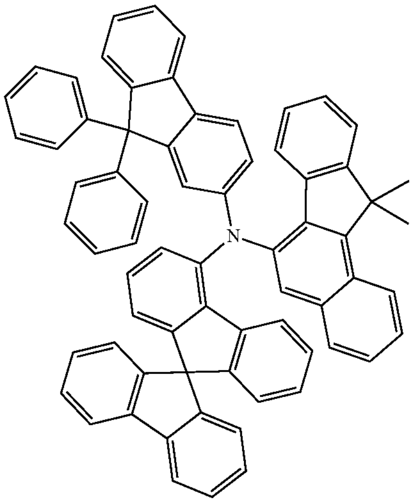

-continued
331
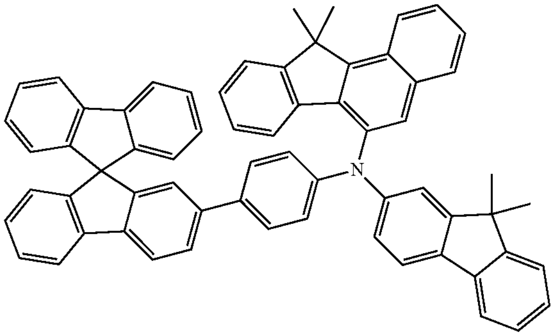
332
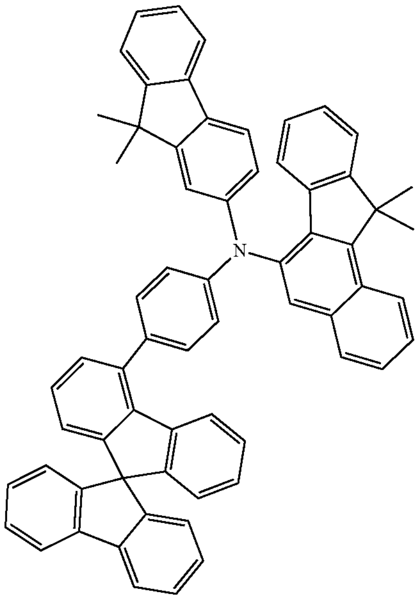
333
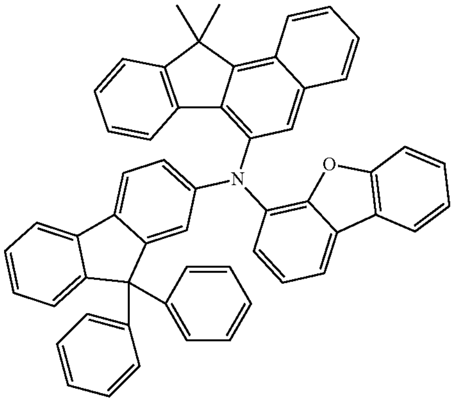
-continued
334
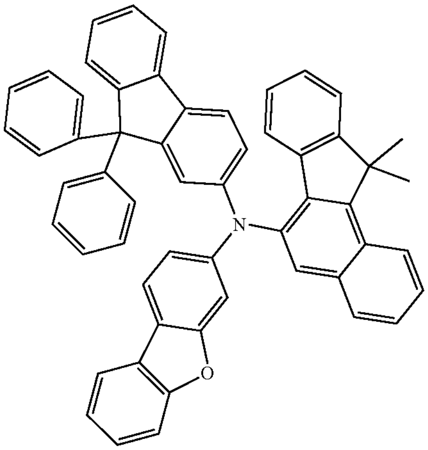
335
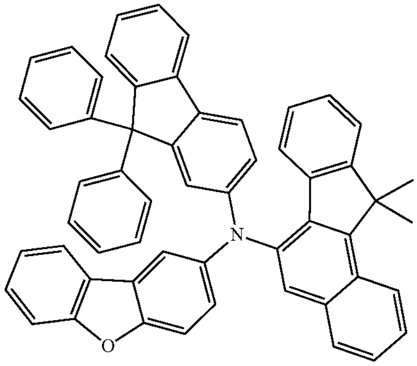
336
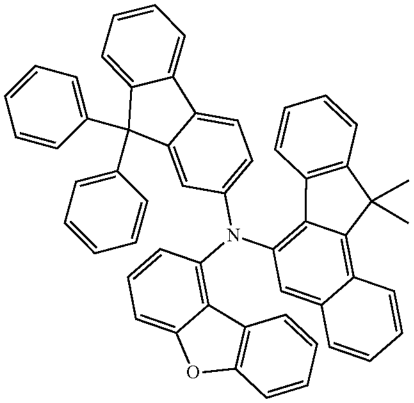

-continued
337
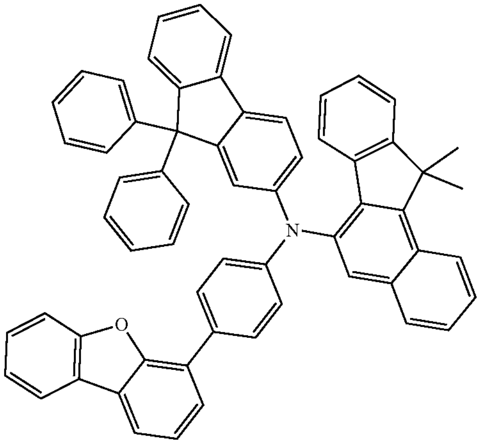
338
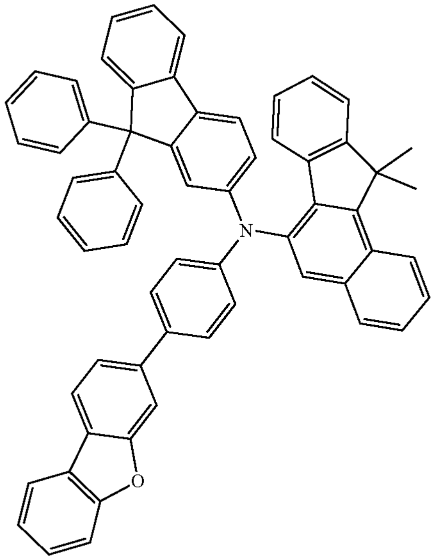
339
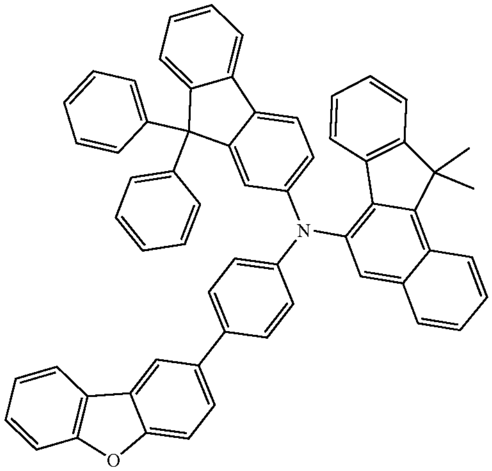
340
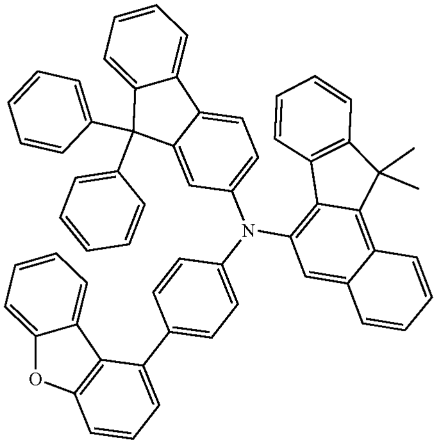
341
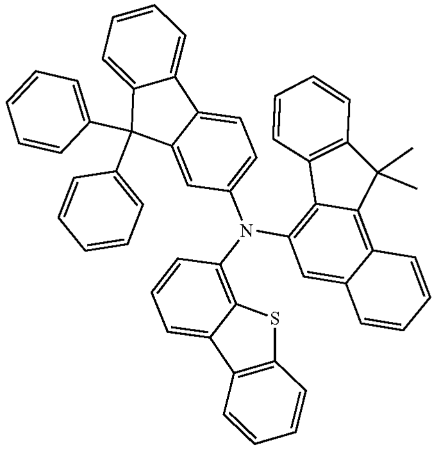
342
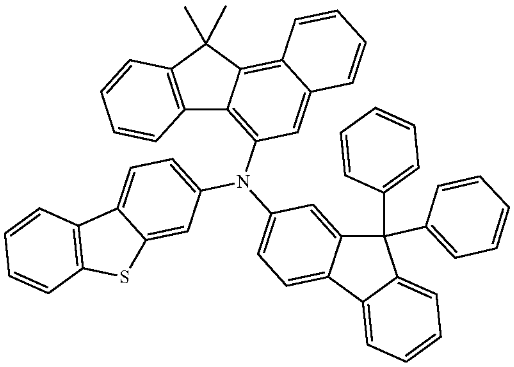

-continued
343
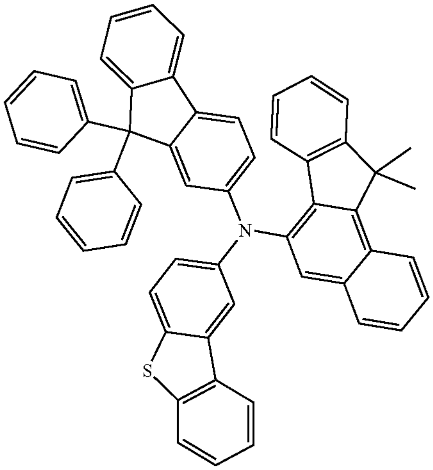
344
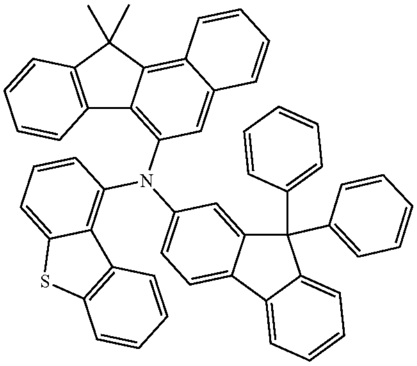
345
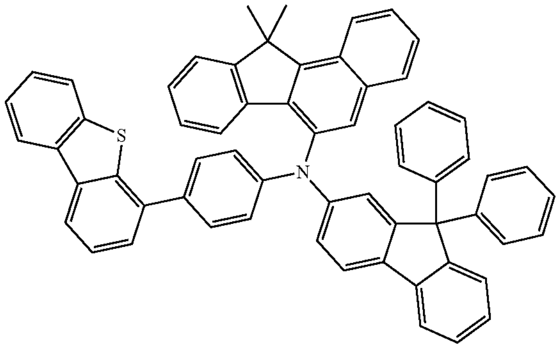
346
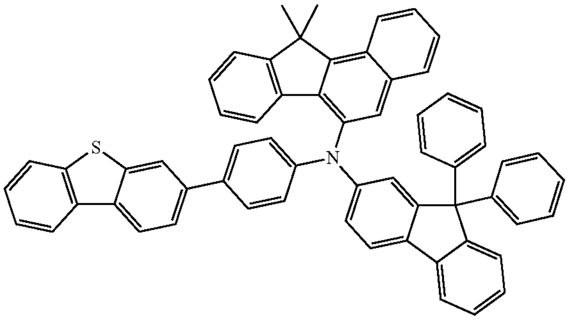
-continued
347
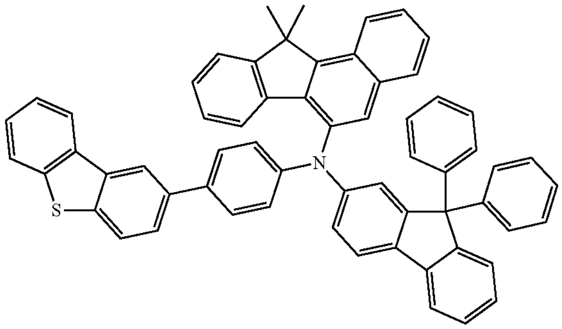
348
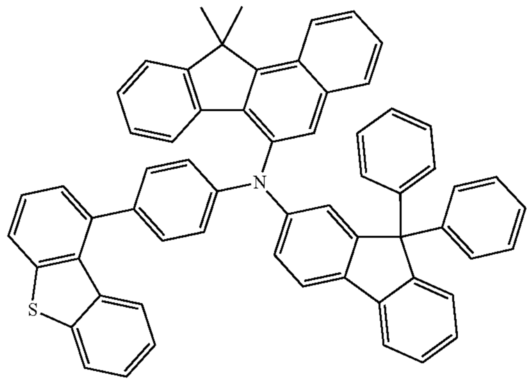
349
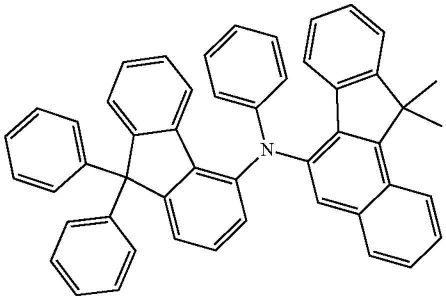
355
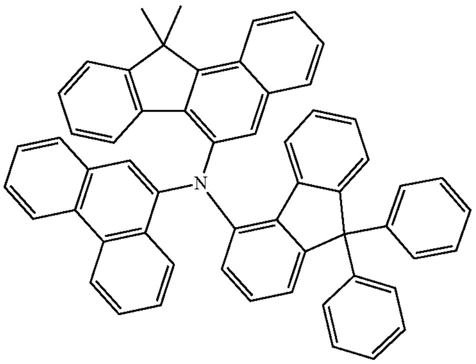

-continued
356
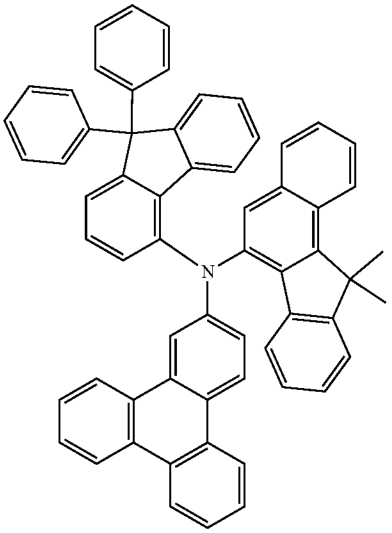
359
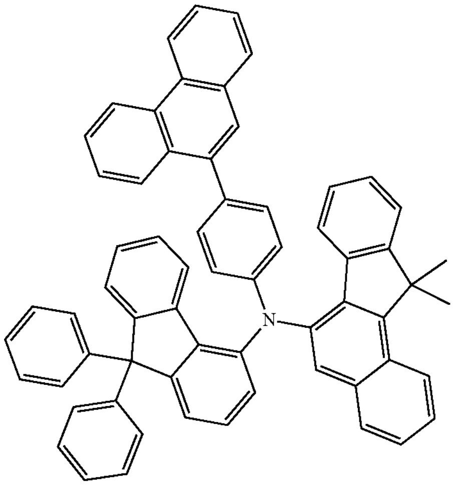
360
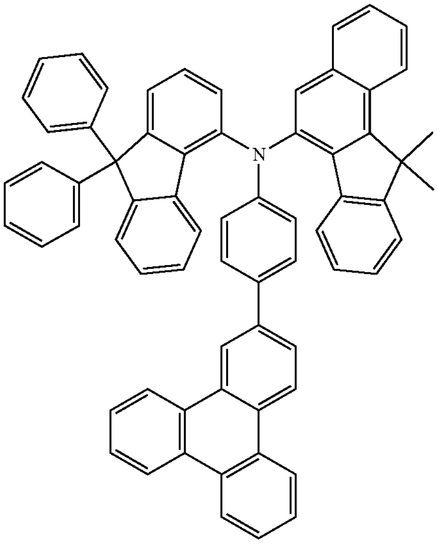
-continued
364
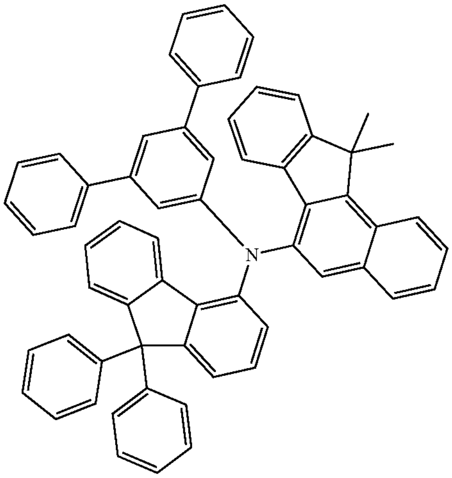
365
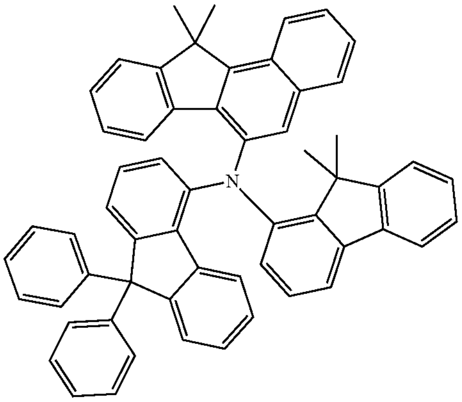
366
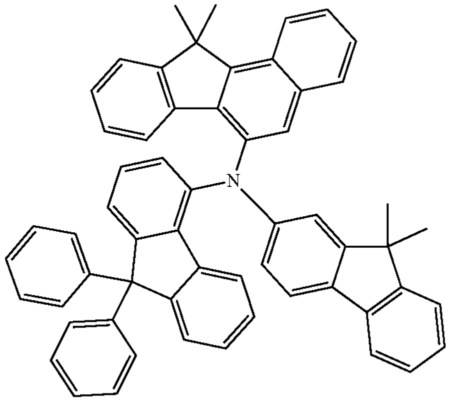

-continued
367
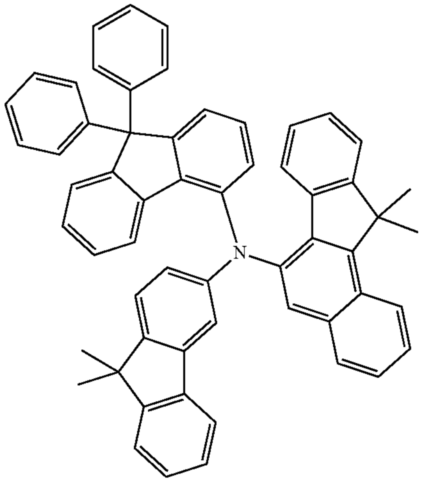
368
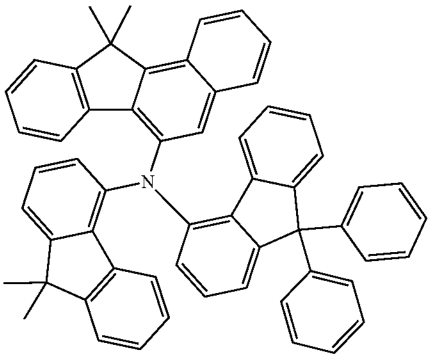
369
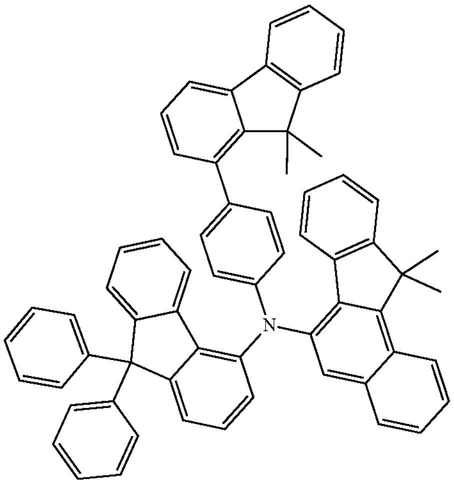
-continued
370
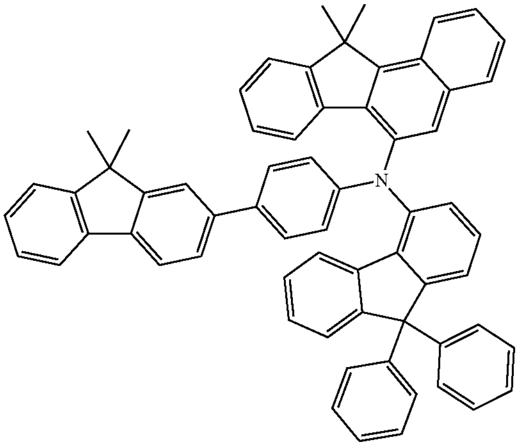
371
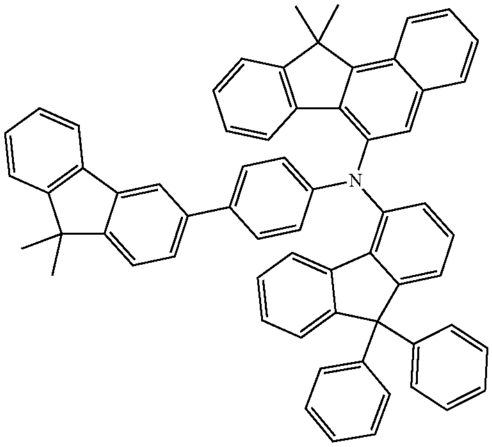
372
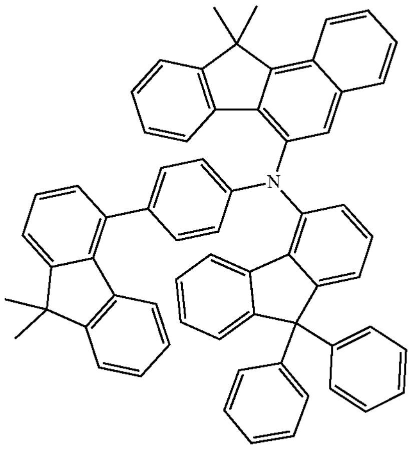

-continued
373
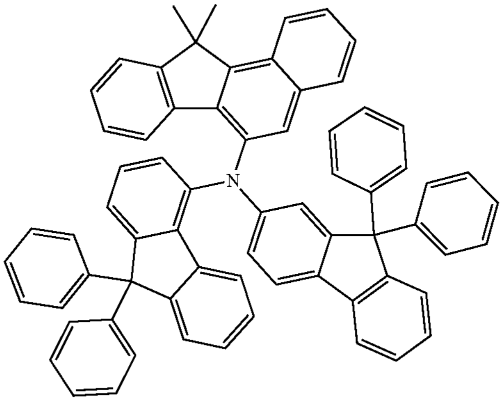
374
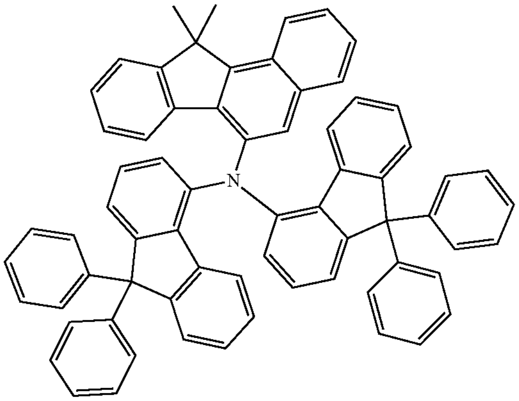
375
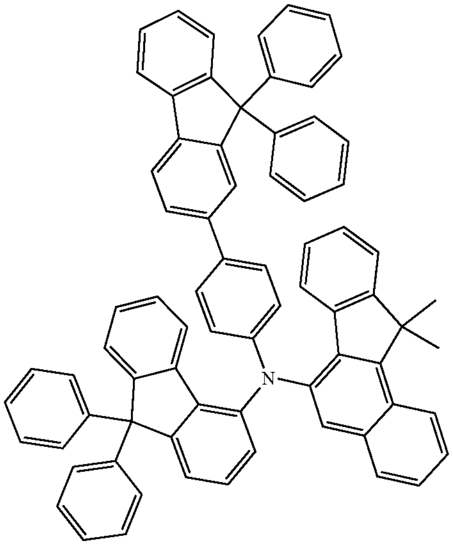
-continued
376
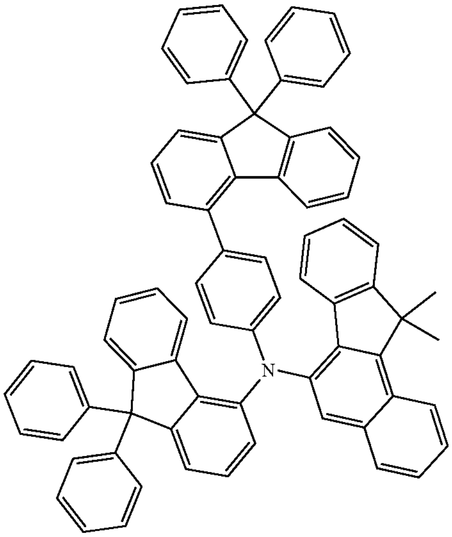
377
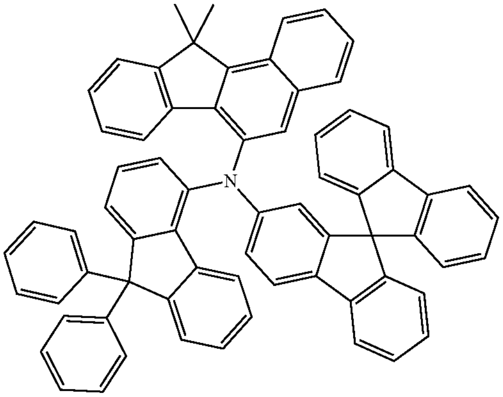
378
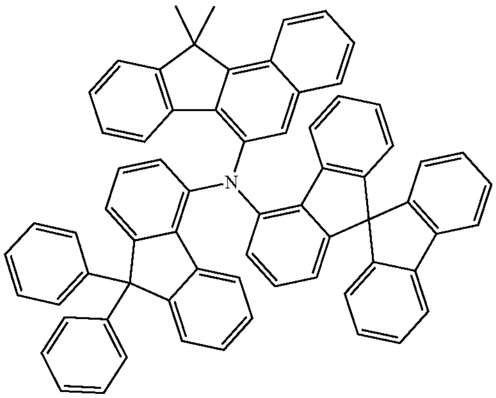

-continued
379
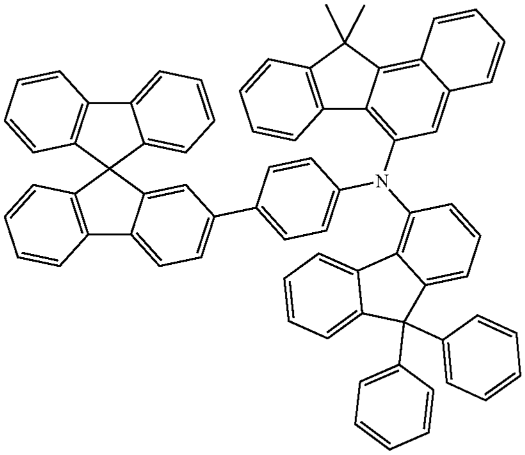
380
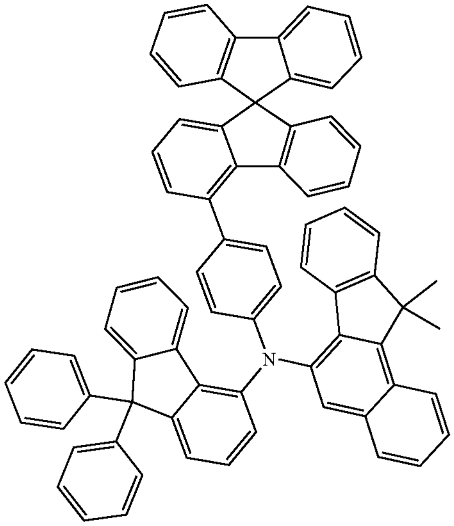
381
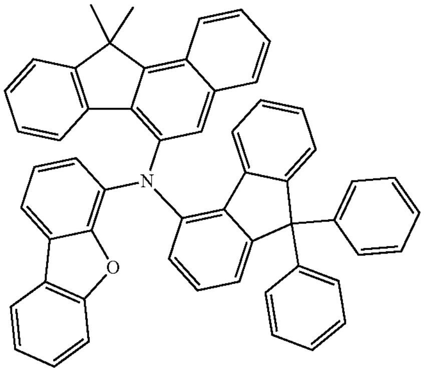
-continued
382
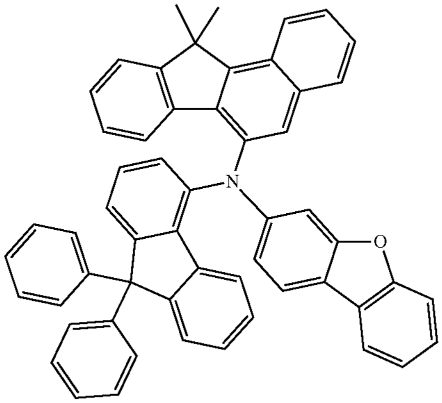
383
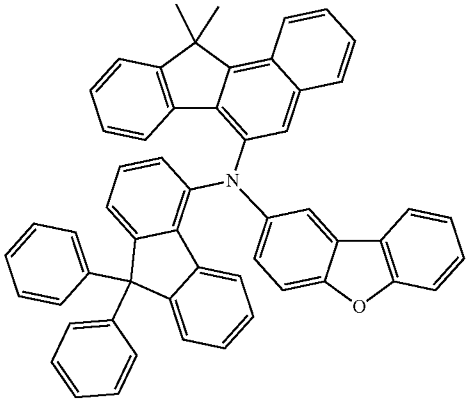
384
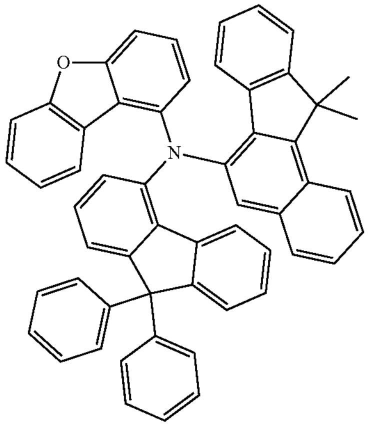
385
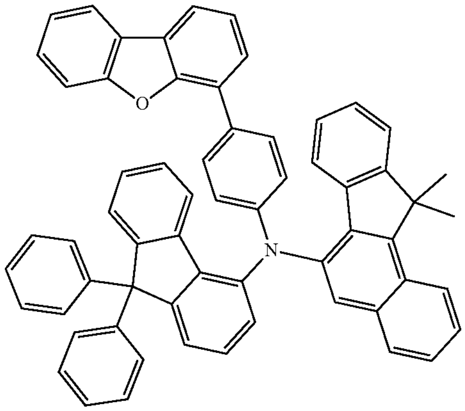

-continued
386
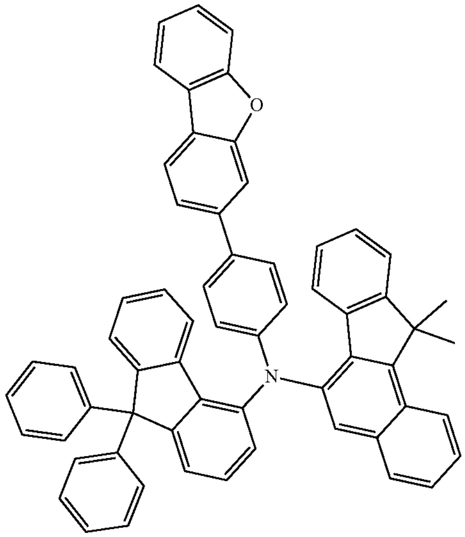
387
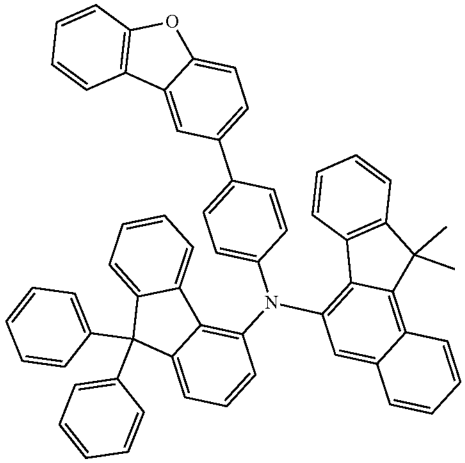
388
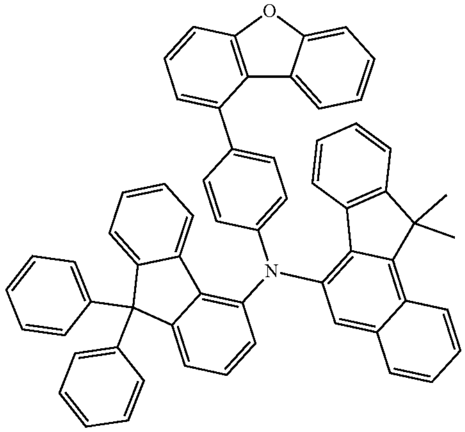
-continued
389
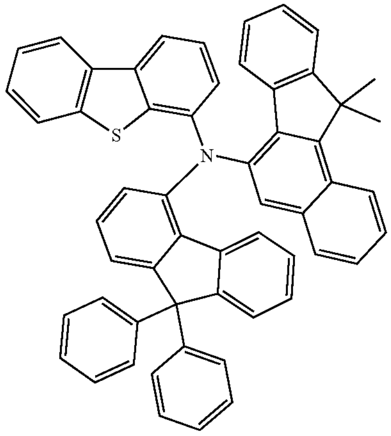
390
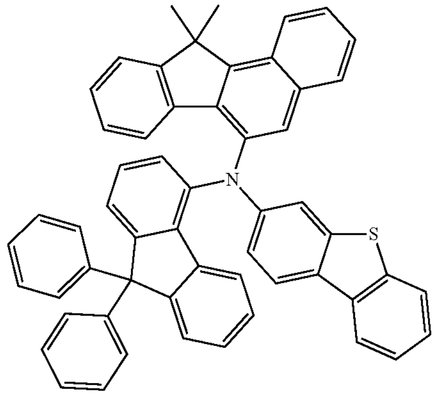
391
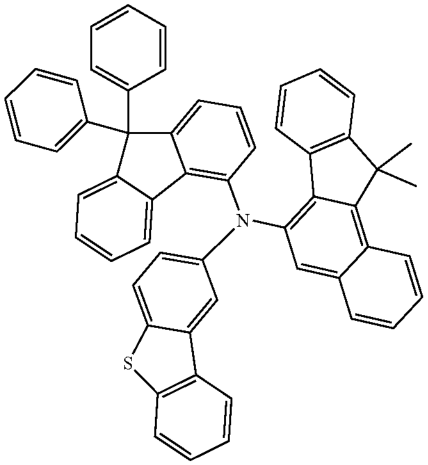

-continued
392
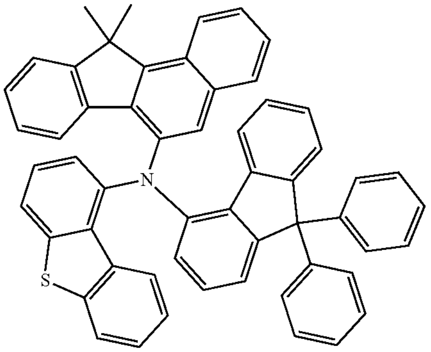
393
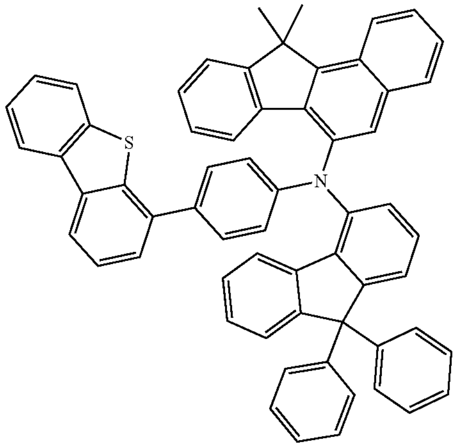
394
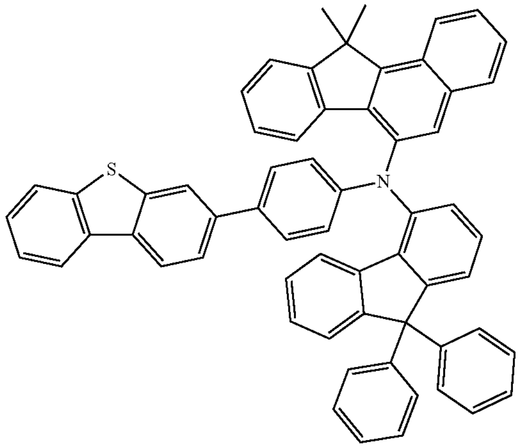
-continued
395
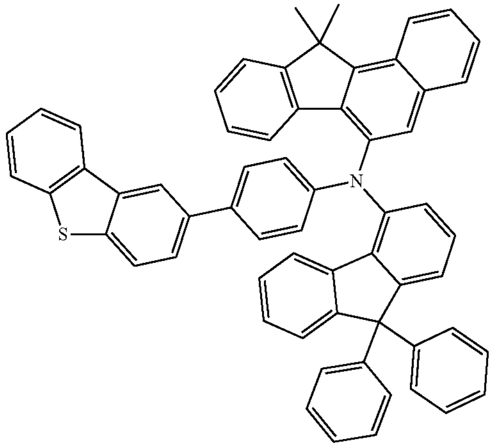
396
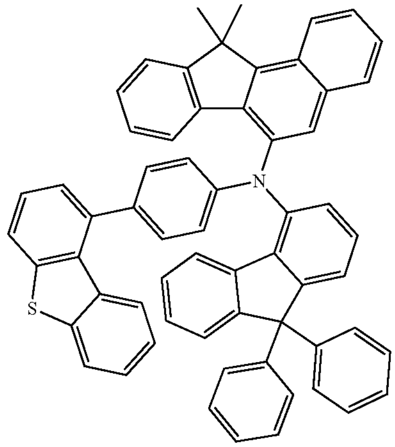
397
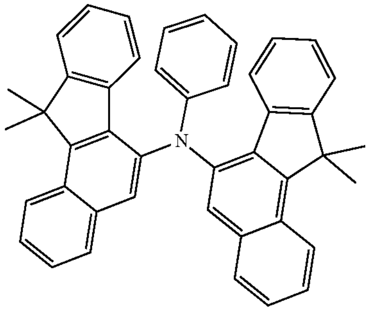
403
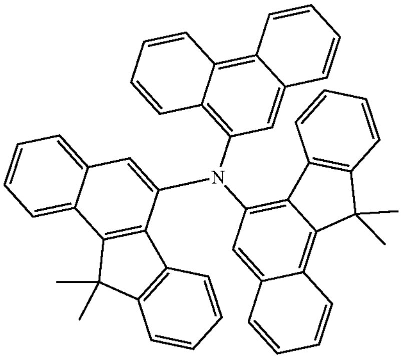

-continued
404
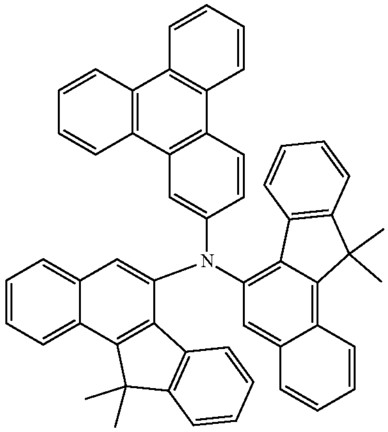
407
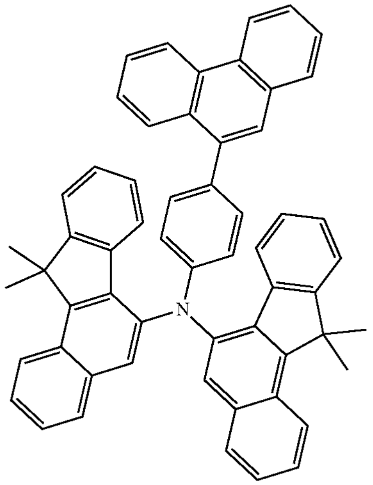
408
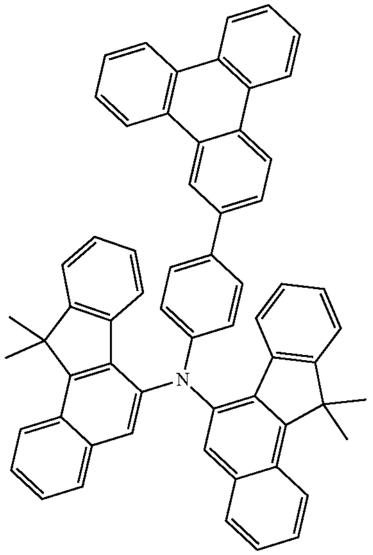
-continued
412
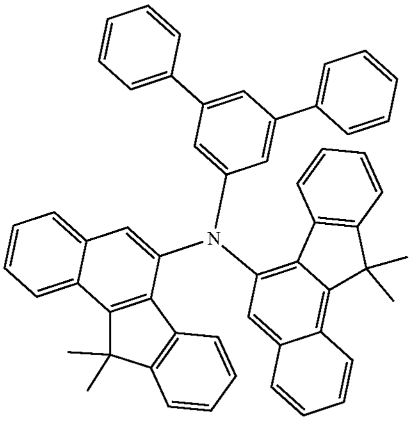
413
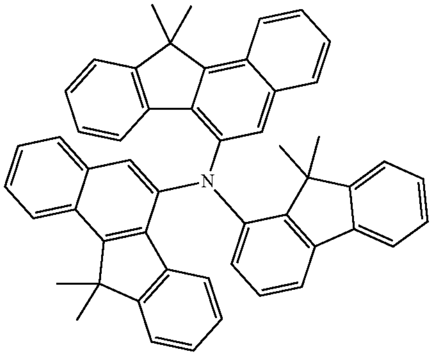
414
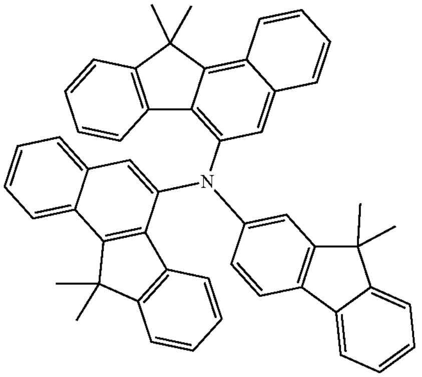
415
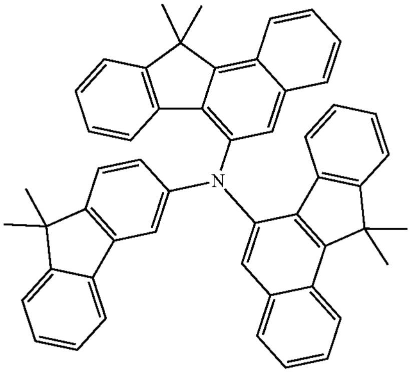

-continued
416
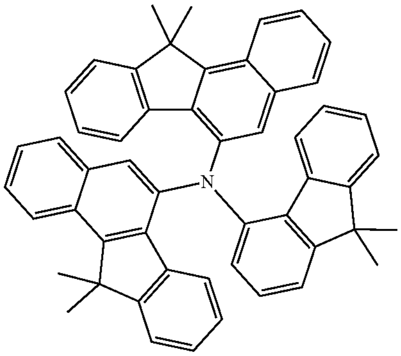
417
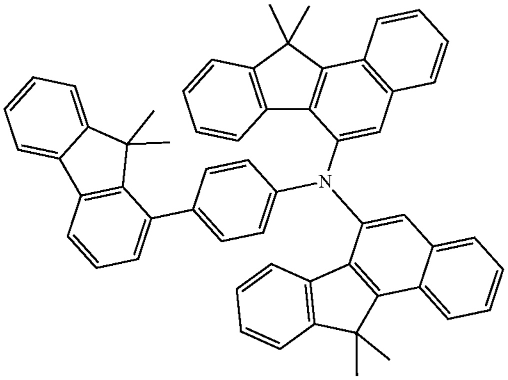
418
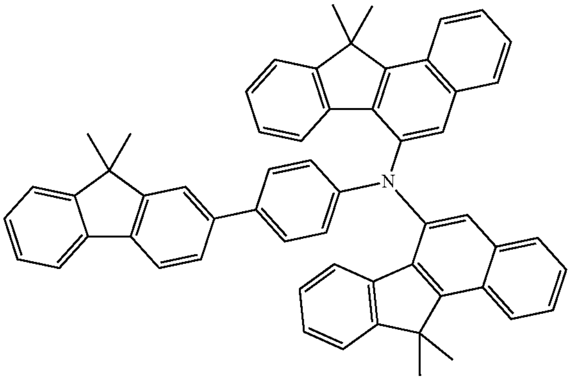
419
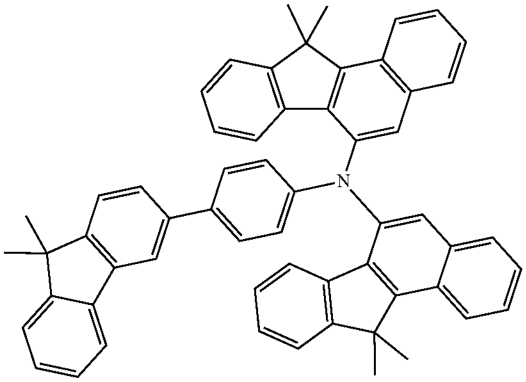
-continued
420
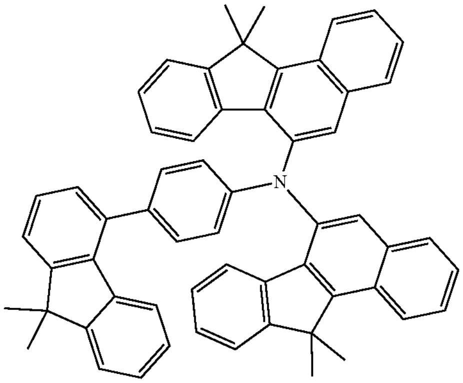
421
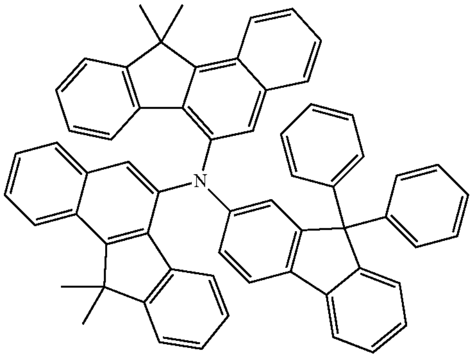
422
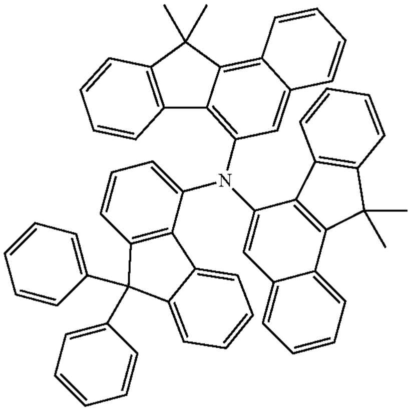
423
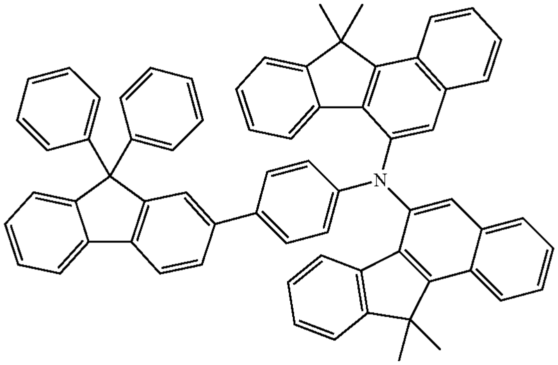

-continued
424
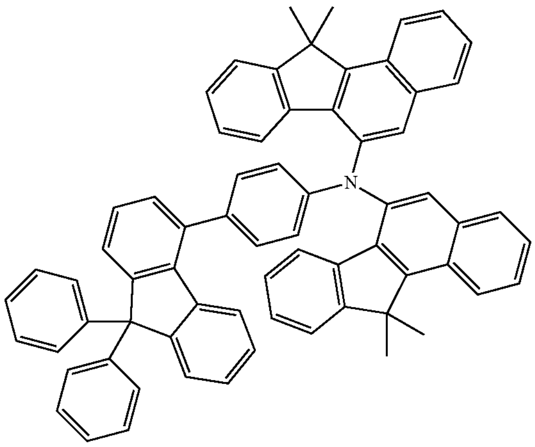
425
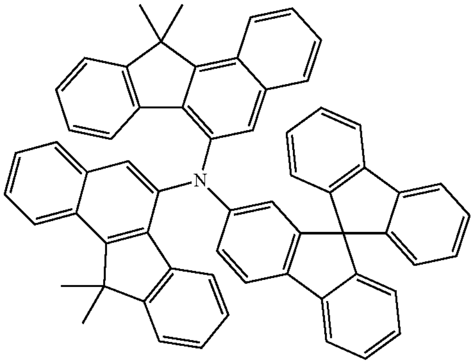
426
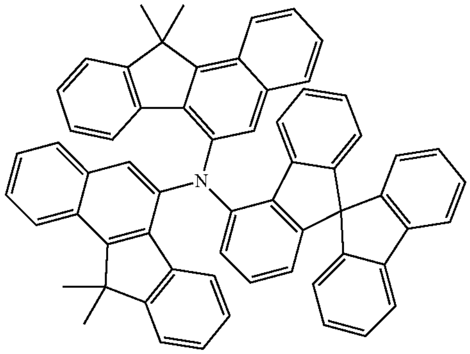
427
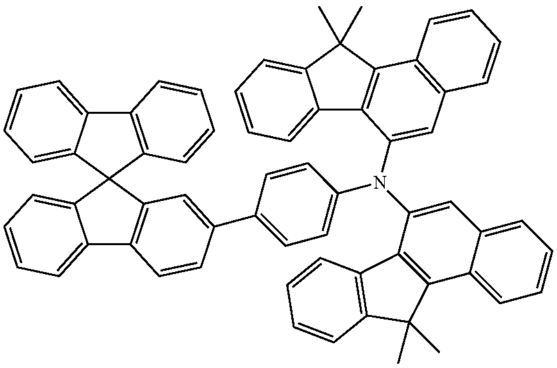
-continued
428
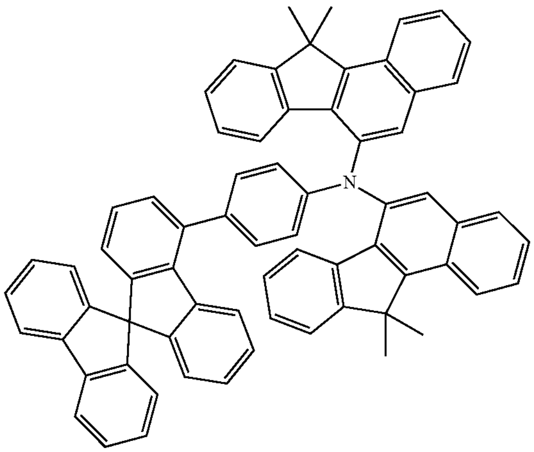
429
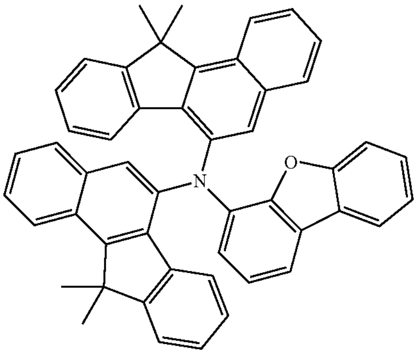
430
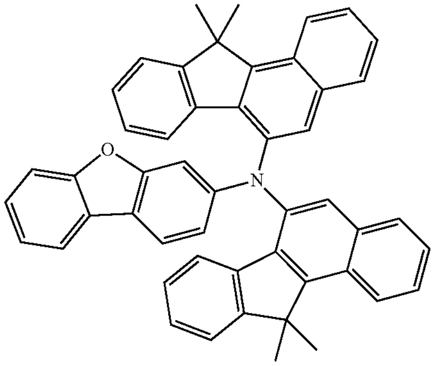
431
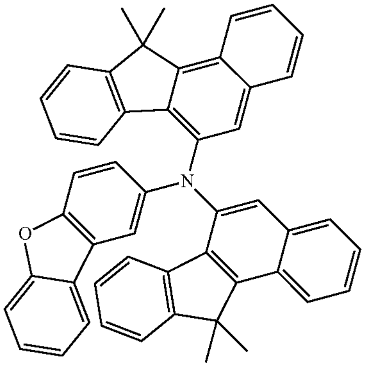

-continued
432
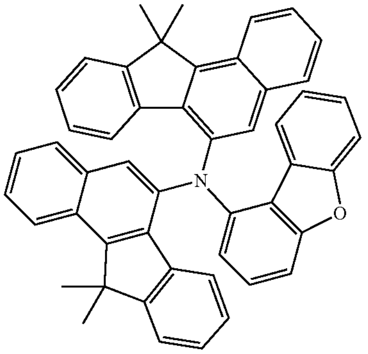
433
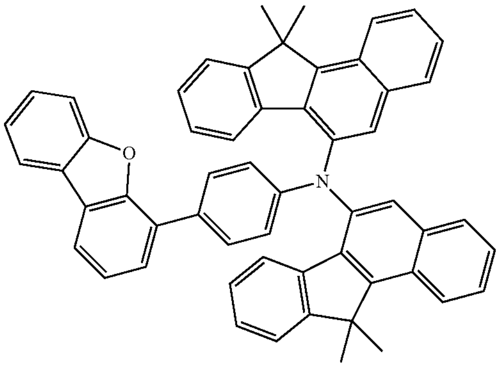
434
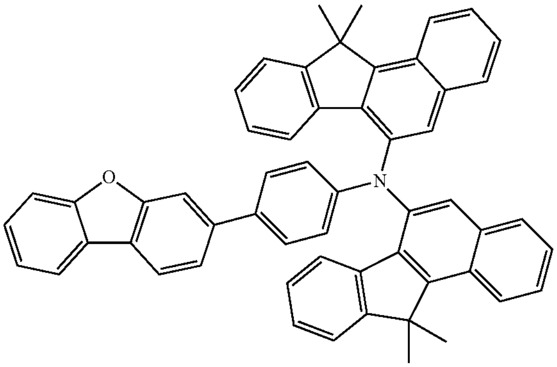
435
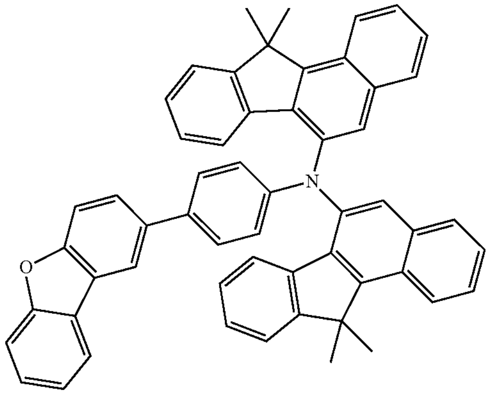
-continued
436
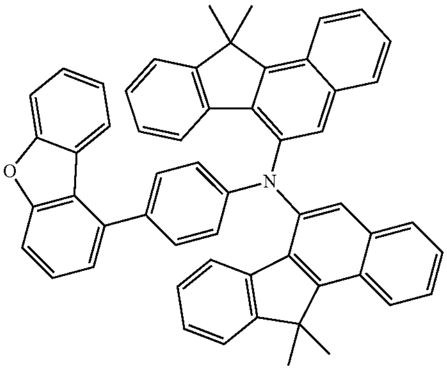
437
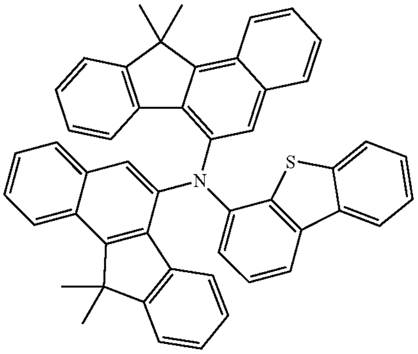
438
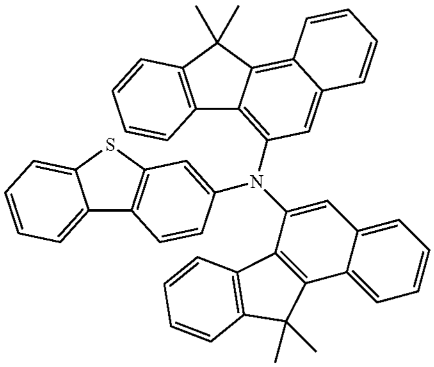
439
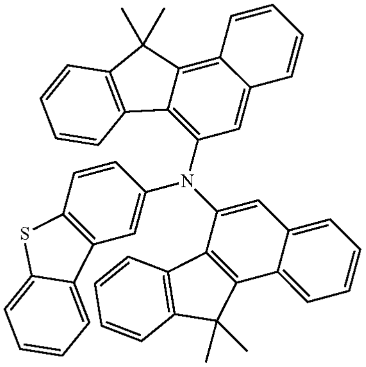

440
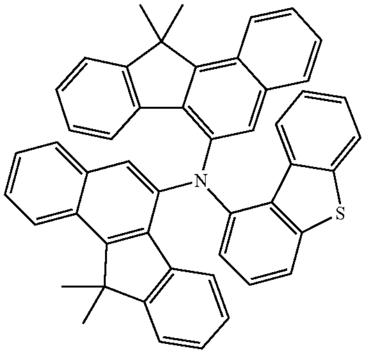
441
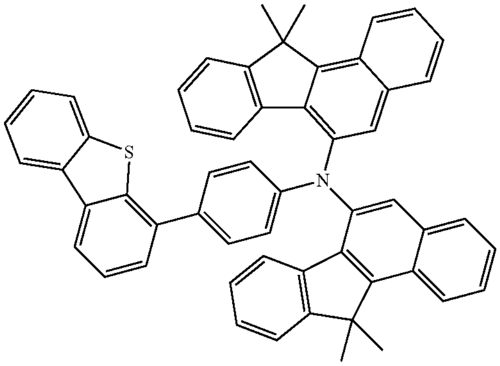
442
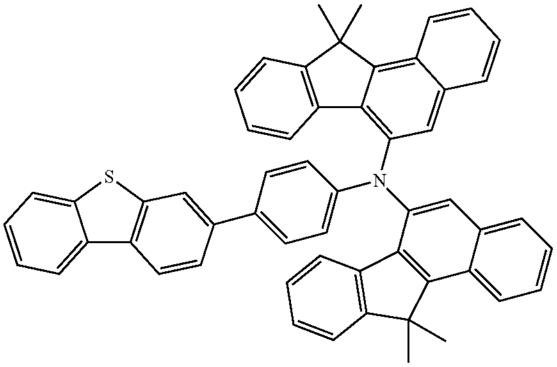
443
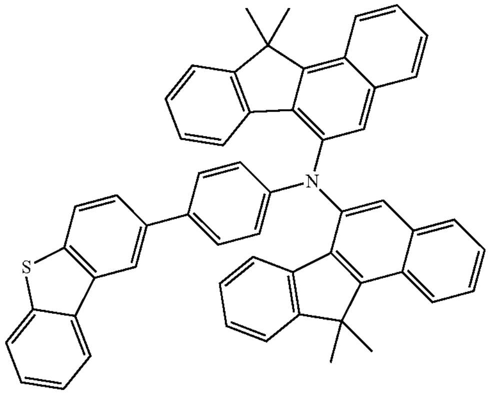
444
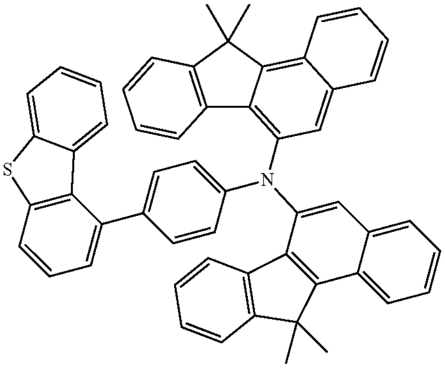
445
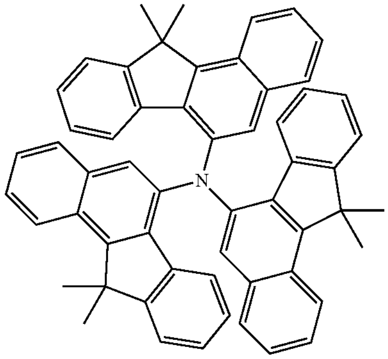
446
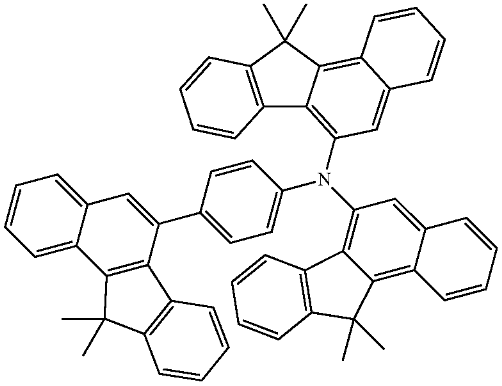
447
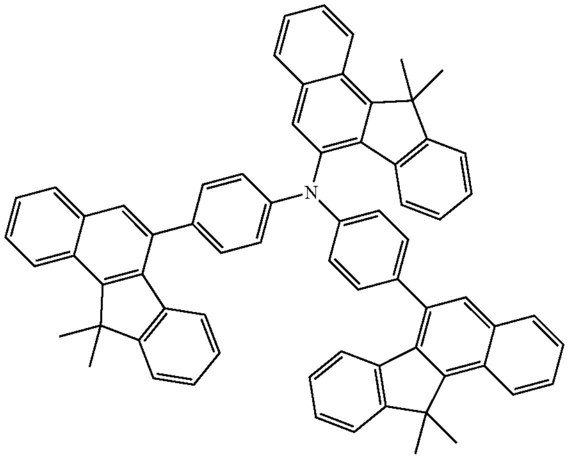

-continued
448
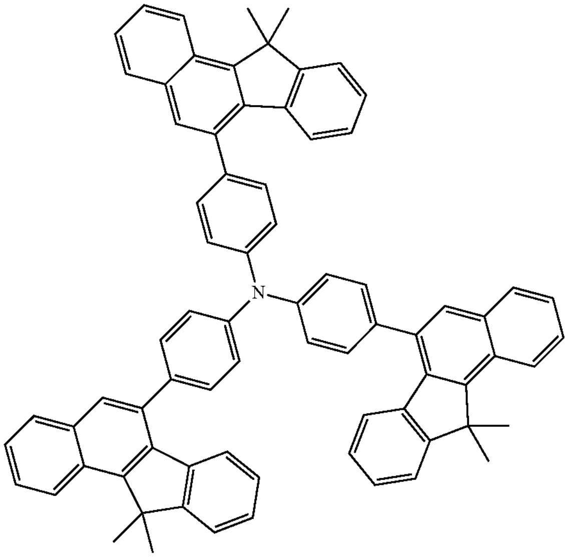
449
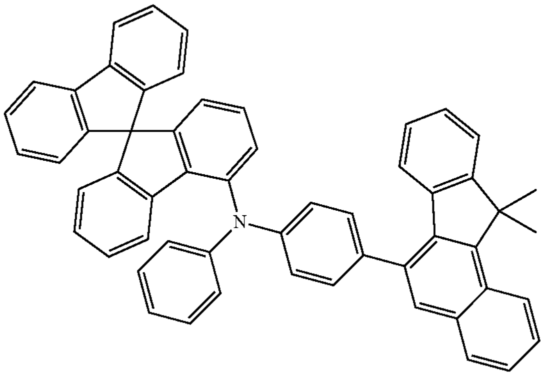
465
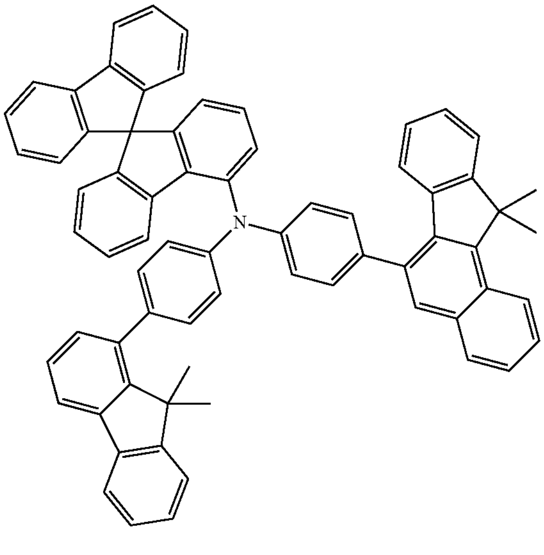
-continued
466
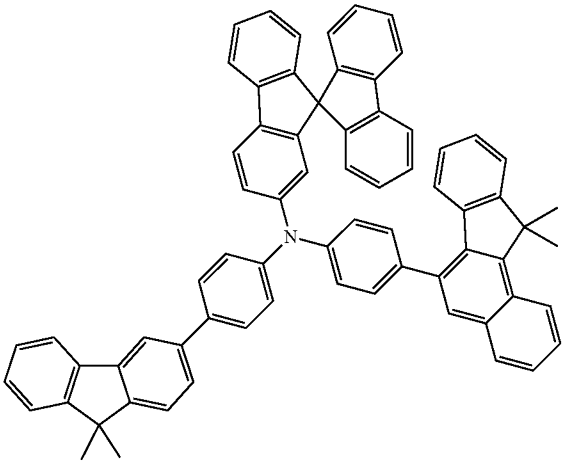
467
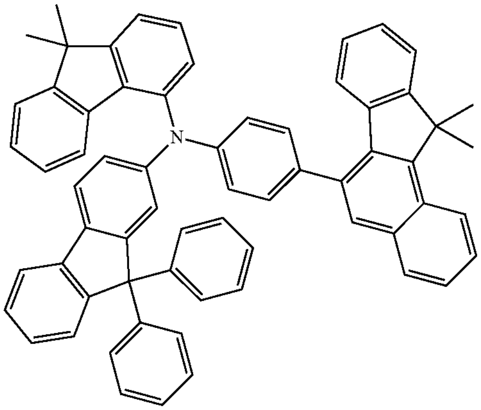
468
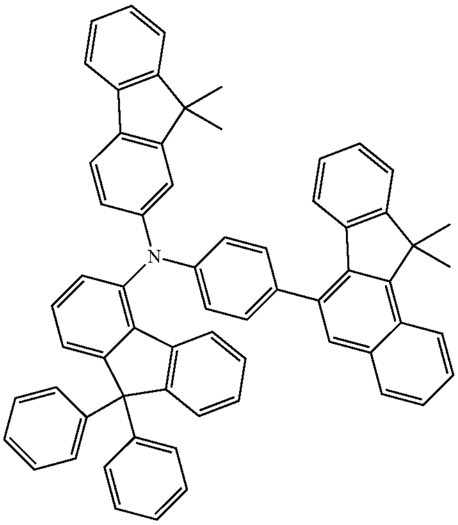

-continued

473

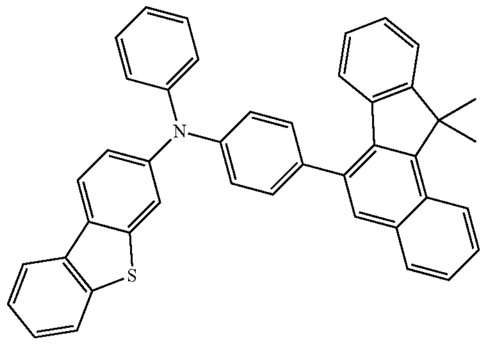

475

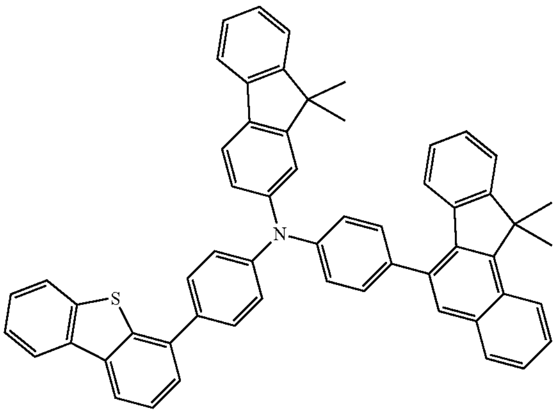

476

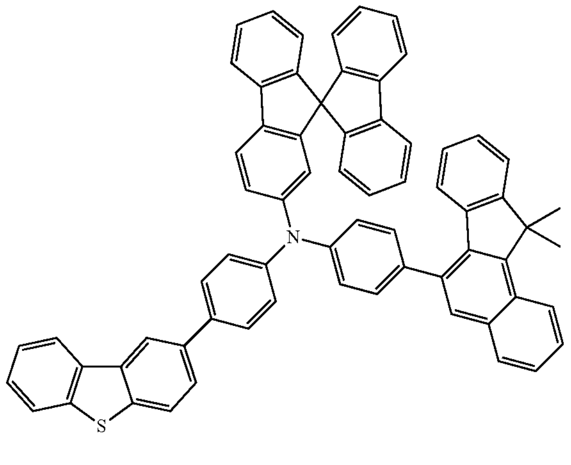

-continued

481

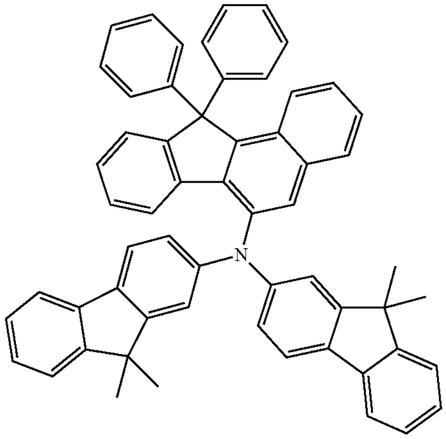

482

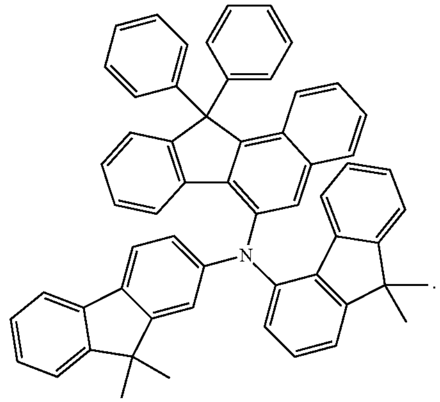

5. An organic light emitting device comprising:

a first electrode;

a second electrode provided opposite to the first electrode; and one or more organic material layers provided between the first electrode and the second electrode, wherein one or more layers of the organic material layers comprise the heterocyclic compound of claim 1.

6. The organic light emitting device of claim 5, wherein the organic material layer comprises a hole transfer layer, and the hole transfer layer comprises the heterocyclic compound.

7. The organic light emitting device of claim 5, wherein the organic material layer comprises an electron injection layer or an electron transfer layer, and the electron injection layer or the electron transfer layer comprises the heterocyclic compound.

8. The organic light emitting device of claim 5, wherein the organic material layer comprises an electron blocking layer or a hole blocking layer, and the electron blocking layer or the hole blocking layer comprises the heterocyclic compound.

9. The organic light emitting device of claim 5, further comprising one, two or more layers selected from the group consisting of a light emitting layer, a hole injection layer, a hole transfer layer, an electron injection layer, an electron transfer layer, an electron blocking layer and a hole blocking layer.

10. The organic light emitting device of claim 5 comprising:

a first electrode;

a first stack provided on the first electrode and comprising a first light emitting layer;

a charge generation layer provided on the first stack;

a second stack provided on the charge generation layer and comprising a second light emitting layer; and a second electrode provided on the second stack.

11. The organic light emitting device of claim 10, wherein the charge generation layer comprises the heterocyclic compound.

* * * * *